(12) United States Patent
Byun et al.

(10) Patent No.: US 12,030,903 B2
(45) Date of Patent: Jul. 9, 2024

(54) ANTIVIRAL COMPOUNDS

(71) Applicant: Gilead Sciences, Inc., Foster City, CA (US)

(72) Inventors: Daniel H. Byun, Foster City, CA (US); Gregory F. Chin, San Francisco, CA (US); Michael O. Clarke, Redwood City, CA (US); Bindu Goyal, Fremont, CA (US); Petr Jansa, Foster City, CA (US); Richard L. Mackman, Millbrae, CA (US); Michael R. Mish, Foster City, CA (US); Dustin S. Siegel, Half Moon Bay, CA (US)

(73) Assignee: Gilead Sciences, Inc., Foster City, CA (US)

( * ) Notice: Subject to any disclaimer, the term of this patent is extended or adjusted under 35 U.S.C. 154(b) by 364 days.

(21) Appl. No.: 17/178,115

(22) Filed: Feb. 17, 2021

(65) Prior Publication Data

US 2021/0292348 A1 Sep. 23, 2021

Related U.S. Application Data

(60) Provisional application No. 62/978,199, filed on Feb. 18, 2020.

(51) Int. Cl.
*C07F 9/6561* (2006.01)
*A61K 45/06* (2006.01)

(52) U.S. Cl.
CPC ............ *C07F 9/6561* (2013.01); *A61K 45/06* (2013.01)

(58) Field of Classification Search
CPC ...... C07F 9/6561; A61K 45/06; A61K 31/706; A61K 31/675; Y02A 50/30; A61P 31/12; A61P 31/14; C07D 487/04
See application file for complete search history.

(56) References Cited

U.S. PATENT DOCUMENTS

| | | |
|---|---|---|
| 4,707,540 A | 11/1987 | Manser et al. |
| 5,446,137 A | 8/1995 | Maag et al. |
| 6,699,994 B1 | 3/2004 | Babu et al. |
| 8,101,745 B2 | 1/2012 | Hostetler et al. |
| 8,119,607 B2 | 2/2012 | Francom et al. |
| 8,242,085 B2 | 8/2012 | Babu et al. |
| 8,318,700 B2 | 11/2012 | Hostetler et al. |
| 8,440,813 B2 | 5/2013 | Babu et al. |
| 9,370,528 B2 | 6/2016 | Schentag et al. |
| 9,388,208 B2 | 7/2016 | Clarke et al. |
| 9,701,682 B2 | 7/2017 | Clarke et al. |
| 9,724,360 B2 | 8/2017 | Chun et al. |
| 9,777,035 B2 | 10/2017 | Girijavallabhan et al. |
| 9,815,864 B2 | 11/2017 | Beigelman et al. |
| 10,004,719 B1 | 6/2018 | Hsu et al. |
| 10,059,716 B2 | 8/2018 | Clarke et al. |
| 10,251,904 B2 | 4/2019 | Clarke et al. |
| 10,377,761 B2 | 8/2019 | Clarke et al. |
| 10,682,368 B2 | 6/2020 | Perron et al. |
| 2002/0035082 A1 | 3/2002 | Grinstaff et al. |
| 2002/0188137 A1 | 12/2002 | Dershem et al. |
| 2003/0170891 A1 | 9/2003 | McSwiggen |
| 2003/0175950 A1 | 9/2003 | McSwiggen |
| 2003/0199516 A1 | 10/2003 | Moser et al. |
| 2004/0009959 A1 | 1/2004 | Potter et al. |
| 2004/0157838 A1 | 8/2004 | Griffith |
| 2004/0157839 A1 | 8/2004 | Griffith |
| 2004/0214837 A1 | 10/2004 | Griffith et al. |
| 2004/0229839 A1 | 11/2004 | Babu et al. |
| 2004/0229840 A1 | 11/2004 | Bhat et al. |
| 2006/0121312 A1 | 6/2006 | Yamada et al. |
| 2006/0194144 A1 | 8/2006 | Sooriyakumaran et al. |
| 2006/0281922 A1 | 12/2006 | Gao et al. |
| 2007/0232635 A1 | 10/2007 | Chelliah et al. |
| 2009/0318380 A1 | 12/2009 | Sofia et al. |
| 2009/0323011 A1 | 12/2009 | He et al. |
| 2009/0323012 A1 | 12/2009 | He et al. |
| 2010/0035836 A1 | 2/2010 | Francom et al. |
| 2010/0040804 A1 | 2/2010 | Zhang |
| 2010/0096603 A1 | 4/2010 | Wang et al. |
| 2010/0184942 A1 | 7/2010 | Chen et al. |
| 2010/0186626 A1 | 7/2010 | Shin et al. |
| 2011/0212994 A1 | 9/2011 | Clem et al. |
| 2011/0216273 A1 | 9/2011 | He et al. |
| 2011/0287927 A1 | 11/2011 | Grasset et al. |
| 2011/0319459 A1 | 12/2011 | Gupta et al. |
| 2012/0009147 A1 | 1/2012 | Cho et al. |
| 2012/0020921 A1 | 1/2012 | Cho et al. |
| 2012/0035115 A1 | 2/2012 | Manoharan et al. |
| 2012/0070411 A1 | 3/2012 | Beigelman et al. |
| 2012/0070415 A1 | 3/2012 | Beigelman et al. |

(Continued)

FOREIGN PATENT DOCUMENTS

| | | |
|---|---|---|
| CN | 102000103 A | 4/2011 |
| CN | 102286047 A | 12/2011 |

(Continued)

OTHER PUBLICATIONS

Office Action and Search Report in Taiwan Application No. 110105140, dated Dec. 7, 2021, 7 pages (3 pages of English Translation and 4 pages of Taiwan Office Action).

(Continued)

*Primary Examiner* — Savitha M Rao
*Assistant Examiner* — Andrew P Lee
(74) *Attorney, Agent, or Firm* — Mintz, Levin, Cohn, Ferris, Glovsky and Popeo, P.C.

(57) ABSTRACT

The present disclosure describes 4'-fluoromethyl nucleosides for treating viral infections, including Dengue.

33 Claims, No Drawings
Specification includes a Sequence Listing.

(56) References Cited

U.S. PATENT DOCUMENTS

| | | |
|---|---|---|
| 2012/0071434 A1 | 3/2012 | Smith et al. |
| 2012/0214735 A1 | 8/2012 | Bhuniya et al. |
| 2012/0214762 A1 | 8/2012 | Staben et al. |
| 2012/0219568 A1 | 8/2012 | Liu et al. |
| 2012/0264649 A1 | 10/2012 | Bazan et al. |
| 2013/0303669 A1 | 11/2013 | Morimoto et al. |
| 2014/0038991 A1 | 2/2014 | Yu et al. |
| 2014/0200215 A1 | 7/2014 | Buckman et al. |
| 2014/0309413 A1 | 10/2014 | Rose et al. |
| 2015/0011497 A1 | 1/2015 | Beigelman et al. |
| 2015/0051167 A1 | 2/2015 | Wang et al. |
| 2015/0105341 A1 | 4/2015 | Beigelman et al. |
| 2015/0252265 A1 | 9/2015 | Archetti et al. |
| 2015/0274767 A1 | 10/2015 | Girijavallabhan et al. |
| 2015/0366887 A1 | 12/2015 | Blatt et al. |
| 2015/0366888 A1 | 12/2015 | Blatt et al. |
| 2016/0024107 A1 | 1/2016 | Clarke et al. |
| 2016/0053175 A1 | 2/2016 | Song et al. |
| 2016/0122374 A1 | 5/2016 | Chun et al. |
| 2016/0244668 A1 | 8/2016 | Saito et al. |
| 2016/0257657 A1 | 9/2016 | Wipf et al. |
| 2017/0071964 A1 | 3/2017 | Clarke et al. |
| 2017/0186964 A1 | 6/2017 | Cho et al. |
| 2018/0002366 A1 | 1/2018 | Girijavallabhan et al. |
| 2018/0044369 A1 | 2/2018 | Beigelman et al. |
| 2018/0079774 A1 | 3/2018 | Beigelman et al. |
| 2018/0226580 A1 | 8/2018 | Fitzgerald et al. |
| 2019/0185748 A1 | 6/2019 | Liao |
| 2019/0185754 A1 | 6/2019 | Archetti et al. |
| 2019/0241807 A1 | 8/2019 | Mizusaki et al. |
| 2021/0060051 A1 | 3/2021 | Schinazi et al. |
| 2021/0284669 A1 | 9/2021 | Chun et al. |
| 2021/0284670 A1 | 9/2021 | Chin et al. |
| 2023/0295201 A1 | 9/2023 | Byun et al. |

FOREIGN PATENT DOCUMENTS

| | | |
|---|---|---|
| CN | 102603836 A | 7/2012 |
| CN | 103709220 A | 4/2014 |
| CN | 104086612 A | 10/2014 |
| CN | 105646629 A | 6/2016 |
| CN | 105777580 A | 7/2016 |
| CN | 106518766 A | 3/2017 |
| CN | 106518767 A | 3/2017 |
| CN | 106892920 A | 6/2017 |
| CN | 107286190 A | 10/2017 |
| CN | 108276352 A | 7/2018 |
| CN | 109748921 A | 5/2019 |
| CN | 109748943 A | 5/2019 |
| CN | 109748944 A | 5/2019 |
| CN | 110215456 A | 9/2019 |
| CN | 110330540 A | 10/2019 |
| CN | 110724174 A | 1/2020 |
| CN | 110776512 A | 2/2020 |
| CN | 111620909 A | 9/2020 |
| DE | 2626792 A1 | 12/1977 |
| DE | 3528753 A1 | 2/1987 |
| DE | 4232852 A1 | 3/1994 |
| DE | 19934799 A1 | 2/2001 |
| DE | 10064823 A1 | 6/2002 |
| EP | 0284952 A2 | 10/1988 |
| EP | 0419944 A2 | 4/1991 |
| EP | 0458214 A1 | 11/1991 |
| EP | 0682098 A2 | 11/1995 |
| EP | 0924265 A2 | 6/1999 |
| EP | 1046631 A1 | 10/2000 |
| EP | 1170353 A2 | 1/2002 |
| EP | 1593713 A1 | 11/2005 |
| EP | 1975718 A2 | 10/2008 |
| EP | 1978077 A1 | 10/2008 |
| EP | 2098226 A1 | 9/2009 |
| EP | 2388069 A1 | 11/2011 |
| EP | 2778169 A1 | 9/2014 |
| EP | 2896678 A1 | 7/2015 |
| EP | 2980182 A1 | 2/2016 |
| FR | 2354774 A1 | 1/1978 |
| FR | 2669639 A1 | 5/1992 |
| IN | 167775 B | 12/1990 |
| JP | S6286363 A | 4/1987 |
| JP | H0931092 A | 2/1997 |
| JP | H09328497 A | 12/1997 |
| JP | 2002326995 A | 11/2002 |
| JP | 2002326996 A | 11/2002 |
| JP | 2003246770 A | 9/2003 |
| JP | 2004315613 A | 11/2004 |
| JP | 2005120172 A | 5/2005 |
| JP | 2006232875 A | 9/2006 |
| JP | 2008007634 A | 1/2008 |
| JP | 2012216832 A | 11/2012 |
| JP | 5295692 B2 | 9/2013 |
| JP | 2014145852 A | 8/2014 |
| JP | 2016132779 A | 7/2016 |
| JP | 2018044028 A | 3/2018 |
| JP | 2018203945 A | 12/2018 |
| KR | 20120135501 A | 12/2012 |
| KR | 20160098975 A | 8/2016 |
| KR | 20160110899 A | 9/2016 |
| KR | 20160110900 A | 9/2016 |
| KR | 20190041918 A | 4/2019 |
| KR | 20190076339 A | 7/2019 |
| NL | 7606413 A | 12/1977 |
| WO | 8807043 A1 | 9/1988 |
| WO | 9110671 A1 | 7/1991 |
| WO | 9201695 A1 | 2/1992 |
| WO | 9201696 A1 | 2/1992 |
| WO | 9214805 A1 | 9/1992 |
| WO | 9316075 A1 | 8/1993 |
| WO | 9614329 A1 | 5/1996 |
| WO | 9640705 A1 | 12/1996 |
| WO | 9816184 A2 | 4/1998 |
| WO | 9900399 A1 | 1/1999 |
| WO | 9914226 A2 | 3/1999 |
| WO | 9926933 A1 | 6/1999 |
| WO | 9926941 A1 | 6/1999 |
| WO | 9951565 A1 | 10/1999 |
| WO | 9961583 A2 | 12/1999 |
| WO | 0001381 A1 | 1/2000 |
| WO | 0032152 A2 | 6/2000 |
| WO | 0034276 A1 | 6/2000 |
| WO | 0063154 A1 | 10/2000 |
| WO | 0066604 A2 | 11/2000 |
| WO | 0100197 A2 | 1/2001 |
| WO | 0110842 A2 | 2/2001 |
| WO | 0114320 A1 | 3/2001 |
| WO | 0119841 A1 | 3/2001 |
| WO | 0121577 A2 | 3/2001 |
| WO | 0123357 A2 | 4/2001 |
| WO | 0147862 A1 | 7/2001 |
| WO | 0164642 A2 | 9/2001 |
| WO | 0177091 A2 | 10/2001 |
| WO | 0207516 A2 | 1/2002 |
| WO | 0234711 A1 | 5/2002 |
| WO | 0234736 A1 | 5/2002 |
| WO | 0239987 A2 | 5/2002 |
| WO | 02062766 A2 | 8/2002 |
| WO | 02094185 A2 | 11/2002 |
| WO | 02100415 A2 | 12/2002 |
| WO | 03039523 A2 | 5/2003 |
| WO | 03041649 A2 | 5/2003 |
| WO | 03049772 A2 | 6/2003 |
| WO | 03088908 A2 | 10/2003 |
| WO | 03090748 A1 | 11/2003 |
| WO | 03091262 A1 | 11/2003 |
| WO | 2004002999 A2 | 1/2004 |
| WO | 2004007472 A1 | 1/2004 |
| WO | 2004014312 A2 | 2/2004 |
| WO | 2004037159 A2 | 5/2004 |
| WO | 2004041752 A2 | 5/2004 |
| WO | 2004080966 A1 | 9/2004 |
| WO | 2004083177 A2 | 9/2004 |
| WO | 2004083263 A1 | 9/2004 |
| WO | 2004087153 A2 | 10/2004 |
| WO | 2004091499 A2 | 10/2004 |
| WO | 2004106356 A1 | 12/2004 |

(56) References Cited

FOREIGN PATENT DOCUMENTS

| | | |
|---|---|---|
| WO | 2004110350 A2 | 12/2004 |
| WO | 2005020885 A2 | 3/2005 |
| WO | 2005021568 A2 | 3/2005 |
| WO | 2005023771 A1 | 3/2005 |
| WO | 2005025515 A2 | 3/2005 |
| WO | 2005040135 A1 | 5/2005 |
| WO | 2005058832 A1 | 6/2005 |
| WO | 2005093476 A1 | 10/2005 |
| WO | 2005095544 A1 | 10/2005 |
| WO | 2005097052 A1 | 10/2005 |
| WO | 2005111099 A1 | 11/2005 |
| WO | 2006001463 A1 | 1/2006 |
| WO | 2006006490 A1 | 1/2006 |
| WO | 2006008438 A1 | 1/2006 |
| WO | 2006016101 A1 | 2/2006 |
| WO | 2006030193 A1 | 3/2006 |
| WO | 2006038594 A1 | 4/2006 |
| WO | 2006048634 A1 | 5/2006 |
| WO | 2006061094 A1 | 6/2006 |
| WO | 2006063717 A2 | 6/2006 |
| WO | 2006066074 A2 | 6/2006 |
| WO | 2006094347 A1 | 9/2006 |
| WO | 2006098380 A1 | 9/2006 |
| WO | 2006105440 A2 | 10/2006 |
| WO | 2006110656 A2 | 10/2006 |
| WO | 2006119800 A1 | 11/2006 |
| WO | 2006130217 A2 | 12/2006 |
| WO | 2007007588 A1 | 1/2007 |
| WO | 2007011759 A2 | 1/2007 |
| WO | 2007024021 A1 | 3/2007 |
| WO | 2007031185 A1 | 3/2007 |
| WO | 2007056143 A2 | 5/2007 |
| WO | 2007056170 A2 | 5/2007 |
| WO | 2007076034 A2 | 7/2007 |
| WO | 2007084667 A2 | 7/2007 |
| WO | 2007095188 A2 | 8/2007 |
| WO | 2007125320 A1 | 11/2007 |
| WO | 2007130783 A2 | 11/2007 |
| WO | 2008001195 A2 | 1/2008 |
| WO | 2008011557 A2 | 1/2008 |
| WO | 2008012555 A2 | 1/2008 |
| WO | 2008021388 A1 | 2/2008 |
| WO | 2008024364 A2 | 2/2008 |
| WO | 2008082601 A2 | 7/2008 |
| WO | 2008092006 A2 | 7/2008 |
| WO | 2008095040 A2 | 8/2008 |
| WO | 2008109177 A2 | 9/2008 |
| WO | 2008109180 A2 | 9/2008 |
| WO | 2008109181 A2 | 9/2008 |
| WO | 2008117047 A1 | 10/2008 |
| WO | 2008121360 A1 | 10/2008 |
| WO | 2008133966 A1 | 11/2008 |
| WO | 2008151437 A1 | 12/2008 |
| WO | 2009001097 A2 | 12/2008 |
| WO | 2009009951 A1 | 1/2009 |
| WO | 2009011228 A1 | 1/2009 |
| WO | 2009011229 A1 | 1/2009 |
| WO | 2009067409 A1 | 5/2009 |
| WO | 2009069095 A2 | 6/2009 |
| WO | 2009076593 A1 | 6/2009 |
| WO | 2009076618 A2 | 6/2009 |
| WO | 2009086192 A1 | 7/2009 |
| WO | 2009086201 A1 | 7/2009 |
| WO | 2009111653 A2 | 9/2009 |
| WO | 2009132123 A1 | 10/2009 |
| WO | 2009132135 A1 | 10/2009 |
| WO | 2009151921 A1 | 12/2009 |
| WO | 2009152095 A2 | 12/2009 |
| WO | 2010001174 A1 | 1/2010 |
| WO | 2010007116 A2 | 1/2010 |
| WO | 2010026153 A1 | 3/2010 |
| WO | 2010036407 A2 | 4/2010 |
| WO | 2010060952 A1 | 6/2010 |
| WO | 2010073126 A2 | 7/2010 |
| WO | 2010084115 A2 | 7/2010 |
| WO | WO2010091386 A2 | 8/2010 |
| WO | 2010108135 A1 | 9/2010 |
| WO | 2010108140 A1 | 9/2010 |
| WO | 2010145778 A1 | 12/2010 |
| WO | 2011005860 A2 | 1/2011 |
| WO | 2011015037 A1 | 2/2011 |
| WO | 2011016430 A1 | 2/2011 |
| WO | 2011031896 A2 | 3/2011 |
| WO | 2011032169 A2 | 3/2011 |
| WO | 2011035231 A1 | 3/2011 |
| WO | 2011035250 A1 | 3/2011 |
| WO | 2011035842 A1 | 3/2011 |
| WO | 2011036557 A1 | 3/2011 |
| WO | 2011038207 A1 | 3/2011 |
| WO | 2011057214 A2 | 5/2011 |
| WO | 2011086075 A1 | 7/2011 |
| WO | 2011097300 A1 | 8/2011 |
| WO | 2011100131 A2 | 8/2011 |
| WO | 2011109799 A1 | 9/2011 |
| WO | 2011119869 A1 | 9/2011 |
| WO | 2011146401 A1 | 11/2011 |
| WO | 2011150288 A1 | 12/2011 |
| WO | 2011156632 A2 | 12/2011 |
| WO | 2012012465 A1 | 1/2012 |
| WO | 2012012776 A1 | 1/2012 |
| WO | 2012031539 A1 | 3/2012 |
| WO | 2012034626 A1 | 3/2012 |
| WO | 2012037038 A1 | 3/2012 |
| WO | 2012040124 A1 | 3/2012 |
| WO | 2012040126 A1 | 3/2012 |
| WO | 2012040127 A1 | 3/2012 |
| WO | 2012068340 A2 | 5/2012 |
| WO | 2012083048 A2 | 6/2012 |
| WO | 2012087596 A1 | 6/2012 |
| WO | 2012088155 A1 | 6/2012 |
| WO | 2012088438 A1 | 6/2012 |
| WO | 2012092471 A2 | 7/2012 |
| WO | 2012121973 A1 | 9/2012 |
| WO | 2012128944 A1 | 9/2012 |
| WO | 2012139028 A2 | 10/2012 |
| WO | 2012142075 A1 | 10/2012 |
| WO | 2012142085 A1 | 10/2012 |
| WO | 2012142523 A2 | 10/2012 |
| WO | 2012160392 A1 | 11/2012 |
| WO | WO2012168348 | 12/2012 |
| WO | 2013000855 A1 | 1/2013 |
| WO | 2013007586 A1 | 1/2013 |
| WO | 2013030288 A1 | 3/2013 |
| WO | 2013033270 A2 | 3/2013 |
| WO | 2013040492 A2 | 3/2013 |
| WO | 2013040568 A1 | 3/2013 |
| WO | 2013044030 A1 | 3/2013 |
| WO | 2013056132 A2 | 4/2013 |
| WO | 2013072466 A1 | 5/2013 |
| WO | 2013087765 A1 | 6/2013 |
| WO | 2013090420 A2 | 6/2013 |
| WO | 2013096679 A1 | 6/2013 |
| WO | 2013096680 A1 | 6/2013 |
| WO | 2013101552 A1 | 7/2013 |
| WO | 2013135339 A2 | 9/2013 |
| WO | 2013138236 A1 | 9/2013 |
| WO | 2013142124 A1 | 9/2013 |
| WO | 2013142157 A1 | 9/2013 |
| WO | 2013142159 A1 | 9/2013 |
| WO | 2013142525 A1 | 9/2013 |
| WO | 2013147795 A1 | 10/2013 |
| WO | 2013151975 A1 | 10/2013 |
| WO | 2013182262 A1 | 12/2013 |
| WO | 2014005125 A2 | 1/2014 |
| WO | 2014008236 A1 | 1/2014 |
| WO | 2014015936 A1 | 1/2014 |
| WO | 2014026198 A1 | 2/2014 |
| WO | 2014031872 A2 | 2/2014 |
| WO | 2014035140 A2 | 3/2014 |
| WO | 2014048998 A1 | 4/2014 |
| WO | 2014057095 A1 | 4/2014 |
| WO | 2014058801 A1 | 4/2014 |
| WO | 2014059901 A1 | 4/2014 |
| WO | 2014059902 A1 | 4/2014 |

(56) References Cited

FOREIGN PATENT DOCUMENTS

| | | |
|---|---|---|
| WO | 2014090369 A1 | 6/2014 |
| WO | 2014100498 A1 | 6/2014 |
| WO | 2014100505 A1 | 6/2014 |
| WO | 2014102077 A1 | 7/2014 |
| WO | 2014124458 A1 | 8/2014 |
| WO | 2014134127 A1 | 9/2014 |
| WO | 2014134251 A1 | 9/2014 |
| WO | 2014149164 A1 | 9/2014 |
| WO | 2014160012 A2 | 10/2014 |
| WO | 2014209979 A1 | 12/2014 |
| WO | 2015003146 A1 | 1/2015 |
| WO | 2015006280 A1 | 1/2015 |
| WO | 2015016187 A1 | 2/2015 |
| WO | 2015024120 A1 | 2/2015 |
| WO | 2015031710 A1 | 3/2015 |
| WO | 2015038596 A1 | 3/2015 |
| WO | 2015046827 A1 | 4/2015 |
| WO | 2015051169 A2 | 4/2015 |
| WO | 2015061742 A2 | 4/2015 |
| WO | 2015069939 A1 | 5/2015 |
| WO | 2015089511 A2 | 6/2015 |
| WO | 2015118898 A1 | 8/2015 |
| WO | 2015120237 A2 | 8/2015 |
| WO | 2015129672 A1 | 9/2015 |
| WO | 2015143712 A1 | 10/2015 |
| WO | 2015148746 A1 | 10/2015 |
| WO | 2015148869 A1 | 10/2015 |
| WO | 2015160251 A1 | 10/2015 |
| WO | 2015196118 A1 | 12/2015 |
| WO | 2015196128 A2 | 12/2015 |
| WO | 2015196130 A2 | 12/2015 |
| WO | 2015198915 A1 | 12/2015 |
| WO | 2015200205 A1 | 12/2015 |
| WO | 2015200219 A1 | 12/2015 |
| WO | 2016010026 A1 | 1/2016 |
| WO | 2016018697 A1 | 2/2016 |
| WO | 2016029186 A1 | 2/2016 |
| WO | 2016031406 A1 | 3/2016 |
| WO | 2016041877 A1 | 3/2016 |
| WO | 2016066582 A1 | 5/2016 |
| WO | 2016069827 A1 | 5/2016 |
| WO | 2016069975 A1 | 5/2016 |
| WO | 2016070952 A1 | 5/2016 |
| WO | 2016074762 A1 | 5/2016 |
| WO | WO2016069825 A1 | 5/2016 |
| WO | WO2016069826 A1 | 5/2016 |
| WO | 2016096076 A1 | 6/2016 |
| WO | 2016100441 A1 | 6/2016 |
| WO | 2016100569 A1 | 6/2016 |
| WO | 2016107664 A1 | 7/2016 |
| WO | 2016115222 A1 | 7/2016 |
| WO | 2016116124 A1 | 7/2016 |
| WO | 2016116254 A1 | 7/2016 |
| WO | 2016116508 A1 | 7/2016 |
| WO | 2016117271 A1 | 7/2016 |
| WO | 2016145142 A1 | 9/2016 |
| WO | 2016148170 A1 | 9/2016 |
| WO | 2016152340 A1 | 9/2016 |
| WO | 2016161176 A1 | 10/2016 |
| WO | 2016162644 A1 | 10/2016 |
| WO | 2016170948 A1 | 10/2016 |
| WO | 2016172631 A2 | 10/2016 |
| WO | 2016178876 A2 | 11/2016 |
| WO | 2016184361 A1 | 11/2016 |
| WO | 2016192902 A1 | 12/2016 |
| WO | 2017005673 A1 | 1/2017 |
| WO | 2017019817 A1 | 2/2017 |
| WO | 2017019822 A1 | 2/2017 |
| WO | 2017019830 A1 | 2/2017 |
| WO | 2017023894 A1 | 2/2017 |
| WO | 2017024310 A1 | 2/2017 |
| WO | 2017027646 A1 | 2/2017 |
| WO | 2017032840 A1 | 3/2017 |
| WO | 2017041893 A1 | 3/2017 |
| WO | 2017045612 A1 | 3/2017 |
| WO | 2017045615 A1 | 3/2017 |
| WO | 2017045616 A1 | 3/2017 |
| WO | 2017045740 A1 | 3/2017 |
| WO | 2017049060 A1 | 3/2017 |
| WO | 2017058807 A1 | 4/2017 |
| WO | 2017059357 A1 | 4/2017 |
| WO | 2017066781 A1 | 4/2017 |
| WO | 2017066782 A1 | 4/2017 |
| WO | 2017066791 A1 | 4/2017 |
| WO | 2017066793 A1 | 4/2017 |
| WO | 2017066797 A1 | 4/2017 |
| WO | 2017068875 A1 | 4/2017 |
| WO | 2017073931 A1 | 5/2017 |
| WO | 2017073932 A1 | 5/2017 |
| WO | 2017073933 A1 | 5/2017 |
| WO | 2017091767 A2 | 6/2017 |
| WO | 2017093214 A1 | 6/2017 |
| WO | 2017097401 A1 | 6/2017 |
| WO | 2017153186 A1 | 9/2017 |
| WO | 2017156262 A1 | 9/2017 |
| WO | 2017161028 A1 | 9/2017 |
| WO | 2017165489 A1 | 9/2017 |
| WO | 2017184668 A1 | 10/2017 |
| WO | 2017205980 A1 | 12/2017 |
| WO | 2017207993 A1 | 12/2017 |
| WO | 2018015323 A2 | 1/2018 |
| WO | 2018031818 A2 | 2/2018 |
| WO | 2018065356 A1 | 4/2018 |
| WO | 2018067615 A1 | 4/2018 |
| WO | 2018098206 A1 | 5/2018 |
| WO | 2018106818 A1 | 6/2018 |
| WO | 2018106820 A1 | 6/2018 |
| WO | 2018110529 A1 | 6/2018 |
| WO | 2018116901 A1 | 6/2018 |
| WO | 2018119263 A1 | 6/2018 |
| WO | 2018138685 A2 | 8/2018 |
| WO | 2018169946 A1 | 9/2018 |
| WO | 2018175746 A1 | 9/2018 |
| WO | 2018183635 A1 | 10/2018 |
| WO | 2018184590 A1 | 10/2018 |
| WO | 2018189134 A1 | 10/2018 |
| WO | 2018204198 A1 | 11/2018 |
| WO | 2018208667 A1 | 11/2018 |
| WO | 2018213185 A1 | 11/2018 |
| WO | 2018218171 A1 | 11/2018 |
| WO | 2018218281 A1 | 12/2018 |
| WO | 2018222172 A1 | 12/2018 |
| WO | 2018226976 A1 | 12/2018 |
| WO | 2018237194 A1 | 12/2018 |
| WO | 2019014247 A1 | 1/2019 |
| WO | 2019018185 A1 | 1/2019 |
| WO | 2019051269 A1 | 3/2019 |
| WO | 2019052935 A1 | 3/2019 |
| WO | 2019053696 A1 | 3/2019 |
| WO | 2019084271 A1 | 5/2019 |
| WO | 2019086400 A1 | 5/2019 |
| WO | 2019092171 A1 | 5/2019 |
| WO | 2019098109 A1 | 5/2019 |
| WO | 2019125974 A1 | 6/2019 |
| WO | 2019129059 A1 | 7/2019 |
| WO | 2019133712 A1 | 7/2019 |
| WO | 2019154953 A1 | 8/2019 |
| WO | 2019154956 A1 | 8/2019 |
| WO | 2019173682 A1 | 9/2019 |
| WO | 2019195056 A1 | 10/2019 |
| WO | 2019215076 A1 | 11/2019 |
| WO | 2019218797 A1 | 11/2019 |
| WO | 2020032152 A1 | 2/2020 |
| WO | 2020033413 A2 | 2/2020 |
| WO | 2021167882 A1 | 8/2021 |
| WO | 2021168008 A1 | 8/2021 |
| WO | 2021168038 A1 | 8/2021 |

OTHER PUBLICATIONS

Office Action and Search Report in Taiwan Application No. 110105397, dated Dec. 3, 2021, 11 pages (5 pages of English Translation and 6 pages of Taiwan Office Action).

(56) References Cited

OTHER PUBLICATIONS

First Office Action and Search Report in Taiwan (ROC) Application 110104869 dated Jan. 24, 2022, 7 pages (3 pages of English Translation and 4 pages of Taiwan Office Action).
First Office Action and Search Report in Taiwan (ROC) Application 110105126 dated Jan. 6, 2022, 7 pages (3 pages of English Translation and 4 pages of Taiwan Office Action).
U.S. Non-Final Office Action dated Jan. 18, 2023 in U.S. Appl. No. 17/178,463, filed Feb. 18, 2021 (11 Pages).
European Patent Office Communication for EP Application No. 21710378.7, dated Sep. 27, 2022, 3 pages.
European Patent Office Communication for EP Application No. 21712279.5, dated Sep. 28, 2022, 3 pages.
International Preliminary Report on Patentability for PCT Application No. PCT/US2021/018415, dated Sep. 1, 2022, 9 Pages.
International Preliminary Report on Patentability received for PCT Application No. PCT/US2021/018458, dated Sep. 1, 2022, 12 Pages.
Notice of Allowance in Taiwan (ROC) Application No. 110104869, dated Sep. 30, 2022, 3 pages.
Notice of Allowance in Taiwan (ROC) Application No. 110105126, dated Nov. 22, 2022, 3 pages.
U.S. Non-Final Office Action issued in U.S. Appl. No. 17/176,497, filed Feb. 16, 2021, dated Jul. 27, 2022, 11 Pages.
Clarke et al. (May 14, 2015) "Pyrrolo [1,2,f] [1,2,4] triazines useful for treating respiratory syncitial virus infections", CAPLUS Chemical Abstract Accession No. 2015:832846, Document 162:643613, 4 Pages.
U.S. Appl. No. 17/176,497, filed Feb. 16, 2021, Byun et al.
International Preliminary Report on Patentability received for PCT Application No. PCT/US2021/018169, dated Dec. 15, 2021, 20 pages.
International Search Report and Written Opinion received for PCT Application No. PCT/US2021/018169, dated Apr. 26, 2021, 19 pages.
International Search Report and Written Opinion received for PCT Application No. PCT/US2021/018410, dated May 10, 2021, 11 pages.
International Search Report and Written Opinion received for PCT Application No. PCT/US2021/018415, dated May 11, 2021, 14 pages.
International Search Report and Written Opinion received for PCT Application No. PCT/US2021/018458, dated May 18, 2021, 17 pages.
Cockerill et al. (2019) "State of the Art in Respiratory Syncytial Virus Drug Discovery and Development", Journal of Medicinal Chemistry, 62(7):3206-3227.
Colombo et al. (1985) "Asymetric Dihydroxylations via Chiral Oxazolidines", Tetrahedron Letters, 26(44):5459-5462.
Griffon et al. (2001) "Synthesis and Antiproliferative Activity of Some 4'-C-Hydroxymethyl-A- and -B-D-Arabino-Pentofuranosyl Pyrimidine Nucleosides", Nucleosides, Nucleotides & Nucleic Acids, 20(4-7):649-652.
Griffon et al. (2006) "Synthesis and Biological Evaluation of Some 4'-C-(Hydroxymethyl)-α- and -β-D-Arabinofuranosyl Pyrimidine and Adenine Nucleosides", Collection of Czechoslovak Chemical Communications, 71(7):1063-1087.
Koshkin et al. (Apr. 2, 1998) "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition", Tetrahedron, 54(14):3607-3630.
Leisvuori Anna (Sep. 2015) "Prodrug Strategies of Antiviral Nucleotides: Studies on Enzymatically and Thermally Removable Phosphate Protecting Groups", University of Turku, Turku, Finland, 86 pages.
Musich et al. (1978) "Synthesis of Anthopleurine, the Alarm Pheromone from Anthopleura Elegantissima", Journal of the American Chemical Society, 100(15):4865-4872.
Overend et al. (1970) "Branched Chain Sugars Part 12 Branched Sugars Derived from Methyl 2, 3-O-Isopropylidene-β-L-erythro-Pentopyranosid-4-Ulose and a Synthesis of L-Apiose", Carbohydrate Research, 15(2):185-195.
Patil et al. (1994) "4-Aza-7,9-Dideazaadenosine, a New Cytotoxic Synthetic C-Nucleoside Analogue of Adenosine", Tetrahedron Letters, 35(30):5339-5342.
Patil et al. (1994) "Synthesis of Pyrrolo[2,1-f][1,2,4]triazine Congeners of Nucleic Acid Purines via the N-Amination of 2-Substituted Pyrroles", Journal of Heterocyclic Chemistry, 31(4):781-786.
Shrestha et al. (2011) "Synthesis and Properties of a Bridged Nucleic Acid with a Perhydro-1,2-oxazin-3-one Ring", Journal of Organic Chemistry, 76(24):9891-9899.
Timpe et al. (Jan. 1975) "3-desoxyhex-2-enono-1,4-lactone aus D-hexofuran(osid)-urono-6,3-lactonen", Carbohydrate Research, 39(1):53-60.
Waga et al. (Jan. 26, 1993) "Synthesis of 4'-C-Methylnucleosides", Bioscience, Biotechnology, Biochemistry, 57(9):1433-1438.
Wenska et al. (2007) "Synthesis of Conformationally Constrained 2'-N,4'-C-Ethylene-Bridged Adenosine (aza-ENA-A)", Heterocycles, 73(1):303-324.
Youssefyeh et al. (1977) "Synthetic Routes to 4'-hydroxymethylnucleosides", Tetrahedron Letters, 18(5):435-438.
Feng et al. (Apr. 2014) "Inhibition of Hepatitis C Virus Replication by GS-6620, a Potent C-Nucleoside Monophosphate Prodrug", Antimicrobial Agents and Chemotherapy, 58(4):1930-1942.
"Clinical Pharmacotherapeutics", edited by Yaocheng Rui et al., published on Apr. 30, 2001, p. 337, "Chronic Obstructive Pulmonary Disease".
CDC "Dengue" (https://www.cdc.gov/dengue/healthcare-providers/treatment.html) (Year: 2023).
CDC "Human metapneumovirus" (https://www.cdc.gov/ncird/human-metapneumovirus.html) (Year: 2023).
Krilov ("Respiratory Syncytial virus infection Medication" Medscape https://emedicine.medscape.com/article971488-medication?form=fpf, 2003). (Year: 2023).
Rueckert, (Chapter 21, Picornaviridae; the viruses and their replication. pp. 609-610. Fields Virology, vol. 1, Third Edition, Bernard Field, 1995.
Wikipedia, "Flaviviridae." (Year: 2023).
Wikipedia, "Pneumoviridae" (Year: 2023).
1st Examination Report in Australia Appl. No. 2021224588.
Office Action in Canada Appl. No. 3,171,648 dated Oct. 17, 2023.
Office Action in China Application No. 202180014070.0.
Office Action in Japan Appl. No. 2022-548501.
Office Action in India Appl. No. 202217051891 dated Dec. 27, 2023.

ANTIVIRAL COMPOUNDS

CROSS-REFERENCES TO RELATED APPLICATIONS

This application claims the benefit of priority to U.S. Provisional Patent Application No. 62/978,199, filed 18 Feb. 2020 and titled "ANTIVIRAL COMPOUNDS," the entirety of which is incorporated herein by reference.

SEQUENCE LISTING

The instant application contains a Sequence Listing which has been submitted electronically in ASCII format and is hereby incorporated by reference in its entirety. Said ASCII copy, created on Feb. 17, 2021, is named 1225-US-NP_SL.txt and is 777 bytes in size.

BACKGROUND OF THE INVENTION

Viruses comprising the Flaviviridae family comprise at least three distinguishable genera including pestiviruses, flaviviruses, and hepaciviruses (Calisher, et al., J. Gen. Virol., 1993, 70, 37-43). While pestiviruses cause many economically important animal diseases such as bovine viral diarrhea virus (BVDV), classical swine fever virus (CSFV, hog cholera) and border disease of sheep (BDV), their importance in human disease is less well characterized (Moennig, V., et al., Adv. Vir. Res. 1992, 48, 53-98). Flaviviruses are responsible for important human diseases such as dengue fever and yellow fever, while hepaciviruses cause hepatitis C virus infections in humans. Other important viral infections caused by the Flaviviridae family include West Nile virus (WNV) Japanese encephalitis virus (JEV), tick-borne encephalitis virus, Junjin virus, Murray Valley encephalitis, St. Louis encephalitis, Omsk hemorrhagic fever virus and Zika virus. Combined, infections from the Flaviviridae virus family cause significant mortality, morbidity and economic losses throughout the world. Therefore, there is a need to develop effective treatments for Flaviviridae virus infections.

Pneumoviridae viruses are negative-sense, single-stranded, RNA viruses that are responsible for many prevalent human and animal diseases. The Pneumoviridae family of viruses includes human respiratory syncytial virus (HRSV) and human metapneumovirus. Almost all children will have had an HRSV infection by their second birthday. HRSV is the major cause of lower respiratory tract infections in infancy and childhood with 0.5% to 2% of those infected requiring hospitalization.

No vaccine to prevent HRSV infection is currently available. The monoclonal antibody palivizumab is available for immunoprophylaxis, but its use is restricted to infants at high risk, e.g., premature infants or those with either congenital heart or lung disease, and the cost for general use is often prohibitive. In addition, nucleoside analog ribavirin has been approved as the only antiviral agent to treat HRSV infections but has limited efficacy. Therefore, there is a need for anti-Pneumoviridae therapeutics.

Examples of pyrrolo[2,3-d]pyrimidine compounds useful for treating viral infections are described in U.S. 2012/0009147 A1 (Cho et al.), U.S. 2012/0020921 A1 (Cho et al.), WO 2008/089105 A2 (Babu et al.), WO 2008/141079 A1 (Babu et al.), WO 2009/132135 A1 (Butler et al.), WO 2010/002877 A2 (Francom), WO 2011/035231 A1 (Cho et al.), WO 2011/035250 A1 (Butler et al.), WO 2011/150288 A1 (Cho et al.), WO 2012/012465 (Cho et al.), WO 2012/012776 A1 (Mackman et al.), WO 2012/037038 (Clarke et al.), WO 2012/087596 A1 (Delaney et al.), and WO 2012/142075 A1 (Girijavallabhan et al.).

Thus, there is a need for compositions and methods for treating Pneumoviridae viral infections, such as HRSV infections, that are effective and have acceptable toxicity profiles, Flaviviridae infections, including dengue, and EBOV infections. The present disclosure addresses these and other needs.

BRIEF SUMMARY OF THE INVENTION

In one embodiment, the present disclosure provides a compound of Formula (I):

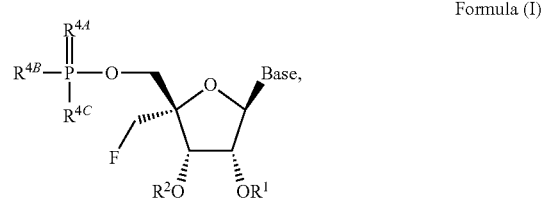

Formula (I)

or a pharmaceutically acceptable salt thereof, wherein:
Base is

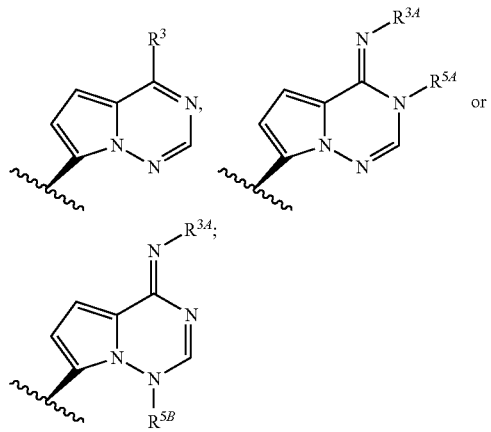

$R^1$ and $R^2$ are each independently H or —C(O)$R^{1A}$, wherein $R^{1A}$ is $C_{1-6}$ alkyl;
$R^3$ is —N(H)$R^{3A}$;
$R^{3A}$ is H, —CH$_2$OP(O)(OH)$_2$, or —C(O)$R^{3D}$, wherein $R^{3D}$ is $C_{6-12}$ aryl or $C_{1-6}$ alkyl optionally substituted with a $C_{3-6}$ cycloalkyl;
$R^{4A}$ is O;
$R^{4B}$ and $R^{4C}$ are each independently:
(A) —OH;
(B) —OR$^{4B1}$, wherein $R^{4B1}$ is $C_{6-12}$ aryl;

(C)
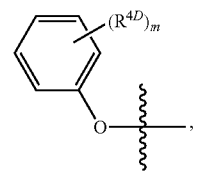

wherein
subscript m is 0, 1, 2, 3, 4, or 5; and
each $R^{4D}$ is independently $C_{1-6}$ alkyl;

(D)

[Chemical structure showing: $R^{4G}$-O-C($R^{4F2}$)($R^{4F1}$)-C($R^{4E2}$)($R^{4E1}$)-N(H)-]

wherein
$R^{4E1}$ and $R^{4E2}$ are each independently H or $C_{1-6}$ alkyl;
$R^{4F1}$ and $R^{4F2}$ together are oxo;
$R^{4G}$ is $C_{1-8}$ alkyl optionally substituted with 1 to 3 $R^{4G1}$, $C_{3-8}$ cycloalkyl, or a 3 to 8 membered heterocyclyl having 1 to 3 heteroatoms selected from N, O and S, optionally substituted with 1 to 3 $R^{4G3}$;
each $R^{4G1}$ is independently —OH, $C_{1-6}$ alkoxy, —(CH$_2$OCH$_2$)$_{1-5}$—CH$_3$, $C_1$-3 haloalkyl, or $C_{3-8}$ cycloalkyl optionally substituted with 1 to 3 $R^{4G9}$.
each $R^{4G3}$ and $R^{4G9}$ is independently $C_{1-6}$ alkyl; or
(E) —(OP(O)(OH))$_{1-2}$—OH; and
$R^{5A}$ and $R^{5B}$ are each independently $C_{1-6}$ alkyl substituted with —OP(O)(OH)$_2$.

In another embodiment, the present disclosure provides a compound, or a pharmaceutically acceptable salt thereof, wherein the compound is:

[Chemical structure of remdesivir-like compound]

In another embodiment, the present disclosure provides a pharmaceutical formulation comprising a pharmaceutically effective amount of a compound of the present disclosure, or a pharmaceutically acceptable salt thereof, and a pharmaceutically acceptable carrier or excipient.

In another embodiment, the present disclosure provides a method of treating a Pneumoviridae virus infection in a human in need thereof, the method comprising administering to the human a therapeutically effective amount of a compound of the present disclosure, or a pharmaceutically acceptable salt thereof.

In another embodiment, the present disclosure provides a method of treating a Picornaviridae virus infection in a human in need thereof, the method comprising administering to the human a therapeutically effective amount of a compound of the present disclosure, or a pharmaceutically acceptable salt thereof.

In another embodiment, the present disclosure provides a method of treating a Flaviviridae virus infection in a human in need thereof, the method comprising administering to the human a therapeutically effective amount of a compound of the present disclosure, or a pharmaceutically acceptable salt thereof.

In another embodiment, the present disclosure provides a method of treating a Filoviridae virus infection in a human in need thereof, the method comprising administering to the human a therapeutically effective amount of a compound of the present disclosure, or a pharmaceutically acceptable salt thereof.

In another embodiment, the present disclosure provides a method for manufacturing a medicament for treating a Pneumoviridae virus infection in a human in need thereof, characterized in that a compound of the present disclosure, or a pharmaceutically acceptable salt thereof, is used.

In another embodiment, the present disclosure provides a method for manufacturing a medicament for treating a Picornaviridae virus infection in a human in need thereof, characterized in that a compound of the present disclosure, or a pharmaceutically acceptable salt thereof, is used.

In another embodiment, the present disclosure provides a method for manufacturing a medicament for treating a Flaviviridae virus infection in a human in need thereof, characterized in that a compound of the present disclosure, or a pharmaceutically acceptable salt thereof, is used.

In another embodiment, the present disclosure provides a method for manufacturing a medicament for treating a Filoviridae virus infection in a human in need thereof, characterized in that a compound of the present disclosure, or a pharmaceutically acceptable salt thereof, is used.

In another embodiment, the present disclosure provides use of a compound of the present disclosure, or a pharmaceutically acceptable salt thereof, for the manufacture of a medicament for the treatment in a human of a Pneumoviridae virus infection.

In another embodiment, the present disclosure provides use of a compound of the present disclosure, or a pharmaceutically acceptable salt thereof, for the manufacture of a medicament for the treatment in a human of a Picornaviridae virus infection.

In another embodiment, the present disclosure provides use of a compound of the present disclosure, or a pharmaceutically acceptable salt thereof, for the manufacture of a medicament for the treatment in a human of a Flaviviridae virus infection.

In another embodiment, the present disclosure provides use of a compound of the present disclosure, or a pharmaceutically acceptable salt thereof, for the manufacture of a medicament for the treatment in a human of a Filoviridae virus infection.

In another embodiment, the present disclosure provides the compound of the present disclosure, or a pharmaceutically acceptable salt thereof, for use in the treatment of a Pneumoviridae virus infection in a human in need thereof.

In another embodiment, the present disclosure provides the compound of the present disclosure, or a pharmaceutically acceptable salt thereof, for use in the treatment of a Picornaviridae virus infection in a human in need thereof.

In another embodiment, the present disclosure provides the compound of the present disclosure, or a pharmaceutically acceptable salt thereof, for use in the treatment of a Flaviviridae virus infection in a human in need thereof.

In another embodiment, the present disclosure provides the compound of the present disclosure, or a pharmaceutically acceptable salt thereof, for use in the treatment of a Filoviridae virus infection in a human in need thereof.

In another embodiment, the present disclosure provides a method for the treatment or prophylaxis of an exacerbation of a respiratory condition by a viral infection in a human in need thereof, the method comprising administering to the human a therapeutically effective amount of a compound of the present disclosure, or a pharmaceutically acceptable salt thereof, wherein the respiratory condition is chronic obstructive pulmonary disease.

In another embodiment, the present disclosure provides a method for manufacturing a medicament for the treatment or prophylaxis of an exacerbation of a respiratory condition by a viral infection in a human in need thereof, characterized in that a compound of the present disclosure, or a pharmaceutically acceptable salt thereof, is used, wherein the respiratory condition is chronic obstructive pulmonary disease.

In another embodiment, the present disclosure provides use of a compound of the present disclosure, or a pharmaceutically acceptable salt thereof, for the manufacture of a medicament for the treatment or prophylaxis in a human of an exacerbation of a respiratory condition by a viral infection, wherein the respiratory condition is chronic obstructive pulmonary disease.

In another embodiment, the present disclosure provides the compound of the present disclosure, or a pharmaceutically acceptable salt thereof, for use in the treatment or prophylaxis of an exacerbation of a respiratory condition by a viral infection in a human in need thereof, wherein the respiratory condition is chronic obstructive pulmonary disease.

DETAILED DESCRIPTION OF THE INVENTION

I. General

The present disclosure provides 2',3'-dihyroxy-4'-fluoromethyl nucleoside and related compounds for the treatment of viral infections, such as Ebola, zika, West Nile, Yellow Fever, Dengue, HBV, HCV, RSV, and others.

II. Definitions

"Alkyl" is a linear or branched saturated monovalent hydrocarbon. For example, an alkyl group can have 1 to 10 carbon atoms (i.e., $C_{1-10}$ alkyl) or 1 to 8 carbon atoms (i.e., $C_{1-8}$ alkyl) or 1 to 6 carbon atoms (i.e., $C_{1-6}$ alkyl) or 1 to 4 carbon atoms (i.e., ($C_{1-4}$ alkyl). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —CH($CH_3$)$CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—CH($CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—CH($CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), and octyl (—$(CH_2)_7CH_3$).

"Alkoxy" refers to an alkyl group having an oxygen atom that connects the alkyl group to the point of attachment: alkyl-O—. As for alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. Alkoxy groups can be substituted or unsubstituted.

"Hydroxy" refers to —OH.

"Halo" or "halogen" as used herein refers to fluoro (—F), chloro (—Cl), bromo (—Br) and iodo (—I).

"Haloalkyl" as used herein refers to an alkyl as defined herein, wherein one or more hydrogen atoms of the alkyl are independently replaced by a halo substituent, which may be the same or different. For example, $C_{1-4}$ haloalkyl is a $C_{1-4}$ alkyl wherein one or more of the hydrogen atoms of the $C_{1-4}$ alkyl have been replaced by a halo substituent. Examples of haloalkyl groups include but are not limited to fluoromethyl, fluorochloromethyl, difluoromethyl, difluorochloromethyl, trifluoromethyl, 1,1,1-trifluoroethyl and pentafluoroethyl.

"Cycloalkyl" refers to a single saturated or partially unsaturated all carbon ring having 3 to 20 annular carbon atoms (i.e., $C_{3-20}$ cycloalkyl), for example from 3 to 12 annular atoms, for example from 3 to 10 annular atoms, or 3 to 8 annular atoms, or 3 to 6 annular atoms, or 3 to 5 annular atoms, or 3 to 4 annular atoms. The term "cycloalkyl" also includes multiple condensed, saturated and partially unsaturated all carbon ring systems (e.g., ring systems comprising 2, 3 or 4 carbocyclic rings). Accordingly, cycloalkyl includes multicyclic carbocycles such as a bicyclic carbocycles (e.g., bicyclic carbocycles having about 6 to 12 annular carbon atoms such as bicyclo[3.1.0]hexane and bicyclo[2.1.1]hexane), and polycyclic carbocycles (e.g. tricyclic and tetracyclic carbocycles with up to about 20 annular carbon atoms). The rings of a multiple condensed ring system can be connected to each other via fused, spiro and bridged bonds when allowed by valency requirements. Non-limiting examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl.

"Heterocyclyl" or "heterocycle" or "heterocycloalkyl" as used herein refers to a single saturated or partially unsaturated non-aromatic ring or a non-aromatic multiple ring system that has at least one heteroatom in the ring (i.e., at least one annular heteroatom selected from oxygen, nitrogen, and sulfur). Unless otherwise specified, a heterocyclyl group has from 3 to about 20 annular atoms, for example from 3 to 12 annular atoms, for example from 3 to 10 annular atoms, or 3 to 8 annular atoms, or 3 to 6 annular atoms, or 3 to 5 annular atoms, or 4 to 6 annular atoms, or 4 to 5 annular atoms. Thus, the term includes single saturated or partially unsaturated rings (e.g., 3, 4, 5, 6 or 7-membered rings) having from about 1 to 6 annular carbon atoms and from about 1 to 3 annular heteroatoms selected from the group consisting of oxygen, nitrogen and sulfur in the ring. The rings of the multiple condensed ring (e.g. bicyclic heterocyclyl) system can be connected to each other via fused, spiro and bridged bonds when allowed by valency requirements. Heterocycles include, but are not limited to, azetidine, aziridine, imidazolidine, morpholine, oxirane (epoxide), oxetane, thietane, piperazine, piperidine, pyrazolidine, piperidine, pyrrolidine, pyrrolidinone, tetrahydrofuran, tetrahydrothiophene, dihydropyridine, tetrahydropyridine, quinuclidine, 2-oxa-6-azaspiro[3.3]heptan-6-yl, 6-oxa-1-azaspiro[3.3]heptan-1-yl, 2-thia-6-azaspiro[3.3]heptan-6-yl, 2,6-diazaspiro[3.3]heptan-2-yl, 2-azabicyclo[3.1.0]hexan-2-yl, 3-azabicyclo[3.1.0]hexanyl, 2-azabicyclo[2.1.1]hexanyl, 2-azabicyclo[2.2.1]heptan-2-yl, 4-azaspiro[2.4]heptanyl, 5-azaspiro[2.4]heptanyl, and the like.

"Aryl" as used herein refers to a single all carbon aromatic ring or a multiple condensed all carbon ring system wherein at least one of the rings is aromatic. For example, in some embodiments, an aryl group has 6 to 20 carbon atoms, 6 to 14 carbon atoms, or 6 to 12 carbon atoms. Aryl includes a phenyl radical. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., carbocycle). Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is also to be understood that when reference is made to a certain atom-range membered aryl (e.g., 6-10 membered aryl), the atom range is for the total ring atoms of the aryl. For example, a 6-membered aryl would include phenyl and a 10-membered aryl would include naphthyl and 1,2,3,4-tetrahydronaphthyl. Non-limiting examples of aryl groups include, but are not limited to, phenyl, indenyl, naphthyl, 1,2,3,4-tetrahydronaphthyl, anthracenyl, and the like.

"Heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from heteroaryls (to form for example 1,8-naphthyridinyl), heterocycles, (to form for example 1,2,3,4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has about 1-20 carbon atoms and about 1-6 heteroatoms within the heteroaryl ring. Such multiple condensed ring systems may be optionally substituted with one or more (e.g., 1, 2, 3 or 4) oxo groups on the carbocycle or heterocycle portions of the condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). It also to be understood that when a reference is made to a certain atom-range membered heteroaryl (e.g., a 5 to 10 membered heteroaryl), the atom range is for the total ring atoms of the heteroaryl and includes carbon atoms and heteroatoms. For example, a 5-membered heteroaryl would include a thiazolyl and a 10-membered heteroaryl would include a quinolinyl. Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl, thianaphthenyl, pyrrolo[2,3-b]pyridinyl, quinazolinyl-4(3H)-one, and triazolyl.

A "compound of the present disclosure" includes compounds disclosed herein, for example a compound of the present disclosure includes compounds of Formula (I), (Ia), (Ib), (Ic), (Id), (Ie), (If), (Ig), (Ih), (Ij), (Ik), (Im) or (In), including the compounds of the Examples.

"Pharmaceutically effective amount" refers to an amount of a compound of the present disclosure in a formulation or combination thereof, that provides the desired therapeutic or pharmaceutical result.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Treatment" or "treat" or "treating" as used herein refers to an approach for obtaining beneficial or desired results. For purposes of the present disclosure, beneficial or desired results include, but are not limited to, alleviation of a symptom and/or diminishment of the extent of a symptom and/or preventing a worsening of a symptom associated with a disease or condition. In one embodiment, "treatment" or "treating" includes one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and c) relieving the disease or condition, e.g., causing the regression of clinical symptoms, ameliorating the disease state, delaying the progression of the disease, increasing the quality of life, and/or prolonging survival.

"Prophylaxis" refers to preventing or retarding the progression of clinical illness in patients suffering from a viral infection.

"Therapeutically effective amount" or "effective amount" as used herein refers to an amount that is effective to elicit the desired biological or medical response, including the amount of a compound that, when administered to a subject for treating a disease, is sufficient to effect such treatment for the disease. The effective amount will vary depending on the compound, the disease, and its severity and the age, weight, etc., of the subject to be treated. The effective amount can include a range of amounts. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (e.g., additive or synergistic effects) of the compounds.

"Co-administration" as used herein refers to administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of a compound of the present disclosure is administered first, followed within seconds or minutes by administration of a unit dose of one or more additional therapeutic agents. Alternatively, in other embodiments, a unit dose of one or more additional therapeutic agents is administered first, followed by administration of a unit dose of a compound of the present disclosure within seconds or minutes. In some embodiments, a unit dose of a compound of the present disclosure is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound of the present disclosure. Co-administration of a compound disclosed herein with one or more additional therapeutic agents generally refers to simultaneous or sequential administration of a compound disclosed herein and one or more additional therapeutic agents, such that therapeutically effective amounts of each agent are present in the body of the patient.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The compounds described herein may be prepared and/or formulated as pharmaceutically acceptable salts or when appropriate as a free base. Pharmaceutically acceptable salts are non-toxic salts of a free base form of a compound that possess the desired pharmacological activity of the free base. These salts may be derived from inorganic or organic acids or bases. For example, a compound that contains a basic nitrogen may be prepared as a pharmaceutically acceptable salt by contacting the compound with an inorganic or organic acid. Non-limiting examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington: The Science and Practice of Pharmacy, 21$^{st}$ Edition, Lippincott Wiliams and Wilkins, Philadelphia, Pa., 2006.

Examples of "pharmaceutically acceptable salts" of the compounds disclosed herein also include salts derived from an appropriate base, such as an alkali metal (for example, sodium, potassium), an alkaline earth metal (for example, magnesium), ammonium and $NX_4^+$ (wherein X is $C_1$-$C_4$ alkyl). Also included are base addition salts, such as sodium or potassium salts.

Provided are also compounds described herein or pharmaceutically acceptable salts, isomers, or a mixture thereof, in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds may increase resistance to metabolism, and thus may be useful for increasing the half-life of the compounds described herein or pharmaceutically acceptable salts, isomer, or a mixture thereof when administered to a mammal. See, e.g., Foster, "Deuterium Isotope Effects in Studies of Drug Metabolism", Trends Pharmacol. Sci., 5(12):524-527 (1984). Such compounds are synthesized, for example by employing starting materials in which one or more hydrogen atoms have been replaced by deuterium.

Examples of isotopes that can be incorporated into the disclosed compounds also include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$ $^{31}P$, $^{32}P$ $^{35}S$, $^{18}F$, $^{36}Cl$, $^{123}I$ and $^{125}I$ respectively. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of Formula (I), (Ia), (Ib), (Ic), (Id), (Ie), (If), (Ig), (Ih), (Ij), (Ik), (Im) or (In), can generally be prepared by processes analogous to those described in the Examples as set out below using an appropriate isotopically-labeled reagent in place of the non-labeled reagent previously employed.

The compounds of the embodiments disclosed herein, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included. Where compounds are represented in their chiral form, it is understood that the embodiment encompasses, but is not limited to, the specific diastereomerically or enantiomerically enriched form. Where chirality is not specified but is present, it is understood that the embodiment is directed to either the specific diastereomerically or enantiomerically enriched form or a racemic or scalemic mixture of such compound(s). As used herein, "scalemic mixture" is a mixture of stereoisomers at a ratio other than 1:1.

"Racemates" refers to a mixture of enantiomers. The mixture can comprise equal or unequal amounts of each enantiomer.

"Stereoisomer" and "stereoisomers" refer to compounds that differ in the chirality of one or more stereocenters. Stereoisomers include enantiomers and diastereomers. The compounds may exist in stereoisomeric form if they possess one or more asymmetric centers or a double bond with asymmetric substitution and, therefore, can be produced as individual stereoisomers or as mixtures. Unless otherwise indicated, the description is intended to include individual stereoisomers as well as mixtures. The methods for the determination of stereochemistry and the separation of stereoisomers are well-known in the art (see, e.g., Chapter 4 of Advanced Organic Chemistry, 4th ed., J. March, John Wiley and Sons, New York, 1992).

"Tautomer" refers to alternate forms of a compound that differ in the position of a proton, such as enol-keto and imine-enamine tautomers, or the tautomeric forms of heteroaryl groups containing a ring atom attached to both a ring —NH— and a ring=N—such as pyrazoles, imidazoles, benzimidazoles, triazoles, and tetrazoles.

Unless defined otherwise, all technical and scientific terms used herein have the same meaning as commonly understood by one of ordinary skill in the art. A dash at the front or end of a chemical group is a matter of convenience; chemical groups may be depicted with or without one or more dashes without losing their ordinary meaning. A wavy line drawn through a line in a structure indicates a point of attachment of a group. A dashed line indicates an optional bond. Unless chemically or structurally required, no directionality is indicated or implied by the order in which a chemical group is written or the point at which it is attached to the remainder of the molecule. For instance, the group "—$SO_2CH_2$—" is equivalent to "—$CH_2SO_2$—" and both may be connected in either direction. Similarly, an "arylalkyl" group, for example, may be attached to the remainder of the molecule at either an aryl or an alkyl portion of the group. A prefix such as "$C_{u-v}$" or ($C_u$-$C_v$) indicates that the following group has from u to v carbon atoms. For example, "$C_{1-6}$ alkyl" and "$C_1$-$C_6$ alkyl" both indicate that the alkyl group has from 1 to 6 carbon atoms.

"Solvate" as used herein refers to the result of the interaction of a solvent and a compound. Solvates of salts of the compounds described herein are also provided. Hydrates of the compounds described herein are also provided.

"Prodrug" as used herein refers to a derivative of a drug that upon administration to the human body is converted to the active drug according to some chemical or enzymatic pathway.

III. Compounds

The present disclosure describes compounds of Formula (I), (Ia), (Ib), (Ic), (Id), (Ie), (If), (Ig), (Ih), (Ij), (Ik), (Im) and (In).

In some embodiments, the present disclosure provides a compound of Formula (I):

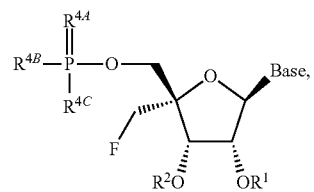

Formula (I)

or a pharmaceutically acceptable salt thereof, wherein:
Base is

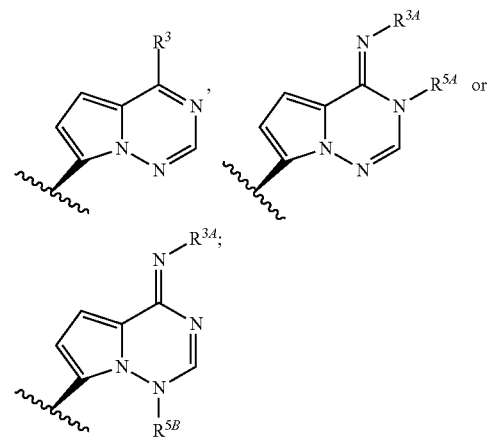

$R^1$ and $R^2$ are each independently H or —$C(O)R^{1A}$, wherein $R^{1A}$ is $C_{1-6}$ alkyl;
$R^3$ is —$N(H)R^{3A}$;
$R^{3A}$ is H, —$CH_2OP(O)(OH)_2$, or —$C(O)R^{3D}$, wherein $R^{3D}$ is $C_{6-12}$ aryl or $C_{1-6}$ alkyl optionally substituted with a $C_{3-6}$ cycloalkyl;
$R^{4A}$ is O;
$R^{4B}$ and $R^{4C}$ are each independently:
(A) —OH;
(B) —$OR^{4B1}$, wherein $R^{4B1}$ is $C_{6-12}$ aryl;

(C)

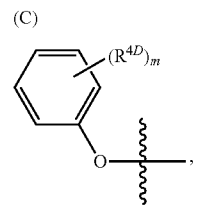

wherein
subscript m is 0, 1, 2, 3, 4, or 5; and
each $R^{4D}$ is independently $C_{1-6}$ alkyl;

(D)

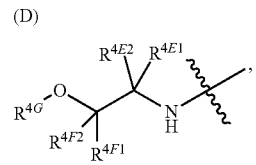

wherein
R$^{4E1}$ and R$^{4E2}$ are each independently H or C$_{1-6}$ alkyl;
R$^{4F1}$ and R$^{4F2}$ together are oxo;
R$^{4G}$ is C$_{1-8}$ alkyl optionally substituted with 1 to 3 R$^{4G1}$, C$_{3-8}$ cycloalkyl, or a 3 to 8 membered heterocyclyl having 1 to 3 heteroatoms selected from N, O and S, optionally substituted with 1 to 3 R$^{4G3}$;
each R$^{4G1}$ is independently —OH, C$_{1-6}$ alkoxy, —(CH$_2$OCH$_2$)$_{1-5}$-CH$_3$, C$_1$. 3 haloalkyl, or C$_{3-8}$ cycloalkyl optionally substituted with 1 to 3 R$^{4G9}$;
each R$^{4G3}$ and R$^{4G9}$ is independently C$_{1-6}$ alkyl; or
(E) —(OP(O)(OH))$_{1-2}$—OH; and
R$^{5A}$ and R$^{5B}$ are each independently C$_{1-6}$ alkyl substituted with —OP(O)(OH)$_2$.

In some embodiments, the compound can be represented by Formula (I), or a pharmaceutically acceptable salt thereof, wherein Base is

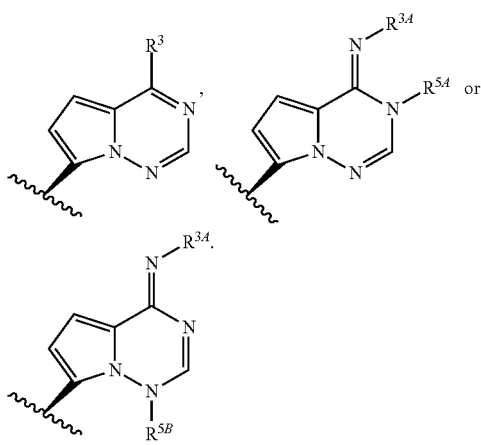

In some embodiments, the compound can be represented by Formula (I), or a pharmaceutically acceptable salt thereof, wherein Base is

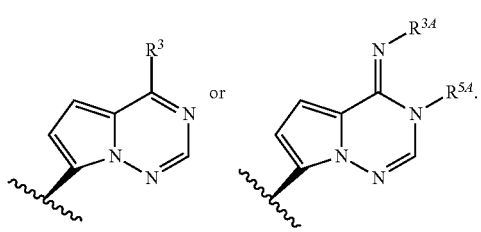

In some embodiments, the compound can be represented by Formula (I), or a pharmaceutically acceptable salt thereof, wherein Base is

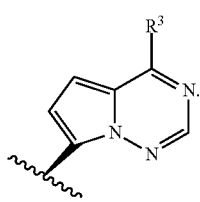

In some embodiments, the compound can be represented by Formula (I), or a pharmaceutically acceptable salt thereof, wherein Base is

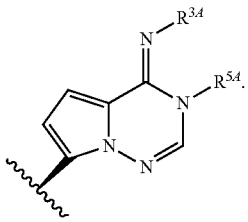

In some embodiments, the compound can be represented by Formula (I), or a pharmaceutically acceptable salt thereof, wherein Base is

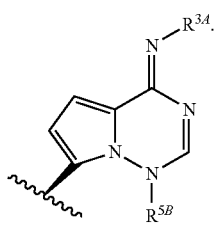

In some embodiments, the compound can be represented by Formula (I), (Ia), (Ib), (Ic), (Id), (Ie), (If), (Ig), (Ih), (Ij), (Ik), (Im) or (In), or a pharmaceutically acceptable salt thereof, wherein R$^1$ and R$^2$ are each independently H or —C(O)R$^{1A}$, wherein R$^{1A}$ is C$_{1-6}$ alkyl. In some embodiments, the compound can be represented by Formula (I), (Ia), (Ib), (Ic), (Id), (Ie), (If), (Ig), (Ih), (Ij), (Ik), (Im) or (In), or a pharmaceutically acceptable salt thereof, wherein R$^1$ and R$^2$ are each H. In some embodiments, the compound can be represented by Formula (I), (Ia), (Ib), (Ic), (Id), (Ie), (If), (Ig), (Ih), (Ij), (Ik), (Im) or (In), or a pharmaceutically acceptable salt thereof, wherein R$^1$ and R$^2$ are each —C(O)R$^{1A}$, wherein R$^{1A}$ is C$_{1-6}$ alkyl. In some embodiments, the compound can be represented by Formula (I), (Ia), (Ib), (Ic), (Id), (Ie), (If), (Ig), (Ih), (Ij), (Ik), (Im) or (In), or a pharmaceutically acceptable salt thereof, wherein R$^1$ and R$^2$ are each —C(O)R$^{1A}$; and R$^{1A}$ is methyl, ethyl, n-propyl, iso-propyl, n-butyl, iso-butyl, sec-butyl or t-butyl. In some embodiments, the compound can be represented by Formula (I), (Ia), (Ib), (Ic), (Id), (Ie), (If), (Ig), (Ih), (Ij), (Ik), (Im) or (In), or a pharmaceutically acceptable salt thereof, wherein R$^1$ and R$^2$ are each —C(O)R$^{1A}$; and R$^{1A}$ is methyl, ethyl, or iso-propyl.

In some embodiments, the compound of the present disclosure, or a pharmaceutically acceptable salt thereof, is represented by Formula (Ia):

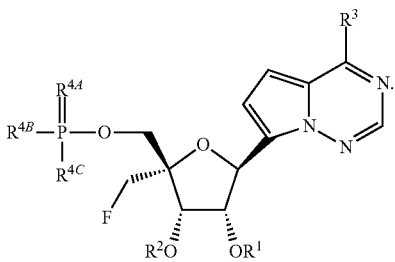

(Ia)

In some embodiments, the compound can be represented by Formula (I), (Ia), (Ib), or (Ic), or a pharmaceutically acceptable salt thereof, wherein $R^3$ is —N(H)$R^{3A}$; $R^{3A}$ is H, —CH$_2$OP(O)(OH)$_2$, or —C(O)$R^{3D}$, wherein $R^{3D}$ is $C_{6-12}$ aryl or $C_{1-6}$ alkyl optionally substituted with a $C_{3-6}$ cycloalkyl. In some embodiments, the compound can be represented by Formula (I), (Ia), (Ib), or (Ic), or a pharmaceutically acceptable salt thereof, wherein $R^{3A}$ is H. In some embodiments, the compound can be represented by Formula (I), (Ia), (Ib), or (Ic), or a pharmaceutically acceptable salt thereof, wherein $R^{3A}$ is —CH$_2$OP(O)(OH)$_2$. In some embodiments, the compound can be represented by Formula (I), (Ia), (Ib), or (Ic), or a pharmaceutically acceptable salt thereof, wherein $R^{3A}$ is —C(O)$R^{3D}$, wherein $R^{3D}$ is $C_{6-12}$ aryl or $C_{1-6}$ alkyl optionally substituted with a $C_{3-6}$ cycloalkyl. In some embodiments, the compound can be represented by Formula (I), (Ia), (Ib), or (Ic), or a pharmaceutically acceptable salt thereof, wherein $R^{3A}$ is —C(O)$R^{3D}$, wherein $R^{3D}$ is phenyl or $C_{1-3}$ alkyl optionally substituted with a $C_{3-6}$ cycloalkyl.

In some embodiments, the compound can be represented by Formula (Ia), or a pharmaceutically acceptable salt thereof, wherein $R^3$ is —N(H)$R^{3A}$; $R^{3A}$ is H or —C(O)$R^{3D}$; and $R^{3D}$ is phenyl or $C_{1-3}$ alkyl optionally substituted with a $C_{3-6}$ cycloalkyl. In some embodiments, the compound can be represented by Formula (Ia), or a pharmaceutically acceptable salt thereof, wherein $R^3$ is —NH$_2$.

In some embodiments, the compound can be represented by Formula (I), (Ia), (Ib), (Ic), or (Id), or a pharmaceutically acceptable salt thereof, wherein $R^{4B}$ and $R^{4C}$ are each independently:
(A) —OH;
(B) —OR$^{4B1}$, wherein $R^{4B1}$ is $C_{6-12}$ aryl;

(C)

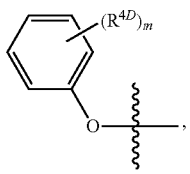

wherein
subscript m is 0, 1, 2, 3, 4, or 5; and
each $R^{4D}$ is independently $C_{1-6}$ alkyl;

(D)

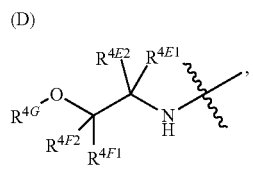

wherein
$R^{4E1}$ and $R^{4E2}$ are each independently H or $C_{1-6}$ alkyl;
$R^{4F1}$ and $R^{4F2}$ together are oxo;
$R^{4G}$ is $C_{1-8}$ alkyl optionally substituted with 1 to 3 $R^{4G1}$, $C_{3-8}$ cycloalkyl, or a 3 to 8 membered heterocyclyl having 1 to 3 heteroatoms selected from N, O and S, optionally substituted with 1 to 3 $R^{4G3}$;
each $R^{4G1}$ is independently —OH, $C_{1-6}$ alkoxy, —(CH$_2$OCH$_2$)$_{1-5}$-CH$_3$, $C_1$-3 haloalkyl, or $C_{3-8}$ cycloalkyl optionally substituted with 1 to 3 $R^{4G9}$.
each $R^{4G3}$ and $R^{4G9}$ is independently $C_{1-6}$ alkyl; or
(E) —(OP(O)(OH))$_{1-2}$—OH.

In some embodiments, the compound can be represented by Formula (I), (Ia), (Ib), (Ic), or (Id), or a pharmaceutically acceptable salt thereof, wherein $R^{4B}$ and $R^{4C}$ are each independently:

(C)

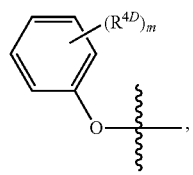

wherein
subscript m is 0, 1, 2, 3, 4, or 5; and
each $R^{4D}$ is independently $C_{1-6}$ alkyl;

(D)

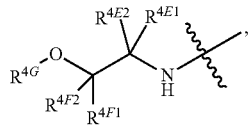

wherein
$R^{4E1}$ and $R^{4E2}$ are each independently H or $C_{1-6}$ alkyl;
$R^{4F1}$ and $R^{4F2}$ together are oxo;
$R^{4G}$ is $C_{1-8}$ alkyl optionally substituted with 1 to 3 $R^{4G1}$, $C_{3-8}$ cycloalkyl, or a 3 to 8 membered heterocyclyl having 1 to 3 heteroatoms selected from N, O and S, optionally substituted with 1 to 3 $R^{4G3}$;
each $R^{4G1}$ is independently —OH, $C_{1-6}$ alkoxy, —(CH$_2$OCH$_2$)$_{1-5}$-CH$_3$, $C_1$- 3 haloalkyl, or $C_{3-8}$ cycloalkyl optionally substituted with 1 to 3 $R^{4G9}$.
each $R^{4G3}$ and $R^{4G9}$ is independently $C_{1-6}$ alkyl; or
(E) —(OP(O)(OH))$_{1-2}$—OH.

In some embodiments, the compound can be represented by Formula (I), (Ia), (Ib), (Ic), or (Id), or a pharmaceutically acceptable salt thereof, wherein $R^{4B}$ and $R^{4C}$ are each independently:
(A) —OH;
(B) —OR$^{4B1}$, wherein $R^{4B1}$ is naphthyl;

(C)

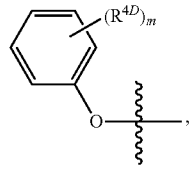

wherein
subscript m is 0 or 1; and
$R^{4D}$ is $C_{1-6}$ alkyl;

(D)

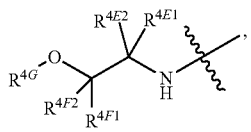

wherein
$R^{4E1}$ is $C_{1-3}$ alkyl;
$R^{4E2}$ is H;
$R^{4F1}$ and $R^{4F2}$ together are oxo;
$R^{4G}$ is $C_{1-8}$ alkyl optionally substituted with 1 $R^{4G1}$, $C_{4-6}$ cycloalkyl, or a 4 to 6 membered heterocyclyl having 1 heteroatom selected from N and O, optionally substituted with 1 $R^{4G3}$.
  each $R^{4G1}$ is independently —OH, $C_{1-4}$ alkoxy, —(CH$_2$OCH$_2$)$_{1-2}$-CH$_3$, $C_1$-3 haloalkyl, or $C_{3-6}$ cycloalkyl optionally substituted with 1 $R^{4G9}$;
  each $R^{4G3}$ and $R^{4G9}$ is independently $C_{1-3}$ alkyl; or
(E) —(OP(O)(OH))$_{1-2}$—OH.

In some embodiments, the compound can be represented by Formula (I), (Ia), (Ib), (Ic), (Id), (Ie), (Ih) or (Ik), or a pharmaceutically acceptable salt thereof, wherein $R^{4B}$ is:
(B) —OR$^{4B1}$, wherein $R^{4B1}$ is naphthyl; or (C)

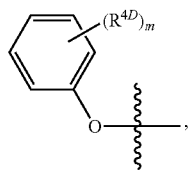

wherein
subscript m is 0 or 1; and
each $R^{4D}$ is independently t-butyl; or
(E) —(OP(O)(OH))$_{1-2}$—OH.

In some embodiments, the compound can be represented by Formula (I), (Ia), (Ib), (Ic), (Id) or (If), or a pharmaceutically acceptable salt thereof, wherein $R^{4C}$ is:
(A) —OH; or (D)

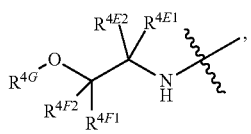

wherein
$R^{4E1}$ is methyl;
$R^{4E2}$ is H;
$R^{4F1}$ and $R^{4F2}$ together are oxo; and
$R^{4G}$ is
  methyl, ethyl, n-propyl, iso-propyl, n-butyl, iso-butyl, sec-butyl, tert-butyl, n-pentyl, neopentyl, n-hexane, 2,2-dimethyl-butyl, 3,3-dimethyl-butyl, 2-ethyl-butyl, or 2-n-propyl-pentyl, each optionally substituted with OH, methoxy, ethoxy, propoxy, butoxy, CF$_3$, Me(CH$_2$OCH$_2$)$_2$—, cyclopropyl or 1-methylcyclopropyl,
  cyclobutyl, cyclopentyl, or cyclohexyl,
  pyrrolidinyl, oxetanyl, or tetrahydropyranyl, each optionally substituted with methyl, ethyl, n-propyl or iso-propyl.

In some embodiments, the compound can be represented by Formula (I), (Ib), or (Ic), or a pharmaceutically acceptable salt thereof, wherein $R^{5A}$ and $R^{5B}$ are each independently $C_{1-6}$ alkyl substituted with —OP(O)(OH)$_2$. In some embodiments, the compound can be represented by Formula (I), (Ib), or (Ic), or a pharmaceutically acceptable salt thereof, wherein $R^{5A}$ and $R^{5B}$ are each independently $C_{1-3}$ alkyl substituted with —OP(O)(OH)$_2$. In some embodiments, the compound can be represented by Formula (I) or (Ic), or a pharmaceutically acceptable salt thereof, wherein $R^{5B}$ is —CH$_2$OP(O)(OH)$_2$. In some embodiments, the compound can be represented by Formula (I) or (Ib), or a pharmaceutically acceptable salt thereof, wherein $R^{5A}$ is —CH$_2$OP(O)(OH)$_2$.

In some embodiments, the compound of the present disclosure, or a pharmaceutically acceptable salt thereof, is represented by Formula (Ib):

Formula (Ib)

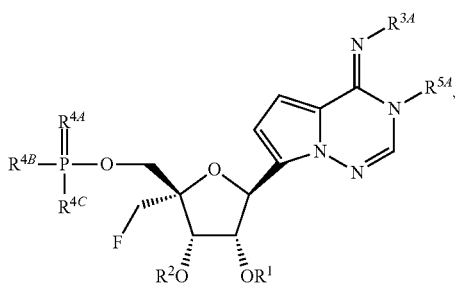

wherein $R^{3A}$ is H; and $R^{5A}$ is —CH$_2$OP(O)(OH)$_2$.

In some embodiments, the compound of the present disclosure, or a pharmaceutically acceptable salt thereof, is represented by Formula (Ic):

Formula (Ic)

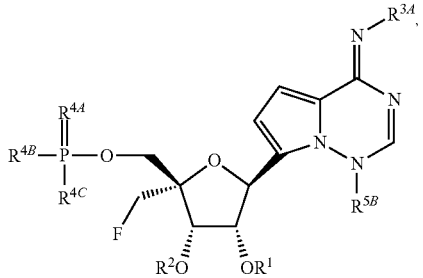

wherein $R^{3A}$ is H; and $R^{5B}$ is —CH$_2$OP(O)(OH)$_2$.

In some embodiments, the compound of the present disclosure, or a pharmaceutically acceptable salt thereof, is represented by Formula (Id):

Formula (Id)

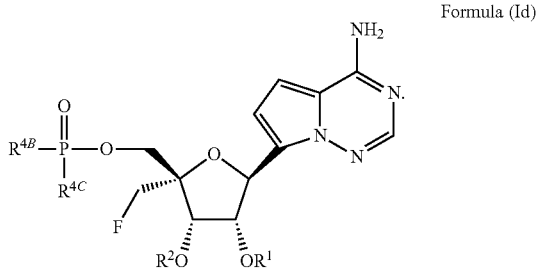

In some embodiments, the compound of the present disclosure, or a pharmaceutically acceptable salt thereof, is represented by Formula (Ie):

Formula (Ie)

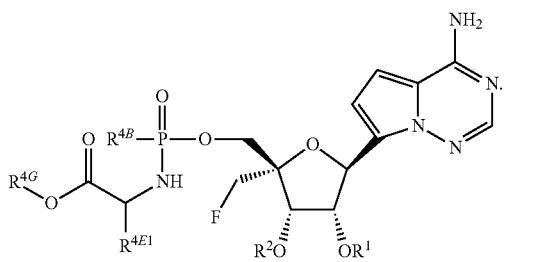

In some embodiments, the compound of the present disclosure, or a pharmaceutically acceptable salt thereof, is represented by Formula (If):

Formula (If)

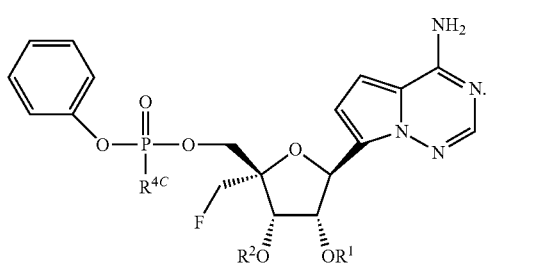

In some embodiments, the compound of the present disclosure, or a pharmaceutically acceptable salt thereof, is represented by Formula (Ig):

Formula (Ig)

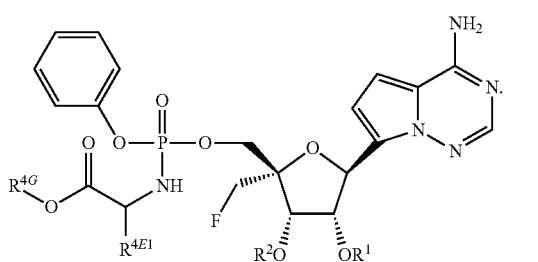

In some embodiments, the compound of the present disclosure, or a pharmaceutically acceptable salt thereof, is represented by Formula (Ih):

Formula (Ih)

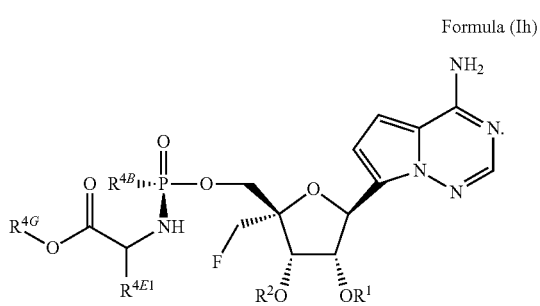

In some embodiments, the compound of the present disclosure, or a pharmaceutically acceptable salt thereof, is represented by Formula (Ij):

Formula (Ij)

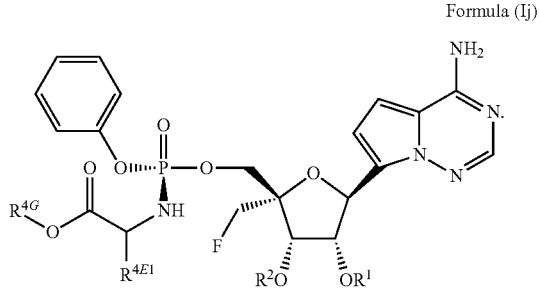

In some embodiments, the compound of the present disclosure, or a pharmaceutically acceptable salt thereof, is represented by Formula (Ik):

Formula (Ik)

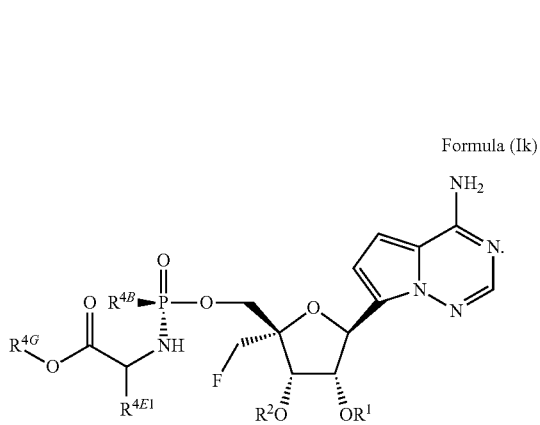

In some embodiments, the compound of the present disclosure, or a pharmaceutically acceptable salt thereof, is represented by Formula (Im):

Formula (Im)

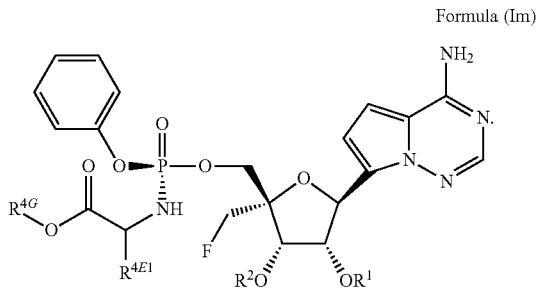

In some embodiments, the compound can be represented by Formula (I), (Ia), (Ib), (Ic), (Id) or (If), or a pharmaceutically acceptable salt thereof, wherein $R^{4C}$ is:

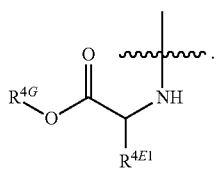

In some embodiments, the compound can be represented by Formula (I), (Ia), (Ib), (Ic), (Id) or (If), or a pharmaceutically acceptable salt thereof, wherein $R^{4C}$ is:

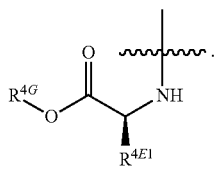

In some embodiments, the compound can be represented by Formula (I), (Ia), (Ib), (Ic), (Id) or (If), or a pharmaceutically acceptable salt thereof, wherein $R^{4C}$ is:

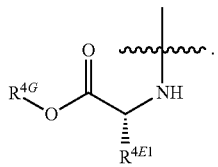

In some embodiments, the compound can be represented by Formula (I), (Ia), (Ib), (Ic), (Id), (Ie), (If), (Ig), (Ih), (Ij), (Ik), (Im) or (In), or a pharmaceutically acceptable salt thereof, wherein $R^{4G}$ is $C_{1-8}$ alkyl optionally substituted with 1 to 3 $R^{4G1}$, $C_{3-8}$ cycloalkyl, or a 3 to 8 membered heterocyclyl having 1 to 3 heteroatoms selected from N, O and S, optionally substituted with 1 to 3 $R^{4G3}$; each $R^{4G1}$ is independently —OH, $C_{1-6}$ alkoxy, —(CH$_2$OCH$_2$)$_{1-5}$-CH$_3$, $C_{1-3}$ haloalkyl, or $C_{3-8}$ cycloalkyl optionally substituted with 1 to 3 $R^{4G9}$; and each $R^{4G3}$ and $R^{4G9}$ is independently $C_{1-6}$ alkyl.

In some embodiments, the compound can be represented by Formula (I), (Ia), (Ib), (Ic), (Id), (Ie), (If), (Ig), (Ih), (Ij), (Ik), (Im) or (In), or a pharmaceutically acceptable salt thereof, wherein $R^{4G}$ is
methyl, ethyl, n-propyl, iso-propyl, n-butyl, iso-butyl, sec-butyl, tert-butyl, n-pentyl, neopentyl, n-hexane, 2,2-dimethyl-butyl, 3,3-dimethyl-butyl, 2-ethyl-butyl, or 2-n-propyl-pentyl, each optionally substituted with OH, methoxy, ethoxy, propoxy, butoxy, CF$_3$, Me(CH$_2$OCH$_2$)$_2$—, cyclopropyl or 1-methylcyclopropyl,
cyclobutyl, cyclopentyl, or cyclohexyl,
pyrrolidinyl, oxetanyl, or tetrahydropyranyl, each optionally substituted with methyl, ethyl, n-propyl or iso-propyl.

In some embodiments, the compound can be represented by Formula (I), (Ia), (Ib), (Ic), (Id), (Ie), (If), (Ig), (Ih), (Ij), (Ik), (Im) or (In), or a pharmaceutically acceptable salt thereof, wherein $R^{4G}$ is
methyl optionally substituted with Me(CH$_2$OCH$_2$)$_2$—, cyclopropyl or 1-methylcyclopropyl,
ethyl optionally substituted with butoxy,
n-propyl optionally substituted with methoxy,
iso-propyl, n-butyl,
iso-butyl optionally substituted with OH, methoxy or CF$_3$,
n-pentyl, neopentyl, n-hexane, 2,2-dimethyl-butyl, 3,3-dimethyl-butyl, 2-ethyl-butyl, 2-n-propyl-pentyl,
cyclobutyl, cyclohexyl,
N-methyl-pyrrolidinyl, oxetanyl, or tetrahydropyranyl.

In some embodiments, the compound can be represented by Formula (I), (Ia), (Ib), (Ic), (Id), (Ie), (If), (Ig), (Ih), (Ij), (Ik), (Im) or (In), or a pharmaceutically acceptable salt thereof, wherein $R^{4G}$ is methyl, ethyl, n-propyl, iso-propyl, n-butyl, iso-butyl, n-pentyl, neopentyl, n-hexane, 2,2-dimethyl-butyl, 3,3-dimethyl-butyl, 2-ethyl-butyl, 2-n-propyl-pentyl, cyclobutyl, cyclohexyl, N-methyl-pyrrolidinyl, oxetanyl, or tetrahydropyranyl. In some embodiments, the compound can be represented by Formula (I), (Ia), (Ib), (Ic), (Id), (Ie), (If), (Ig), (Ih), (Ij), (Ik), (Im) or (In), or a pharmaceutically acceptable salt thereof, wherein $R^{4G}$ is methyl, ethyl, n-propyl, iso-propyl, n-butyl, iso-butyl, n-pentyl, neopentyl, n-hexane, 2,2-dimethyl-butyl, 3,3-dimethyl-butyl, 2-ethyl-butyl, or 2-n-propyl-pentyl. In some embodiments, the compound can be represented by Formula (I), (Ia), (Ib), (Ic), (Id), (Ie), (If), (Ig), (Ih), (Ij), (Ik), (Im) or (In), or a pharmaceutically acceptable salt thereof, wherein $R^{4G}$ is iso-propyl, n-hexane, 2,2-dimethyl-butyl, 3,3-dimethyl-butyl, or 2-ethyl-butyl. In some embodiments, the compound can be represented by Formula (I), (Ia), (Ib), (Ic), (Id), (Ie), (If), (Ig), (Ih), (Ij), (Ik), (Im) or (In), or a pharmaceutically acceptable salt thereof, wherein $R^{4G}$ is iso-propyl. In some embodiments, the compound can be represented by Formula (I), (Ia), (Ib), (Ic), (Id), (Ie), (If), (Ig), (Ih), (Ij), (Ik), (Im) or (In), or a pharmaceutically acceptable salt thereof, wherein $R^{4G}$ is n-hexane. In some embodiments, the compound can be represented by Formula (I), (Ia), (Ib), (Ic), (Id), (Ie), (If), (Ig), (Ih), (Ij), (Ik), (Im) or (In), or a pharmaceutically acceptable salt thereof, wherein $R^{4G}$ is 2,2-dimethyl-butyl. In some embodiments, the compound can be represented by Formula (I), (Ia), (Ib), (Ic), (Id), (Ie), (If), (Ig), (Ih), (Ij), (Ik), (Im) or (In), or a pharmaceutically acceptable salt thereof, wherein $R^{4G}$ is 3,3-dimethyl-butyl. In some embodiments, the compound can be represented by Formula (I), (Ia), (Ib), (Ic), (Id), (Ie), (If), (Ig), (Ih), (Ij), (Ik), (Im) or (In), or a pharmaceutically acceptable salt thereof, wherein $R^{4G}$ is 2-ethyl-butyl.

In some embodiments, the compound can be represented by Formula (Ia), or a pharmaceutically acceptable salt thereof, wherein
$R^1$ and $R^2$ are both H or —C(O)$R^{1A}$, wherein $R^{1A}$ is methyl, ethyl or iso-propyl;
$R^3$ is —NH$_2$;

$R^{4B}$ is:
—OPh; and
$R^{4C}$ is:

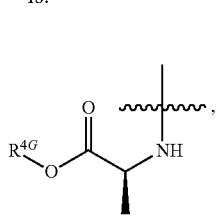

wherein
$R^{4G}$ is
methyl, ethyl, n-propyl, iso-propyl, n-butyl, iso-butyl, sec-butyl, tert-butyl, n-pentyl, neopentyl, n-hexane, 2,2-dimethyl-butyl, 3,3-dimethyl-butyl, 2-ethyl-butyl, or 2-n-propyl-pentyl, each optionally substituted with OH, methoxy, ethoxy, propoxy, butoxy, $CF_3$, $Me(CH_2OCH_2)_2$—, cyclopropyl or 1-methylcyclopropyl, cyclobutyl, cyclopentyl, or cyclohexyl, pyrrolidinyl, oxetanyl, or tetrahydropyranyl, each optionally substituted with methyl, ethyl, n-propyl or iso-propyl.

In some embodiments, the compound of the present disclosure, or a pharmaceutically acceptable salt thereof, is represented by Formula (In):

Formula (In)

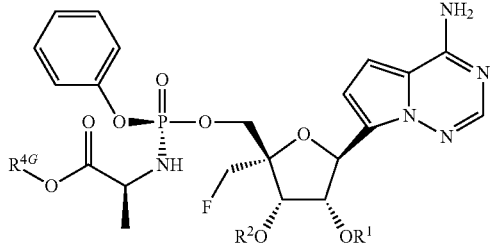

wherein
$R^1$ and $R^2$ are both H or —C(O)$R^{1A}$, wherein $R^{1A}$ is methyl, ethyl or iso-propyl; and
$R^{4G}$ is
methyl, ethyl, n-propyl, iso-propyl, n-butyl, iso-butyl, sec-butyl, tert-butyl, n-pentyl, neopentyl, n-hexane, 2,2-dimethyl-butyl, 3,3-dimethyl-butyl, 2-ethyl-butyl, or 2-n-propyl-pentyl, each optionally substituted with OH, methoxy, ethoxy, propoxy, butoxy, $CF_3$, $Me(CH_2OCH_2)_2$—, cyclopropyl or 1-methylcyclopropyl, cyclobutyl, cyclopentyl, or cyclohexyl, pyrrolidinyl, oxetanyl, or tetrahydropyranyl, each optionally substituted with methyl, ethyl, n-propyl or iso-propyl.

In some embodiments, the compound can be represented by Formula (I), (Ia), (Ib), (Ic), (Id), (Ie), (If), (Ig), (Ih), (Ij), (Ik), (Im) or (In), or a pharmaceutically acceptable salt thereof, wherein the compound is selected from the compounds of Table 1A, Table 1B, Table 1C and Table 1D.

TABLE 1A

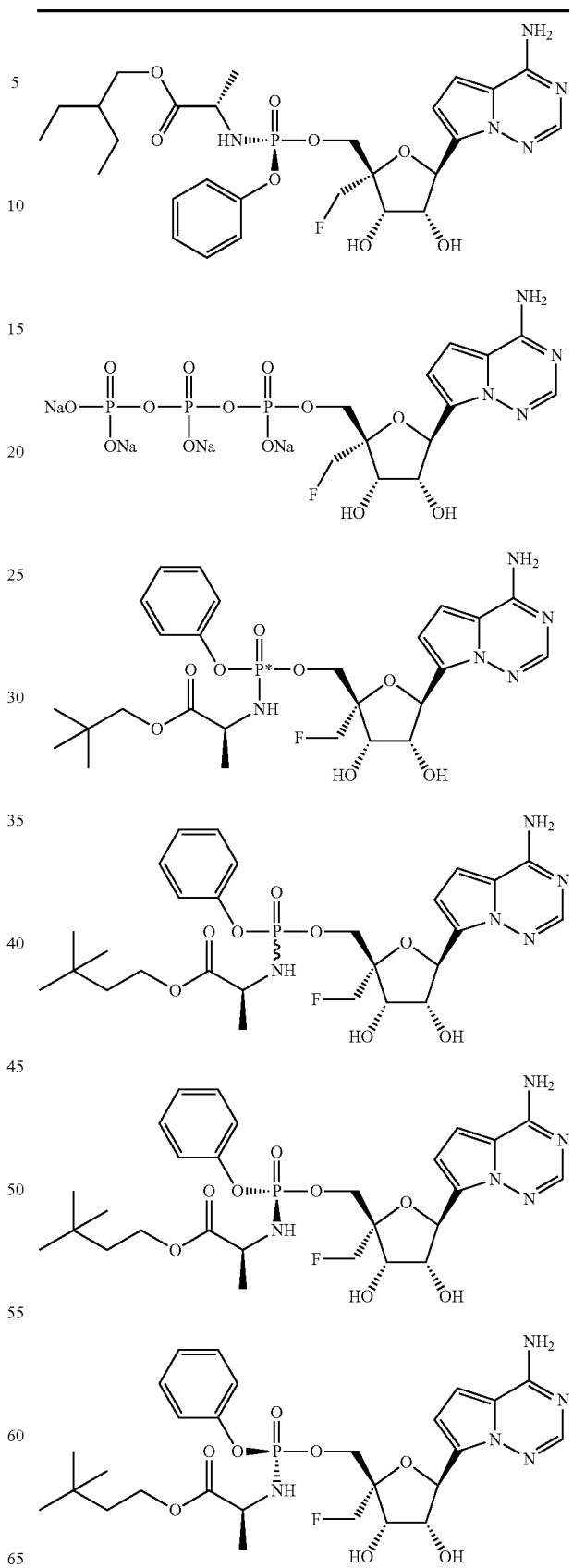

TABLE 1A-continued
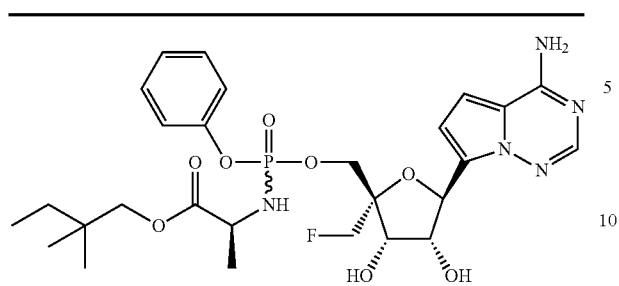
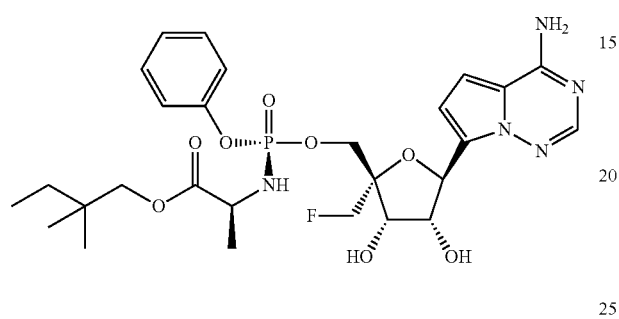
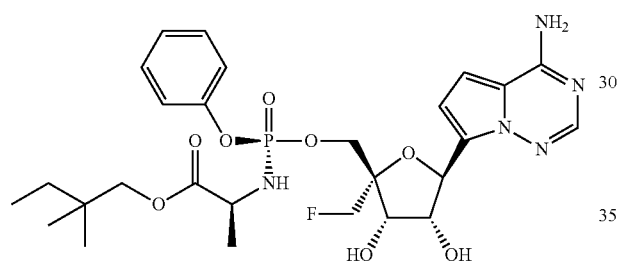
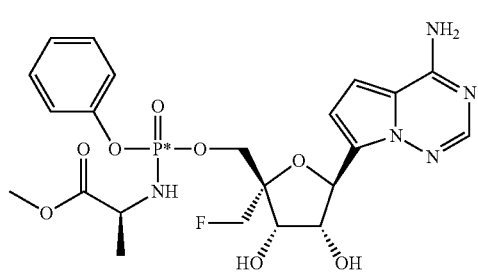
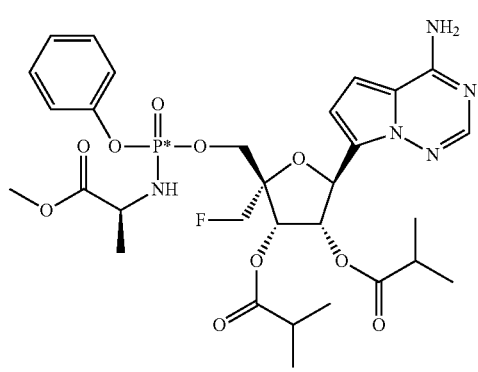
TABLE 1A-continued
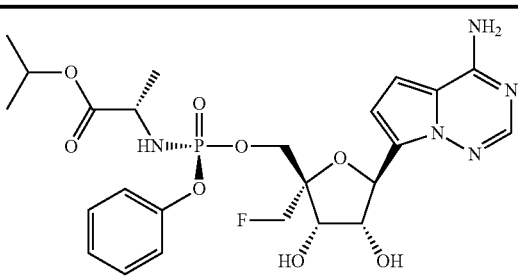
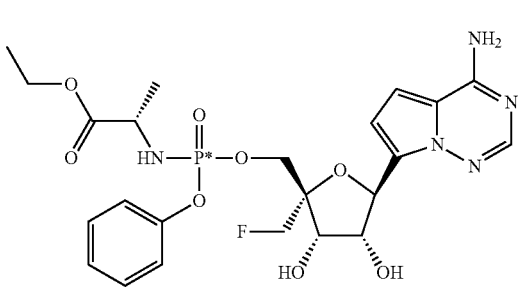
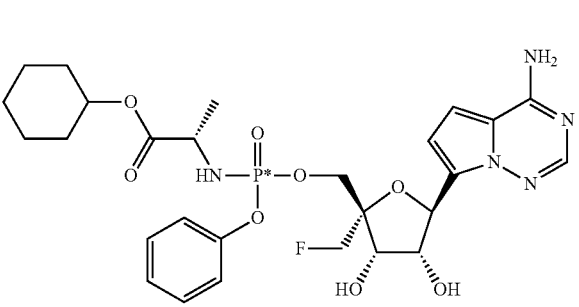
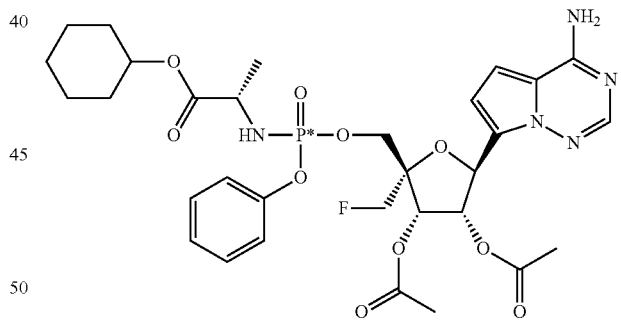
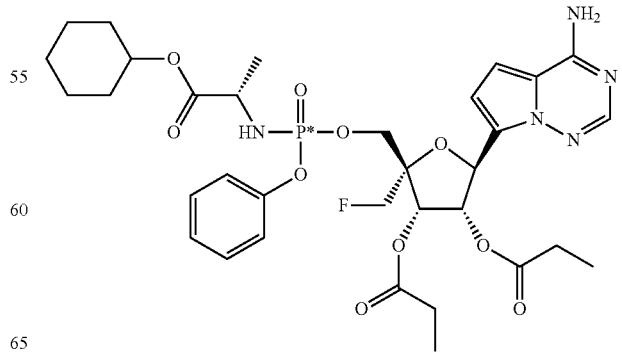

TABLE 1A-continued
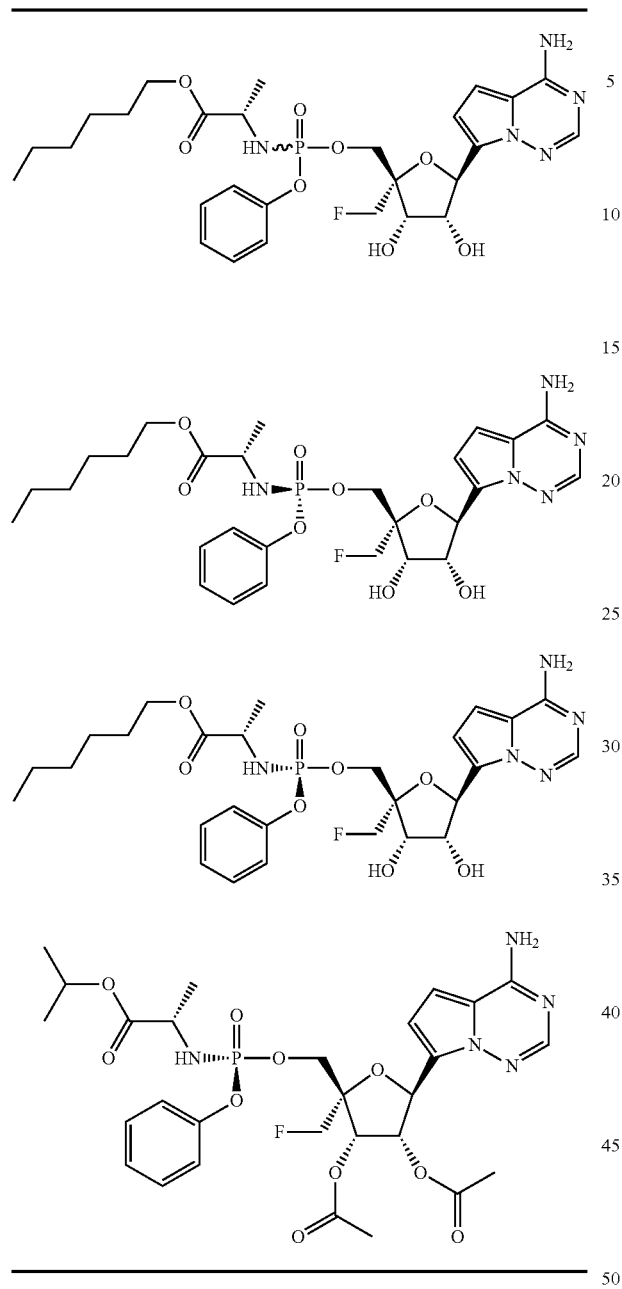
TABLE 1B
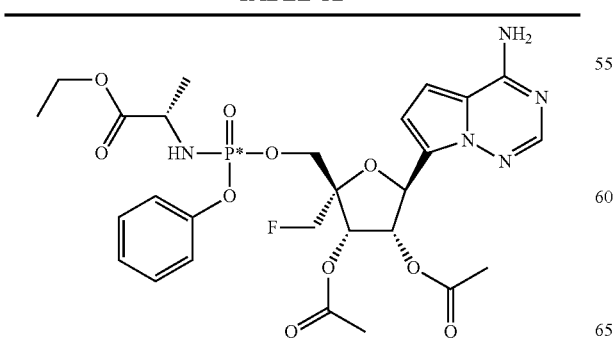
TABLE 1B-continued
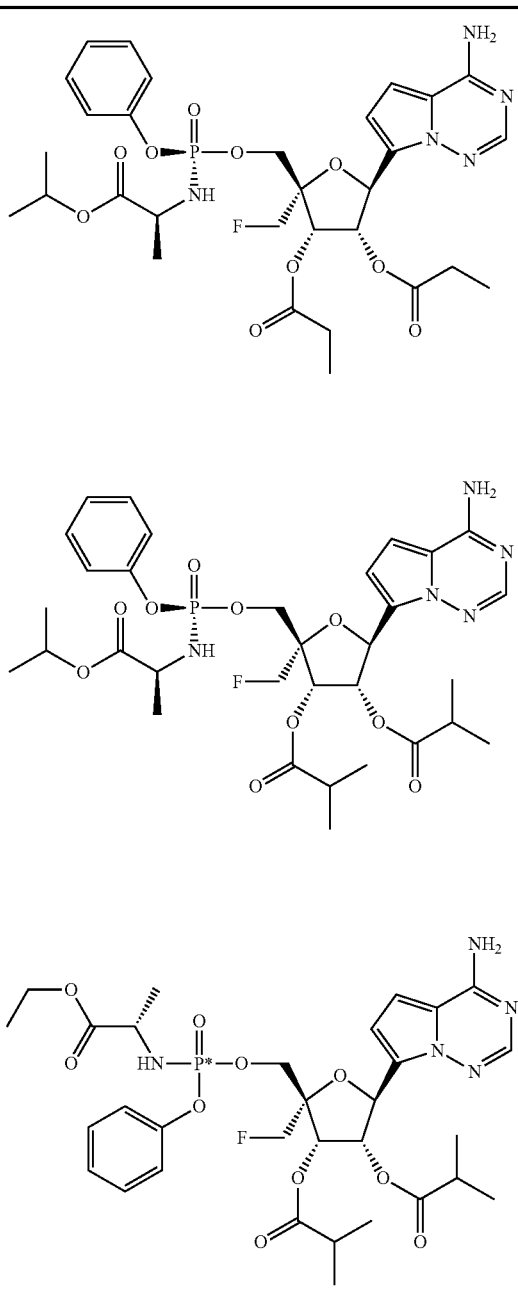
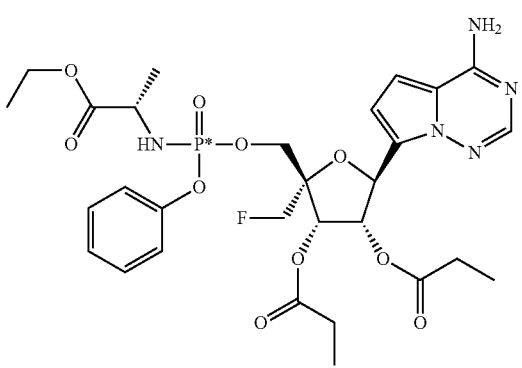

TABLE 1B-continued
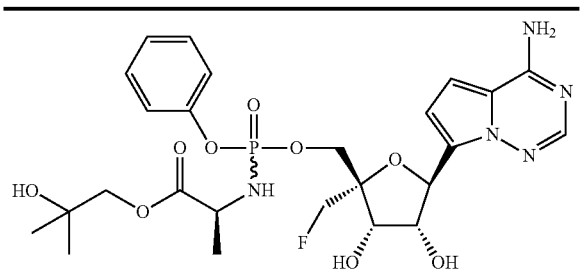
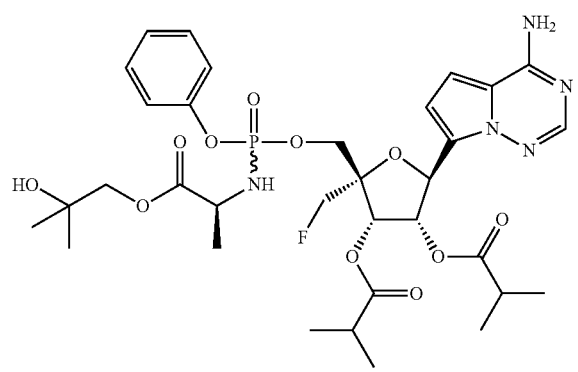 [SMILES: CC(C)C(=O)O[C@H]1[C@H](c2ccc3c(N)ncnn23)O[C@](CF)(COP(=O)(N[C@@H](C)C(=O)OCC(C)(C)O)Oc2ccccc2)[C@H]1OC(=O)C(C)C]
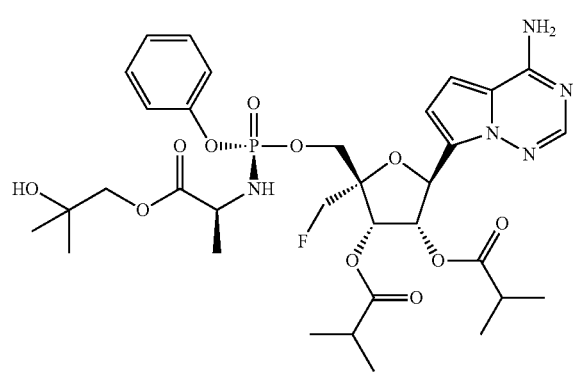 [SMILES: CC(C)C(=O)O[C@H]1[C@H](c2ccc3c(N)ncnn23)O[C@](CF)(CO[P@](=O)(N[C@@H](C)C(=O)OCC(C)(C)O)Oc2ccccc2)[C@H]1OC(=O)C(C)C]
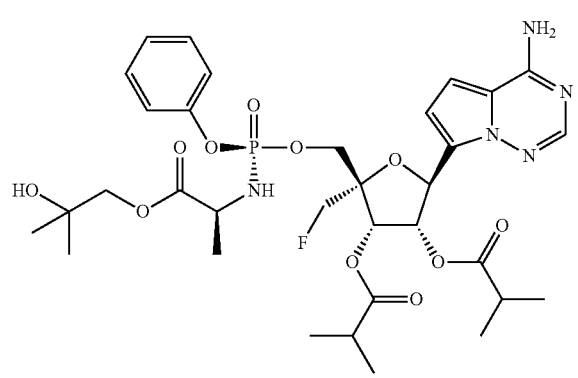 [SMILES: CC(C)C(=O)O[C@H]1[C@H](c2ccc3c(N)ncnn23)O[C@](CF)(CO[P@@](=O)(N[C@@H](C)C(=O)OCC(C)(C)O)Oc2ccccc2)[C@H]1OC(=O)C(C)C]
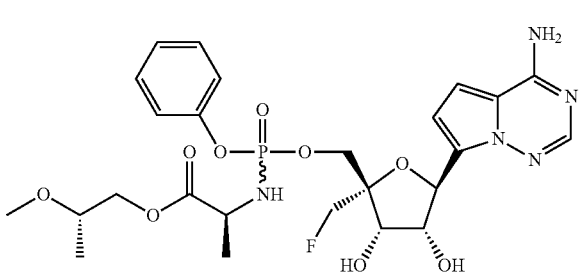 [SMILES: CO[C@@H](C)COC(=O)[C@H](C)N[P@@](=O)(OC[C@@]1(CF)O[C@@H](c2ccc3c(N)ncnn23)[C@H](O)[C@@H]1O)Oc1ccccc1]
TABLE 1B-continued
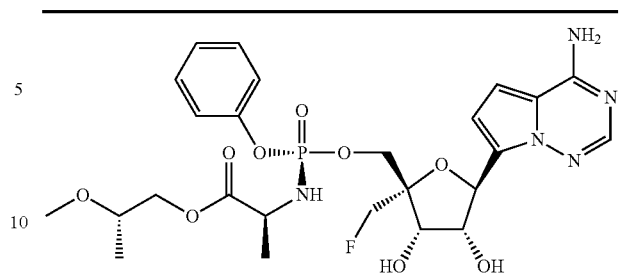
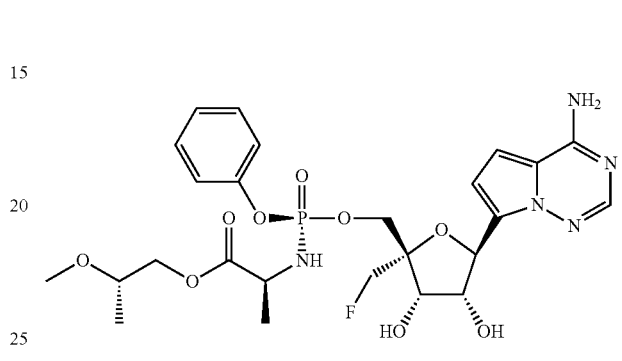
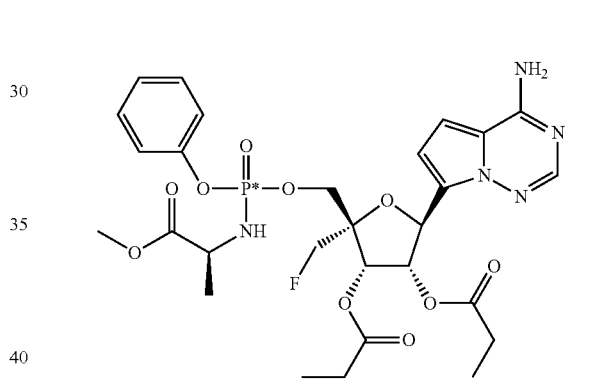
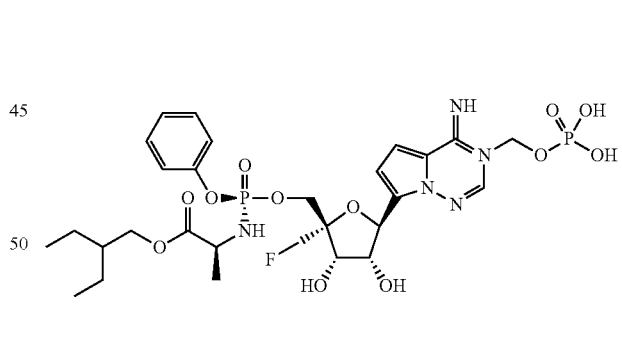
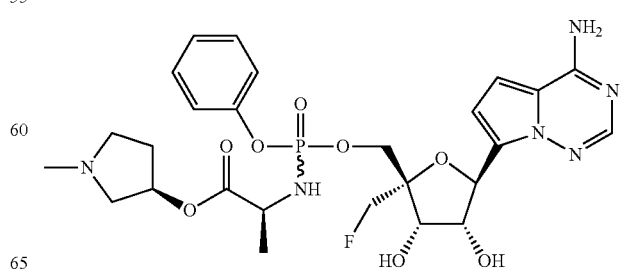

TABLE 1B-continued
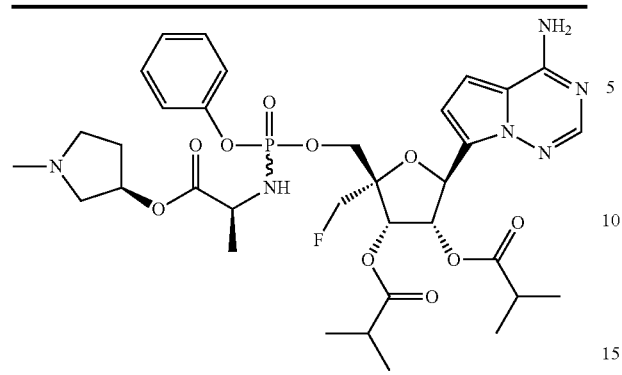
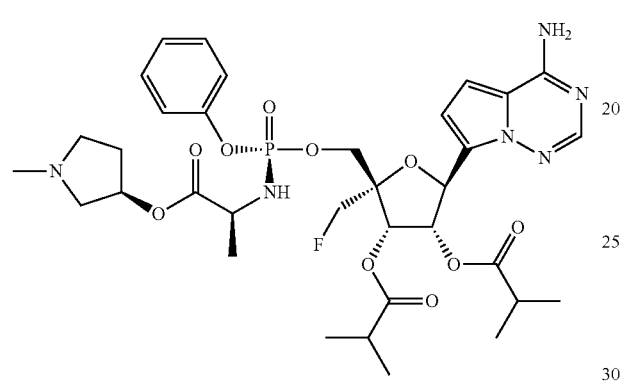
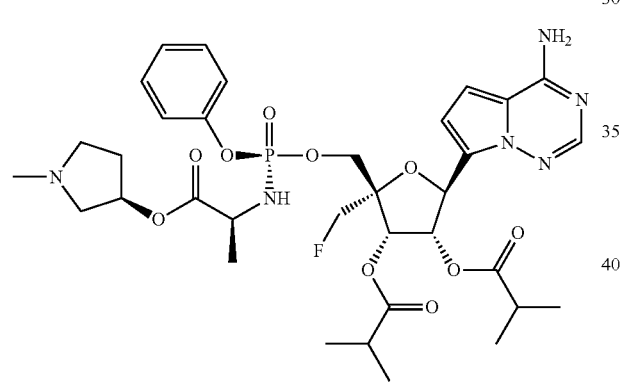
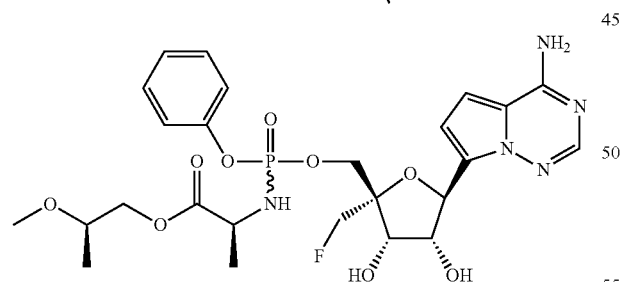
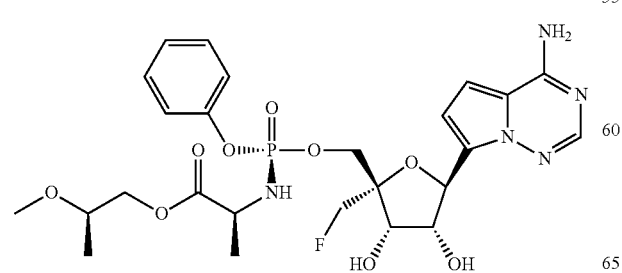
TABLE 1B-continued
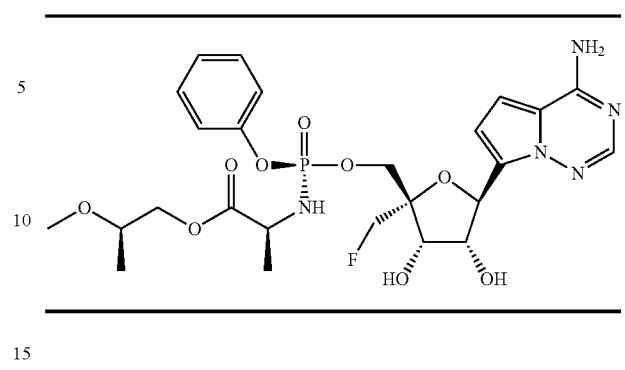
TABLE 1C
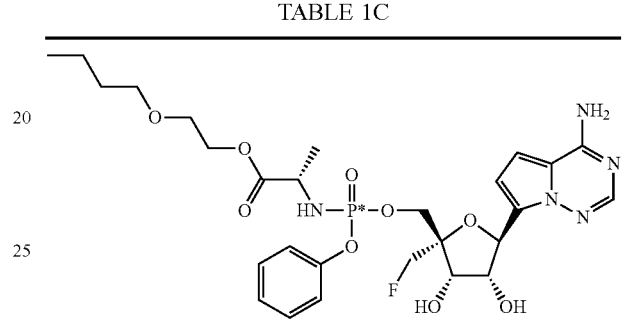
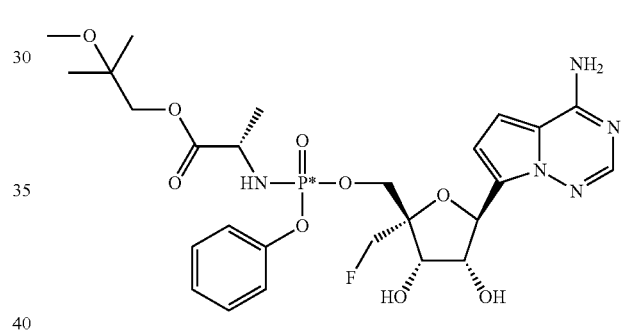
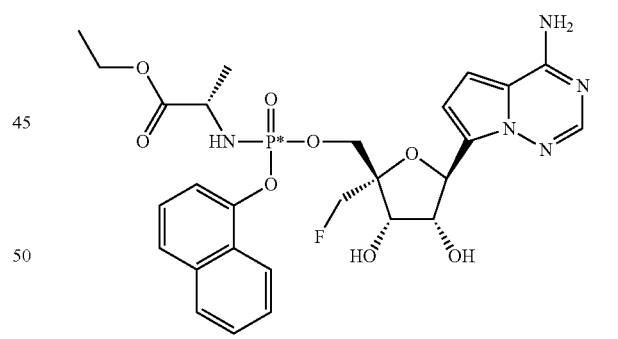
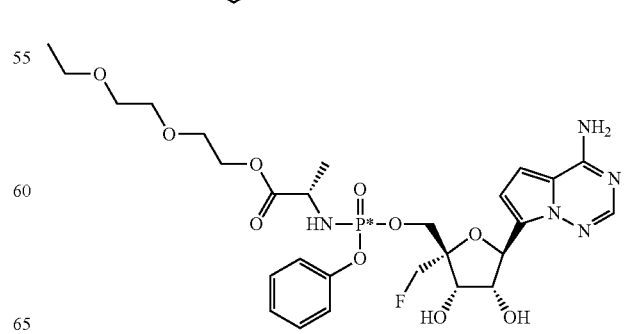

TABLE 1C-continued
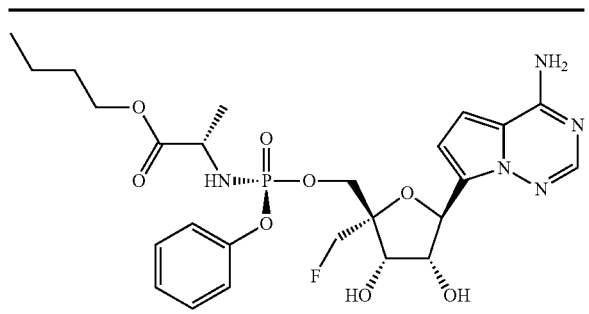
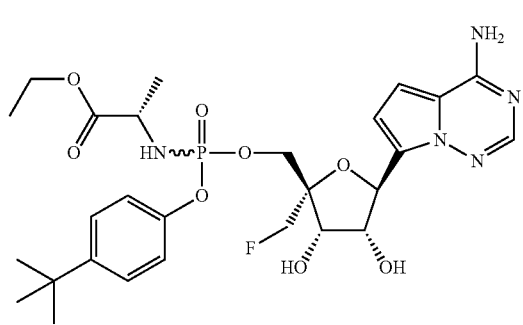 [SMILES: CCOC(=O)[C@H](C)NP(=O)(OC[C@@]1(CF)O[C@@H](c2ccc3c(N)ncnn23)[C@H](O)[C@@H]1O)Oc1ccc(C(C)(C)C)cc1]
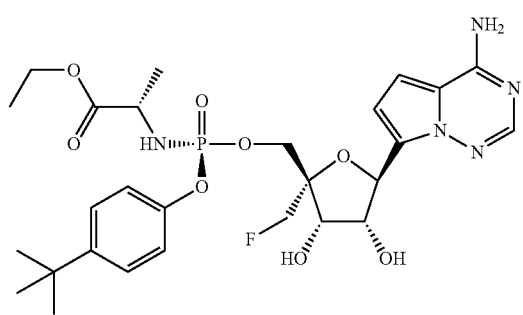 [SMILES: CCOC(=O)[C@H](C)N[P@](=O)(OC[C@@]1(CF)O[C@@H](c2ccc3c(N)ncnn23)[C@H](O)[C@@H]1O)Oc1ccc(C(C)(C)C)cc1]
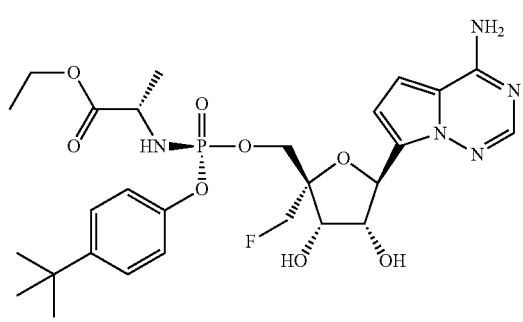 [SMILES: CCOC(=O)[C@H](C)N[P@@](=O)(OC[C@@]1(CF)O[C@@H](c2ccc3c(N)ncnn23)[C@H](O)[C@@H]1O)Oc1ccc(C(C)(C)C)cc1]
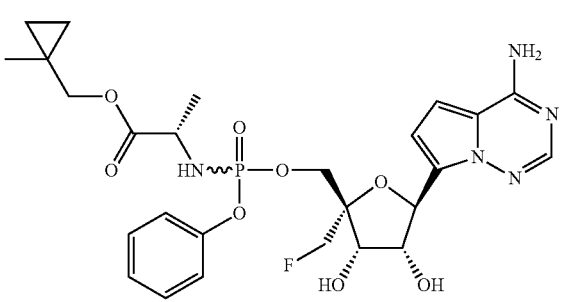 [SMILES: C[C@H](NP(=O)(OC[C@@]1(CF)O[C@@H](c2ccc3c(N)ncnn23)[C@H](O)[C@@H]1O)Oc1ccccc1)C(=O)OCC1(C)CC1]
TABLE 1C-continued
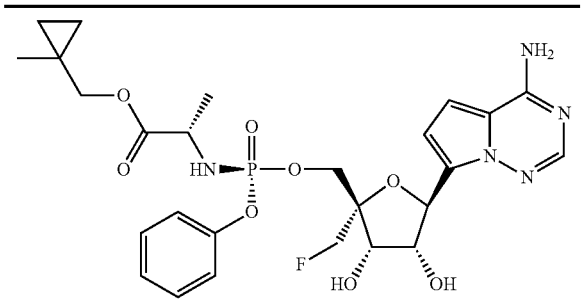
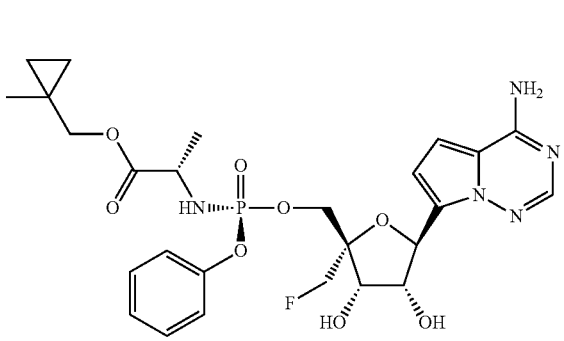 [SMILES: C[C@H](N[P@](=O)(OC[C@@]1(CF)O[C@@H](c2ccc3c(N)ncnn23)[C@H](O)[C@@H]1O)Oc1ccccc1)C(=O)OCC1(C)CC1]
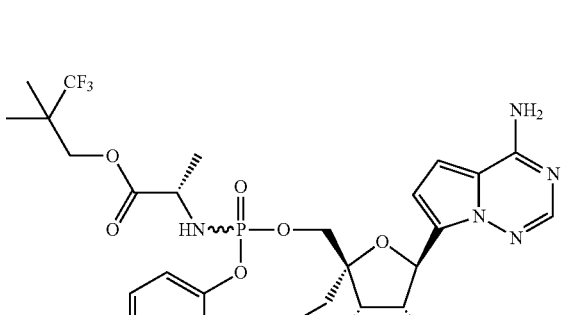
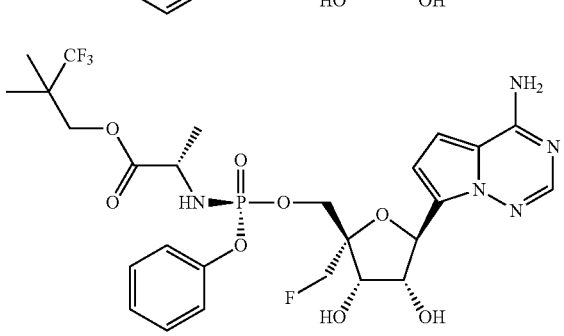
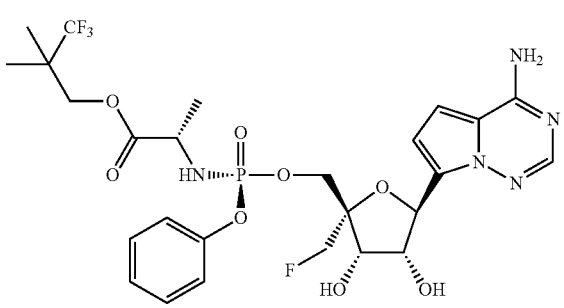 [SMILES: C[C@H](N[P@](=O)(OC[C@@]1(CF)O[C@@H](c2ccc3c(N)ncnn23)[C@H](O)[C@@H]1O)Oc1ccccc1)C(=O)OCC(C)(C)C(F)(F)F]

TABLE 1C-continued
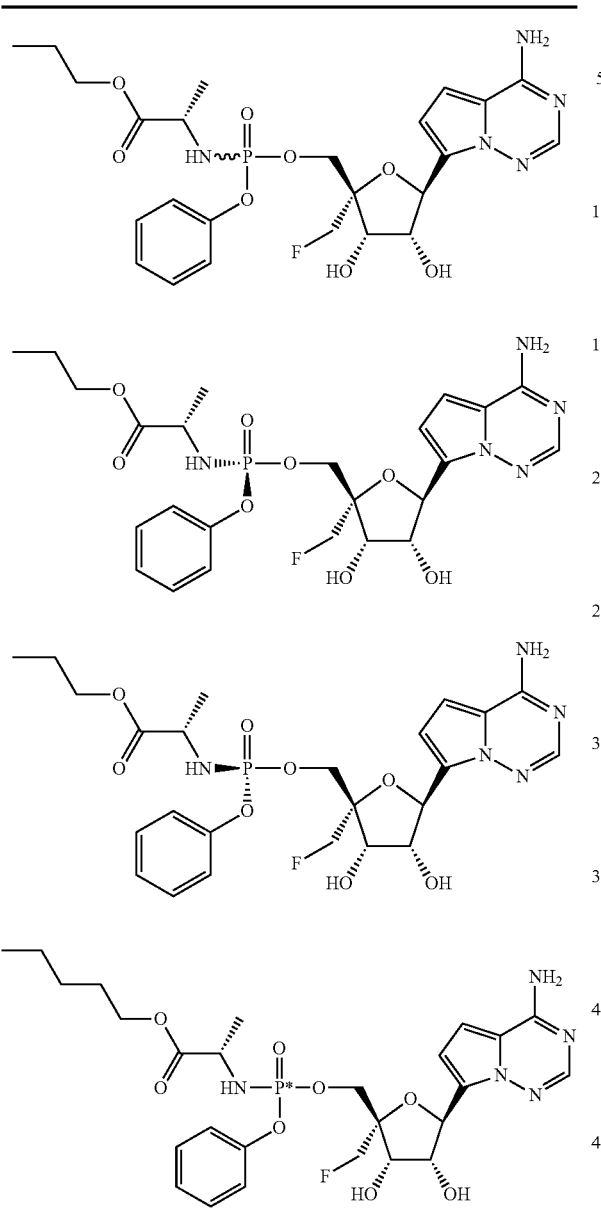
TABLE 1D
TABLE 1D-continued
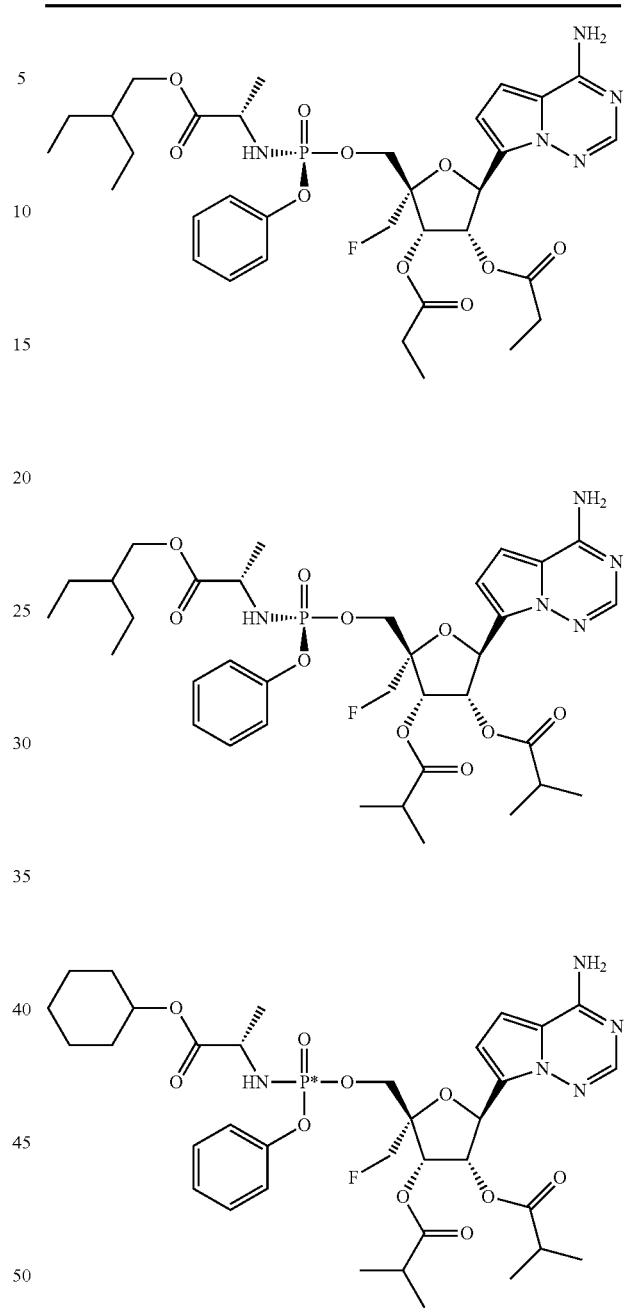

TABLE 1D-continued
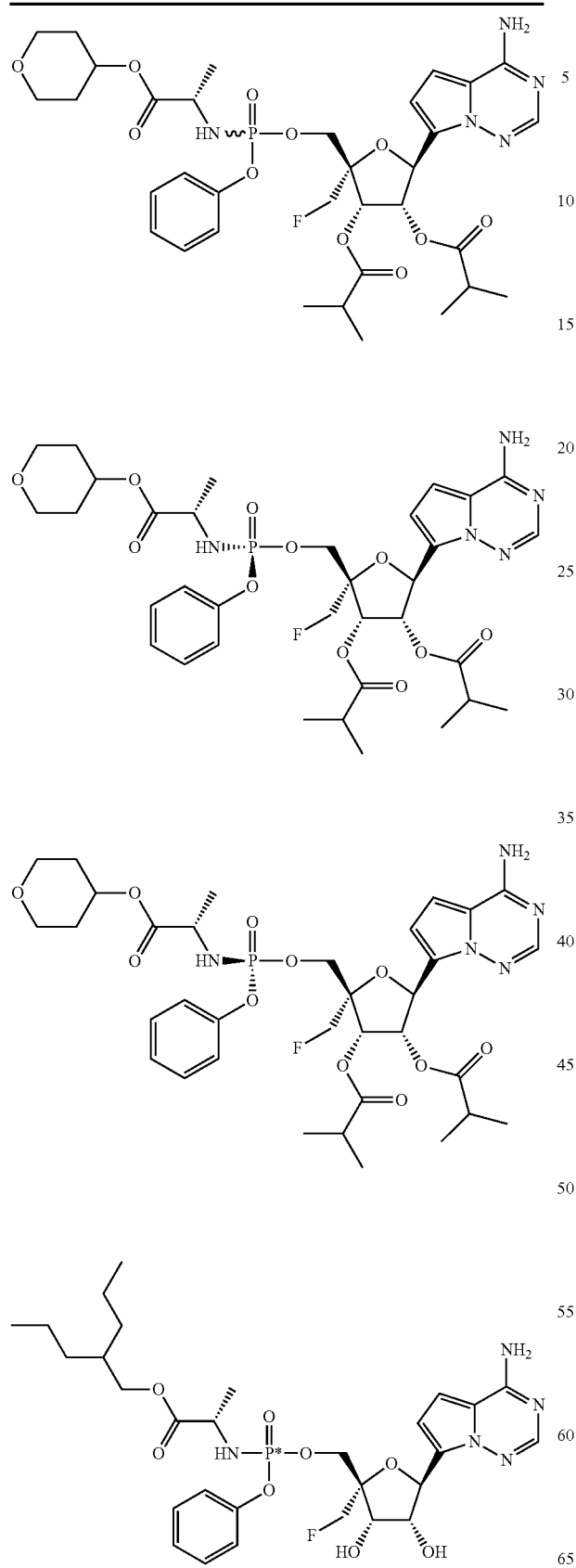
TABLE 1D-continued
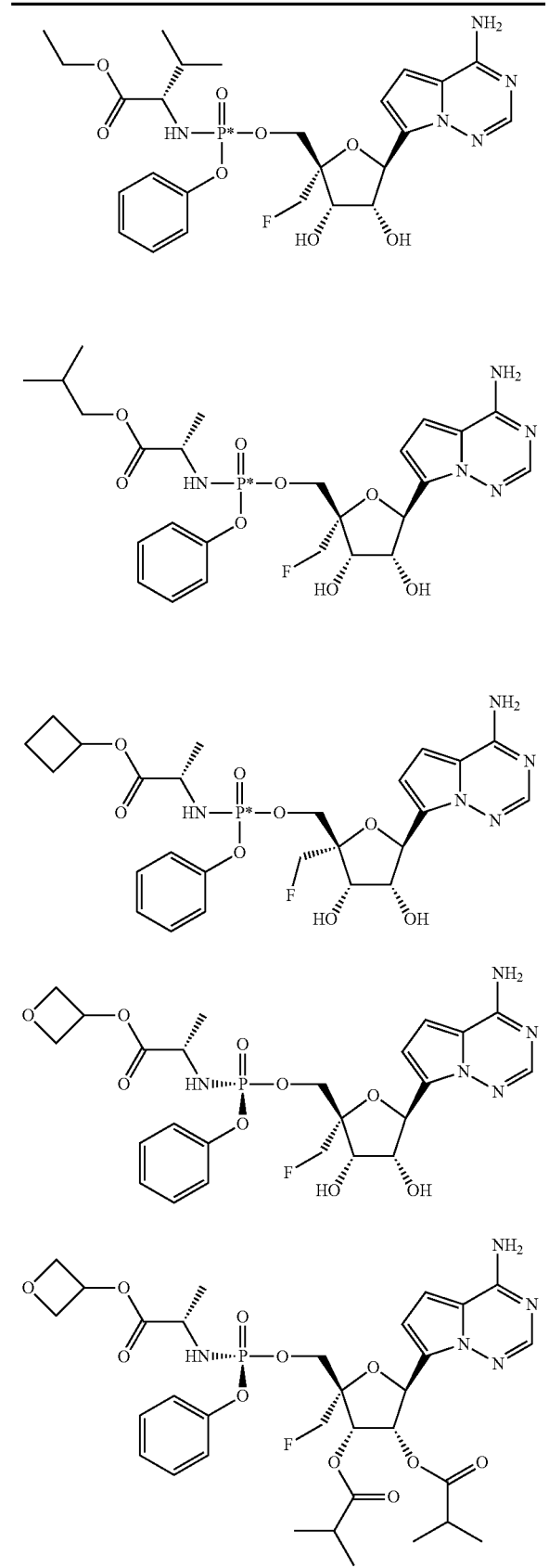

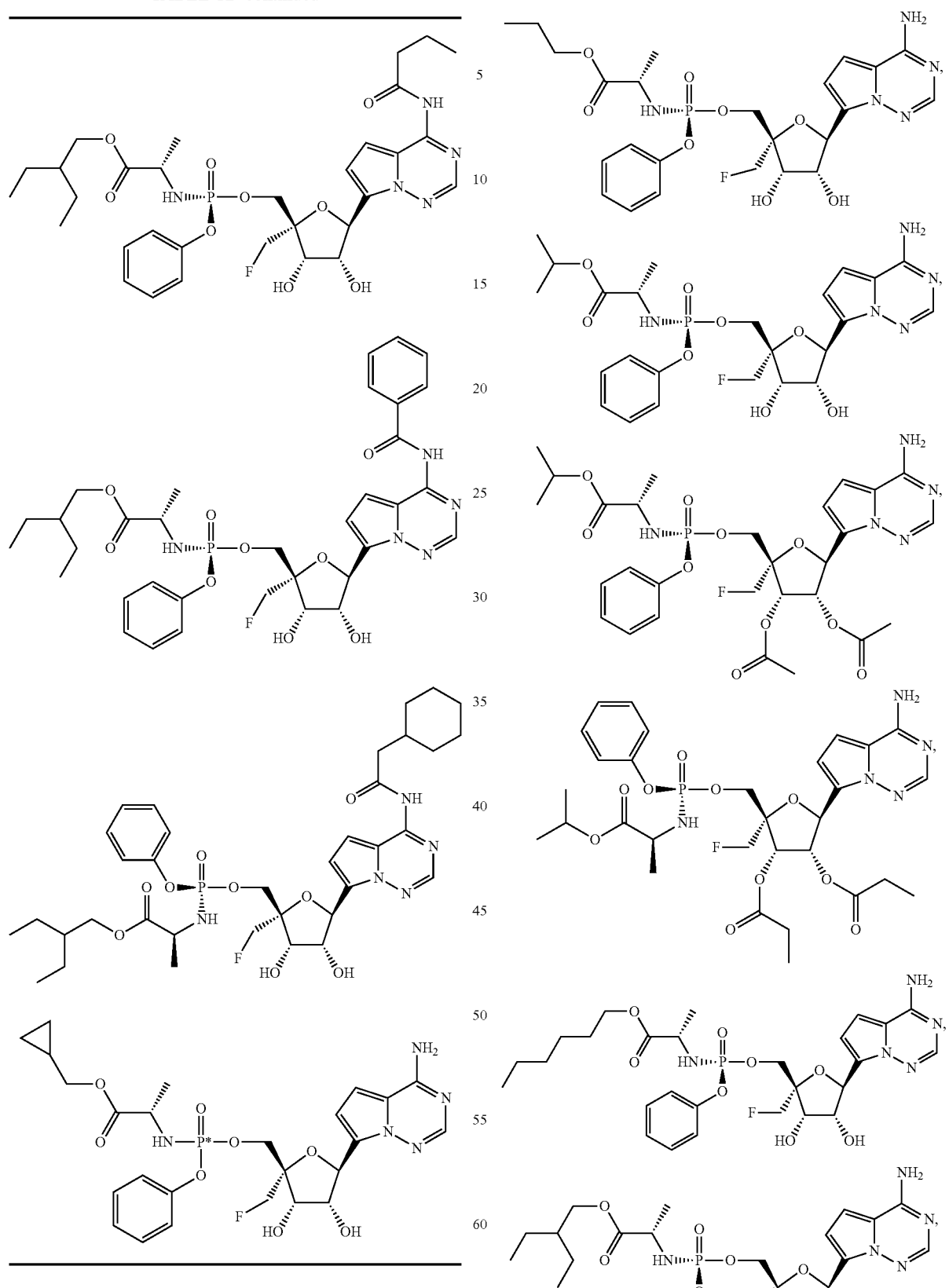
In some embodiments, the compound can be represented by Formula (I), (Ia), (Ib), (Ic), (Id), (Ie), (If), (Ig), (Ih), (Ij), (Ik), (Im) or (In), or a pharmaceutically acceptable salt thereof, wherein the compound is:

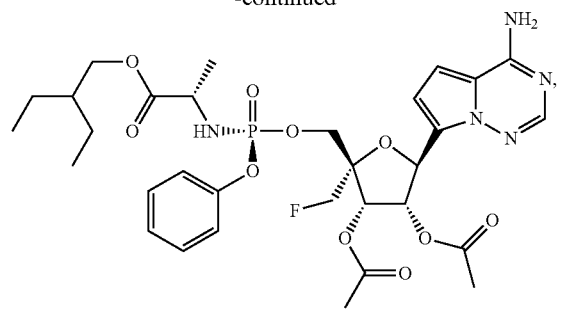
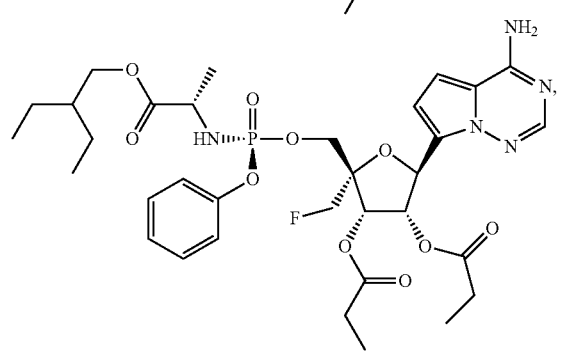
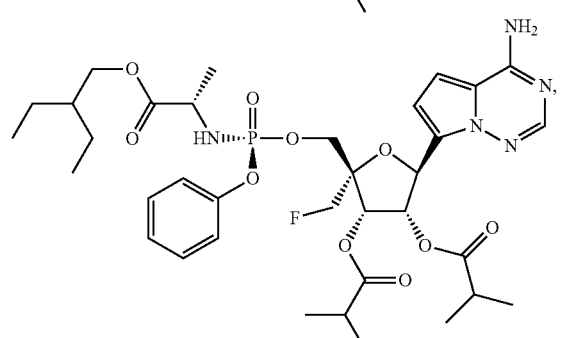
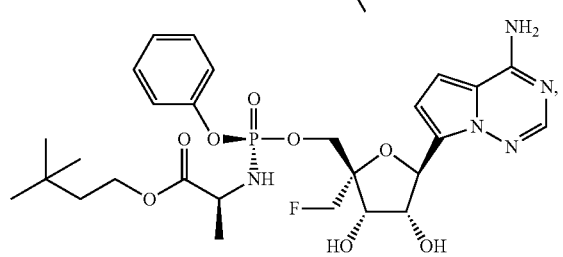
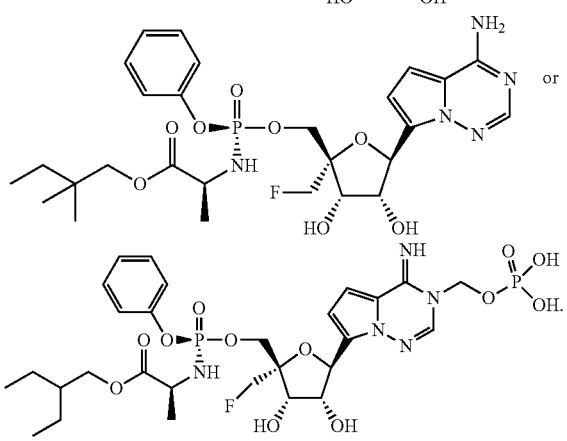

In some embodiments, the compound can be represented by Formula (I), (Ia), (Ib), (Ic), (Id), (Ie), (If), (Ig), (Ih), (Ij), (Ik), (Im) or (In), or a pharmaceutically acceptable salt thereof, wherein the compound is:

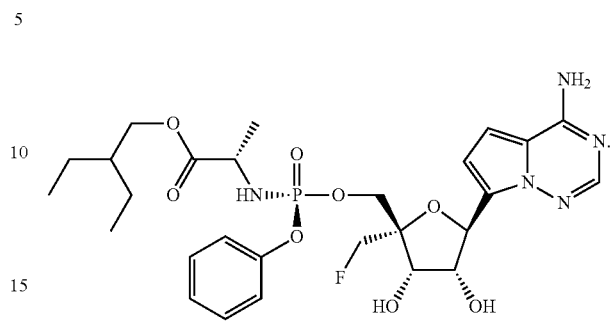

In some embodiments, the compound can be represented by Formula (I), (Ia), (Ib), (Ic), (Id), (Ie), (If), (Ig), (Ih), (Ij), (Ik), (Im) or (In), or a pharmaceutically acceptable salt thereof, wherein the compound is:

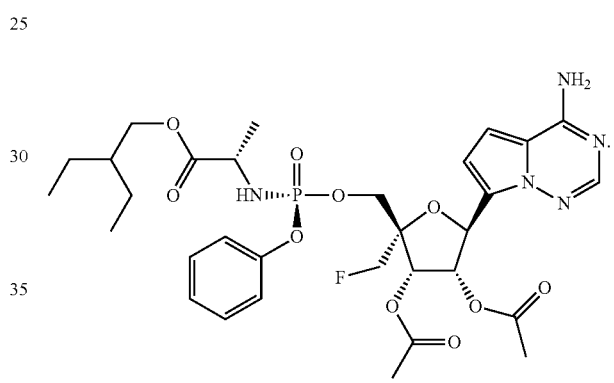

In some embodiments, the compound can be represented by Formula (I), (Ia), (Ib), (Ic), (Id), (Ie), (If), (Ig), (Ih), (Ij), (Ik), (Im) or (In), or a pharmaceutically acceptable salt thereof, wherein the compound is:

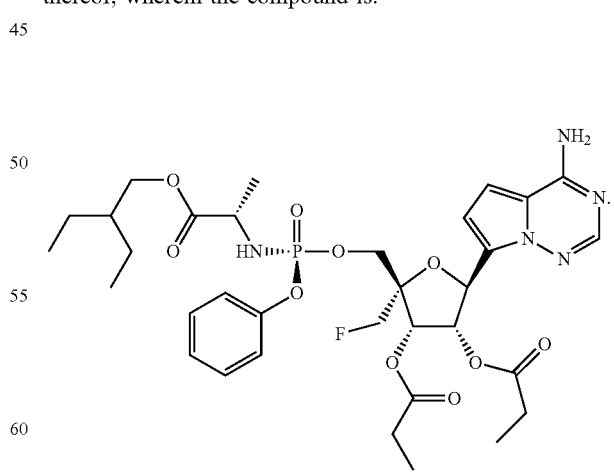

In some embodiments, the compound can be represented by Formula (I), (Ia), (Ib), (Ic), (Id), (Ie), (If), (Ig), (Ih), (Ij), (Ik), (Im) or (In), or a pharmaceutically acceptable salt thereof, wherein the compound is:

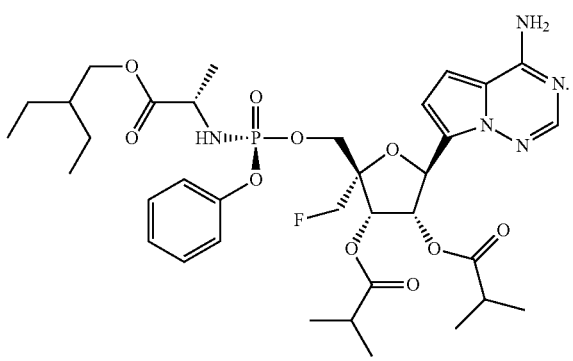 [SMILES: CCC(CC)COC(=O)[C@H](C)N[P@](=O)(OC[C@@]1(CF)O[C@@H](c2ccc3c(N)ncnn23)[C@H](OC(=O)C(C)C)[C@@H]1OC(=O)C(C)C)Oc1ccccc1]

In some embodiments, the compound can be represented by Formula (I), (Ia), (Ib), (Ic), (Id), (Ie), (If), (Ig), (Ih), (Ij), (Ik), (Im) or (In), or a pharmaceutically acceptable salt thereof, wherein the compound is:

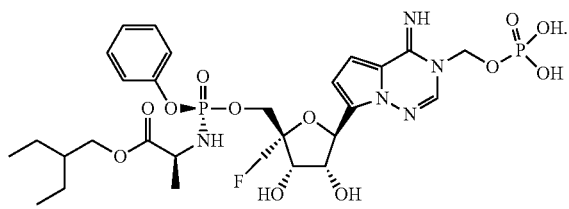 [SMILES: CCC(CC)COC(=O)[C@H](C)N[P@](=O)(OC[C@@]1(CF)O[C@@H](c2ccc3c(=N)n(COP(=O)(O)O)cnn23)[C@H](O)[C@@H]1O)Oc1ccccc1]

In some embodiments, the present disclosure provides a compound, or a pharmaceutically acceptable salt thereof, wherein the compound is:

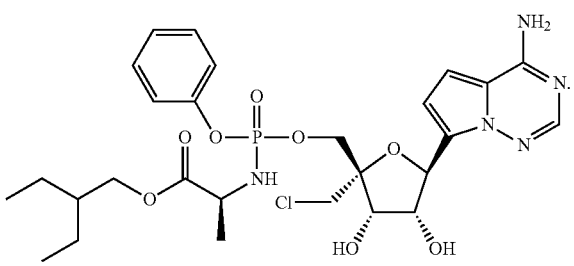 [SMILES: CCC(CC)COC(=O)[C@H](C)NP(=O)(OC[C@@]1(CCl)O[C@@H](c2ccc3c(N)ncnn23)[C@H](O)[C@@H]1O)Oc1ccccc1]

Also falling within the scope herein are the in vivo metabolic products of the compounds described herein, to the extent such products are novel and unobvious over the prior art. Such products may result for example from the oxidation, reduction, hydrolysis, amidation, esterification and the like of the administered compound, primarily due to enzymatic processes. Accordingly, included are novel and unobvious compounds produced by a process comprising contacting a compound with a mammal for a period of time sufficient to yield a metabolic product thereof. Such products typically are identified by preparing a radiolabelled (e.g. $^{14}$C or $^3$H) compound, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds even if they possess no HSV antiviral activity of their own.

Recipes and methods for determining stability of compounds in surrogate gastrointestinal secretions are known. Compounds are defined herein as stable in the gastrointestinal tract where less than about 50 mole percent of the protected groups are deprotected in surrogate intestinal or gastric juice upon incubation for 1 hour at 37° C. Simply because the compounds are stable to the gastrointestinal tract does not mean that they cannot be hydrolyzed in vivo. The prodrugs typically will be stable in the digestive system but may be substantially hydrolyzed to the parental drug in the digestive lumen, liver, lung or other metabolic organ, or within cells in general. As used herein, a prodrug is understood to be a compound that is chemically designed to efficiently liberate the parent drug after overcoming biological barriers to oral delivery.

IV. Pharmaceutical Formulations

In some embodiments, the present disclosure provides a pharmaceutical formulation comprising a pharmaceutically effective amount of a compound of the present disclosure, or a pharmaceutically acceptable salt thereof, and a pharmaceutically acceptable carrier or excipient. Also provided herein is a pharmaceutical formulation comprising a pharmaceutically effective amount of a compound of Formula (I), (Ia), (Ib), (Ic), (Id), (Ie), (If), (Ig), (Ih), (Ij), (Ik), (Im) and (In), or a pharmaceutically acceptable salt, solvate, and/or ester thereof, and a pharmaceutically acceptable carrier or excipient.

The compounds herein are formulated with conventional carriers and excipients. Tablets will contain excipients, glidants, fillers, binders and the like. Aqueous formulations are prepared in sterile form, and when intended for delivery by other than oral administration generally will be isotonic. All formulations will optionally contain excipients such as those set forth in the "Handbook of Pharmaceutical Excipients" (1986). Excipients include ascorbic acid and other antioxidants, chelating agents such as EDTA, carbohydrates such as dextran, hydroxyalkylcellulose, hydroxyalkylmethylcellulose, stearic acid and the like. The pH of the formulations ranges from about 3 to about 11, for example about 7 to 10.

While it is possible for the active ingredients to be administered alone it may be preferable to present them as pharmaceutical formulations. The formulations, both for veterinary and for human use, comprise at least one active ingredient, as above defined, together with one or more acceptable carriers and optionally other therapeutic ingredients, particularly those additional therapeutic ingredients as discussed herein. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any suitable method. Techniques and formulations generally are found in Remington's Pharmaceutical Sciences (Mack Publishing Co., Easton, PA). Such methods include the step of bringing into association the active ingredient with the carrier which constitutes one or more accessory ingredients.

In general, the formulations are prepared by uniformly and intimately bringing into association the active ingredient with liquid carriers or finely divided solid carriers or both, and then, if necessary, shaping the product.

Formulations suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For infections of the eye or other external tissues e.g. mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation include Tween® 60, Span® 80, cetostearyl alcohol, benzyl alcohol, myristyl alcohol, glyceryl monostearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations herein comprise a combination together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, solutions, syrups or elixirs may be prepared. Compositions intended for oral use may be prepared according to any method for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally-occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally-occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions may be in the form of a sterile injectable or intravenous preparations, such as a sterile injectable aqueous or oleaginous suspension. This suspension may be formulated according to the known art using those suitable dispersing or wetting agents and suspending agents which have been mentioned above. The sterile injectable or intravenous preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10%, and particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns, such as 0.5, 1, 30, 35 etc., which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of Pneumoviridae infections as described below.

Another embodiments provides a novel, efficacious, safe, nonirritating and physiologically compatible inhalable composition comprising a compound of Formula (I), (Ia), (Ib), (Ic), (Id), (Ie), (If), (Ig), (Ih), (Ij), (Ik), (Im) or (In), or a pharmaceutically acceptable salt thereof, suitable for treating Pneumoviridae infections and potentially associated bronchiolitis. Preferred pharmaceutically acceptable salts are inorganic acid salts including hydrochloride, hydrobromide, sulfate or phosphate salts as they may cause less pulmonary irritation. Preferably, the inhalable formulation is delivered to the endobronchial space in an aerosol comprising particles with a mass median aerodynamic diameter (MMAD) between about 1 and about 5 μm. Preferably, the compound of Formula (I), (Ia), (Ib), (Ic), (Id), (Ie), (If), (Ig), (Ih), (Ij), (Ik), (Im) or (In) is formulated for aerosol delivery using a nebulizer, pressurized metered dose inhaler (pMDI), or dry powder inhaler (DPI).

Non-limiting examples of nebulizers include atomizing, jet, ultrasonic, pressurized, vibrating porous plate, or equivalent nebulizers including those nebulizers utilizing adaptive aerosol delivery technology (Denyer, J. *Aerosol medicine Pulmonary Drug Delivery* 2010, 23 Supp 1, S1-S10). A jet nebulizer utilizes air pressure to break a liquid solution into aerosol droplets. An ultrasonic nebulizer works by a piezoelectric crystal that shears a liquid into small aerosol droplets. A pressurized nebulization system forces solution under pressure through small pores to generate aerosol droplets. A vibrating porous plate device utilizes rapid vibration to shear a stream of liquid into appropriate droplet sizes.

In a preferred embodiment, the formulation for nebulization is delivered to the endobronchial space in an aerosol comprising particles with a MMAD predominantly between about 1 μm and about 5 μm using a nebulizer able to aerosolize the formulation of the compound of Formula (I), (Ia), (Ib), (Ic), (Id), (Ie), (If), (Ig), (Ih), (Ij), (Ik), (Im) or (In) into particles of the required MMAD. To be optimally therapeutically effective and to avoid upper respiratory and systemic side effects, the majority of aerosolized particles should not have a MMAD greater than about 5 μm. If an aerosol contains a large number of particles with a MMAD larger than 5 μm, the particles are deposited in the upper airways decreasing the amount of drug delivered to the site of inflammation and bronchoconstriction in the lower respiratory tract. If the MMAD of the aerosol is smaller than about 1 μm, then the particles have a tendency to remain suspended in the inhaled air and are subsequently exhaled during expiration.

When formulated and delivered according to the method herein, the aerosol formulation for nebulization delivers a therapeutically efficacious dose of the compound of Formula (I), (Ia), (Ib), (Ic), (Id), (Ie), (If), (Ig), (Ih), (Ij), (Ik), (Im) or (In) to the site of Pneumoviridae infection sufficient to treat the Pneumoviridae infection. The amount of drug administered must be adjusted to reflect the efficiency of the delivery of a therapeutically efficacious dose of the compound of Formula (I), (Ia), (Ib), (Ic), (Id), (Ie), (If), (Ig), (Ih), (Ij), (Ik), (Im) or (In). In a preferred embodiment, a combination of the aqueous aerosol formulation with the atomizing, jet, pressurized, vibrating porous plate, or ultrasonic nebulizer permits, depending on the nebulizer, about, at least, 20, to about 90%, typically about 70% delivery of the administered dose of the compound of Formula (I), (Ia), (Ib), (Ic), (Id), (Ie), (If), (Ig), (Ih), (Ij), (Ik), (Im) or (In) into the airways. In a preferred embodiment, at least about 30 to about 50% of the active compound is delivered. More preferably, about 70 to about 90% of the active compound is delivered.

In another embodiment, a compound of Formula (I), (Ia), (Ib), (Ic), (Id), (Ie), (If), (Ig), (Ih), (Ij), (Ik), (Im) or (In) or a pharmaceutically acceptable salt thereof, is delivered as a dry inhalable powder. The compounds are administered endobronchially as a dry powder formulation to efficacious deliver fine particles of compound into the endobronchial space using dry powder or metered dose inhalers. For delivery by DPI, the compound of Formula (I), (Ia), (Ib), (Ic), (Id), (Ie), (If), (Ig), (Ih), (Ij), (Ik), (Im) or (In) is processed into particles with, predominantly, MMAD between about 1 μm and about 5 μm by milling spray drying, critical fluid processing, or precipitation from solution. Media milling, jet milling and spray-drying devices and procedures capable of producing the particle sizes with a MMAD between about 1 μm and about 5 μm are well known in the art. In one embodiment, excipients are added to the compound of Formula (I), (Ia), (Ib), (Ic), (Id), (Ie), (If), (Ig), (Ih), (Ij), (Ik), (Im) or (In) before processing into particles of the required sizes. In another embodiment, excipients are blended with the particles of the required size to aid in dispersion of the drug particles, for example by using lactose as an excipient.

Particle size determinations are made using devices well known in the art. For example a multi-stage Anderson cascade impactor or other suitable method such as those specifically cited within the US Pharmacopoeia Chapter 601 as characterizing devices for aerosols within metered-dose and dry powder inhalers.

In another preferred embodiment, a compound of Formula (I), (Ia), (Ib), (Ic), (Id), (Ie), (If), (Ig), (Ih), (Ij), (Ik), (Im) or (In) is delivered as a dry powder using a device such as a dry powder inhaler or other dry powder dispersion devices. Non-limiting examples of dry powder inhalers and devices include those disclosed in U.S. Pat. Nos. 5,458,135; 5,740,794; 5,775,320; 5,785,049; 3,906,950; 4,013,075; 4,069,819; 4,995,385; 5,522,385; 4,668,218; 4,667,668; 4,805,811 and 5,388,572. There are two major designs of dry powder inhalers. One design is a metering device in which a reservoir for the drug is place within the device and the patient adds a dose of the drug into the inhalation chamber. The second design is a factory-metered device in which each individual dose has been manufactured in a separate container. Both systems depend on the formulation of the drug into small particles of MMAD from 1 μm and about 5 μm and often involve co-formulation with larger excipient particles such as, but not limited to, lactose. Drug powder is placed in the inhalation chamber (either by device metering or by breakage of a factory-metered dosage) and the inspiratory flow of the patient accelerates the powder out of the device and into the oral cavity. Non-laminar flow characteristics of the powder path cause the excipient-drug aggregates to decompose, and the mass of the large excipient particles causes their impaction at the back of the throat, while the smaller drug particles are deposited deep in the lungs. In preferred embodiments, a compound of Formula (I), (Ia), (Ib), (Ic), (Id), (Ie), (If), (Ig), (Ih), (Ij), (Ik), (Im) or (In), or a pharmaceutically acceptable salt thereof, is delivered as a dry powder using either type of dry powder inhaler as described herein, wherein the MMAD of the dry powder, exclusive of any excipients, is predominantly in the range of 1 μm to about 5 μm.

In another embodiment, a compound of Formula (I), (Ia), (Ib), (Ic), (Id), (Ie), (If), (Ig), (Ih), (Ij), (Ik), (Im) or (In) is delivered as a dry powder using a metered dose inhaler. Non-limiting examples of metered dose inhalers and devices include those disclosed in U.S. Pat. Nos. 5,261,538; 5,544,647; 5,622,163; 4,955,371; 3,565,070; 3,361,306 and 6,116,234. In preferred embodiments, a compound of Formula (I), (Ia), (Ib), (Ic), (Id), (Ie), (If), (Ig), (Ih), (Ij), (Ik), (Im) or (In), or a pharmaceutically acceptable salt thereof, is delivered as a dry powder using a metered dose inhaler wherein the MMAD of the dry powder, exclusive of any excipients, is predominantly in the range of about 1-5 μm.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations may include other agents conventional in the art having regard to the type of formulation in question, for example those suitable for oral administration may include flavoring agents.

Further provided are veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds herein are used to provide controlled release pharmaceutical formulations containing as active ingredient one or more of the compounds ("controlled release formulations") in which the release of the active ingredient is controlled and regulated to allow less frequency dosing or to improve the pharmacokinetic or toxicity profile of a given active ingredient.

Effective dose of active ingredient depends at least on the nature of the condition being treated, toxicity, whether the compound is being used prophylactically (lower doses) or against an active viral infection, the method of delivery, and the pharmaceutical formulation, and will be determined by the clinician using conventional dose escalation studies. It can be expected to be from about 0.0001 to about 100 mg/kg body weight per day; typically, from about 0.01 to about 10 mg/kg body weight per day; more typically, from about 0.01 to about 5 mg/kg body weight per day; most typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

V. Routes of Administration

One or more of the compounds of Formula (I), (Ia), (Ib), (Ic), (Id), (Ie), (If), (Ig), (Ih), (Ij), (Ik), (Im) or (In) (herein referred to as the active ingredients) are administered by any route appropriate to the condition to be treated. Suitable routes include oral, rectal, nasal, pulmonary, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds herein is that they are orally bioavailable and can be dosed orally.

The compounds of the present disclosure (also referred to herein as the active ingredients), can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intrathecal and epidural), and the like. It will be appreciated that the preferred route may vary with for example the condition of the recipient. An advantage of certain compounds disclosed herein is that they are orally bioavailable and can be dosed orally.

A compound of the present disclosure, may be administered to an individual in accordance with an effective dosing regimen for a desired period of time or duration, such as at least about one month, at least about 2 months, at least about 3 months, at least about 6 months, or at least about 12 months or longer. In one variation, the compound is administered on a daily or intermittent schedule for the duration of the individual's life.

The dosage or dosing frequency of a compound of the present disclosure may be adjusted over the course of the treatment, based on the judgment of the administering physician.

The compound may be administered to an individual (e.g., a human) in an effective amount. In some embodiments, the compound is administered once daily.

The compound can be administered by any useful route and means, such as by oral or parenteral (e.g., intravenous) administration. Therapeutically effective amounts of the compound may include from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day, or such as from about 0.3 mg to about 30 mg per day, or such as from about 30 mg to about 300 mg per day.

A compound of the present disclosure may be combined with one or more additional therapeutic agents in any dosage amount of the compound of the present disclosure (e.g., from 1 mg to 1000 mg of compound). Therapeutically effective amounts may include from about 1 mg per dose to about 1000 mg per dose, such as from about 50 mg per dose to about 500 mg per dose, or such as from about 100 mg per dose to about 400 mg per dose, or such as from about 150 mg per dose to about 350 mg per dose, or such as from about 200 mg per dose to about 300 mg per dose. Other therapeutically effective amounts of the compound of the present disclosure are about 100, 125, 150, 175, 200, 225, 250, 275, 300, 325, 350, 375, 400, 425, 450, 475, or about 500 mg per dose. Other therapeutically effective amounts of the compound of the present disclosure are about 100 mg per dose, or about 125, 150, 175, 200, 225, 250, 275, 300, 350, 400, 450, or about 500 mg per dose. A single dose can be administered hourly, daily, or weekly. For example, a single dose can be administered once every 1 hour, 2, 3, 4, 6, 8, 12, 16 or once every 24 hours. A single dose can also be administered once every 1 day, 2, 3, 4, 5, 6, or once every 7 days. A single dose can also be administered once every 1 week, 2, 3, or once every 4 weeks. In some embodiments, a single dose can be administered once every week. A single dose can also be administered once every month.

Other therapeutically effective amounts of the compound of the present disclosure are about 20, 25, 30, 35, 40, 45, 50, 55, 60, 65, 70, 75, 80, 85, 90, 95, or about 100 mg per dose.

The frequency of dosage of the compound of the present disclosure are will be determined by the needs of the individual patient and can be, for example, once per day or twice, or more times, per day. Administration of the compound continues for as long as necessary to treat the viral infection. For example, a compound can be administered to a human being infected with a virus for a period of from 20 days to 180 days or, for example, for a period of from 20 days to 90 days or, for example, for a period of from 30 days to 60 days.

Administration can be intermittent, with a period of several or more days during which a patient receives a daily dose of the compound of the present disclosure followed by a period of several or more days during which a patient does not receive a daily dose of the compound. For example, a patient can receive a dose of the compound every other day, or three times per week. Again by way of example, a patient can receive a dose of the compound each day for a period of from 1 to 14 days, followed by a period of 7 to 21 days during which the patient does not receive a dose of the compound, followed by a subsequent period (e.g., from 1 to 14 days) during which the patient again receives a daily dose of the compound. Alternating periods of administration of the compound, followed by non-administration of the compound, can be repeated as clinically required to treat the patient.

In one embodiment, pharmaceutical compositions comprising a compound of the present disclosure, or a pharmaceutically acceptable salt thereof, in combination with one or more (e.g., one, two, three, four, one or two, one to three, or one to four) additional therapeutic agents, and a pharmaceutically acceptable excipient are provided.

In one embodiment, kits comprising a compound of the present disclosure, or a pharmaceutically acceptable salt thereof, in combination with one or more (e.g., one, two, three, four, one or two, one to three, or one to four) additional therapeutic agents are provided.

In some embodiments, a compound of the present disclosure, or a pharmaceutically acceptable salt thereof, is combined with one, two, three, four or more additional therapeutic agents. In some embodiments, a compound of the present disclosure, or a pharmaceutically acceptable salt thereof, is combined with two additional therapeutic agents. In other embodiments, a compound of the present disclosure, or a pharmaceutically acceptable salt thereof, is combined with three additional therapeutic agents. In further embodiments, a compound of the present disclosure, or a pharmaceutically acceptable salt thereof, is combined with four additional therapeutic agents. The one, two, three, four or more additional therapeutic agents can be different therapeutic agents selected from the same class of therapeutic agents, and/or they can be selected from different classes of therapeutic agents.

In some embodiments, when a compound of the present disclosure is combined with one or more additional therapeutic agents as described herein, the components of the composition are administered as a simultaneous or sequential regimen. When administered sequentially, the combination may be administered in two or more administrations.

In some embodiments, a compound of the present disclosure is combined with one or more additional therapeutic agents in a unitary dosage form for simultaneous administration to a patient, for example as a solid dosage form for oral administration.

In some embodiments, a compound of the present disclosure is co-administered with one or more additional therapeutic agents.

In order to prolong the effect of a compound of the present disclosure, it is often desirable to slow the absorption of a compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending a compound in an oil vehicle. Injectable depot forms are made by forming microencapsule matrices of a compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping a compound in liposomes or microemulsions that are compatible with body tissues.

VI. Combination Therapy

The compounds of Formula (I), (Ia), (Ib), (Ic), (Id), (Ie), (If), (Ig), (Ih), (Ij), (Ik), (Im) or (In) and compositions provided herein are also used in combination with other active therapeutic agents for the treatment of virus infections, such as Pneumoviridae, Picornaviridae, Flaviviridae, or Filoviridae virus infections.

Combination Therapy for the treatment of Pneumoviridae

The compounds and compositions provided herein are also used in combination with other active therapeutic agents. For the treatment of Pneumoviridae virus infections, preferably, the other active therapeutic agent is active against Pneumoviridae virus infections, particularly respiratory syncytial virus infections and/or metapneumovirus infections. Non-limiting examples of these other active therapeutic agents active against RSV are ribavirin, palivizumab, motavizumab, RSV-IGIV (RespiGam®), MEDI-557, A-60444 (also known as RSV604), MDT-637, BMS-433771, ALN-RSV0, ALX-0171 and mixtures thereof. Other non-limiting examples of other active therapeutic agents active against respiratory syncytial virus infections include respiratory syncytial virus protein F inhibitors, such as AK-0529; RV-521, ALX-0171, JNJ-53718678, BTA-585, and presatovir; RNA polymerase inhibitors, such as lumicitabine and ALS-8112; anti-RSV G protein antibodies, such as anti-G-protein mAb; viral replication inhibitors, such as nitazoxanide.

In some embodiments, the other active therapeutic agent may be a vaccine for the treatment or prevention of RSV, including but not limited to MVA-BN RSV, RSV-F, MEDI-8897, JNJ-64400141, DPX-RSV, SynGEM, GSK-3389245A, GSK-300389-1A, RSV-MEDI deltaM2-2 vaccine, VRC-RSVRGP084-00VP, Ad35-RSV-FA2, Ad26-RSV-FA2, and RSV fusion glycoprotein subunit vaccine.

Non-limiting examples of other active therapeutic agents active against metapneumovirus infections include sialidase modulators such as DAS-181; RNA polymerase inhibitors, such as ALS-8112; and antibodies for the treatment of Metapneumovirus infections, such as EV-046113.

In some embodiments, the other active therapeutic agent may be a vaccine for the treatment or prevention of metapneumovirus infections, including but not limited to mRNA-1653 and rHMPV-Pa vaccine.

Combination Therapy for the treatment of Picornaviridae

The compounds and compositions provided herein are also used in combination with other active therapeutic agents. For the treatment of Picornaviridae virus infections, preferably, the other active therapeutic agent is active against Picornaviridae virus infections, particularly Enterovirus infections. Non-limiting examples of these other active therapeutic agents are capsid binding inhibitors such as pleconaril, BTA-798 (vapendavir) and other compounds disclosed by Wu, et al. (U.S. Pat. No. 7,078,403) and Watson (U.S. Pat. No. 7,166,604); fusion sialidase protein such as DAS-181; a capsid protein VP1 inhibitor such as VVX-003 and AZN-001; a viral protease inhibitor such as CW-33; a phosphatidylinositol 4 kinase beta inhibitor such as GSK-480 and GSK-533; anti-EV71 antibody;

In some embodiments, the other active therapeutic agent may be a vaccine for the treatment or prevention of Picornaviridae virus infections, including but not limited to EV71 vaccines, TAK-021, and EV-D68 adenovector-based vaccine.

Combination Therapy for Respiratory Infections

Many of the infections of the Pneumoviridae and Picornaviridae viruses are respiratory infections. Therefore, additional active therapeutics used to treat respiratory symptoms and sequelae of infection may be used in combination with the compounds provided herein. The additional agents are preferably administered orally or by direct inhalation. For example, other preferred additional therapeutic agents in combination with the compounds provided herein for the treatment of viral respiratory infections include, but are not limited to, bronchodilators and corticosteroids.

Glucocorticoids

Glucocorticoids, which were first introduced as an asthma therapy in 1950 (Carryer, Journal of Allergy, 21, 282-287, 1950), remain the most potent and consistently effective therapy for this disease, although their mechanism of action is not yet fully understood (Morris, J. Allergy Clin. Immunol., 75 (1 Pt) 1-13, 1985). Unfortunately, oral glucocorticoid therapies are associated with profound undesirable side effects such as truncal obesity, hypertension, glaucoma, glucose intolerance, acceleration of cataract formation, bone mineral loss, and psychological effects, all of which limit their use as long-term therapeutic agents (Goodman and Gilman, 10th edition, 2001). A solution to systemic side effects is to deliver steroid drugs directly to the site of inflammation. Inhaled corticosteroids (ICS) have been developed to mitigate the severe adverse effects of oral steroids. Non-limiting examples of corticosteroids that may be used in combinations with the compounds provided herein are dexamethasone, dexamethasone sodium phosphate, fluorometholone, fluorometholone acetate, loteprednol, loteprednol etabonate, hydrocortisone, prednisolone, fludrocortisones, triamcinolone, triamcinolone acetonide, betamethasone, beclomethasone diproprionate, methylprednisolone, fluocinolone, fluocinolone acetonide, flunisolide, fluocortin-21-butylate, flumethasone, flumetasone pivalate, budesonide, halobetasol propionate, mometasone furoate, fluticasone, AZD-7594, ciclesonide; or a pharmaceutically acceptable salts thereof.

Anti-Inflammatory Agents

Other anti-inflammatory agents working through anti-inflammatory cascade mechanisms are also useful as additional therapeutic agents in combination with the compounds provided herein for the treatment of viral respiratory infections. Applying "anti-inflammatory signal transduction modulators" (referred to in this text as AISTM), like phosphodiesterase inhibitors (e.g. PDE-4, PDE-5, or PDE-7 specific), transcription factor inhibitors (e.g. blocking NFκB through IKK inhibition), or kinase inhibitors (e.g. blocking P38 MAP, INK, PI3K, EGFR or Syk) is a logical approach to switching off inflammation as these small molecules target a limited number of common intracellular pathways—those signal transduction pathways that are critical points for the anti-inflammatory therapeutic intervention (see review by P. J. Barnes, 2006). These non-limiting additional therapeutic agents include: 5-(2,4-Difluoro-phenoxy)-1-isobutyl-1H-indazole-6-carboxylic acid (2-dimethylamino-ethyl)-amide (P38 Map kinase inhibitor ARRY-797); 3-Cyclopropylmethoxy-N-(3,5-dichloro-pyridin-4-yl)-4-difluorormethoxy-benzamide (PDE-4 inhibitor Roflumilast); 4-[2-(3-cyclopentyloxy-4-methoxyphenyl)-2-phenyl-ethyl]-pyridine (PDE-4 inhibitor CDP-840); N-(3,5-dichloro-4-pyridinyl)-4-(difluoromethoxy)-8-[(methylsulfonyl)amino]-1-dibenzofurancarboxamide (PDE-4 inhibitor Oglemilast); N-(3,5-Dichloro-pyridin-4-yl)-2-[1-(4-fluorobenzyl)-5-hydroxy-1H-indol-3-yl]-2-oxo-acetamide (PDE-4 inhibitor AWD 12-281); 8-Methoxy-2-trifluoromethyl-quinoline-5-carboxylic acid (3,5-dichloro-1-oxy-pyridin-4-yl)-amide (PDE-4 inhibitor Sch 351591); 4-[5-(4-Fluorophenyl)-2-(4-methanesulfinyl-phenyl)-1H-imidazol-4-yl]-pyridine (P38 inhibitor SB-203850); 4-[4-(4-Fluoro-phenyl)-1-(3-phenyl-propyl)-5-pyridin-4-yl-1H-imidazol-2-yl]-but-3-yn-1-ol (P38 inhibitor RWJ-67657); 4-Cyano-4-(3-cyclopentyloxy-4-methoxy-phenyl)-cyclohexanecarboxylic acid 2-diethylamino-ethyl ester (2-diethyl-ethyl ester prodrug of Cilomilast, PDE-4 inhibitor); (3-Chloro-4-fluorophenyl)-[7-methoxy-6-(3-morpholin-4-yl-propoxy)-quinazolin-4-yl]-amine (Gefitinib, EGFR inhibitor); and 4-(4-Methyl-piperazin-1-ylmethyl)-N-[4-methyl-3-(4-pyridin-3-yl-pyrimidin-2-ylamino)-phenyl]-benzamide (Imatinib, EGFR inhibitor).

β2-Adrenoreceptor Agonist Bronchodilators

Combinations comprising inhaled β2-adrenoreceptor agonist bronchodilators such as formoterol, albuterol or salmeterol with the compounds provided herein are also suitable, but non-limiting, combinations useful for the treatment of respiratory viral infections.

Combinations of inhaled β2-adrenoreceptor agonist bronchodilators such as formoterol or salmeterol with ICS's are also used to treat both the bronchoconstriction and the inflammation (Symbicort® and Advair®, respectively). The combinations comprising these ICS and β2-adrenoreceptor agonist combinations along with the compounds provided herein are also suitable, but non-limiting, combinations useful for the treatment of respiratory viral infections.

Other examples of Beta 2 adrenoceptor agonists are bedoradrine, vilanterol, indacaterol, olodaterol, tulobuterol, formoterol, abediterol, salbutamol, arformoterol, levalbuterol, fenoterol, and TD-5471.

Anticholinergics

For the treatment or prophylaxis of pulmonary bronchoconstriction, anticholinergics are of potential use and, therefore, useful as an additional therapeutic agent in combination with the compounds provided herein for the treatment of viral respiratory infections. These anticholinergics include, but are not limited to, antagonists of the muscarinic receptor (particularly of the M3 subtype) which have shown therapeutic efficacy in man for the control of cholinergic tone in COPD (Witek, 1999); 1-{4-Hydroxy-1-[3,3,3-tris-(4-fluoro-phenyl)-propionyl]-pyrrolidine-2-carbonyl}-pyrrolidine-2-carboxylic acid (1-methyl-piperidin-4-ylmethyl)-amide; 3-[3-(2-Diethylamino-acetoxy)-2-phenyl-propionyloxy]-8-isopropyl-8-methyl-8-azonia-bicyclo [3.2.1]octane (Ipratropium-N,N-diethylglycinate); 1-Cyclohexyl-3,4-dihydro-1H-isoquinoline-2-carboxylic acid 1-aza-bicyclo[2.2.2]oct-3-yl ester (Solifenacin); 2-Hydroxymethyl-4-methanesulfinyl-2-phenyl-butyric acid 1-aza-bicyclo[2.2.2]oct-3-yl ester (Revatropate); 2-{1-[2-(2,3-Dihydro-benzofuran-5-yl)-ethyl]-pyrrolidin-3-yl}-2,2-diphenyl-acetamide (Darifenacin); 4-Azepan-1-yl-2,2-diphenyl-butyramide (Buzepide); 7-[3-(2-Diethylamino-acetoxy)-2-phenyl-propionyloxy]-9-ethyl-9-methyl-3-oxa-9-azonia-tricyclo[3.3.1.02,4]nonane (Oxitropium-N,N-diethylglycinate); 7-[2-(2-Diethylamino-acetoxy)-2,2-di-thiophen-2-yl-acetoxy]-9,9-dimethyl-3-oxa-9-azonia-tricyclo[3.3.1.02,4]nonane (Tiotropium-N,N-diethylglycinate); Dimethylamino-acetic acid 2-(3-diisopropylamino-1-phenyl-propyl)-4-methyl-phenyl ester (Tolterodine-N,N-dimethylglycinate); 3-[4,4-Bis-(4-fluoro-phenyl)-2-oxo-imidazolidin-1-yl]-1-methyl-1-(2-oxo-2-pyridin-2-yl-ethyl)-pyrrolidinium; 1-[1-(3-Fluoro-benzyl)-piperidin-4-yl]-4,4-bis-(4-fluoro-phenyl)-imidazolidin-2-one; 1-Cyclooctyl-3-(3-methoxy-1-aza-bicyclo[2.2.2]oct-3-yl)-1-phenyl-prop-2-yn-1-ol; 3-[2-(2-Diethylamino-acetoxy)-2,2-di-thiophen-2-yl-acetoxy]-1-(3-phenoxy-propyl)-1-azonia-bicyclo[2.2.2]octane (Aclidinium-N,N-diethylglycinate); or (2-Diethylamino-acetoxy)-di-thiophen-2-yl-acetic acid 1-methyl-1-(2-phenoxy-ethyl)-piperidin-4-yl ester; revefenacin, glycopyrronium bromide, umeclidinium bromide, tiotropium bromide, aclidinium bromide, bencycloquidium bromide.

Mucolytic Agents

The compounds provided herein and the compositions provided herein may also be combined with mucolytic agents to treat both the infection and symptoms of respiratory infections. A non-limiting example of a mucolytic agent is ambroxol. Similarly, the compounds of Formula (I), (Ia), (Ib), (Ic), (Id), (Ie), (If), (Ig), (Ih), (Ij), (Ik), (Im) or (In) may be combined with expectorants to treat both the infection and symptoms of respiratory infections. A non-limiting example of an expectorant is guaifenesin.

Nebulized hypertonic saline is used to improve immediate and long-term clearance of small airways in patients with lung diseases (Kuzik, *J. Pediatrics* 2007, 266). Thus, the compounds provided herein may also be combined with nebulized hypertonic saline particularly when the Pneumoviridae virus infection is complicated with bronchiolitis. The combination of the compounds of Formula (I) or Formula (II) with hypertonic saline may also comprise any of the additional agents discussed above. In one embodiment, nebulized about 3% hypertonic saline is used.

Combination Therapy for the Treatment of COPD

The compounds and compositions provided herein are also used in combination with other active therapeutic agents. For the treatment of respiratory exacerbations of COPD, the other active therapeutic agents include other active against COPD. Non-limiting examples of these other active therapeutic agents include anti-IL5 antibodies, such as benralizumab, mepolizumab; dipeptidyl peptidase I (DPP1) inhibitors, such as AZD-7986 (INS-1007); DNA gyrase inhibitor/topoisomerase IV inhibitors, such as ciprofloxacin hydrochloride; MDR associated protein 4/phosphodiesterase (PDE) 3 and 4 inhibitors, such as RPL-554; CFTR stimulators, such as ivacaftor, QBW-251; MMP-9/MMP-12 inhibitors, such as RBx-10017609; Adenosine A1 receptor antagonists, such as PBF-680; GATA 3 transcription factor inhibitors, such as SB-010; muscarinic receptor modulator/nicotinic acetylcholine receptor agonists, such as ASM-024; MARCKS protein inhibitors, such as BIO-11006; kit tyrosine kinase/PDGF inhibitors such as masitinib; phosphodiesterase (PDE) 4 inhibitors, such as roflumilast, CHF-6001; phosphoinositide-3 kinase delta inhibitors, such as nemiralisib; 5-Lipoxygenase inhibitors, such as TA-270; muscarinic receptor antagonist/beta 2 adrenoceptor agonist, such as batefenterol succinate, AZD-887, ipratropium bromide; TRN-157; elastase inhibitors, such as erdosteine; metalloprotease-12 inhibitors such as FP-025; interleukin 18 ligand inhibitors, such as tadekinig alfa; skeletal muscle troponin activators, such as CK-2127107; p38 MAP kinase inhibitors, such as acumapimod; IL-17 receptor modulators, such as CNTO-6785; CXCR2 chemokine antagonists, such as danirixin; leukocyte elastase inhibitors, such as POL-6014; epoxide hydrolase inhibitors, such as GSK-2256294; HNE inhibitors, such as CHF-6333; VIP agonists, such as aviptadil; phosphoinositide-3 kinase delta/gamma inhibitors, such as RV-1729; complement C3 inhibitors, such as APL-1; and G-protein coupled receptor-44 antagonists, such as AM-211.

Other non-limiting examples of active therapeutic agents also include budesonide, adipocell, nitric oxide, PUR-1800, YLP-001, LT-4001, azithromycin, gamunex, QBKPN, sodium pyruvate, MUL-1867, mannitol, MV-130, MEDI-3506, BI-443651, VR-096, OPK-0018, TEV-48107, doxofylline, TEV-46017, OligoG-COPD-5/20, Stempeucel®, ZP-051, lysine acetylsalicylate.

In some embodiments, the other active therapeutic agent may be a vaccine that is active against COPD, including but not limited to MV-130 and GSK-2838497A.

Combination Therapy for the Treatment of Dengue

The compounds and compositions provided herein are also used in combination with other active therapeutic agents. For the treatment of Flaviviridae virus infections, preferably, the other active therapeutic agent is active against Flaviviridae virus infections, particularly dengue infections. Non-limiting examples of these other active therapeutic agents are host cell factor modulators, such as GBV-006; fenretinide ABX-220, BRM-211; alpha-glucosidase 1 inhibitors, such as celgosivir; platelet activating factor receptor (PAFR) antagonists, such as modipafant; cadherin-5/Factor Ia modulators, such as FX-06; NS4B inhibitors, such as JNJ-8359; viral RNA splicing modulators, such as ABX-202; a NS5 polymerase inhibitor; a NS3 protease inhibitor; and a TLR modulator.

In some embodiments, the other active therapeutic agent may be a vaccine for the treatment or prevention of dengue, including but not limited to TetraVax-DV, Dengvaxia®, DPIV-001, TAK-003, live attenuated dengue vaccine, tetravalent dengue fever vaccine, tetravalent DNA vaccine, rDEN2delta30-7169; and DENV-1 PIV.

Combination Therapy for the Treatment of Ebola

The compounds and compositions provided herein are also used in combination with other active therapeutic agents. For the treatment of Filoviridae virus infections, preferably, the other active therapeutic agent is active against Filoviridae virus infections, particularly Marburg virus, Ebola virus and Cueva virus infections. Non-limiting examples of these other active therapeutic agents are: ribavirin, palivizumab, motavizumab, RSV-IGIV (RespiGam©), MEDI-557, A-60444, MDT-637, BMS-433771, amiodarone, dronedarone, verapamil, Ebola Convalescent Plasma (ECP), TKM-100201, BCX4430 ((2S,3S,4R,5R)-2-(4-amino-5H-pyrrolo[3,2-d]pyrimidin-7-yl)-5-(hydroxymethyl)pyrrolidine-3,4-diol), TKM-Ebola, T-705 monophosphate, T-705 diphosphate, T-705 triphosphate, FGI-106 (1-N,7-N-bis[3-(dimethylamino)propyl]-3,9-dimethylquinolino[8,7-h]quinolone-1,7-diamine), rNAPc2, OS-2966, brincidofovir, remdesivir; RNA polymerase inhibitors, such as galidesivir, favipiravir (also known as T-705 or Avigan), JK-05; host cell factor modulators, such as GMV-006; cadherin-5/factor Ia modulators, such as FX-06; and antibodies for the treatment of Ebola, such as REGN-3470-3471-3479 and ZMapp.

Other non-limiting active therapeutic agents active against Ebola include an alpha-glucosidase 1 inhibitor, a cathepsin B inhibitor, a CD29 antagonist, a dendritic ICAM-3 grabbing nonintegrin 1 inhibitor, an estrogen receptor antagonist, a factor VII antagonist HLA class II antigen modulator, a host cell factor modulator, a Interferon alpha ligand, a neutral alpha glucosidase AB inhibitor, a niemann-Pick C1 protein inhibitor, a nucleoprotein inhibitor, a polymerase cofactor VP35 inhibitor, a Serine protease inhibitor, a tissue factor inhibitor, a TLR-3 agonist, a viral envelope glycoprotein inhibitor, and an Ebola virus entry inhibitors (NPC1 inhibitors).

In some embodiments, the other active therapeutic agent may be a vaccine for the treatment or prevention of Ebola, including but not limited to VRC-EBOADC076-00-VP, adenovirus-based Ebola vaccine, rVSV-EBOV, rVSVN4CT1-EBOVGP, MVA-BN Filo+Ad26-ZEBOV regimen, INO-4212, VRC-EBODNA023-00-VP, VRC-EBOADC069-00-VP, GamEvac-combi vaccine, SRC VB Vector, HPIV3/EboGP vaccine, MVA-EBOZ, Ebola recombinant glycoprotein vaccine, Vaxart adenovirus vector 5-based Ebola vaccine, FiloVax vaccine, GOVX-E301, and GOVX-E302.

The compounds and compositions provided herein may also be used in combination with phosphoramidate morpholino oligomers (PMOs), which are synthetic antisense oligonucleotide analogs designed to interfere with translational processes by forming base-pair duplexes with specific RNA sequences. Examples of PMOs include but are not limited to AVI-7287, AVI-7288, AVI-7537, AVI-7539, AVI-6002, and AVI-6003.

The compounds and compositions provided herein are also intended for use with general care provided to patients with Filoviridae viral infections, including parenteral fluids (including dextrose saline and Ringer's lactate) and nutrition, antibiotic (including metronidazole and cephalosporin antibiotics, such as ceftriaxone and cefuroxime) and/or antifungal prophylaxis, fever and pain medication, antiemetic (such as metoclopramide) and/or antidiarrheal agents, vitamin and mineral supplements (including Vitamin K and zinc sulfate), anti-inflammatory agents (such as ibuprofen), pain medications, and medications for other common diseases in the patient population, such anti-malarial agents (including artemether and artesunate-lumefantrine combination therapy), typhoid (including quinolone antibiotics, such as ciprofloxacin, macrolide antibiotics, such as azithromycin, cephalosporin antibiotics, such as ceftriaxone, or aminopenicillins, such as ampicillin), or shigellosis.

VII. Methods of Treating Viral Infections

The present disclosure provides methods for treating a variety of diseases, such as respiratory syncytial virus (RSV), ebola, Zika, West Nile, Dengue, HCV and HBV using compounds of the present disclosure. The present disclosure provides methods for treating a variety of diseases, such as respiratory syncytial virus (RSV), ebola, Zika, West Nile, Dengue, HCV and HBV using compounds of Formula (I), (Ia), (Ib), (Ic), (Id), (Je), (If), (Ig), (Ih), (Ij), (Ik), (Im) or (In).

Paramyxoviridae

In some embodiments, the present disclosure provides methods for treating a Paramyxoviridae infection, comprising administering to an individual (e.g. a human) infected with Paramyxoviridae virus a therapeutically effective amount a compound of the present disclosure or a pharmaceutically acceptable salt thereof. Paramyxoviridae viruses include, but are not limited to, Nipah virus and parainfluenze virus.

Pneumoviridae

In some embodiments, the present disclosure provides a method of treating a Pneumoviridae virus infection in a human in need thereof, the method comprising administering to the human a therapeutically effective amount of a compound of the present disclosure, or a pharmaceutically acceptable salt thereof. Pneumoviridae viruses include, but are not limited to, respiratory snycytial virus, and human metapneumovirus. In some embodiments, the Pneumoviridae virus infection is a respiratory syncytial virus infection. In some embodiments, the Pneumoviridae virus infection is human metapneumovirus infection.

In some embodiments, the present disclosure provides a method for manufacturing a medicament for treating a Pneumoviridae virus infection in a human in need thereof, characterized in that the compound of the present disclosure, or a pharmaceutically acceptable salt thereof, is used. In some embodiments, the present disclosure provides use of a compound of the present disclosure, or a pharmaceutically acceptable salt thereof, for the manufacture of a medicament for the treatment in a human of a Pneumoviridae virus infection. In some embodiments, the Pneumoviridae virus infection is a respiratory syncytial virus infection. In some embodiments, the Pneumoviridae virus infection is human metapneumovirus infection.

In some embodiments, the present disclosure provides a compound of the present disclosure, or a pharmaceutically acceptable salt thereof, for use in the treatment of a Pneumoviridae virus infection in a human in need thereof. In some embodiments, the Pneumoviridae virus infection is a respiratory syncytial virus infection. In some embodiments, the Pneumoviridae virus infection is human metapneumovirus infection.

In some embodiments, the present disclosure provides methods for treating a RSV infection, comprising administering to an individual (e.g. a human) infected with respiratory syncytial virus a therapeutically effective amount a compound of the present disclosure or a pharmaceutically acceptable salt thereof. Typically, the individual is suffering from a chronic respiratory syncytial viral infection, although it is within the scope of the present disclosure to treat people who are acutely infected with RSV.

In some embodiments, a method of inhibiting RSV replication is provided, comprising administering a compound of the present disclosure, or a pharmaceutically acceptable salt thereof, to an individual (e.g. a human).

In some embodiments, the present disclosure provides a method for reducing the viral load associated with RSV infection, wherein the method comprises administering to an individual (e.g. a human) infected with RSV a therapeutically effective amount of a compound of the present disclosure, or a pharmaceutically acceptable salt thereof, wherein the therapeutically effective amount is sufficient to reduce the RSV viral load in the individual.

As described more fully herein, compounds of the present disclosure can be administered with one or more additional therapeutic agent(s) to an individual (e.g. a human) infected with RSV. The additional therapeutic agent(s) can be administered to the infected individual (e.g. a human) at the same time as a compound of the present disclosure or before or after administration of a compound of the present disclosure.

In some embodiments, a compound of the present disclosure, or a pharmaceutically acceptable salt thereof, for use in treating or preventing a RSV infection is provided. In some embodiments, a compound of the present disclosure (e.g. a compound of Formula (I), (Ia), (Ib), (Ic), (Id), (Je), (If), (Ig), (Ih), (Ij), (Ik), (Im) or (In)), or a pharmaceutically acceptable salt thereof, for the manufacture of a medicament for treating or preventing a RSV infection is provided.

As described more fully herein, compounds of the present disclosure can be administered with one or more additional therapeutic agent(s) to an individual (e.g. a human) infected with RSV. Further, in some embodiments, when used to treat or prevent RSV, a compound of the present disclosure may be administered with one or more (e.g. one, two, three, four or more) additional therapeutic agent(s) selected from the group consisting of RSV combination drugs, RSV vaccines, RSV DNA polymerase inhibitors, immunomodulators toll-like receptor (TLR) modulators, interferon alpha receptor ligands, hyaluronidase inhibitors, respiratory syncytial surface antigen inhibitors, cytotoxic T-lymphocyte-associated protein 4 (ipi4) inhibitors, cyclophilin inhibitors, RSV viral entry inhibitors, antisense oligonucleotide targeting viral mRNA, short interfering RNAs (siRNA) and ddRNAi endonuclease modulators, ribonucelotide reductase inhibitors, RSV E antigen inhibitors, covalently closed circular DNA (cccDNA) inhibitors, farnesoid X receptor agonists, RSV antibodies, CCR2 chemokine antagonists, thymosin agonists, cytokines, nucleoprotein modulators, retinoic acidinducible gene 1 stimulators, NOD2 stimulators, phosphatidylinositol 3-kinase (PI3K) inhibitors, indoleamine-2,3-dioxygenase (IDO) pathway inhibitors, PD-1 inhibitors, PD-L1 inhibitors, recombinant thymosin alpha-1, bruton's tyrosine kinase (BTK) inhibitors, KDM inhibitors, RSV replication inhibitors, arginase inhibitors, and other RSV drugs.

Picornaviridae

In some embodiments, the present disclosure provides a method of treating a Picornaviridae virus infection in a human in need thereof, the method comprising administering to the human a therapeutically effective amount of a compound of the present disclosure, or a pharmaceutically acceptable salt thereof. Picornaviridae viruses are eneteroviruses causing a heterogeneous group of infections including herpangina, aseptic meningitis, a common-cold-like syndrome (human rhinovirus infection), a non-paralytic poliomyelitis-like syndrome, epidemic pleurodynia (an acute, febrile, infectious disease generally occurring in epidemics), hand-foot-mouth syndrome, pediatric and adult pancreatitis and serious myocarditis. In some embodiments, the Picornaviridae virus infection is human rhinovirus infection.

In some embodiments, the present disclosure provides a method for manufacturing a medicament for treating a Picornaviridae virus infection in a human in need thereof, characterized in that the compound of the present disclosure, or a pharmaceutically acceptable salt thereof, is used. In some embodiments, the present disclosure provides use of a compound of the present disclosure, or a pharmaceutically acceptable salt thereof, for the manufacture of a medicament for the treatment in a human of a Picornaviridae virus infection. In some embodiments, the Picornaviridae virus infection is human rhinovirus infection.

In some embodiments, the present disclosure provides a compound of the present disclosure, or a pharmaceutically acceptable salt thereof, for use in the treatment of a Picornaviridae virus infection in a human in need thereof. In some embodiments, the Picornaviridae virus infection is human rhinovirus infection.

Flaviviridae

In some embodiments, the present disclosure provides a method of treating a Flaviviridae virus infection in a human in need thereof, the method comprising administering to the human a therapeutically effective amount of a compound of the present disclosure, or a pharmaceutically acceptable salt thereof. Representative Flaviviridae viruses include, but are not limited to, dengue, Yellow fever, West Nile, Zika, Japanese encephalitis virus, Hepatitis C (HCV), and Hepatitis B (HBV). In some embodiments, the Flaviviridae virus infection is a dengue virus infection. In some embodiments, the Flaviviridae virus infection is a Yellow fever virus infection. In some embodiments, the Flaviviridae virus infection is a West Nile virus infection. In some embodiments, the Flaviviridae virus infection is a Zika virus infection. In some embodiments, the Flaviviridae virus infection is a Japanese ensephalitis virus infection. In some embodiments, the Flaviviridae virus infection is a Hepatitis C virus infection. In some embodiments, the Flaviviridae virus infection is a Hepatitis B virus infection.

In some embodiments, the present disclosure provides a method for manufacturing a medicament for treating a Flaviviridae virus infection in a human in need thereof, characterized in that the compound of the present disclosure, or a pharmaceutically acceptable salt thereof, is used. In some embodiments, the present disclosure provides use of a compound of the present disclosure, or a pharmaceutically acceptable salt thereof, for the manufacture of a medicament for the treatment in a human of a Flaviviridae virus infection. In some embodiments, the Flaviviridae virus infection is a dengue virus infection. In some embodiments, the Flaviviridae virus infection is a Yellow fever virus infection. In some embodiments, the Flaviviridae virus infection is a West Nile virus infection. In some embodiments, the Flaviviridae virus infection is a Zika virus infection. In some embodiments, the Flaviviridae virus infection is a Hepatitis C virus infection. In some embodiments, the Flaviviridae virus infection is a Hepatitis B virus infection.

In some embodiments, the present disclosure provides a compound of the present disclosure, or a pharmaceutically acceptable salt thereof, for use in the treatment of a Flaviviridae virus infection in a human in need thereof. In some embodiments, the Flaviviridae virus infection is a dengue virus infection. In some embodiments, the Flaviviridae virus infection is a Yellow fever virus infection. In some embodiments, the Flaviviridae virus infection is a West Nile virus infection. In some embodiments, the Flaviviridae virus infection is a Zika virus infection. In some embodiments, the Flaviviridae virus infection is a Hepatitis C virus infection. In some embodiments, the Flaviviridae virus infection is a Hepatitis B virus infection.

Filoviridae

In some embodiments, the present disclosure provides a method of treating a Filoviridae virus infection in a human in need thereof, the method comprising administering to the human a therapeutically effective amount of a compound of the present disclosure, or a pharmaceutically acceptable salt thereof. Representative Filoviridae viruses include, but are not limited to, ebola and Marburg. In some embodiments, the Filoviridae virus infection is an ebola virus infection.

In some embodiments, the present disclosure provides a method for manufacturing a medicament for treating a Filoviridae virus infection in a human in need thereof, characterized in that the compound of the present disclosure, or a pharmaceutically acceptable salt thereof, is used. In some embodiments, the present disclosure provides use of a compound of the present disclosure, or a pharmaceutically acceptable salt thereof, for the manufacture of a medicament for the treatment in a human of a Filoviridae virus infection. In some embodiments, the Filoviridae virus infection is an ebola virus infection.

In some embodiments, the present disclosure provides a compound of the present disclosure, or a pharmaceutically acceptable salt thereof, for use in the treatment of a Filoviridae virus infection in a human in need thereof. In some embodiments, the Filoviridae virus infection is an ebola virus infection.

VIII. Methods of Treatment or Prophylaxis of an Exacerbation of a Respiratory Condition by a Virus Infection The compounds of the present disclosure can also be used for the treatment or prophylaxis of an exacerbation of a respiratory condition by a viral infection in a human in need thereof. The compounds of Formula (I), (Ia), (Ib), (Ic), (Id), (Ie), (If), (Ig), (Ih), (Ij), (Ik), (Im) or (In) can also be used for the treatment or prophylaxis of an exacerbation of a respiratory condition by a viral infection in a human in need thereof.

In some embodiments, the present disclosure provides a method for the treatment or prophylaxis of an exacerbation of a respiratory condition by a viral infection in a human in need thereof, the method comprising administering to the human a therapeutically effective amount of a compound of the present disclosure, or a pharmaceutically acceptable salt thereof, wherein the respiratory condition is chronic obstructive pulmonary disease. In some embodiments, the viral infection is caused by respiratory syncytial virus, rhinovirus or metapneumovirus.

In some embodiments, the present disclosure provides a method for the treatment or prophylaxis of an exacerbation of a respiratory condition by a viral infection in a human in need thereof, the method comprising administering to the human a therapeutically effective amount of the compound of the present disclosure, or a pharmaceutically acceptable salt thereof, wherein the respiratory condition is asthma. In some embodiments, the viral infection is caused by respiratory syncytial virus, rhinovirus, enteroviruses or metapneumovirus.

In some embodiments, the present disclosure provides a method for manufacturing a medicament for the treatment or prophylaxis of an exacerbation of a respiratory condition by a viral infection in a human in need thereof, characterized in that a compound of the present disclosure, or a pharmaceutically acceptable salt thereof, is used, wherein the respiratory condition is chronic obstructive pulmonary disease. In some embodiments, the viral infection is caused by respiratory syncytial virus, rhinovirus or metapneumovirus.

In some embodiments, the present disclosure provides a method for manufacturing a medicament for the treatment or prophylaxis of an exacerbation of a respiratory condition by a viral infection in a human in need thereof, characterized in that the compound of the present disclosure, or a pharmaceutically acceptable salt thereof, is used, wherein the respiratory condition is asthma. In some embodiments, the viral infection is caused by respiratory syncytial virus, rhinovirus, enteroviruses or metapneumovirus.

In some embodiments, the present disclosure provides use of a compound of the present disclosure, or a pharmaceutically acceptable salt thereof, for the manufacture of a medicament for the treatment or prophylaxis in a human of an exacerbation of a respiratory condition by a viral infection, wherein the respiratory condition is chronic obstructive pulmonary disease. In some embodiments, the viral infection is caused by respiratory syncytial virus, rhinovirus or metapneumovirus.

In some embodiments, the present disclosure provides use of the compound of the present disclosure, or a pharmaceutically acceptable salt thereof, for the manufacture of a medicament for the treatment or prophylaxis in a human of an exacerbation of a respiratory condition by a viral infection, wherein the respiratory condition is asthma. In some embodiments, the viral infection is caused by respiratory syncytial virus, rhinovirus, enteroviruses or metapneumovirus.

In some embodiments, the present disclosure provides the compound of the present disclosure, or a pharmaceutically acceptable salt thereof, for use in the treatment or prophylaxis of a respiratory condition by a viral infection in a human in need thereof, wherein the respiratory condition is chronic obstructive pulmonary disease. In some embodiments, the viral infection is caused by respiratory syncytial virus, rhinovirus or metapneumovirus.

In some embodiments, the present disclosure provides the compound of the present disclosure, or a pharmaceutically acceptable salt thereof, for use in the treatment or prophylaxis of an exacerbation of a respiratory condition by a viral infection in a human in need thereof, wherein the respiratory condition is asthma. In some embodiments, the viral infection is caused by respiratory syncytial virus, rhinovirus, enteroviruses or metapneumovirus.

IX. Examples

Abbreviations. Certain abbreviations and acronyms are used in describing the experimental details. Although most of these would be understood by one skilled in the art, Table 1 contains a list of many of these abbreviations and acronyms.

TABLE 2

List of abbreviations and acronyms.

| Abbreviation | Meaning |
| --- | --- |
| Ac | acetate |
| ACN | acetonitrile |
| AIBN | azobisisobutyronitrile |
| Bn | benzyl |
| Bu | butyl |
| Bz | benzoyl |
| BzCl | benzoyl chloride |
| CDI | 1,1'-carbonyldiimidazole |
| DAST | diethylaminosulfur trifluoride |
| DCE | 1,2-dichloroethane |
| DCM | dichloromethane |
| DMAP | 4-dimethylamiopyridine |
| DMDO | dimethydioxirane |
| DMSO | dimethylsulfoxide |
| DMF | dimethylformamide |
| DMTrCl | 4,4'-dimethoxytritylchloride |
| DMTr | 4,4'-dimethoxytrityl |
| EDCI | N-(3-dimethylaminopropyl)-N'-ethylcarbodiimide hydrochloride |
| Et | ethyl |
| Imid | imidazole |
| KOtBu | potassium tert-butoxide |
| LC | liquid chromatography |
| MCPBA | meta-chloroperbenzoic acid |
| Me | methyl |
| m/z | mass to charge ratio |
| MS or ms | mass spectrum |
| NIS | N-iodosuccinimide |
| NMP | N-methyl-2-pyrrolidone |
| Ph | phenyl |
| $Ph_3P$ | triphenylphosphine |
| PMB | para-methoxybenzyl |
| PMBCl | para-methoxybenzyl chloride |
| PhOC(S)Cl | phenylchlorothionoformate |
| $(PhO)_3PMeI$ | methyltriphenoxyphosphonium iodide |
| Pyr | pyridine |
| RT | room temperature |
| TBAF | tetrabutylammonium flouride |
| TBS | tert-butyldimethylsilyl |
| TBSCl | tert-Butyldimethylsilyl chloride |
| $TMSN_3$ | trimethylsilyl azide |
| TEA | triethylamine |
| TES | triethylsilane |
| TFA | trifluoroacetic acid |
| THF | tetrahydrofuran |
| TMS | trimethylsilyl |
| TMSCl | trimethylsilyl chloride |
| Ts | 4-toluenesulfonyl |
| TsOH | tosylic acid |
| δ | parts per million referenced to residual non-deuterated solvent peak |

Compound structures using a "P*" notation refers to the isolated (R)- or (S)-isomer where the specific stereochemistry at that position is unassigned.

A. Intermediates

Intermediate 1. ((3aS,4S,6S,6aS)-6-(4-((tert-butoxy-carbonyl)amino)pyrrolo[2,1-f][1,2,4]triazin-7-yl)-2,2-dimethyl-4-((((trifluoromethyl)sulfonyl)oxy)methyl) tetrahydrofuro[3,4-d][1,3]dioxol-4-yl) methyl acetate Intermediate 2. ((3aS,4S,6S,6aS)-6-(4-((tert-butoxy-carbonyl)amino)pyrrolo[2,1-f][1,2,4]triazin-7-yl)-2,2-dimethyl-4-((((trifluoromethyl)sulfonyl)oxy)methyl) tetrahydrofuro[3,4-d][1,3]dioxol-4-yl) methyl acetate

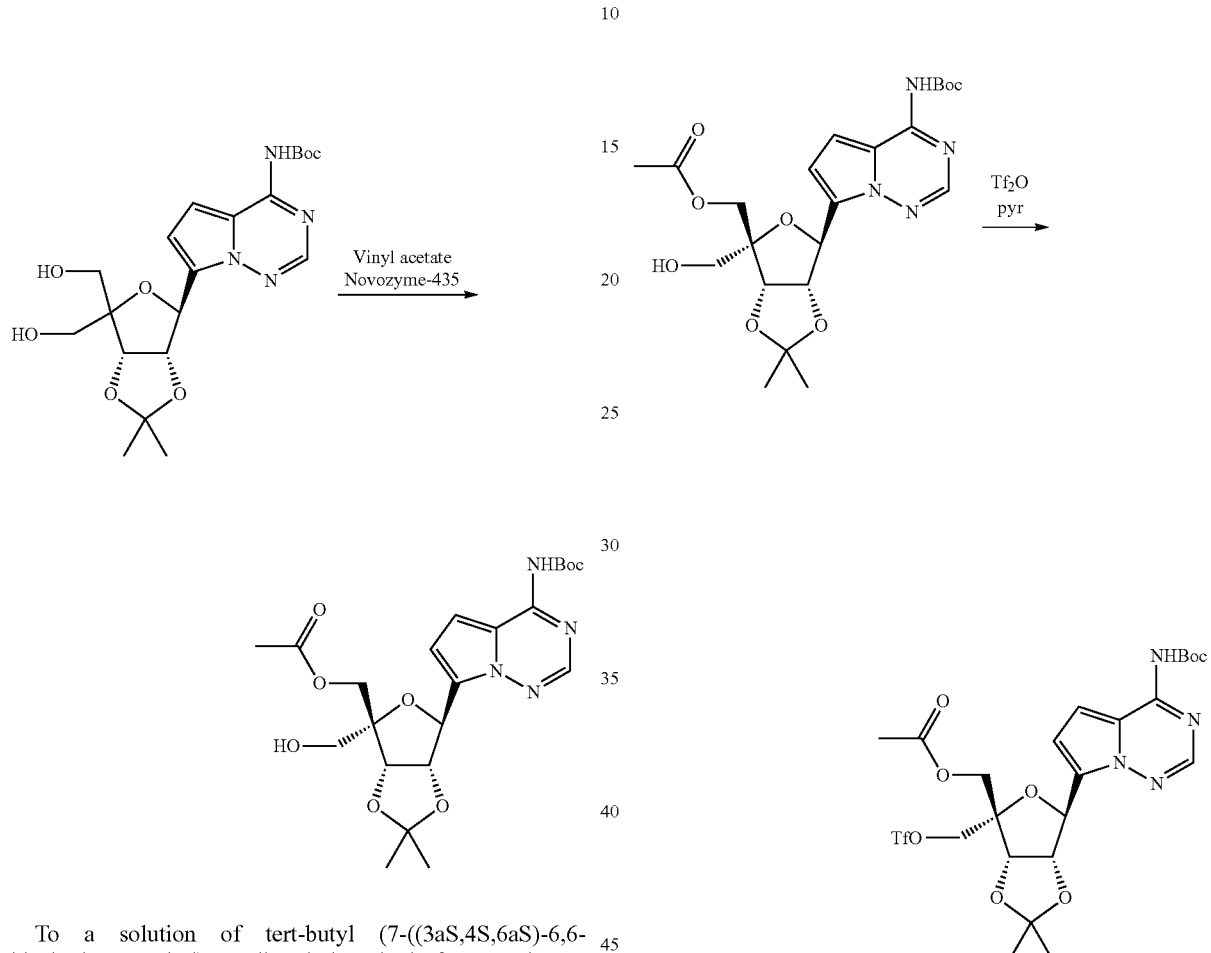

To a solution of tert-butyl (7-((3aS,4S,6aS)-6,6-bis9hydroxymethyl)-2,2-dimethyltetrahydrofuro[3,4-d][1,3]dioxol-4-yl)pyrrolo[2,1-f][1,2,4]triazin-4-yl)carbamate (WO2015069939; 100 mg, 0.229 mmol) and Novozyme-435 (50 mg, 50% w/w) in an anhydrous tetrahydrofuran (1 mL) was added vinyl acetate(0.03 mL, 0.321 mmol) and the reaction mixture was stirred at 45° C. for 7 h. The reaction mixture was filtered and enzyme was repeatedly washed with THF. Combined filtrate was concentrated and residue obtained was purified by silica gel chromatography 30-100% ethyl acetate/hexane to afford the compound. $^1$H NMR (400 MHz, DMSO-$d_6$) δ 10.46 (s, 1H), 8.21 (s, 1H), 7.21 (s, 1H), 6.88 (d, J=4.6 Hz, 1H), 5.39 (d, J=4.9 Hz, 1H), 5.17 (dd, J=6.1, 4.9 Hz, 1H), 4.78 (d, J=6.1 Hz, 1H), 4.03 (q, J=11.2 Hz, 2H), 3.63 (s, 2H), 1.96 (s, 3H), 1.50 (d, J=3.0 Hz, 12H), 1.29 (s, 3H). LCMS: MS m/z=478.92 [M+1]; $t_R$=0.96 min; LC system: Thermo Accela 1250 UHPLC; MS system: Thermo LCQ Fleet; Column: Phenomenex Kinetex 2.6 μXB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min.

To a solution of trifluoromethanesuflonic anhydride in dichloromethane (1 M, 1.46 mL, 1.46 mmol) was added to a solution of Intermediate 1 (350 mg, 0.731 mmol) and pyridine (0.300 mL, 3.66 mmol) in dichloromethane (3.67 mL) at 0° C. After 20 min, the reaction mixture was diluted with water (5 mL) and the resulting mixture was extracted with dichloromethane (2×5 mL). The combined organic extracts were dried over anhydrous sodium sulfate and concentrated under reduced pressure. The resulting crude compound was used directly in the next step. LCMS: MS m/z=610.79 [M+1], $t_R$=1.51 min; LC system: Thermo Accela 1250 UHPLC; MS system: Thermo LCQ Fleet; Column: Kinetex 2.6 μXB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min.

Intermediate 3. ((3aS,4R,6S,6aS)-6-(4-((tert-butoxycarbonyl)amino)pyrrolo[2,1-f][1,2,4]triazin-7-yl)-4-(fluoromethyl)-2,2-dimethyltetrahydrofuro[3,4-d][1,3]dioxol-4-yl)methyl acetate Intermediate 4. ((3aS,4R,6S,6aS)-6-(4-aminopyrrolo[2,1-f][1,2,4]triazin-7-yl)-4-(fluoromethyl)-2,2-dimethyltetrahydrofuro[3,4-d][1,3]dioxol-4-yl)methanol

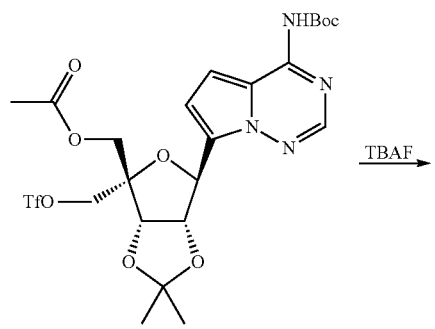

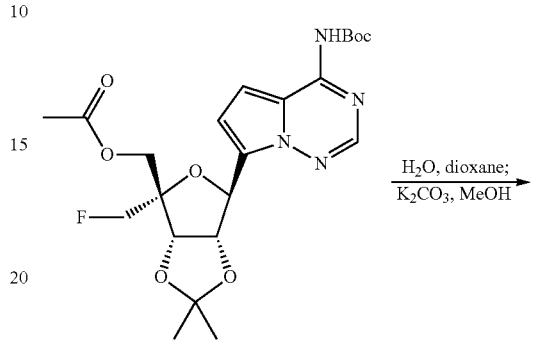

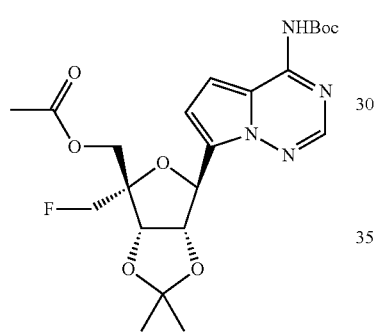

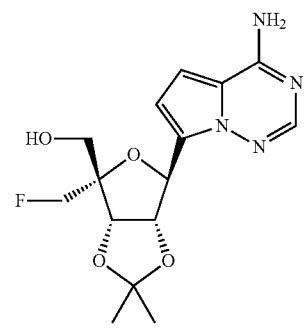

A solution of tetrabutylammonium fluoride in tetrahydrofuran (1 M, 2.87 mL, 2.87 mmol) was added to a solution of crude Intermediate 2 (350 mg, 0.573 mmol) in tetrahydrofuran (3 mL) at rt. After 4 h, the reaction mixture was diluted with ethyl acetate (5 mL) and was washed with water (2×5 mL). The organic extract was dried over anhydrous sodium sulfate and concentrated under reduced pressure. The crude residue was purified by silica gel chromatography eluting with 0-100% ethyl acetate in hexanes to afford the compound. $^1$H NMR (400 MHz, Methanol-$d_4$) δ 8.12 (br s, 1H), 7.18 (d, J=4.7 Hz, 1H), 6.89 (d, J=4.7 Hz, 1H), 5.55 (d, J=4.4 Hz, 1H), 5.29 (dd, J=6.5, 4.5 Hz, 1H), 4.96 (d, J=6.4 Hz, 1H), 4.77-4.68 (m, 1H), 4.65-4.56 (m, 1H), 4.24-4.13 (m, 2H), 2.02 (s, 3H), 1.58 (br s, 12H), 1.37 (s, 3H). LCMS: MS m/z=480.97 [M+1], $t_R$=1.39 min; LC system: Thermo Accela 1250 UHPLC; MS system: Thermo LCQ Fleet; Column: Kinetex 2.6 µXB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 µL/min. HPLC: $t_R$=3.04 min; HPLC system: Agilent 1100 series; Column: Gemini 5 µC18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

A solution of Intermediate 3 (189 mg, 0.393 mmol) in water (0.6 mL) and dioxane (2.4 mL) was heated to 100° C. After 4 h, the resulting mixture was concentrated under reduced pressure. The crude residue was dissolved in methanol (2 mL) and 1 N potassium carbonate solution (1 mL) was added to the mixture at rt. After 1.25 h, the reaction mixture was concentrated under reduced pressure and The crude residue was purified by silica gel chromatography eluting with 0-100% ethyl acetate in hexanes to afford the compound. $^1$H NMR (400 MHz, Methanol-$d_4$) δ 7.79 (s, 1H), 6.86 (d, J=4.5 Hz, 1H), 6.74 (d, J=4.5 Hz, 1H), 5.36 (d, J=5.7 Hz, 1H), 5.24 (t, J=5.9 Hz, 1H), 4.99 (d, J=6.3 Hz, 1H), 4.71 (dd, J=31.9, 10.0 Hz, 1H), 4.59 (dd, J=33.4, 10.0 Hz, 1H), 3.73 (dd, J=11.5, 1.6 Hz, 1H), 3.64 (dd, J=11.5, 2.2 Hz, 1H), 1.58 (s, 3H), 1.35 (s, 3H). LCMS: MS m/z=339.24 [M+1], $t_R$=1.02 min; LC system: Thermo Accela 1250 UHPLC; MS system: Thermo LCQ Fleet; Column: Kinetex 2.6 µXB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 µL/min. HPLC: $t_R$=1.94 min; HPLC system: Agilent 1100 series; Column: Gemini 5 µC18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

Intermediate 5. (2R,3S,4R,5S)-5-(4-aminopyrrolo[2,1-f][1,2,4]triazin-7-yl)-2-(fluoromethyl)-2-(hydroxymethyl)tetrahydrofuran-3,4-diol Intermediate 6. 2-ethylbutyl ((S)-(((3aS,4R,6S,6aS)-6-(4-aminopyrrolo[2,1-f][1,2,4]triazin-7-yl)-2-(fluoromethyl)-2,2-dimethyltetrahydrofuro[3,4-d][1,3]dioxol-4-yl)methoxy)(phenoxy)phosphoryl)-L-alaninate

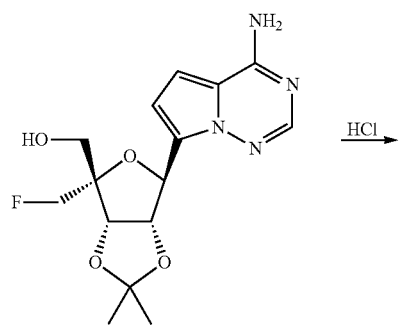

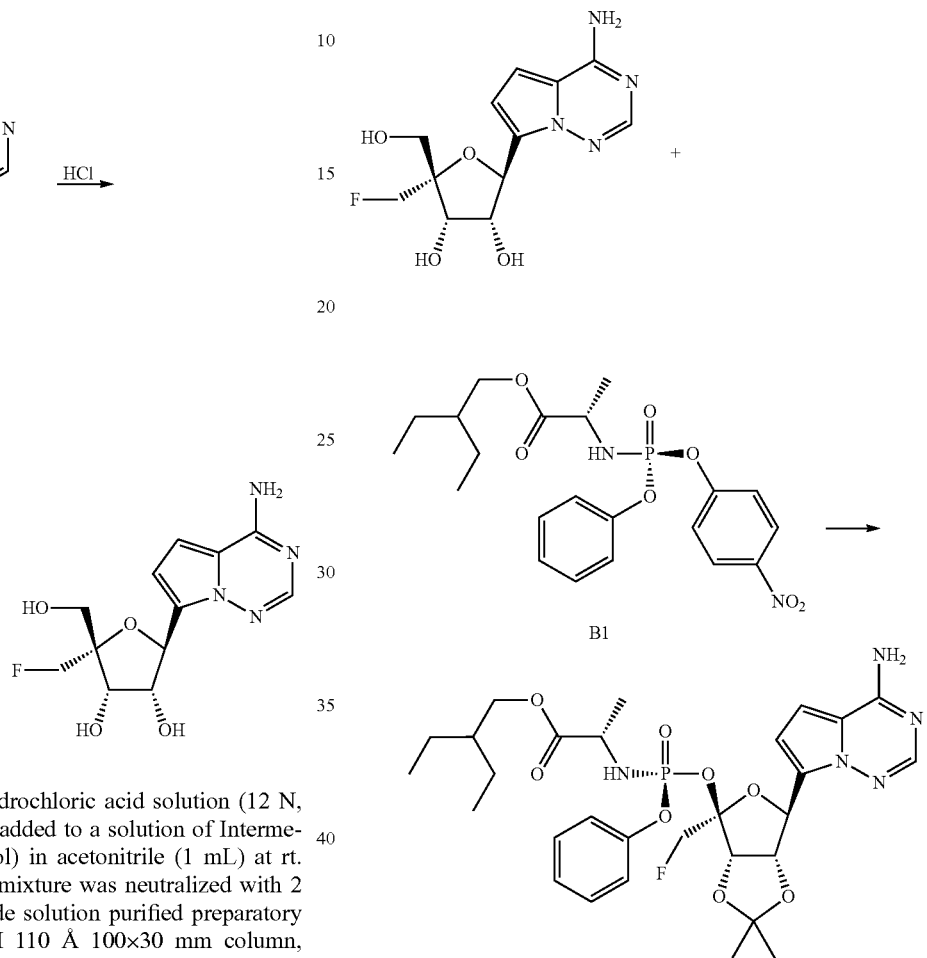

Concentrated aqueous hydrochloric acid solution (12 N, 0.172 mL, 2.07 mmol) was added to a solution of Intermediate 4 (50 mg, 0.148 mmol) in acetonitrile (1 mL) at rt. After 45 min, the resulting mixture was neutralized with 2 N aqueous sodium hydroxide solution purified preparatory HPLC (Gemeni C18 5 uM 110 Å 100×30 mm column, 5-100% acetonitrile/water gradient) to afford the compound. $^1$H NMR (400 MHz, Methanol-$d_4$) δ 7.78 (s, 1H), 6.87 (d, J=4.5 Hz, 1H), 6.75 (d, J=4.5 Hz, 1H), 5.21 (d, J=8.9 Hz, 1H), 4.80-4.74 (m, 1.5H), 4.65 (dd, J=9.9, 6.1 Hz, 1H), 4.52 (d, J=9.9 Hz, 0.5H), 4.32 (d, J=5.4 Hz, 1H), 3.71 (t, J=1.9 Hz, 2H). $^{19}$F NMR (376 MHz, Methanol-$d_4$) δ-237.67 (t, J=47.7 Hz). LCMS: MS m/z=299.20 [M+1], $t_R$=0.48 min; LC system: Thermo Accela 1250 UHPLC; MS system: Thermo LCQ Fleet; Column: Kinetex 2.6 µXB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 µL/min. HPLC: $t_R$=1.10 min; HPLC system: Agilent 1100 series; Column: Gemini 5 µC$_{18\ 110}$A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min. HPLC: $t_R$=2.05 min; HPLC system: Agilent 1290 II; Column: Phenomenex Kinetex C18, 2.6µ 110A, 100×4.6 mm; Solvents: A: Water with 0.1% TFA, B: Acetonitrile with 0.1% TFA; Gradient: 2-98% B with 8.5 min gradient at 1.5 mL/min.

Tetrahydrofuran (18.75 mL) was added to a mixture of Intermediate 4 (1.5 g, 4.433 mmol), intermediate B1 (J. Med. Chem. 2017, 60(5), pp 1648-1661; 2.197 g, 4.877 mmol), and magnesium chloride (0.633 g, 6.65 mmol) followed by the addition of N,N-diisopropylethylamine (1.931 mL, 11.08 mmol) at rt. After 2 h at 50° C., the reaction mixture was diluted with ethyl acetate (400 mL) and the resulting mixture was washed with water (2×100 mL) and brine (200 mL). The organic layer was dried over anhydrous sodium sulfate, filtered and concentrated under reduced pressure. The crude residue was subjected to silica gel chromatography eluting with 0-20% methanol in dichloromethane to afford the intermediate. LCMS: MS m/z=650.28 [M+1], $t_R$=1.74 min; LC system: Dionex Ultimate 3000 UHPLC; Column: Phenomenex Kinetex 2.6 µC18 100A, 50×3.0 mm; Solvents: acetonitrile with 0.1% formic acid, water with 0.1% formic acid; Gradient: 0 min-1.6 min 2-100% acetonitrile, 1.6 min-1.8 min 100% acetonitrile, 1.80 min-1.90 min 100%-2% acetonitrile, 1.90 min-2.20 min 2% acetonitrile at 1100 µl/min.

B. Compounds

Example 1. 2-ethylbutyl ((S)-(((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate

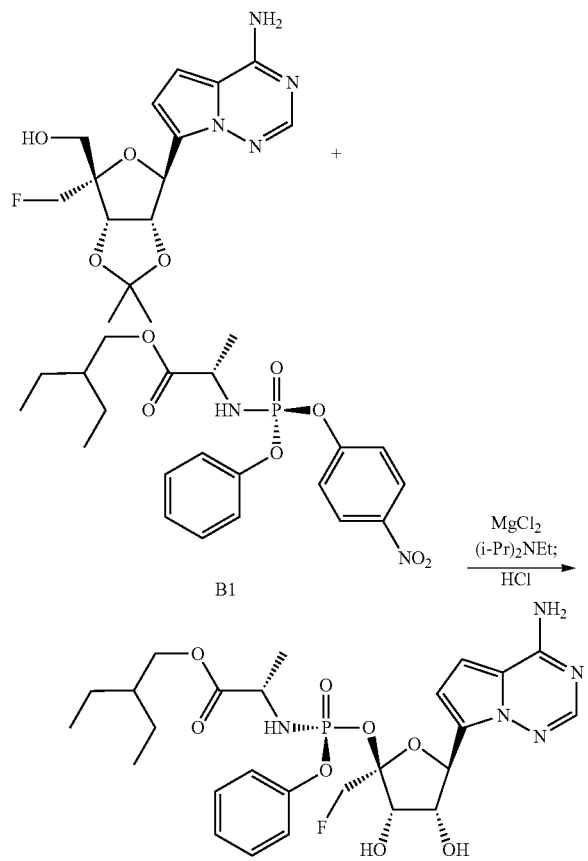

Acetonitrile (0.4 mL) was added to a mixture of Intermediate 4 (27 mg, 0.080 mmol), intermediate B1 (J. Med. Chem. 2017, 60(5), pp 1648-1661; 36 mg, 0.080 mmol), and magnesium chloride (8 mg, 0.08 mmol) at rt. The mixture was heated to 50° C. for 10 min, and N,N-diisopropylethylamine (0.035 mL, 0.20 mmol) was added. After 5 h, the reaction mixture was allowed to cool to rt, and concentrated aqueous hydrochloric acid solution (0.093 mL) was added dropwise. After 30 min, the reaction mixture was diluted with ethyl acetate (20 mL) and the resulting mixture was washed with saturated aqueous sodium bicarbonate solution (20 mL) and brine (20 mL). The organic layer was dried over anhydrous sodium sulfate and concentrated under reduced pressure. The crude residue was subjected to silica gel chromatography eluting with 0-100% ethyl acetate in hexanes to afford the product which was determined to be a single diastereomer by NMR spectroscopy. $^1$H NMR (400 MHz, Methanol-$d_4$) δ 7.79 (s, 1H), 7.40-7.31 (m, 2H), 7.26-7.14 (m, 3H), 6.85 (d, J=4.5 Hz, 1H), 6.73 (d, J=4.6 Hz, 1H), 5.36 (d, J=8.3 Hz, 1H), 4.80-4.70 (m, 1H), 4.70-4.58 (m, 2H), 4.33 (d, J=5.2 Hz, 1H), 4.21 (dd, J=5.7, 1.7 Hz, 2H), 4.07-3.87 (m, 3H), 1.48 (app p, J=6.2 Hz, 1H), 1.39-1.27 (m, 7H), 0.86 (t, J=7.5 Hz, 6H). $^{19}$F NMR (376 MHz, Methanol-$d_4$) δ -238.79 (t, J=47.7 Hz). $^{31}$P NMR (162 MHz, Methanol-$d_4$) δ 3.53. LCMS: MS m/z=610.32 [M+1], $t_R$=1.22 min; LC system: Thermo Accela 1250 UHPLC; MS system: Thermo LCQ Fleet; Column: Kinetex 2.6 µXB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 µL/min. HPLC: $t_R$=3.03 min; HPLC system: Agilent 1100 series; Column: Gemini 5 µC18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min. HPLC: $t_R$=5.11 min; HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 2. sodium ((2R,3S,4R,5S)-5-(4-aminopyrrolo[2,1-f][1,2,4]triazin-7-yl)-2-(fluoromethyl)-3,4-dihydroxytetrahydrofuran-2-yl)methyl triphosphate

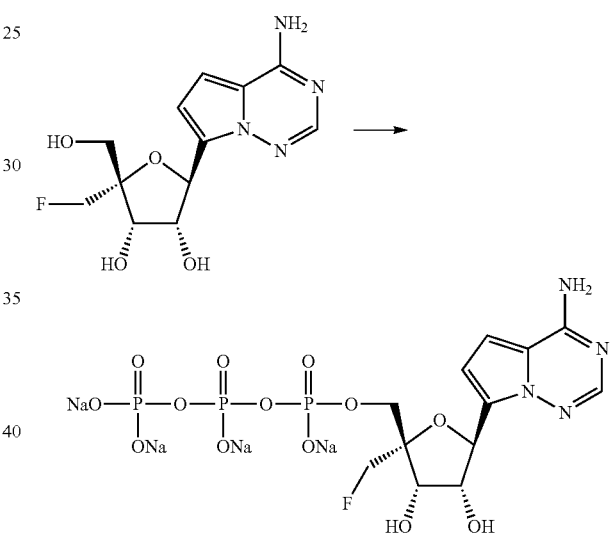

To a solution of Intermediate 5 (10 mg, 0.034 mmol) in PO(OMe)$_3$ (0.5 mL) at 0° C. was added NaHCO$_3$ (10 mg, 0.12 mmol) and POCl$_3$ (0.03 mL, 0.33 mmol). The reaction mixture was stirred at 0° C. for 4 h at which point a solution of tributylammonium pyrophosphate (250 mg, 0.46 mmol) in ACN (0.5 mL) was added, followed by tributylamine (0.14 mL, 0.59 mmol). The reaction mixture was stirred at 0° C. and monitored by ion-exchange HPLC. After 1 h, the reaction was quenched with triethylammonium bicarbonate buffer (1 M, 8 mL). The reaction mixture was stirred at rt for 0.5 h, then concentrated and co-evaporated with water twice. The residue was dissolved in water (2 mL) and NaHCO$_3$ (400 mg) was added. The resulting mixture was concentrated. The residue was dissolved in water (~2 mL) and loaded to a C-18 column, eluted with water. The fractions containing product were combined, acidified with HCl (1 N, 150 uL) and concentrated to ~4 mL volume, loaded to a ion-exchange column, eluted with water, then 10-40% triethylammonium bicarbonate buffer (1 M)—H$_2$O. The fractions containing product were combined and concentrated. The residue was dissolved in water (1 mL) and NaOH (1 N, 0.1 mL) was added. The resulting mixture was concentrated to about ~0.2 mL volume and was purified with a C-18 column, eluting with water. The fractions containing product were combined and concentrated to afford the product. $^1$H NMR (400 MHz, water-d$_2$) δ 7.88 (s, 1H), 7.06 (d, J=4.7 Hz, 1H), 6.96 (d, J=4.7 Hz, 1H), 5.46 (d, J=9.2 Hz, 1H), 4.94-4.84 (m, 2H), 4.82-4.75 (m, 1H), 4.72 (d, J=5.3 Hz, 1H), 4.13 (dd, J=10.8, 5.8 Hz, 1H), 3.96 (dd, J=10.6, 5.1 Hz, 1H). $^{31}$P NMR (162 MHz, water-d$_2$) δ-5.74 (d, J=19.7 Hz), −11.10 (d, J=19.4 Hz), −21.68 (t, J=19.7 Hz). LCMS: MS m/z=538.88 [M+1], t$_R$=0.45 min; LC system: Thermo Accela 1250 UHPLC; MS system: Thermo LCQ Fleet; Column: Kinetex 2.6 μXB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μl/min. Ion Exchange HPLC: t$_R$=10.303 min; Ion Exchange 0-80 Milli-Q water/0.5 M TEAB with 14 min gradient; 1 mL/min.

Example 3. neopentyl ((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate

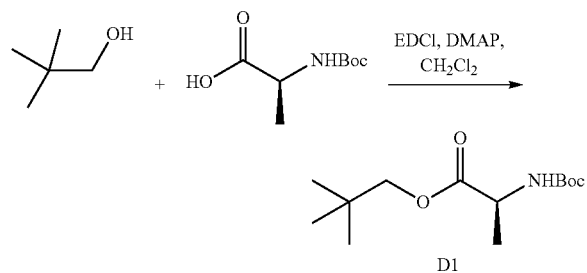

D1 neopentyl (tert-butoxycarbonyl)-L-alaninate. (tert-butoxycarbonyl)-L-alanine (20.61 g, 0.109 mol) was taken up in acetonitrile (100 mL) and 2,2-dimethylpropan-1-ol (8 g, 0.091 mol) was added followed by EDCI (18.32 g, 0.118 mol) and DMAP (16.63 g, 0.136 mol). The reaction was allowed to stir at room temperature for 4 h. The reaction was diluted with dichloromethane and water. The layers were split and the organic layer was dried over anhydrous sodium sulfate, filtered and was concentrated under reduced pressure. Purification was conducted by silica gel chromatography 0-25% ethylacetate/hexane to afford intermediate D1. $^1$H NMR (400 MHz, DMSO-d$_6$) δ 7.27 (d, J=7.5 Hz, 1H), 4.00 (p, J=7.4 Hz, 1H), 3.79 (d, J=10.5 Hz, 1H), 3.64 (d, J=10.5 Hz, 1H), 1.35 (s, 9H), 1.23 (d, J=7.4 Hz, 3H), 0.87 (s, 9H).

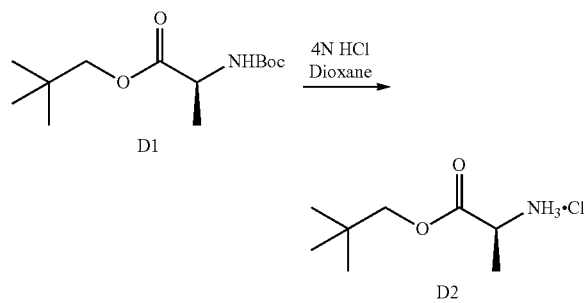

(S)-1-(neopentyloxy)-1-oxopropan-2-aminium chloride. Neopentyl (tert-butoxycarbonyl)-L-alaninate (17.45 g, 0.067 mol) was taken up in anhydrous dichloromethane (175 mL) and 4 N HCl in dioxane (84.11 mL, 0.336 mol). The reaction was stirred at ambient temperature for 4 h. The reaction was concentrated under reduced pressure and co-evaporated with dichloromethane. The resulting residue was placed under high vacuum overnight to obtain the intermediate D2, which was used as is without purification for the next step. $^1$H NMR (400 MHz, DMSO-d$_6$) δ 8.60 (s, 3H), 4.08 (q, J=7.2 Hz, 1H), 3.90 (d, J=10.4 Hz, 1H), 3.78 (d, J=10.4 Hz, 1H), 1.43 (d, J=7.2 Hz, 3H), 0.90 (s, 9H).

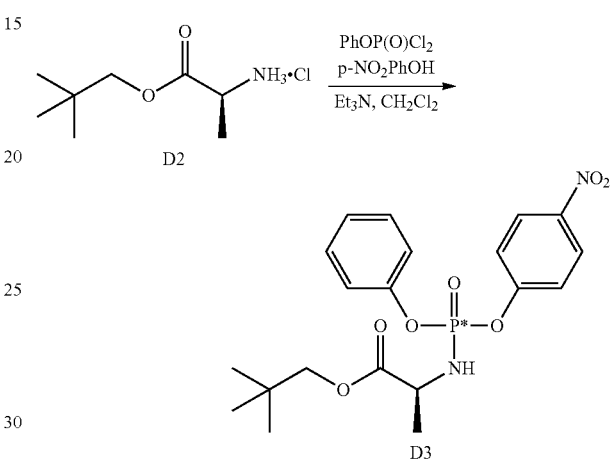

neopentyl ((4-nitrophenoxy)(phenoxy)phosphoryl)-L-alaninate. To a solution of intermediate D2 (13.15 g, 67.2 mmol) and phenyl dichlorophosphate (10 mL, 67.2 mmol) in anhydrous dichloromethane (227 mL) was added triethylamine (20.78 mL, 147.84 mmol) at 0° C. under argon atmosphere. The resulting mixture was stirred for 1 h at 0° C. 4-Nitrophenol (9.348 g, 67.2 mmol) and triethylamine (10.39 mL, 73.92 mmol) were then added. After 1 h stirring at 0° C., the reaction mixture was diluted with Et$_2$O and the solids were filtered off. The crude was concentrated under reduced pressure and was purified by silica gel chromatography (80 g SiO$_2$ Combiflash HP Gold Column, 100% dichloromethane followed by 0-45% ethyl acetate/hexanes) to afford the desired compound as a diastereomeric mixture (19 g, 64.79%, diastereomeric mixture). Compound obtained was dried under high vacuum, causing partial solidification. Diisopropyl ether was added to the partially solidified material and was sonicated to obtain a fine solid. The solids were isolated by filtration. Another round of sonication with diisopropyl ether and filtration afforded intermediate D3. Intermediate D3 was determined to be a single diastereomer by NMR spectroscopy. $^1$H NMR (400 MHz, Methanol-d$_4$) δ 8.31-8.23 (m, 2H), 7.52-7.43 (m, 2H), 7.38 (dd, J=8.6, 7.2 Hz, 2H), 7.28-7.18 (m, 3H), 4.09 (dq, J=9.8, 7.2 Hz, 1H), 3.83-3.72 (m, 2H), 1.34 (dd, J=7.2, 1.2 Hz, 3H), 0.91 (s, 9H). $^{31}$P NMR (162 MHz, Methanol-d$_4$) δ-1.32 (s). LCMS: MS m/z=436.85 [M+1]; t$_R$=1.67 min; LC system: Thermo Accela 1250 UHPLC; MS system: Thermo LCQ Fleet; Column: Phenomenex Kinetex 2.6 μXB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min.

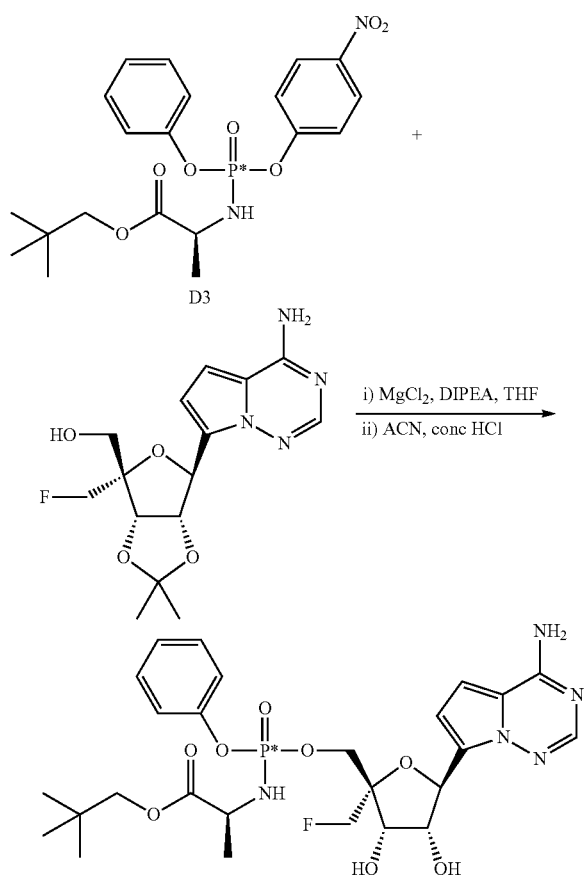

neopentyl ((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate. To a mixture of Intermediate 4 (0.015 g, 0.044 mmol), intermediate D3 (0.021 g, 0.049 mmol), and magnesium chloride (0.006 g, 0.067 mmol) was added tetrahydrofuran (0.5 mL) at room temperature followed by the addition of N,N-diisopropylethylamine (0.019 mL, 0.111 mmol). The resulting mixture was stirred at 50° C. for 1.5 h. The reaction mixture was then concentrated under reduced pressure and the residue obtained was diluted with saturated sodium chloride solution and ethyl acetate. The layers were split and the organic layer was dried over anhydrous sodium sulfate, filtered and was concentrated under reduced pressure. The residue obtained was dissolved in an anhydrous acetonitrile (0.5 mL) and was cooled in an ice bath followed by the dropwise addition of concentrated hydrochloric acid (0.088 mL, 1.058 mmol). The reaction mixture was stirred at room temperature for 1 h. After 1 h the reaction mixture was cooled in an ice bath and was neutralized with 3 N aqueous sodium hydroxide solution. The resulting mixture was purified by preparative HPLC (Phenominex Synergi 4u Hydro-RR 80 Å 150×30 mm column, 15%-85% acetonitrile/water gradient in 30 min run) to afford the product which was determined to be a single diastereomer by NMR spectroscopy. $^1$H NMR (400 MHz, Methanol-d$_4$) δ 7.78 (s, 1H), 7.34 (dd, J=8.6, 7.1 Hz, 2H), 7.27-7.13 (m, 3H), 6.84 (d, J=4.5 Hz, 1H), 6.73 (d, J=4.5 Hz, 1H), 5.35 (d, J=8.4 Hz, 1H), 4.81-4.55 (m, 3H), 4.33 (d, J=5.2 Hz, 1H), 4.24-4.17 (m, 2H), 4.02-3.86 (m, 1H), 3.83 (d, J=10.5 Hz, 1H), 3.73 (d, J=10.5 Hz, 1H), 1.33 (dd, J=7.1, 1.0 Hz, 3H), 0.91 (s, 9H).

$^{31}$P NMR (162 MHz, Methanol-d$_4$) δ 3.54. LCMS: MS m/z=596.10 [M+1]; t$_R$=1.16 min; LC system: Thermo Accela 1250 UHPLC; MS system: Thermo LCQ Fleet; Column: Phenomenex Kinetex 2.6 µXB-C$_{18\ 100}$A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µl/min. HPLC: t$_R$=4.848 min; HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 4. 3,3-dimethylbutyl ((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate

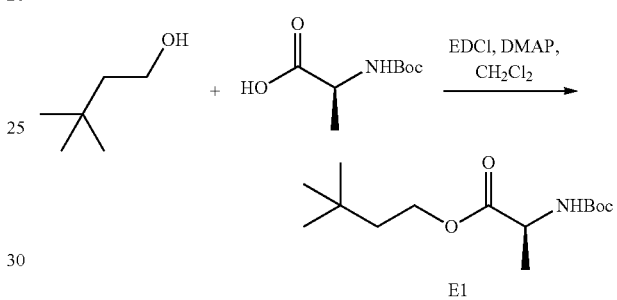

3,3-dimethylbutyl (tert-butoxycarbonyl)-L-alaninate. (tert-butoxycarbonyl)-L-alanine (22.38 g, 0.118 mol) was taken up in acetonitrile (100 mL) and 3,3-dimethylbutan-1-ol (10.07 g, 0.099 mol) followed by EDCI (19.89 g, 0.128 mol) and DMAP (18.06 g, 0.148 mol) were added in one portion. The reaction was allowed to stir at room temperature for 4 h. The reaction was diluted with dichloromethane and water. The layers were split and the organic layer was dried over anhydrous sodium sulfate, filtered and was concentrated under reduced pressure. Purification by silica gel chromatography 0-25% ethylacetate/hexane afforded intermediate E1. $^1$H NMR (400 MHz, DMSO-d$_6$) δ 7.22 (d, J=7.4 Hz, 1H), 4.13-3.82 (m, 3H), 1.47 (t, J=7.2 Hz, 2H), 1.35 (s, 9H), 1.19 (d, J=7.3 Hz, 3H), 0.88 (s, 9H).

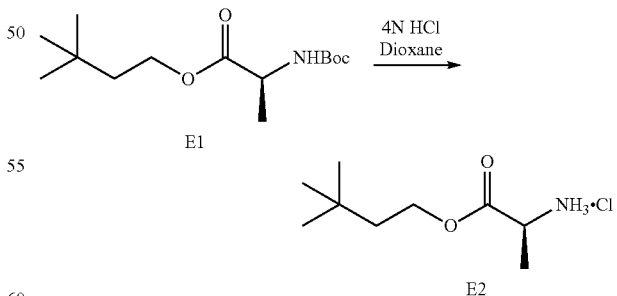

(S)-1-(3,3-dimethylbutoxy)-1-oxopropan-2-aminium chloride. Intermediate E1 (20.9 g, 0.076 mol) was taken up in anhydrous dichloromethane (200 mL) and 4 N HCl in dioxane (95.57 mL, 0.382 mol). The reaction was stirred at ambient temperature for 4 h. The reaction was concentrated under reduced pressure and co-evaporated with dichloromethane. The resulting residue was placed under high vacuum overnight and intermediate E2 was used as is without purification for the next step. ¹H NMR (400 MHz, DMSO-d₆) δ 8.67 (s, 3H), 4.32-4.07 (m, 2H), 3.97 (d, J=7.2 Hz, 1H), 1.52 (t, J=7.3 Hz, 2H), 1.39 (d, J=7.1 Hz, 3H), 0.89 (s, 9H).

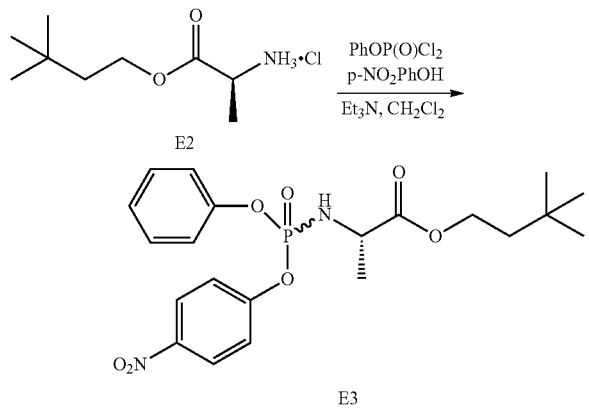

3,3-dimethylbutyl ((4-nitrophenoxy)(phenoxy)phosphoryl)-L-alaninate. To a solution of intermediate E2 (15.93 g, 75.96 mmol) and phenyl dichlorophosphate (11.3 mL, 75.96 mmol) in anhydrous dichloromethane (300 mL) was added triethylamine (23.5 mL, 167.1 mmol) at 0° C. under argon atmosphere. The resulting mixture was stirred for 1 h at 0° C. 4-Nitrophenol (10.57 g, 75.96 mmol) and triethylamine (11.74 mL, 83.56 mmol) were then added. After 1 h stirring at 0° C., the reaction mixture was diluted with Et₂O and the solids were filtered off. The crude was concentrated under reduced pressure and was purified by silica gel chromatography (80 g SiO₂ Combiflash (HP Gold Column, 100% dichloromethane followed by 0-35% ethyl acetate/hexanes) to afford intermediate E3 as a diasteromeric mixture. ¹H NMR (400 MHz, DMSO-d₆) δ 8.28 (d, J=9.1 Hz, 2H), 7.53-7.34 (m, 4H), 7.30-7.16 (m, 3H), 6.66 (td, J=13.2, 10.0 Hz, 1H), 4.06-3.88 (m, 3H), 1.40-1.29 (m, 2H), 1.24-1.11 (m, 3H), 0.83 (s, 9H). ³¹P NMR (162 MHz, DMSO-d₆) δ-1.26, -1.57. LCMS: MS m/z=450.96 [M+1]; t_R-1.71 min; LC system: Thermo Accela 1250 UHPLC; MS system: Thermo LCQ Fleet; Column: Phenomenex Kinetex 2.6 μXB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min.

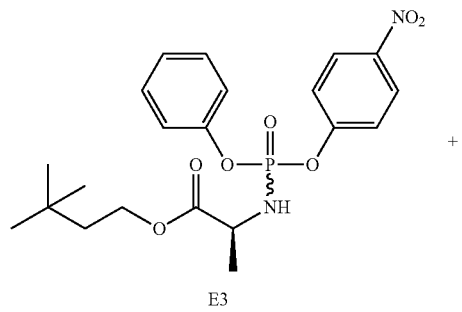

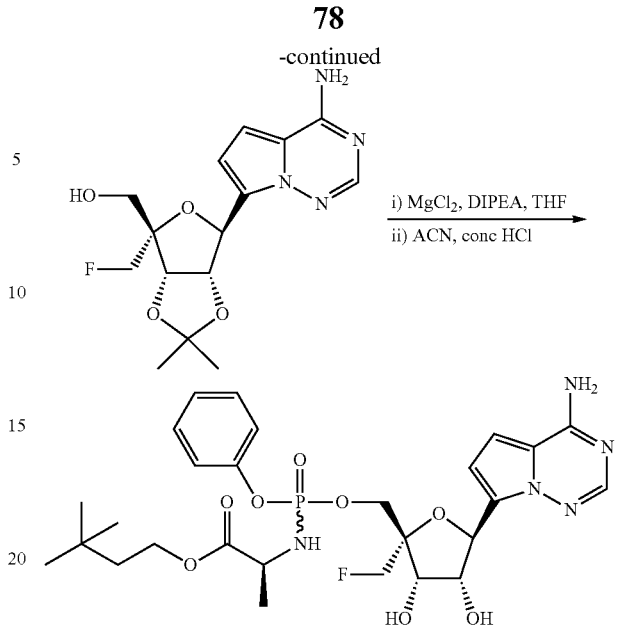

3,3-dimethylbutyl ((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate. To a mixture of Intermediate 4 (0.015 g, 0.044 mmol), intermediate E3 (0.022 g, 0.049 mmol), and magnesium chloride (0.006 g, 0.067 mmol) was added tetrahydrofuran (0.5 mL) at room temperature followed by the addition of N,N-diisopropylethylamine (0.019 mL, 0.111 mmol). The resulting mixture was stirred at 50° C. for 1.5 h. The reaction mixture was then concentrated under reduced pressure and the residue obtained was diluted with saturated sodium chloride solution and ethyl acetate. The layers were split and the organic layer was dried over anhydrous sodium sulfate, filtered and was concentrated under reduced pressure. The residue obtained was dissolved in an anhydrous acetonitrile (0.5 mL) and was cooled in an ice bath followed by the dropwise addition of concentrated hydrochloric acid (0.088 mL, 1.058 mmol). The reaction mixture was stirred at room temperature for 1 h. After 1 h the reaction mixture was cooled in an ice bath and was neutralized with 3 N aqueous sodium hydroxide solution. The resulting mixture was purified by preparative HPLC (Phenominex Synergi 4u Hydro-RR 80 Å 150×30 mm column, 15%-85% acetonitrile/water gradient in 30 min run) to afford the product. ¹H NMR (400 MHz, Methanol-d₄) δ 7.78 (d, J=1.8 Hz, 1H), 7.39-7.28 (m, 2H), 7.28-7.12 (m, 3H), 6.85 (dd, J=5.7, 4.5 Hz, 1H), 6.75 (dd, J=8.7, 4.5 Hz, 1H), 5.37 (dd, J=8.2, 6.2 Hz, 1H), 4.83-4.53 (m, 3H), 4.36 (dd, J=18.1, 5.2 Hz, 1H), 4.30-4.04 (m, 4H), 3.96-3.81 (m, 1H), 1.51 (td, J=7.5, 2.2 Hz, 2H), 1.27 (ddd, J=19.5, 7.1, 1.1 Hz, 3H), 0.90 (d, J=1.9 Hz, 9H). ³¹P NMR (162 MHz, Methanol-d₄) δ 3.7, 3.51. ¹⁹F NMR (376 MHz, Methanol-d₄) δ-238.40-238.89 (m). LCMS: MS m/z=610.05 [M+1]; t_R=1.20 min (minor isomer), 1.22 min (major isomer); LC system: Thermo Accela 1250 UHPLC; MS system: Thermo LCQ Fleet; Column: Phenomenex Kinetex 2.6 μXB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μl/min. HPLC: t_R=5.024 min (minor isomer), 5.1 min (major isomer); HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Resolution of the Sp and Rp diastereomers. The diastereomers were isolated from each other by chiral preparatory HPLC (Chiralpak IA 5 μm, 21×250 mm; 100% ethanol):

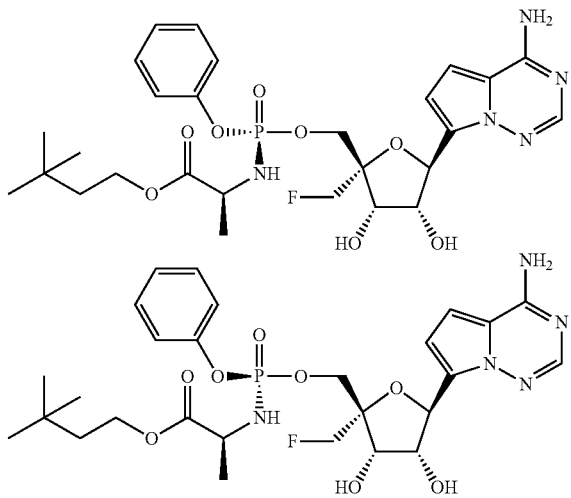

Example 5

First Eluting Diastereomer of Example 4: $^1$H NMR (400 MHz, Methanol-d$_4$) δ 7.78 (s, 1H), 7.32 (t, J=7.9 Hz, 2H), 7.23-7.13 (m, 3H), 6.86 (d, J=4.6 Hz, 1H), 6.75 (d, J=4.5 Hz, 1H), 5.37 (d, J=8.1 Hz, 1H), 4.83-4.71 (m, 1H), 4.71-4.59 (m, 2H), 4.38 (d, J=5.3 Hz, 1H), 4.26 (dd, J=5.1, 1.7 Hz, 2H), 4.16-4.07 (m, 2H), 3.93-3.74 (m, 1H), 1.56-1.47 (m, 2H), 1.24 (dd, J=7.2, 1.2 Hz, 3H), 0.90 (s, 9H). $^{31}$P NMR (162 MHz, Methanol-d$_4$) δ 3.73. $^{19}$F NMR (376 MHz, Methanol-d$_4$) δ-238.61 (t, J=47.7 Hz). LCMS: MS m/z=610.13 [M+1]; t$_R$=1.20 min; LC system: Thermo Accela 1250 UHPLC; MS system: Thermo LCQ Fleet; Column: Phenomenex Kinetex 2.6 μXB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μl/min. HPLC: t$_R$=4.996 min; HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 6

Second Eluting Diastereomer of Example 4: 1H NMR (400 MHz, Methanol-d$_4$) δ 7.79 (s, 1H), 7.35 (dd, J=8.6, 7.1 Hz, 2H), 7.27-7.14 (m, 3H), 6.84 (d, J=4.6 Hz, 1H), 6.73 (d, J=4.6 Hz, 1H), 5.36 (d, J=8.3 Hz, 1H), 4.82-4.56 (m, 3H), 4.33 (d, J=5.2 Hz, 1H), 4.24-4.04 (m, 4H), 3.94-3.80 (m, 1H), 1.50 (t, J=7.4 Hz, 2H), 1.29 (dd, J=7.1, 1.0 Hz, 3H), 0.90 (s, 9H). $^{31}$P NMR (162 MHz, Methanol-d$_4$) δ 3.51. $^{19}$F NMR (376 MHz, Methanol-d$_4$) δ-238.84 (t, J=47.7 Hz). LCMS: MS m/z=610.14 [M+1]; t$_R$=1.21 min; LC system: Thermo Accela 1250 UHPLC; MS system: Thermo LCQ Fleet; Column: Phenomenex Kinetex 2.6 μXB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: t$_R$=5.079 min; HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 7. 2,2-dimethylbutyl ((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate

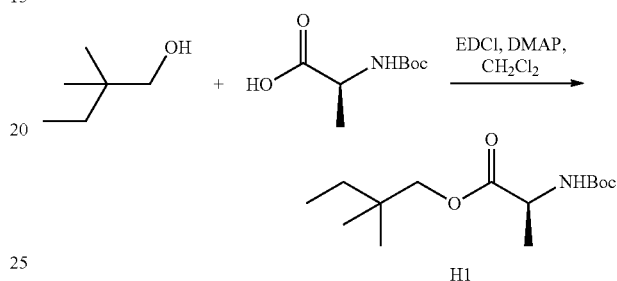

2,2-dimethylbutyl (tert-butoxycarbonyl)-L-alaninate. (tert-butoxycarbonyl)-L-alanine (11.11 g, 0.059 mol) was taken up in acetonitrile (60 mL) and 2,2-dimethylbutan-1-ol (5.0 g, 0.049 mol) followed by EDCI (9.876 g, 0.064 mol) and DMAP (8.967 g, 0.073 mol) were added. The reaction was allowed to stir at room temperature for 4 h. The reaction was diluted with dichloromethane and water. The layers were split and the organic layer was dried over anhydrous sodium sulfate, filtered and was concentrated under reduced pressure. Purification was conducted using silica gel chromatography 0-20% ethylacetate/hexane to afford intermediate H1. $^1$H NMR (400 MHz, DMSO-d$_6$) δ 7.26 (d, J=7.5 Hz, 1H), 3.99 (p, J=7.4 Hz, 1H), 3.81 (d, J=10.6 Hz, 1H), 3.66 (d, J=10.6 Hz, 1H), 1.35 (s, 9H), 1. 23 (m, 5H), 0.84-0.72 (m, 9H).

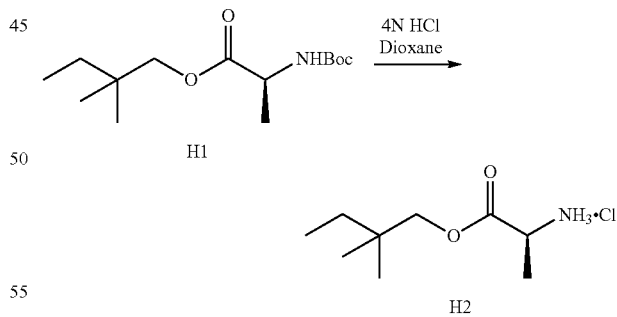

(S)-1-(2,2-dimethylbutoxy)-1-oxopropan-2-aminium chloride. Intermediate H1 (10.34 g, 0.038 mol) was taken up in anhydrous dichloromethane (100 mL) and 4 N HCl in dioxane (47.28 mL, 0.189 mol). The reaction was stirred at ambient temperature for 4 h. The reaction was concentrated under reduced pressure and co-evaporated with dichloromethane. The residue was placed under high vacuum overnight and intermediate H2 was used as is without purification for the next step. $^1$H NMR (400 MHz, DMSO-d$_6$) δ 8.65 (s, 3H), 4.05 (q, J=7.2 Hz, 1H), 3.91 (d, J=10.6

Hz, 1H), 3.79 (d, J=10.6 Hz, 1H), 1.42 (d, J=7.2 Hz, 3H), 1.26 (q, J=7.6 Hz, 2H), 0.87-0.73 (m, 9H).

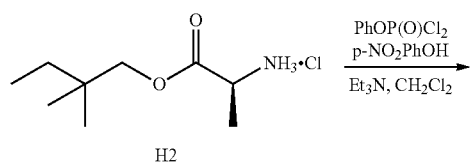

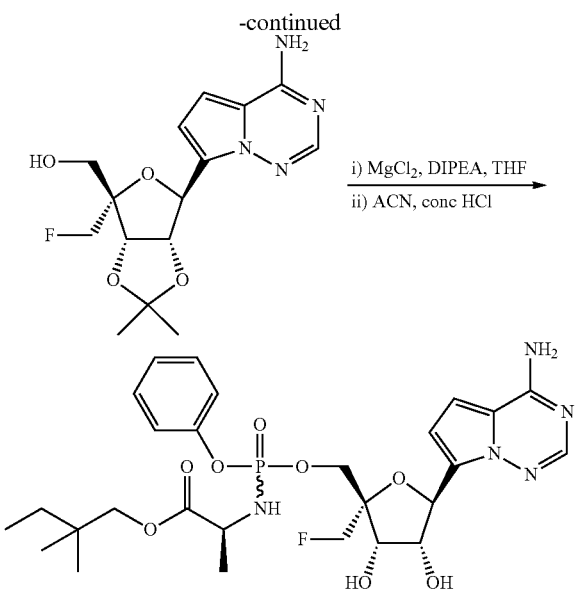

2,2-dimethylbutyl ((4-nitrophenoxy)(phenoxy)phosphoryl)-L-alaninate. To a solution of intermediate H2 (7.9 g, 37.67 mmol) and phenyl dichlorophosphate (5.605 mL, 37.67 mmol) in anhydrous dichloromethane (150 mL) was added triethylamine (11.64 mL, 82.87 mmol) at 0° C. under argon atmosphere. The resulting mixture was stirred for 1 h at 0° C. 4-Nitrophenol (5.24 g, 37.67 mmol) and triethylamine (5.82 mL, 41.43 mmol) were then added. After 1 h stirring at 0° C., the reaction mixture was diluted with Et$_2$O and the solids were filtered off. The crude was concentrated under reduced pressure and was purified by silica gel chromatography (80 g SiO$_2$ Combiflash HP Gold Column, 100% dichloromethane followed by 0-35% ethyl acetate/hexanes) to afford intermediate H3. $^1$H NMR (400 MHz, Methanol-d$_4$) δ 8.32-8.23 (m, 2H), 7.52-7.34 (m, 4H), 7.31-7.18 (m, 3H), 4.15-4.02 (m, 1H), 3.86-3.74 (m, 2H), 1.39-1.28 (m, 3H), 1.32-1.19 (m, 2H), 0.89-0.76 (m, 9H). $^{31}$P NMR (162 MHz, Methanol-d$_4$) δ -1.35, -1.57. LCMS: MS m/z=450.94 [M+1]; t$_R$=1.71 min; LC system: Thermo Accela 1250 UHPLC; MS system: Thermo LCQ Fleet; Column: Phenomenex Kinetex 2.6 µXB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µL/min.

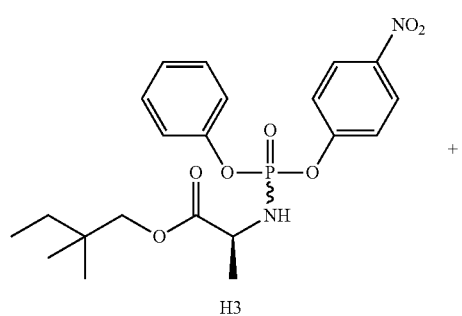

2,2-dimethylbutyl ((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate. To a mixture of Intermediate 4 (0.015 g, 0.044 mmol), intermediate H3 (0.022 g, 0.049 mmol), and magnesium chloride (0.006 g, 0.067 mmol) was added tetrahydrofuran (0.5 mL) at room temperature followed by the addition of N,N-diisopropylethylamine (0.019 mL, 0.111 mmol). The resulting mixture was stirred at 50° C. for 1.5 h. The reaction mixture was then concentrated under reduced pressure and the residue obtained was diluted with saturated sodium chloride solution and ethyl acetate. The layers were split and the organic layer was dried over anhydrous sodium sulfate, filtered and was concentrated under reduced pressure. The residue obtained was dissolved in an anhydrous acetonitrile (0.5 mL) and was cooled in an ice bath followed by the dropwise addition of concentrated hydrochloric acid (0.088 mL, 1.058 mmol). The reaction mixture was stirred at room temperature for 1 h. After 1 h the reaction mixture was cooled in an ice bath and was neutralized with 3 N aqueous sodium hydroxide solution. The resulting mixture was purified by preparative HPLC (Phenominex Synergi 4u Hydro-RR 80 Å 150×30 mm column, 15%-85% acetonitrile/water gradient in 30 min run) to afford the product. $^1$H NMR (400 MHz, Methanol-d$_4$) δ 7.78 (d, J=1.4 Hz, 1H), 7.37-7.27 (m, 2H), 7.27-7.12 (m, 3H), 6.85 (dd, J=5.8, 4.5 Hz, 1H), 6.74 (dd, J=9.9, 4.5 Hz, 1H), 5.37 (dd, J=8.2, 6.7 Hz, 1H), 4.83-4.53 (m, 3H), 4.36 (dd, J=16.6, 5.3 Hz, 1H), 4.24 (ddd, J=21.2, 5.7, 1.8 Hz, 2H), 4.01-3.72 (m, 3H), 1.36-1.24 (m, 5H), 0.90-0.77 (m, 9H). $^{31}$P NMR (162 MHz, Methanol-d$_4$) δ 3.72, 3.54. $^{19}$F NMR (376 MHz, Methanol-d$_4$) δ-238.38-238.82 (m). LCMS: MS m/z=610.05 [M+1]; t$_R$=1.32 min (minor isomer), 1.33 min (major isomer); LC system: Thermo Accela 1250 UHPLC; MS system: Thermo LCQ Fleet; Column: Phenomenex Kinetex 2.6 µXB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µL/min. HPLC: t$_R$=5.021 min (minor isomer), 5.093 min (major isomer); HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Resolution of the Sp and Rp diastereomers. The diastereomers were isolated from each other by chiral preparatory HPLC (Chiralpak IA 5 μm, 21×250 mm; 100% ethanol).

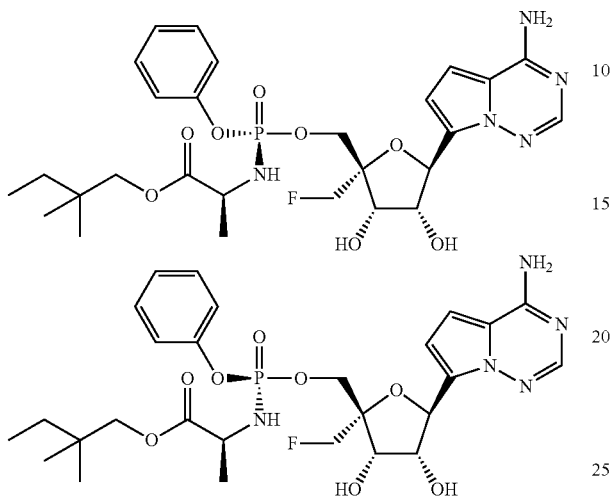

Example 8

First Eluting Diastereomer of Example 7: $^1$H NMR (400 MHz, Methanol-$d_4$) δ 7.78 (s, 1H), 7.32 (t, J=7.8 Hz, 2H), 7.19 (m, 3H), 6.86 (d, J=4.5 Hz, 1H), 6.75 (d, J=4.5 Hz, 1H), 5.37 (d, J=8.2 Hz, 1H), 4.81-4.56 (m, 3H), 4.37 (d, J=5.3 Hz, 1H), 4.26 (d, J=4.9 Hz, 2H), 3.99-3.66 (m, 3H), 1.36-1.19 (m, 5H), 0.87 (s, 6H), 0.82 (t, J=7.6 Hz, 3H). $^{31}$P NMR (162 MHz, Methanol-$d_4$) δ 3.72. $^{19}$F NMR (376 MHz, Methanol-$d_4$) δ-238.59 (t, J=47.7 Hz). LCMS: MS m/z=610.11 [M+1]; $t_R$=1.21 min; LC system: Thermo Accela 1250 UHPLC; MS system: Thermo LCQ Fleet; Column: Phenomenex Kinetex 2.6 μXB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μl/min. HPLC: $t_R$=5.007 min; HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 9

Second Eluting Diastereomer of Example 7: $^1$H NMR (400 MHz, Methanol-$d_4$) δ 7.79 (s, 1H), 7.34 (t, J=7.9 Hz, 2H), 7.27-7.14 (m, 3H), 6.84 (d, J=4.5 Hz, 1H), 6.73 (d, J=4.5 Hz, 1H), 5.35 (d, J=8.3 Hz, 1H), 4.81-4.55 (m, 3H), 4.33 (d, J=5.2 Hz, 1H), 4.21 (d, J=5.8 Hz, 2H), 3.94 (dd, J=9.9, 7.1 Hz, 1H), 3.85 (d, J=10.7 Hz, 1H), 3.76 (d, J=10.6 Hz, 1H), 1.36-1.24 (m, 5H), 0.89-0.77 (m, 9H). $^{31}$P NMR (162 MHz, Methanol-$d_4$) δ 3.54. $^{19}$F NMR (376 MHz, Methanol-$d_4$) δ-238.76 (t, J=47.7 Hz). LCMS: MS m/z=610.14 [M+1]; $t_R$=1.22 min; LC system: Thermo Accela 1250 UHPLC; MS system: Thermo LCQ Fleet; Column: Phenomenex Kinetex 2.6 μXB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=5.085 min; HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 10. methyl (((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate

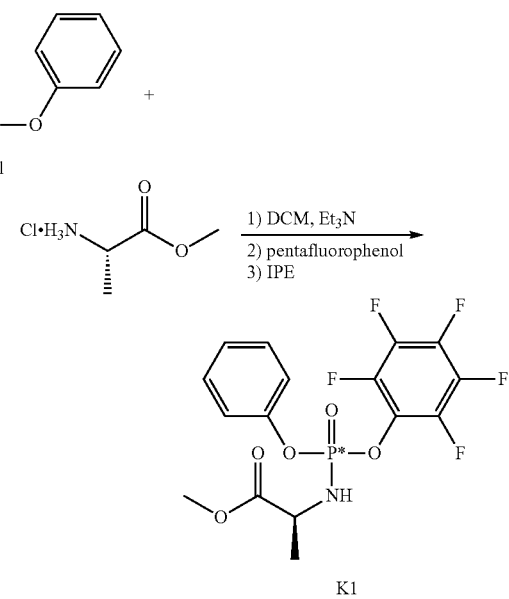

methyl ((perfluorophenoxy)(phenoxy)phosphoryl)-L-alaninate. L-Alanine methyl ester hydrochloride (14 g, 100 mmol) was mixed with 50 mL of anhydrous DCM and stirred under atmospheric nitrogen in an ice bath. Phenyl dichlorophosphate (16.4 mL, 110 mmol) was added to the reaction mixture dropwise, and the reaction mixture was stirred for 30 mins. Triethylamine (29.4 mL, 210 mmol) was mixed with 20 mL anhydrous DCM and added to the reaction dropwise. Reaction was stirred for 1 hr. Pentafluorophenol (18.4 g, 100 mmol) was added in one portion. Triethylamine (14.7 mL, 105 mmol) was mixed with 30 mL of anhydrous DCM and added to reaction dropwise. The reaction mixture was stirred for 16 hrs at RT. The reaction was diluted with DCM (50 mL) and washed with water (5×10 mL). The organic layer was dried over anhydrous sodium sulfate and then concentrated under reduced pressure to give solid. Isopropyl ether (130 mL) was added to the solid. Big pieces of solid were broke down and then sonicated for 20 mins, after which the mixture was then stirred for 24 hrs. Solid was collected and washed with small amount of isopropyl ether (30 mL), and dried under high vacuum to give intermediate K1. Intermediate K1 was determined to be a single diastereomer by NMR spectroscopy. $^1$H NMR (400 MHz, Chloroform-d) δ 7.40-7.32 (m, 2H), 7.28-7.19 (m, 3H), 4.20 (m, 1H), 3.96-3.85 (m, 1H), 3.74 (s, 3H), 1.47 (d, J=7.1 Hz, 3H). $^{31}$P NMR (162 MHz, Chloroform-d) 6-1.62. $^{19}$F NMR (376 MHz, Chloroform-d) 6-153.82 (dd, J=18.5, 2.7 Hz), −159.99 (td, J=21.8, 3.8 Hz), −162.65 (dd, J=22.2, 17.6 Hz). LCMS: MS m/z=425.9 [M+1], 423.9 [M−1], $t_R$=1.68 min; LC system: Thermo Dionex Ultimate 3000 UHPLC; Column: Phenomenex Kinetex 2.6 μC18 100A, 50×3 mm; Solvents: A: Water with 0.1% acetic acid, B: Acetonitrile with 0.1% acetic acid; Gradient: 0 min-0.3 min 5% B, 0.3 min-1.5 min 5-100% B, 1.5 min-2 min 100% B, 2 min-2.2 min 100-5% B at 2 mL/min. HPLC: $t_R$=3.76 min; HPLC system: Agilent 1100 series; Column: Phenomenex Gemini 5 μC18 110A, 50×4.6 mm; Solvent: A: Water with 0.1% TFA, B: Acetonitrile with 0.1% TFA; Gradient: 2-98% B in 5 min at 2 mL/min.

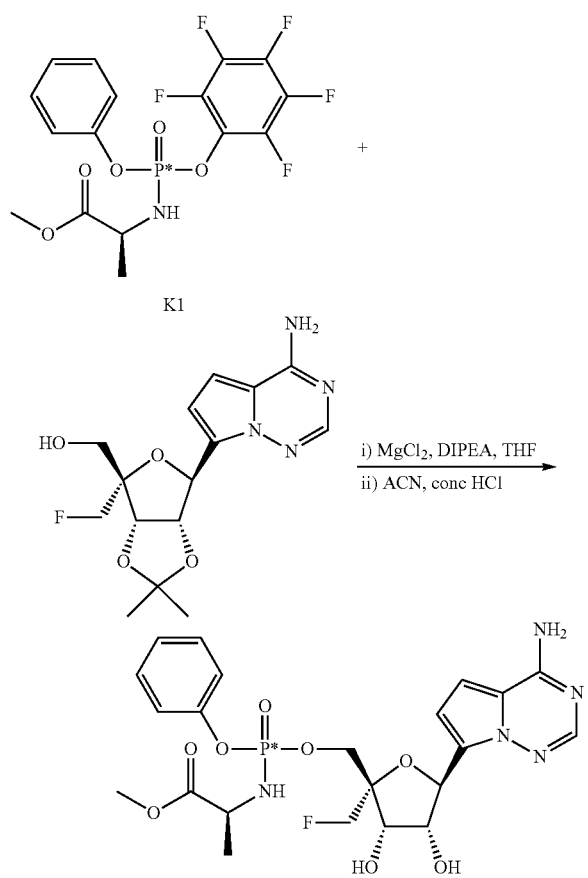

methyl ((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate. Intermediate 4 (56 mg, 0.165 mmol) and intermediate K1 (74 mg, 0.174 mmol) were mixed and dissolved in 5 mL of anhydrous THF. Magnesium chloride (47 mg, 0.495 mmol) was added in one portion. DIPEA (72 μL, 0.414 mmol) was added, and the reaction was stirred at 45° C. for 20 hrs. More of intermediate K1 (74 mg, 0.174 mmol) was added, and the reaction was stirred at 45° C. for 8 hrs. Reaction was then stirred at rt for 16 hrs. Reaction was diluted with EtOAc (10 mL) and washed with water (3×5 mL) and then with brine (5 mL). Organic extract was dried over anhydrous sodium sulfate and concentrated under reduced pressure. The crude residue was purified via SiO₂ column chromatography (4 g SiO₂ Combiflash HP Gold Column, 0-100% ethyl acetate/hexanes). Fractions were combined and concentrated under reduced pressure. Residue was dissolved in ACN (5 mL) and stirred in an ice bath. Concentrated aqueous hydrochloric acid (250 μL) was added dropwise. Reaction was stirred in an ice bath for 1 hr. Ice bath was removed, and the reaction was stirred at rt for 1 hr. Reaction was diluted with EtOAc (15 mL) and added saturated aqueous sodium bicarbonate solution (20 mL). Mixture was stirred for 10 mins. Organic extract was collected and washed with brine (10 mL). Organic extract was dried over anhydrous sodium sulfate and concentrated under reduced pressure. The crude residue was purified via C18 column chromatography (Phenomenex Gemini column, 5-95% ACN/water). Fractions were combined and freeze-dried to give the product. The product was determined to be a single diastereomer by NMR spectroscopy. $^1$H NMR (400 MHz, Methanol-$d_4$) δ 7.79 (s, 1H), 7.38-7.30 (m, 2H), 7.26-7.15 (m, 3H), 6.85 (d, J=4.5 Hz, 1H), 6.73 (d, J=4.5 Hz, 1H), 5.36 (d, J=8.4 Hz, 1H), 4.81-4.57 (m, 3H), 4.34 (d, J=5.2 Hz, 1H), 4.20 (dt, J=5.7, 1.9 Hz, 2H), 3.91 (dq, J=10.0, 7.1 Hz, 1H), 3.65 (s, 3H), 1.29 (dd, J=7.1, 1.1 Hz, 3H). $^{31}$P NMR (162 MHz, Methanol-$d_4$) δ 3.49. LCMS: MS m/z=540.0 [M+1], 538.2 [M−1], $t_R$=1.14 min; LC system: Thermo Dionex Ultimate 3000 UHPLC; Column: Phenomenex Kinetex 2.6 μC$_{18}$ $_{100}$A, 50×3 mm; Solvents: A: Water with 0.1% acetic acid, B: Acetonitrile with 0.1% acetic acid; Gradient: 0 min-0.3 min 5% B, 0.3 min-1.5 min 5-100% B, 1.5 min-2 min 100% B, 2 min-2.2 min 100-5% B at 2 mL/min. HPLC: $t_R$=2.23 min; HPLC system: Agilent 1100 series; Column: Phenomenex Gemini 5 μC18 110A, 50×4.6 mm; Solvent: A: Water with 0.1% TFA, B: Acetonitrile with 0.1% TFA; Gradient: 2-98% B in 5 min at 2 mL/min. HPLC: $t_R$=3.770 min; HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 11. (2R,3S,4S,5S)-5-(4-aminopyrrolo[2,1-f][1,2,4]triazin-7-yl)-2-(fluoromethyl)-2-((((((S)-1-methoxy-1-oxopropan-2-yl)amino)(Phenoxy)phosphoryl)oxy) methyl)tetrahydrofuran-3,4-diyl bis(2-methylpropanoate)

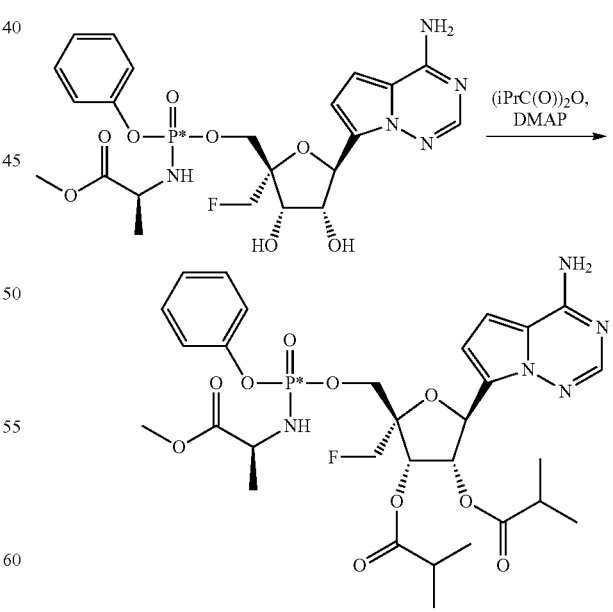

Example 10 (13 mg, 0.024 mmol) was dissolved in 2 mL anhydrous THF and stirred at rt. Isobutyric anhydride (8 μL, 0.048 mmol) and DMAP (0.3 mg, 0.0024 mmol) were added, and the reaction was stirred for 30 mins. More isobutyric anhydride (4 μL, 0.024 mmol) was added, and the reaction was stirred for 30 mins. Reaction was then diluted with EtOAc (10 mL) and washed with saturated aqueous sodium bicarbonate solution (2×5 mL) followed with brine (5 mL). Organic extract was dried over anhydrous sodium sulfate and then concentrated under reduced pressure. The crude residue was purified via SiO₂ column chromatography (4 g SiO₂ Combiflash HP Gold Column, 0-10% methanol/DCM). Fractions were combined and concentrated under reduced pressure. Residue was dissolved in ACN, diluted with water and freeze-dried to give the product, which was determined to be a single diastereomer by NMR spectroscopy. $^1$H NMR (400 MHz, Methanol-d₄) δ 7.79 (s, 1H), 7.38-7.13 (m, 5H), 6.79 (d, J=4.5 Hz, 1H), 6.61 (d, J=4.6 Hz, 1H), 5.88-5.77 (m, 2H), 5.60 (d, J=7.8 Hz, 1H), 4.79-4.52 (m, 2H), 4.39-4.21 (m, 2H), 3.96 (dq, J=10.2, 7.1 Hz, 1H), 3.66 (s, 3H), 2.68 (p, J=7.0 Hz, 1H), 2.46 (p, J=7.0 Hz, 1H), 1.31 (dd, J=7.1, 1.0 Hz, 3H), 1.22 (dd, J=7.0, 1.1 Hz, 6H), 1.07 (d, J=7.0 Hz, 3H), 1.03 (d, J=7.0 Hz, 3H). $^{31}$P NMR (162 MHz, Methanol-d₄) δ 3.38. LCMS: MS m/z=680.2 [M+1], 678.3 [M−1], $t_R$=1.60 min; LC system: Thermo Dionex Ultimate 3000 UHPLC; Column: Phenomenex Kinetex 2.6 μC18 100A, 50×3 mm; Solvents: A: Water with 0.1% acetic acid, B: Acetonitrile with 0.1% acetic acid; Gradient: 0 min-0.3 min 5% B, 0.3 min-1.5 min 5-100% B, 1.5 min-2 min 100% B, 2 min-2.2 min 100-5% B at 2 mL/min. HPLC: $t_R$=3.17 min; HPLC system: Agilent 1100 series; Column: Phenomenex Gemini 5 μC18 110A, 50×4.6 mm; Solvent: A: Water with 0.1% TFA, B: Acetonitrile with 0.1% TFA; Gradient: 2-98% B in 5 min at 2 mL/min. HPLC: $t_R$=5.460 min; HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 12. isopropyl ((S)-(((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate

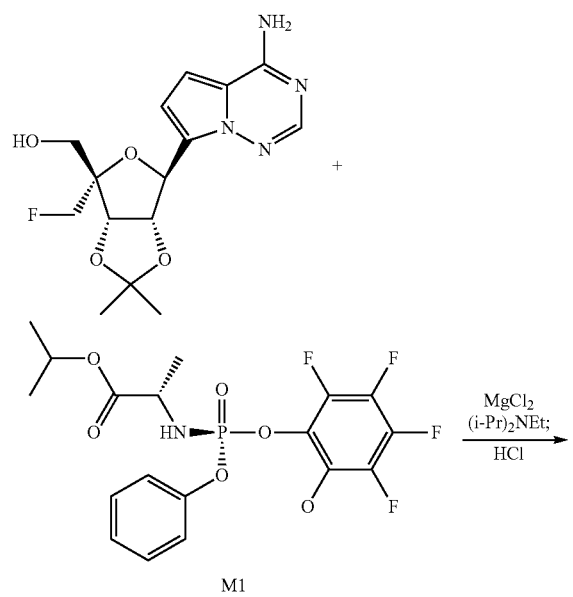

M1

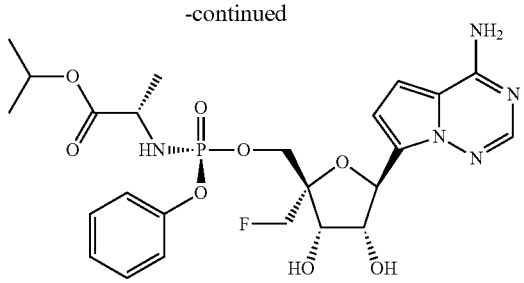

Tetrahydrofuran (1 mL) was added to a mixture of Intermediate 4 (200 mg, 0.591 mmol), intermediate M1 (*J. Org. Chem.* 2011, 76(20), pp 8311-8319; 322 mg, 0.709 mmol), and magnesium chloride (84 mg, 0.887 mmol) at rt. The mixture was heated to 40° C. for 10 min, and N,N-diisopropylethylamine (0.257 mL, 1.478 mmol) was added. After stirring for 2 hours at 40° C., the reaction mixture was allowed to cool to rt, and was concentrated down under reduced pressure. The crude residue was dissolved in ethyl acetate (20 mL) and the resulting mixture was washed with water (20 mL) and brine (20 mL). The organic layer was separated, dried over anhydrous sodium sulfate and concentrated under reduced pressure. The crude residue was dissolved in acetonitrile (7 mL) and concentrated aqueous hydrochloric acid solution (0.493 mL) was added dropwise at 0° C. After 2 hours at 0° C., the reaction mixture was diluted with ethyl acetate (30 mL) and water (20 mL) at 0° C. and the resulting mixture was washed with saturated aqueous sodium bicarbonate solution (20 mL) and brine (20 mL). The organic layer was dried over anhydrous sodium sulfate and concentrated under reduced pressure. The crude residue was purified by preparatory HPLC (Phenomenex Gemini 5 μm C18 110 Å 100×30 mm column) using gradient from 10-100% acetonitrile in water to afford the product, which was determined to be a single diastereomer by NMR spectroscopy. $^1$H NMR (400 MHz, DMSO-d₆) δ 7.83 (s, 1H), 7.71 (bs, 2H), 7.43-7.30 (m, 2H), 7.25-7.15 (m, 3H), 6.84 (d, J=4.5 Hz, 1H), 6.68 (d, J=4.5 Hz, 1H), 6.04 (dd, J=13.2, 10.1 Hz, 1H), 5.29-5.22 (m, 2H), 5.14 (d, J=7.3 Hz, 1H), 4.86 (hept, J=6.2 Hz, 1H), 4.70-4.58 (m, 1H), 4.57-4.44 (m, 2H), 4.20 (t, J=4.8 Hz, 1H), 4.05-3.91 (m, 2H), 3.85-3.68 (m, 1H), 1.21 (d, J=7.0 Hz, 3H), 1.15 (dd, J=6.3, 2.8 Hz, 6H). $^{19}$F NMR (376 MHz, DMSO-d₆) δ-236.69 (t, J=48.1 Hz). $^{31}$P NMR (162 MHz, DMSO-d₆) δ 3.51. LCMS: MS m/z=568.15 [M+1], $t_R$=1.19 min; LC system: Thermo Accela 1250 UHPLC; MS system: Thermo LCQ Fleet; Column: Kinetex 2.6 μXB-C18 100A, 50×4.6 mm; Solvents: acetonitrile with 0.1% acetic acid, water with 0.1% acetic acid; Gradient: 0 min-0.2 min 2% acetonitrile, 0.2 min-1.5 min 2-100% acetonitrile, 1.5 min-2.2 min 100% acetonitrile, 2.2 min-2.4 min 100%-2% acetonitrile, 2.4 min-2.5 min 2% acetonitrile at 2 μL/min. HPLC: $t_R$=2.55 min; HPLC system: Agilent 1100 series; Column: Gemini 5 μC18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min. HPLC: $t_R$=4.32 min; HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 13. ethyl ((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate

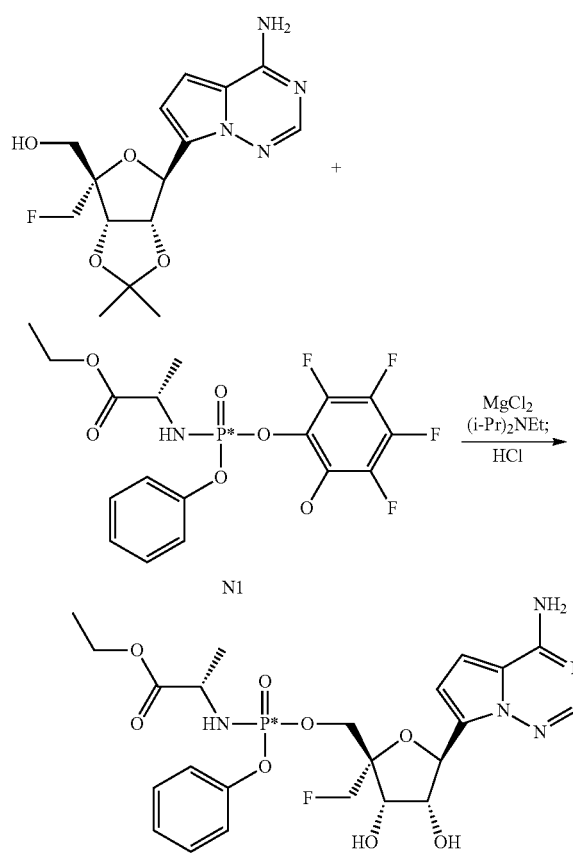

Tetrahydrofuran (4 mL) was added to a mixture of Intermediate 4 (200 mg, 0.591 mmol), intermediate Ni (WO2012075140; 415 mg, 0.946 mmol), and magnesium chloride (84 mg, 0.887 mmol) at rt. The mixture was heated to 40° C. for 10 min, and N,N-diisopropylethylamine (0.257 mL, 1.478 mmol) was added. After stirring for 2 hours at 40° C., the reaction mixture was allowed to cool to rt, and was concentrated down under reduced pressure. The crude residue was dissolved in ethyl acetate (20 mL) and the resulting mixture was washed with water (20 mL) and brine (20 mL). The organic layer was separated, dried over anhydrous sodium sulfate and concentrated under reduced pressure. The crude residue was dissolved in acetonitrile (3 mL) and concentrated aqueous hydrochloric acid solution (0.514 mL) was added dropwise at 0° C. After 2 hours at 0° C., the reaction mixture was diluted with ethyl acetate (30 mL) and water (20 mL) at 0° C. and the resulting mixture was washed with saturated aqueous sodium bicarbonate solution (20 mL) and brine (20 mL). The organic layer was dried over anhydrous sodium sulfate and concentrated under reduced pressure. The crude residue was purified by preparatory HPLC (Phenomenex Gemini 5 μm C18 110 Å 100×30 mm column) using gradient from 10-100% acetonitrile in water to afford the product, which was determined to be a single diastereomer by NMR spectroscopy. $^1$H NMR (400 MHz, DMSO-d$_6$) δ 7.83 (s, 1H), 7.71 (bs, 2H), 7.45-7.33 (m, 2H), 7.31-7.09 (m, 3H), 6.84 (d, J=4.5 Hz, 1H), 6.68 (d, J=4.5 Hz, 1H), 6.08 (dd, J=13.3, 10.1 Hz, 1H), 5.32-5.22 (m, 2H), 5.14 (d, J=7.3 Hz, 1H), 4.70-4.44 (m, 3H), 4.19 (t, J=4.8 Hz, 1H), 4.11-3.94 (m, 4H), 3.88-3.74 (m, 1H), 1.22 (d, J=6.7 Hz, 3H), 1.15 (t, J=7.1 Hz, 3H). $^{19}$F NMR (376 MHz, DMSO-d$_6$) δ-236.69 (t, J=48.0 Hz). $^{31}$P NMR (162 MHz, DMSO-d$_6$) δ 3.46. LCMS: MS m/z=554.11 [M+1], t$_R$=1.13 min; LC system: Thermo Accela 1250 UHPLC; MS system: Thermo LCQ Fleet; Column: Kinetex 2.6 μXB-C18 100A, 50×4.6 mm; Solvents: acetonitrile with 0.1% acetic acid, water with 0.1% acetic acid; Gradient: 0 min-0.2 min 2% acetonitrile, 0.2 min-1.5 min 2-100% acetonitrile, 1.5 min-2.2 min 100% acetonitrile, 2.2 min-2.4 min 100%-2% acetonitrile, 2.4 min-2.5 min 2% acetonitrile at 2 μl/min. HPLC: t$_R$=2.42 min; HPLC system: Agilent 1100 series; Column: Gemini 5 μC18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min. HPLC: t$_R$=4.05 min; HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 14. cyclohexyl ((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate

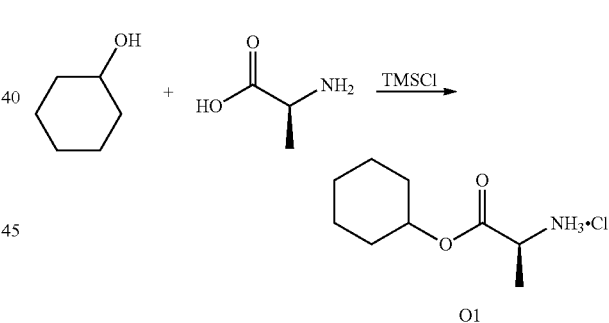

(S)-1-(cyclohexyloxy)-1-oxopropan-2-aminium chloride. To a mixture of L-alanine (20.0 g, 224.48 mmol) and cyclohexanol (213.6 g, 2132.6 mmol) was added trimethylsilyl chloride (76.56 mL, 695.9 mmol). The reaction was allowed to stir at 80° C. overnight. The reaction was concentrated and the residue obtained was coevaporated with toluene 2×100 mL followed by hexane 500 mL. The residue obtained was dried under high vacuum for 15 min and hexane was slowly added while stirring. The mixture as stirred for 30 min at room temperature and solids were separated by filtration, washed with hexane and dried under high vacuum overnight to afford intermediate O1. $^1$H NMR (400 MHz, DMSO-d$_6$) δ 8.53 (d, J=17.7 Hz, 3H), 4.77 (tt, J=8.4, 3.7 Hz, 1H), 3.99 (t, J=6.9 Hz, 1H), 1.88-1.59 (m, 4H), 1.54-1.12 (m, 8H).

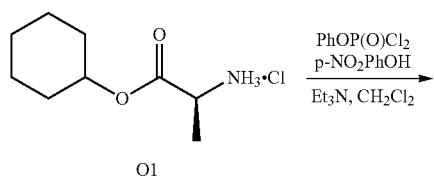

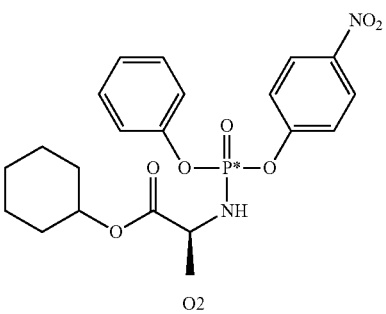

O2

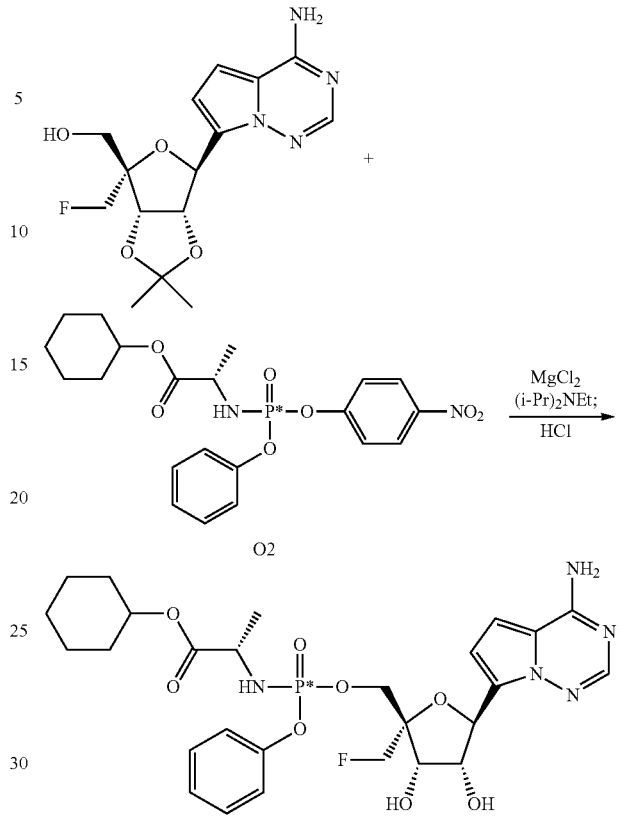

cyclohexyl ((4-nitrophenoxy)(phenoxy)phosphoryl)-L-alaninate. To a solution of intermediate O1 (23.2 g, 111.7 mmol) and phenyl dichlorophosphate (16.2 mL, 108.91 mmol) in anhydrous dichloromethane (400 mL) was added triethylamine (35 mL, 251.33 mmol) at 0° C. under argon atmosphere. The resulting mixture was stirred for 1.5 h at room temperature. 4-Nitrophenol (14.53 g, 104.44 mmol) and triethylamine (18 mL, 125.66 mmol) were then added at 0° C. The reaction mixture was stirred at room temperature for 1 h and was diluted with Et$_2$O and the solids were filtered off. The crude was concentrated under reduced pressure and residue obtained was dissolved in ethyl acetate and was washed with saturated aqueous sodium carbonate solution and brine. Organic layer was separated, dried over sodium sulfate, filtered and concentrated. Crude material was purified by silica gel chromatography (330 g SiO$_2$ Combiflash HP Gold Column, 0-10% methanol/dichloromethane) to afford desired compound as a diastereomeric mixture (41.3 g, 83%, diastereomeric mixture). The material thus obtained was dried under high vacuum overnight resulting solidification. Diisopropyl ether (225 mL) was added to the solidified material and extensive sonication resulted in a fine solid. Isolation of the solids by filtration afforded intermediate 02 as a single isomer by $^1$H NMR and $^{31}$P NMR. $^1$H NMR (400 MHz, Methanol-d$_4$) δ 8.32-8.23 (m, 2H), 7.52-7.40 (m, 2H), 7.38 (dd, J=8.6, 7.2 Hz, 2H), 7.29-7.17 (m, 3H), 4.68 (dp, J=8.7, 3.8 Hz, 1H), 4.02 (dq, J=9.8, 7.1 Hz, 1H), 1.78-1.64 (m, 3H), 1.57-1.46 (m, 1H), 1.44-1.22 (m, 9H). $^{31}$P NMR (162 MHz, Methanol-d$_4$) δ-1.32 (s) LCMS: MS m/z=448.86 [M+1]; t$_R$=1.3 min; LC system: Thermo Accela 1250 UHPLC; MS system: Thermo LCQ Fleet; Column: Phenomenex Kinetex 2.6 μXB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min cyclohexyl (((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate. Tetrahydrofuran (2 mL) was added to a mixture of Intermediate 4 (200 mg, 0.591 mmol), intermediate 02 (318 mg, 0.709 mmol), and magnesium chloride (84 mg, 0.887 mmol) at rt. The mixture was heated to 50° C. for 10 min, and N,N-diisopropylethylamine (0.257 mL, 1.478 mmol) was added. After stirring for 3 hours at 50° C., the reaction mixture was allowed to cool to rt, and was concentrated down under reduced pressure. The crude residue was dissolved in ethyl acetate (20 mL) and the resulting mixture was washed with water (20 mL) and brine (20 mL). The organic layer was separated, dried over anhydrous sodium sulfate and concentrated under reduced pressure. The crude residue was dissolved in acetonitrile (7 mL) and concentrated aqueous hydrochloric acid solution (0.493 mL) was added dropwise at 0° C. After 2 hours at 0° C., the reaction mixture was diluted with ethyl acetate (30 mL) and water (20 mL) at 0° C. and the resulting mixture was washed with saturated aqueous sodium bicarbonate solution (20 mL) and brine (20 mL). The organic layer was dried over anhydrous sodium sulfate and concentrated under reduced pressure. The crude residue was purified by preparatory HPLC (Phenomenex Gemini 5 μm C18 110 Å 100×30 mm column) using gradient from 10-100% acetonitrile in water to afford the product, which was determined to be a single diastereomer by NMR spectroscopy. $^1$H NMR (400 MHz, DMSO-d$_6$) δ 7.83 (s, 1H), 7.71 (s, 2H), 7.43-7.30 (m, 2H), 7.27-7.11 (m, 3H), 6.85 (d, J=4.4 Hz, 1H), 6.69 (d, J=4.5 Hz, 1H), 6.17-5.94 (m, 1H), 5.36-5.19 (m, 2H), 5.14 (dd, J=7.3, 1.0 Hz, 1H), 4.70-4.59 (m, 2H), 4.58-4.45 (m, 2H), 4.21 (t, J=4.8 Hz, 1H), 4.05-3.91 (m, 2H), 3.85-3.70 (m, 1H), 1.76-1.55 (m, 4H), 1.50-1.12 (m, 9H). $^{19}$F NMR (376 MHz, DMSO-$d_6$) δ -236.73 (t, J=48.1 Hz). $^{31}$P NMR (162 MHz, DMSO-$d_6$) δ 3.52. LCMS: MS m/z=608.19 [M+1], $t_R$=1.31 min; LC system: Thermo Accela 1250 UHPLC; MS system: Thermo LCQ Fleet; Column: Kinetex 2.6 µXB-C18 100A, 50×4.6 mm; Solvents: acetonitrile with 0.1% acetic acid, water with 0.1% acetic acid; Gradient: 0 min-0.2 min 2% acetonitrile, 0.2 min-1.5 min 2-100% acetonitrile, 1.5 min-2.2 min 100% acetonitrile, 2.2 min-2.4 min 100%-2% acetonitrile, 2.4 min-2.5 min 2% acetonitrile at 2 µL/min. HPLC: $t_R$=2.89 min; HPLC system: Agilent 1100 series; Column: Gemini 5 µC18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min. HPLC: $t_R$=4.90 min; HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 15. (2R,3S,4S,5S)-5-(4-aminopyrrolo[2,1-f][1,2,4]triazin-7-yl)-2-(((((S)-1-(cyclohexyloxy)-1-oxopropan-2-yl)amino)(Phenoxy)phosphoryl)oxy)methyl)-2-(fluoromethyl)tetrahydrofuran-3,4-diyl diacetate

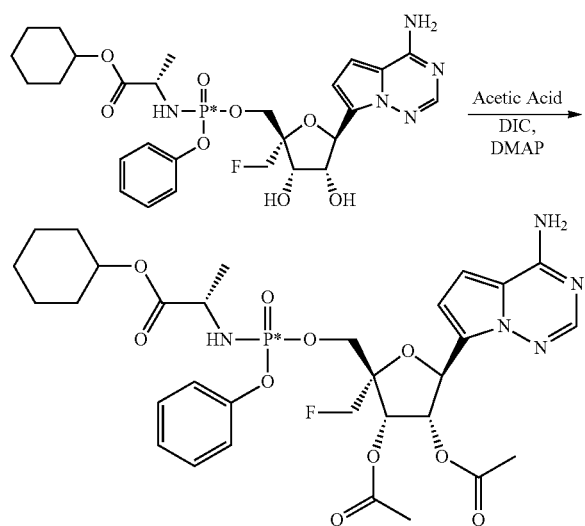

N,N'-Diisopropylcarbodiimide (42 mg, 0.33 mmol) and acetic acid (20 mg, 0.33 mmol) were dissolved in anhydrous tetrahydrofuran (1.0 mL) under argon and the mixture was stirred at rt for 30 minutes. Example 14 (40 mg, 0.07 mmol) and 4-dimethylaminopyridine (8 mg, 0.07 mmol) were added and the reaction mixture was stirred at rt. After 2 hours, methanol (0.5 mL) was added and the mixture was stirred for 20 minutes, then diluted with ethyl acetate (10 mL) and washed twice with saturated aqueous sodium bicarbonate solution (10 mL) and once with brine (10 mL). The organic layer was dried over anhydrous sodium sulfate and concentrated under reduced pressure. The crude residue was purified by preparatory HPLC (Phenomenex Gemini 5 µm C18 110 Å 100×30 mm column) using gradient from 10-100% acetonitrile in water to afford the product, which was determined to be a single diastereomer by NMR spectroscopy. $^1$H NMR (400 MHz, Chloroform-d) δ 7.92 (s, 1H), 7.32-7.25 (m, 3H), 7.25-7.20 (m, 2H), 7.17-7.10 (m, 1H), 6.62 (d, J=4.6 Hz, 1H), 6.51 (d, J=4.6 Hz, 1H), 5.86 (dd, J=7.5, 5.4 Hz, 1H), 5.80 (d, J=5.4 Hz, 1H), 5.64 (d, J=7.5 Hz, 1H), 4.75 (tt, J=8.8, 3.9 Hz, 1H), 4.71-4.63 (m, 1H), 4.60-4.52 (m, 1H), 4.33 (ddd, J=10.8, 5.7, 1.9 Hz, 1H), 4.25 (ddd, J=10.8, 5.8, 2.2 Hz, 1H), 4.08-3.97 (m, 2H), 2.12 (s, 3H), 2.00 (s, 3H), 1.96-1.62 (m, 4H), 1.57-1.17 (m, 7H). $^{19}$F NMR (376 MHz, Chloroform-d) 6-234.25 (t, J=46.8 Hz). $^{31}$P NMR (162 MHz, Chloroform-d) δ 2.69. LCMS: MS m/z=692.34 [M+1], $t_R$=1.51 min; LC system: Thermo Accela 1250 UHPLC; MS system: Thermo LCQ Fleet; Column: Kinetex 2.6 µXB-C18 100A, 50×4.6 mm; Solvents: acetonitrile with 0.1% acetic acid, water with 0.1% acetic acid; Gradient: 0 min-0.2 min 2% acetonitrile, 0.2 min-1.5 min 2-100% acetonitrile, 1.5 min-2.2 min 100% acetonitrile, 2.2 min-2.4 min 100%-2% acetonitrile, 2.4 min-2.5 min 2% acetonitrile at 2 µL/min. HPLC: $t_R$=3.30 min; HPLC system: Agilent 1100 series; Column: Gemini 5 µC18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

Example 16. (2R,3S,4S,5S)-5-(4-aminopyrrolo[2,1-f][1,2,4]triazin-7-yl)-2-(((((S)-1-(cyclohexyloxy)-1-oxopropan-2-yl)amino)(Phenoxy)phosphoryl)oxy)methyl)-2-(fluoromethyl)tetrahydrofuran-3,4-diyl dipropionate

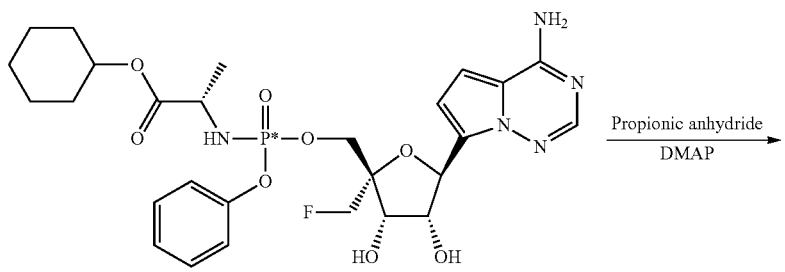

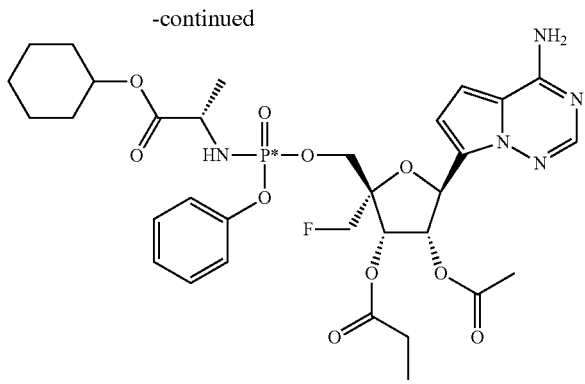

Proprionic anhydride (17 mg, 0.13 mmol) and Example 14 (40 mg, 0.07 mmol) were dissolved in anhydrous tetrahydrofuran (1.0 mL) under argon and the mixture was stirred at rt for 5 minutes. 4-Dimethylaminopyridine (8 mg, 0.07 mmol) was added and the reaction mixture was stirred at rt. After 2 hours, methanol (0.5 mL) was added and the mixture was stirred for 20 minutes, then diluted with ethyl acetate (10 mL) and washed twice with saturated aqueous sodium bicarbonate solution (10 mL) and once with brine (10 mL). The organic layer was dried over anhydrous sodium sulfate and concentrated under reduced pressure. The crude residue was purified by preparatory HPLC (Phenomenex Gemini 5 μm C18 110 Å 100×30 mm column) using gradient from 10-100% acetonitrile in water to afford the product, which was determined to be a single diastereomer by NMR spectroscopy. $^1$H NMR (400 MHz, Chloroform-d) δ 7.91 (s, 1H), 7.32-7.25 (m, 3H), 7.24-7.20 (m, 2H), 7.16-7.11 (m, 1H), 6.60 (d, J=4.6 Hz, 1H), 6.50 (d, J=4.6 Hz, 1H), 5.98-5.91 (m, 2H), 5.88 (dd, J=7.3, 5.4 Hz, 1H), 5.83 (d, J=5.4 Hz, 1H), 5.63 (d, J=7.3 Hz, 1H), 4.79-4.71 (m, 1H), 4.67 (d, J=4.0 Hz, 1H), 4.56 (d, J=5.0 Hz, 1H), 4.33 (ddd, J=10.8, 5.6, 1.8 Hz, 1H), 4.25 (ddd, J=10.8, 5.8, 2.2 Hz, 1H), 4.11-4.06 (m, 1H), 4.05-3.97 (m, 1H), 2.39 (q, J=7.6 Hz, 2H), 2.26 (qd, J=7.6, 1.9 Hz, 2H), 1.98 (d, J=14.2 Hz, 1H), 1.83-1.75 (m, 2H), 1.68 (t, J=8.1 Hz, 2H), 1.55-1.28 (m, 6H), 1.17 (t, J=7.6 Hz, 3H), 1.07 (t, J=7.6 Hz, 3H). $^{19}$F NMR (376 MHz, Chloroform-d) δ -234.18 (t, J=46.9 Hz). $^{31}$P NMR (162 MHz, Chloroform-d) δ 2.73. LCMS: MS m/z=720.60 [M+1], $t_R$=1.63 min; LC system: Thermo Accela 1250 UHPLC; MS system: Thermo LCQ Fleet; Column: Kinetex 2.6 μXB-C18 100A, 50×4.6 mm; Solvents: acetonitrile with 0.1% acetic acid, water with 0.1% acetic acid; Gradient: 0 min-0.2 min 2% acetonitrile, 0.2 min-1.5 min 2-100% acetonitrile, 1.5 min-2.2 min 100% acetonitrile, 2.2 min-2.4 min 100%-2% acetonitrile, 2.4 min-2.5 min 2% acetonitrile at 2 μl/min. HPLC: $t_R$=3.52 min; HPLC system: Agilent 1100 series; Column: Gemini 5 μC18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

Example 17. hexyl (((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate

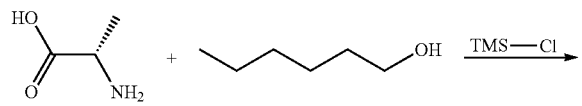

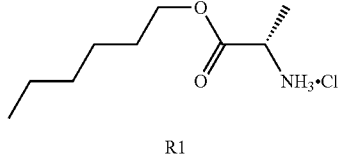

hexyl L-alaninate hydrochloride. L-Alanine (4.45 g, 50 mmol) was mixed with 1-hexanol (30 mL). TMS-Cl (19.1 mL, 150 mmol) was added dropwise and the reaction was stirred at RT for 16 hrs. More 1-hexanol (10 mL) and TMS-Cl (5 mL) were added. The reaction mixture was heated to 80° C. and stirred for 20 hrs. The reaction mixture was concentrated under reduced pressure. The resulting oil was dried under high vacuum and the oil slowly solidified to afford intermediate R1 as the hydrochloride salt. $^1$H NMR (400 MHz, Chloroform-d) δ 8.77 (s, 3H), 4.20 (m, 3H), 1.71 (m, 5H), 1.47-1.19 (m, 6H), 1.01-0.78 (m, 3H).

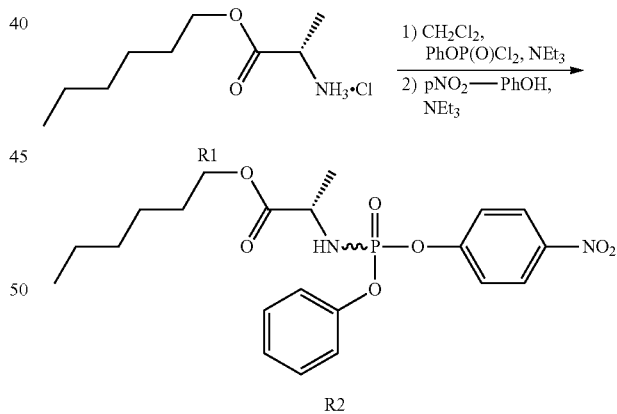

hexyl ((4-nitrophenoxy)(phenoxy)phosphoryl)-L-alaninate. Phenyl dichlorophosphate (3.7 mL, 25 mmol) was dissolved in anhydrous DCM (50 mL) and stirred in an ice bath under atmospheric nitrogen. Intermediate R1 (5.2 g, 25 mmol) was added in one portion. The reaction was stirred for 30 minutes. Triethylamine (8.4 mL, 60 mmol) was added dropwise and then stirred for 60 minutes. p-Nitrophenol (3.1 g, 22.5 mmol) and triethylamine (4.2 mL, 30 mmol) were added. Ice bath was removed and the reaction mixture was stirred for 16 hours at RT. Reaction was diluted with DCM (100 mL) and washed with water (3×20 mL). Organic was dried over anhydrous sodium sulfate and concentrated under reduced pressure. The crude residue was purified via SiO₂ column chromatography (120 g SiO₂ Combiflash HP Gold Column, 0-20% ethyl acetate/hexanes). Fractions were combined and concentrated under reduced pressure to afford intermediate R2 (diastereomeric mixture). $^1$H NMR (400 MHz, Chloroform-d) δ 8.25 (d, J=9.1 Hz, 2H), 7.51-7.32 (m, 4H), 7.32-7.15 (m, 3H), 4.14 (m, 3H), 3.93 (m, 1H), 1.62 (m, 2H), 1.44 (m, 3H), 1.39-1.20 (m, 6H), 0.99-0.82 (m, 3H). $^{31}$P NMR (162 MHz, Chloroform-d) δ-3.03 (s), −3.08 (s).

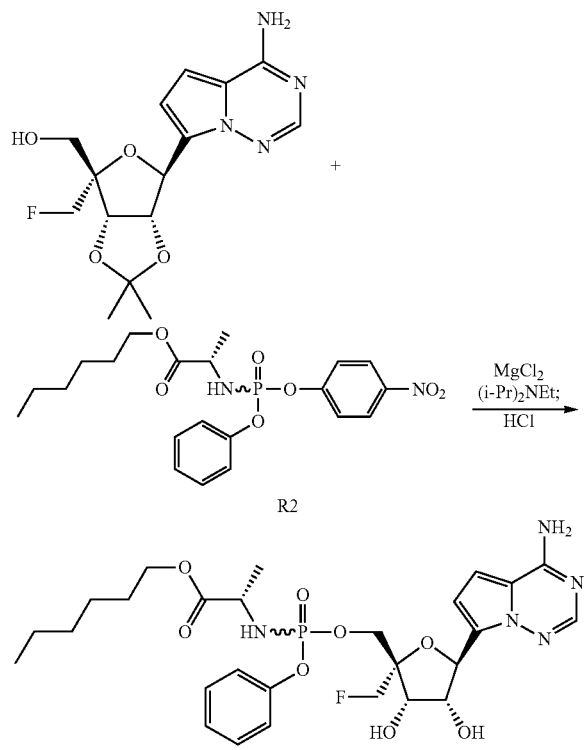

hexyl ((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate.

Tetrahydrofuran (1 mL) was added to a mixture of Intermediate 4 (100 mg, 0.296 mmol), intermediate R2 (173 mg, 0.384 mmol), and magnesium chloride (42 mg, 0.443 mmol) at rt. The mixture was heated to 50° C. for 10 min, and N,N-diisopropylethylamine (0.129 mL, 0.739 mmol) was added. After stirring for 3 hours at 50° C., the reaction mixture was allowed to cool to rt, and was concentrated down under reduced pressure. The crude residue was dissolved in ethyl acetate (20 mL) and the resulting mixture was washed with water (20 mL) and brine (20 mL). The organic layer was separated, dried over anhydrous sodium sulfate and concentrated under reduced pressure. The crude residue was dissolved in acetonitrile (7 mL) and concentrated aqueous hydrochloric acid solution (0.246 mL) was added dropwise at 0° C. After 2 hours at 0° C., the reaction mixture was diluted with ethyl acetate (30 mL) and water (20 mL) at 0° C. and the resulting mixture was washed with saturated aqueous sodium bicarbonate solution (20 mL) and brine (20 mL). The organic layer was dried over anhydrous sodium sulfate and concentrated under reduced pressure.

The crude residue was purified by preparatory HPLC (Phenomenex Gemini 5 μm C18 110 Å 100×30 mm column) using gradient from 10-100% acetonitrile in water to afford the product (diastereomeric mixture). $^1$H NMR (400 MHz, DMSO-d₆) δ 7.83 (s, 0.24 H), 7.83 (s, 0.76 H), 7.72 (bs, 2H), 7.41-7.33 (m, 2H), 7.26-7.14 (m, 3H), 6.88-6.82 (m, 1H), 6.70 (d, J=4.5 Hz, 0.26 H), 6.68 (d, J=4.5 Hz, 0.74 H), 6.13-5.99 (m, 1H), 5.37-5.06 (m, 3H), 4.74-4.44 (m, 3H), 4.25-4.11 (m, 1H), 4.06-3.93 (m, 4H), 3.90-3.76 (m, 1H), 1.58-1.44 (m, 2H), 1.34-1.11 (m, 9H), 0.87-0.74 (m, 3H). $^{19}$F NMR (376 MHz, DMSO-d₆) δ-236.47 (t, J=48.1 Hz), −236.76 (t, J=48.1 Hz). $^{31}$P NMR (162 MHz, DMSO-d₆) δ 3.55, 3.47. LCMS: MS m/z=610.16 [M+1], $t_R$=1.35 min (minor isomer) and 1.37 min (major isomer); LC system: Thermo Accela 1250 UHPLC; MS system: Thermo LCQ Fleet; Column: Kinetex 2.6 μXB-C18 100A, 50×4.6 mm; Solvents: acetonitrile with 0.1% acetic acid, water with 0.1% acetic acid; Gradient: 0 min-0.2 min 2% acetonitrile, 0.2 min-1.5 min 2-100% acetonitrile, 1.5 min-2.2 min 100% acetonitrile, 2.2 min-2.4 min 100%-2% acetonitrile, 2.4 min-2.5 min 2% acetonitrile at 2 μL/min. HPLC: $t_R$=3.02 min (minor isomer) and 3.06 min (major isomer); HPLC system: Agilent 1100 series; Column: Gemini 5 μC18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min. HPLC: $t_R$=5.16 min (minor isomer) and 5.23 min (major isomer); HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Resolution of the Sp and Rp diastereomers. The diastereomers were isolated from each other by chiral preparatory SFC (Chiralpak AD-H 5 μm, 21×250 mm; 30% methanol) to provide Example 18 and Example 19.

Example 18. hexyl ((R)-(((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate

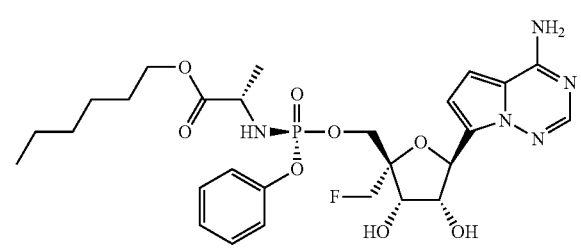 [SMILES: CCCCCCOC(=O)[C@H](C)N[P@@](=O)(OC[C@@]1(CF)O[C@@H](c2ccc3c(N)ncnn23)[C@H](O)[C@@H]1O)Oc1ccccc1]

First Eluting Diastereomer of Example 17: $^1$H NMR (400 MHz, DMSO-d₆) δ 7.83 (s, 1H), 7.36-7.28 (m, 2H), 7.23-7.09 (m, 3H), 6.88 (d, J=4.6 Hz, 1H), 6.69 (d, J=4.5 Hz, 1H), 5.99 (dd, J=13.0, 10.1 Hz, 1H), 5.22 (d, J=8.6 Hz, 1H), 4.69-4.57 (m, 1H), 4.54-4.42 (m, 2H), 4.17 (d, J=5.2 Hz, 1H), 4.03-3.90 (m, 4H), 3.84-3.69 (m, 1H), 1.53-1.40 (m, 2H), 1.30-1.05 (m, 9H), 0.82-0.73 (m, 3H). $^{19}$F NMR (376 MHz, DMSO-d$_6$) δ-236.46 (t, J=48.1 Hz). $^{31}$P NMR (162 MHz, DMSO-d$_6$) δ 3.54. LCMS: MS m/z=610.16 [M+1], $t_R$=1.35 min; LC system: Thermo Accela 1250 UHPLC; MS system: Thermo LCQ Fleet; Column: Kinetex 2.6 µXB-C18 100A, 50×4.6 mm; Solvents: acetonitrile with 0.1% acetic acid, water with 0.1% acetic acid; Gradient: 0 min-0.2 min 2% acetonitrile, 0.2 min-1.5 min 2-100% acetonitrile, 1.5 min-2.2 min 100% acetonitrile, 2.2 min-2.4 min 100%-2% acetonitrile, 2.4 min-2.5 min 2% acetonitrile at 2 µL/min. HPLC: $t_R$=3.02 min; HPLC system: Agilent 1100 series; Column: Gemini 5 µC18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min. HPLC: $t_R$=5.16 min; HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 19. hexyl ((S)-(((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate

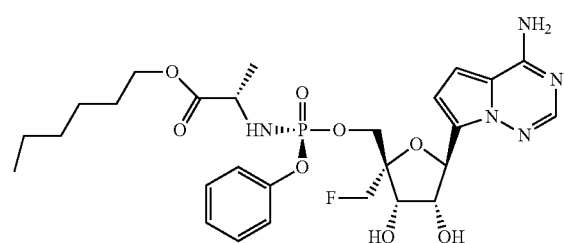 [SMILES: CCCCCCOC(=O)[C@H](C)N[P@](=O)(OC[C@@]1(CF)O[C@@H](c2ccc3c(N)ncnn23)[C@H](O)[C@@H]1O)Oc1ccccc1]

Second Eluting Diastereomer of Example 17: $^1$H NMR (400 MHz, DMSO-d$_6$) δ 7.83 (s, 1H), 7.73 (bs, 2H), 7.45-7.27 (m, 2H), 7.29-7.10 (m, 3H), 6.86 (d, J=4.5 Hz, 1H), 6.68 (d, J=4.5 Hz, 1H), 6.06 (dd, J=13.2, 10.1 Hz, 1H), 5.28-5.19 (m, 2H), 5.18-5.09 (m, 1H), 4.70-4.57 (m, 1H), 4.58-4.45 (m, 2H), 4.23-4.17 (m, 1H), 4.05-3.95 (m, 4H), 3.88-3.79 (m, 1H), 1.57-1.48 (m, 2H), 1.30-1.18 (m, 9H), 0.85-0.80 (m, 3H). $^{19}$F NMR (376 MHz, DMSO-d$_6$) δ-236.75 (t, J=48.1 Hz). $^{31}$P NMR (162 MHz, DMSO-d$_6$) δ 3.47. LCMS: MS m/z=610.16 [M+1], $t_R$=1.37 min; LC system: Thermo Accela 1250 UHPLC; MS system: Thermo LCQ Fleet; Column: Kinetex 2.6 µXB-C18 100A, 50×4.6 mm; Solvents: acetonitrile with 0.1% acetic acid, water with 0.1% acetic acid; Gradient: 0 min-0.2 min 2% acetonitrile, 0.2 min-1.5 min 2-100% acetonitrile, 1.5 min-2.2 min 100% acetonitrile, 2.2 min-2.4 min 100%-2% acetonitrile, 2.4 min-2.5 min 2% acetonitrile at 2 µl/min. HPLC: $t_R$=3.06 min; HPLC system: Agilent 1100 series; Column: Gemini 5 µC18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min. HPLC: $t_R$=5.23 min; HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 20. (2R,3S,4S,5S)-5-(4-aminopyrrolo[2,1-f][1,2,4]triazin-7-yl)-2-(fluoromethyl)-2-((((S)-(((S)-1-isopropoxy-1-oxopropan-2-yl)amino)(phenoxy)phosphoryl)oxy)methyl) tetrahydrofuran-3,4-diyl diacetate

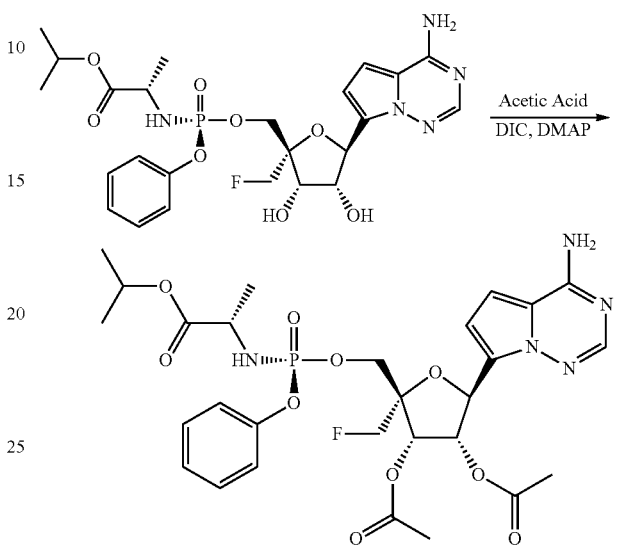

N,N'-Diisopropylcarbodiimide (56 mg, 0.44 mmol) and acetic acid (26 mg, 0.44 mmol) were dissolved in anhydrous tetrahydrofuran (2.0 mL) under argon and the mixture was stirred at rt for 30 minutes. Example 12 (50 mg, 0.09 mmol) and 4-dimethylaminopyridine (11 mg, 0.09 mmol) were added and the reaction mixture was stirred at rt. After 2 hours, methanol (0.5 mL) was added and the mixture was stirred for 20 minutes, then diluted with ethyl acetate (10 mL) and washed twice with saturated aqueous sodium bicarbonate solution (10 mL) and once with brine (10 mL). The organic layer was dried over anhydrous sodium sulfate and concentrated under reduced pressure. The crude residue was purified by preparatory HPLC (Phenomenex Gemini 5 µm C18 110 Å 100×30 mm column) using gradient from 10-100% acetonitrile in water to afford the product, which was determined to be a single diastereomer by NMR spectroscopy. $^1$H NMR (400 MHz, DMSO-d$_6$) δ 7.86 (s, 1H), 7.80 (bs, 2H), 7.41-7.32 (m, 2H), 7.28-7.11 (m, 3H), 6.83 (d, J=4.5 Hz, 1H), 6.66 (d, J=4.5 Hz, 1H), 6.13 (dd, J=13.2, 10.1 Hz, 1H), 5.75 (dd, J=8.7, 5.5 Hz, 1H), 5.67 (d, J=5.4 Hz, 1H), 5.53 (d, J=8.7 Hz, 1H), 4.86 (hept, J=6.2 Hz, 1H), 4.73-4.61 (m, 1H), 4.61-4.49 (m, 1H), 4.21-4.07 (m, 2H), 3.89-3.71 (m, 1H), 2.13 (s, 3H), 1.93 (s, 3H), 1.21 (d, J=7.0 Hz, 3H), 1.15 (dd, J=6.2, 2.8 Hz, 6H). $^{19}$F NMR (376 MHz, DMSO-d$_6$) δ-234.62 (t, J=46.9 Hz). $^{31}$P NMR (162 MHz, DMSO-d$_6$) δ3.49. LCMS: MS m/z=652.41 [M+1], $t_R$=1.38 min; LC system: Thermo Accela 1250 UHPLC; MS system: Thermo LCQ Fleet; Column: Kinetex 2.6 µXB-C18 100A, 50×4.6 mm; Solvents: acetonitrile with 0.1% acetic acid, water with 0.1% acetic acid; Gradient: 0 min-0.2 min 2% acetonitrile, 0.2 min-1.5 min 2-100% acetonitrile, 1.5 min-2.2 min 100% acetonitrile, 2.2 min-2.4 min 100%-2% acetonitrile, 2.4 min-2.5 min 2% acetonitrile at 2 µL/min. HPLC: $t_R$=2.98 min; HPLC system: Agilent 1100 series; Column: Gemini 5 µC18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min. HPLC: $t_R$=5.03 min; HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 21. (2R,3S,4S,5S)-5-(4-aminopyrrolo[2,1-f][1,2,4]triazin-7-yl)-2-(((((S)-1-ethoxy-1-oxopropan-2-yl)amino)(phenoxy)phosphoryl)oxy)methyl)-2-(fluoromethyl)tetrahydrofuran-3,4-diyl diacetate

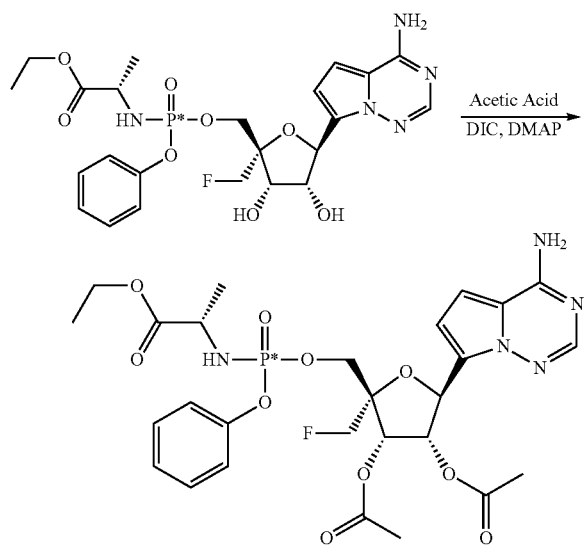

N,N'-Diisopropylcarbodiimide (57 mg, 0.45 mmol) and acetic acid (27 mg, 0.45 mmol) were dissolved in anhydrous tetrahydrofuran (2.0 mL) under argon and the mixture was stirred at rt for 30 minutes. Example 13 (50 mg, 0.09 mmol) and 4-dimethylaminopyridine (11 mg, 0.09 mmol) were added and the reaction mixture was stirred at rt. After 2 hours, methanol (0.5 mL) was added and the mixture was stirred for 20 minutes, then diluted with ethyl acetate (10 mL) and washed twice with saturated aqueous sodium bicarbonate solution (10 mL) and once with brine (10 mL). The organic layer was dried over anhydrous sodium sulfate and concentrated under reduced pressure. The crude residue was purified by preparatory HPLC (Phenomenex Gemini 5 μm C18 110 Å 100×30 mm column) using gradient from 10-100% acetonitrile in water to afford the product, which was determined to be a single diastereomer by NMR spectroscopy. $^1$H NMR (400 MHz, DMSO-$d_6$) δ 7.86 (s, 1H), 7.80 (bs, 2H), 7.40-7.33 (m, 2H), 7.25-7.16 (m, 3H), 6.83 (d, J=4.5 Hz, 1H), 6.66 (d, J=4.5 Hz, 1H), 6.16 (dd, J=13.3, 10.1 Hz, 1H), 5.75 (dd, J=8.7, 5.5 Hz, 1H), 5.67 (d, J=5.4 Hz, 1H), 5.53 (d, J=8.7 Hz, 1H), 4.74-4.44 (m, 2H), 4.21-4.09 (m, 2H), 4.05-3.97 (m, 2H), 3.91-3.75 (m, 1H), 2.13 (s, 3H), 1.93 (s, 3H), 1.22 (d, J=7.0 Hz, 3H), 1.14 (t, J=7.1 Hz, 3H). $^{19}$F NMR (376 MHz, DMSO-$d_6$) δ-234.59 (t, J=46.8 Hz). $^{31}$P NMR (162 MHz, DMSO-$d_6$) δ 3.44. LCMS: MS m/z=638.26 [M+1], $t_R$=1.32 min; LC system: Thermo Accela 1250 UHPLC; MS system: Thermo LCQ Fleet; Column: Kinetex 2.6 μXB-C18 100A, 50×4.6 mm; Solvents: acetonitrile with 0.1% acetic acid, water with 0.1% acetic acid; Gradient: 0 min-0.2 min 2% acetonitrile, 0.2 min-1.5 min 2-100% acetonitrile, 1.5 min-2.2 min 100% acetonitrile, 2.2 min-2.4 min 100%-2% acetonitrile, 2.4 min-2.5 min 2% acetonitrile at 2 μL/min. HPLC: $t_R$=2.84 min; HPLC system: Agilent 1100 series; Column: Gemini 5 μC18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min. HPLC: $t_R$=4.78 min; HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 22. (2R,3S,4S,5S)-5-(4-aminopyrrolo[2,1-f][1,2,4]triazin-7-yl)-2-(fluoromethyl)-2-((((S)-(((S)-1-isopropoxy-1-oxopropan-2-yl)amino)(phenoxy)phosphoryl)oxy)methyl) tetrahydrofuran-3,4-diyl dipropionate

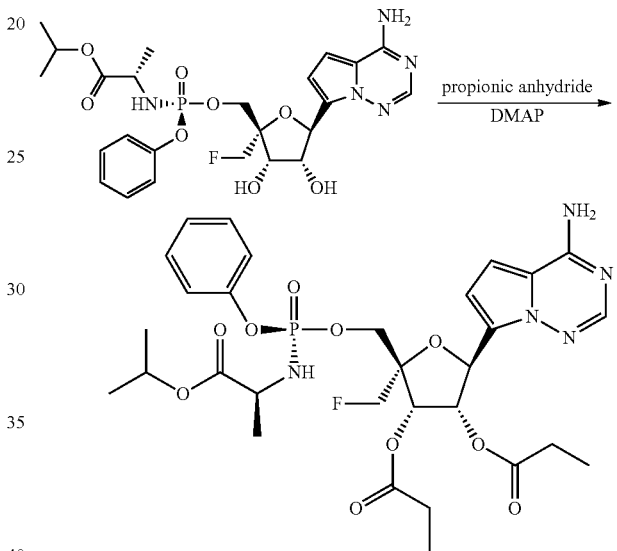

Example 12 (50 mg, 0.09 mmol) was dissolved in anhydrous tetrahydrofuran (2.0 mL) under argon. Propionic anhydride (24 mg, 0.19 mmol) and 4-dimethylaminopyridine (1 mg, 0.01 mmol) were added and the reaction mixture was stirred at rt. After 30 minutes, the reaction mixture was diluted with ethyl acetate (10 mL) and washed twice with saturated aqueous sodium bicarbonate solution (10 mL) and once with brine (10 mL). The organic layer was dried over anhydrous sodium sulfate and concentrated under reduced pressure. The crude residue was purified by preparatory HPLC (Phenomenex Gemini 5 μm C18 110 Å 100×30 mm column) using gradient from 10-100% acetonitrile in water to afford the product, which was determined to be a single diastereomer by NMR spectroscopy. $^1$H NMR (400 MHz, DMSO-$d_6$) δ 7.85 (s, 1H), 7.80 (bs, 2H), 7.41-7.32 (m, 2H), 7.28-7.13 (m, 3H), 6.83 (d, J=4.5 Hz, 1H), 6.66 (d, J=4.5 Hz, 1H), 6.13 (dd, J=13.2, 10.1 Hz, 1H), 5.78 (dd, J=8.5, 5.5 Hz, 1H), 5.69 (d, J=5.5 Hz, 1H), 5.53 (d, J=8.5 Hz, 1H), 4.96-4.76 (m, 1H), 4.73-4.62 (m, 1H), 4.62-4.47 (m, 1H), 4.26-4.05 (m, 2H), 3.91-3.68 (m, 1H), 2.46-2.37 (m, 2H), 2.31-2.00 (m, 2H), 1.21 (d, J=7.1 Hz, 3H), 1.14 (dd, J=6.2, 2.4 Hz, 6H), 1.07 (t, J=7.5 Hz, 3H), 0.93 (t, J=7.5 Hz, 3H). $^{19}$F NMR (376 MHz, DMSO-$d_6$) δ-234.55 (t, J=46.8 Hz). $^{31}$P NMR (162 MHz, DMSO-$d_6$) δ 3.50. LCMS: MS m/z=680.51 [M+1], $t_R$=1.48 min; LC system: Thermo Accela 1250 UHPLC; MS system: Thermo LCQ Fleet;

Column: Kinetex 2.6 μXB-C18 100A, 50×4.6 mm; Solvents: acetonitrile with 0.1% acetic acid, water with 0.1% acetic acid; Gradient: 0 min-0.2 min 2% acetonitrile, 0.2 min-1.5 min 2-100% acetonitrile, 1.5 min-2.2 min 100% acetonitrile, 2.2 min-2.4 min 100%-2% acetonitrile, 2.4 min-2.5 min 2% acetonitrile at 2 μl/min. HPLC: $t_R$=3.23 min; HPLC system: Agilent 1100 series; Column: Gemini 5 μC18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min. HPLC: $t_R$=5.50 min; HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 23. (2R,3S,4S,5S)-5-(4-aminopyrrolo[2,1-f][1,2,4]triazin-7-yl)-2-(fluoromethyl)-2-((((S)-(((S)-1-isopropoxy-1-oxopropan-2-yl)amino)(phenoxy)phosphoryl)oxy)methyl) tetrahydrofuran-3,4-diyl bis(2-methylpropanoate)

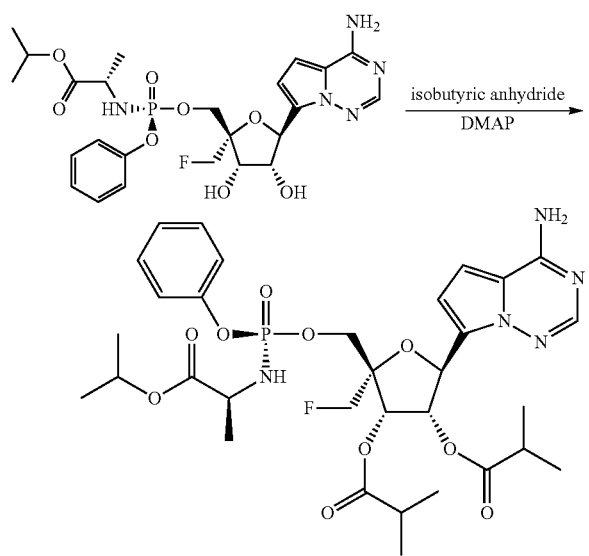

Example 12 (50 mg, 0.09 mmol) was dissolved in anhydrous tetrahydrofuran (2.0 mL) under argon. Isobutyric anhydride (29 mg, 0.19 mmol) and 4-dimethylaminopyridine (1 mg, 0.01 mmol) were added and the reaction mixture was stirred at rt. After 4 hours, the reaction mixture was diluted with ethyl acetate (10 mL) and washed twice with saturated aqueous sodium bicarbonate solution (10 mL) and once with brine (10 mL). The organic layer was dried over anhydrous sodium sulfate and concentrated under reduced pressure. The crude residue was purified by preparatory HPLC (Phenomenex Gemini 5 μm C18 110 Å 100×30 mm column) using gradient from 10-100% acetonitrile in water to afford the product, which was determined to be a single diastereomer by NMR spectroscopy. $^1$H NMR (400 MHz, DMSO-d$_6$) δ 7.85 (s, 1H), 7.78 (bs, 2H), 7.41-7.31 (m, 2H), 7.26-7.13 (m, 3H), 6.82 (d, J=4.5 Hz, 1H), 6.64 (d, J=4.5 Hz, 1H), 6.13 (dd, J=13.2, 10.0 Hz, 1H), 5.75 (dd, J=8.3, 5.4 Hz, 1H), 5.69 (d, J=5.5 Hz, 1H), 5.53 (d, J=8.3 Hz, 1H), 4.86 (hept, J=6.3 Hz, 1H), 4.74-4.63 (m, 1H), 4.63-4.51 (m, 1H), 4.23-4.06 (m, 2H), 3.90-3.70 (m, 1H), 2.73-2.58 (m, 1H), 2.41 (hept, J=7.0 Hz, 1H), 1.21 (d, J=7.1 Hz, 3H), 1.17-1.10 (m, 12H), 0.95 (dd, J=17.5, 7.0 Hz, 6H). $^{19}$F NMR (376 MHz, DMSO-d$_6$) δ-234.04 (t, J=46.7 Hz). $^{31}$P NMR (162 MHz, DMSO-d$_6$) δ 3.53. LCMS: MS m/z=708.42 [M+1], $t_R$=1.61 min; LC system: Thermo Accela 1250 UHPLC; MS system: Thermo LCQ Fleet; Column: Kinetex 2.6 μXB-C18 100A, 50×4.6 mm; Solvents: acetonitrile with 0.1% acetic acid, water with 0.1% acetic acid; Gradient: 0 min-0.2 min 2% acetonitrile, 0.2 min-1.5 min 2-100% acetonitrile, 1.5 min-2.2 min 100% acetonitrile, 2.2 min-2.4 min 100%-2% acetonitrile, 2.4 min-2.5 min 2% acetonitrile at 2 μl/min. HPLC: $t_R$=3.46 min; HPLC system: Agilent 1100 series; Column: Gemini 5 μC18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min. HPLC: $t_R$=5.92 min; HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 24. (2R,3S,4S,5S)-5-(4-aminopyrrolo[2,1-f][1,2,4]triazin-7-yl)-2-((((((S)-1-ethoxy-1-oxopropan-2-yl)amino)(phenoxy)phosphoryl)oxy)methyl)-2-(fluoromethyl) tetrahydrofuran-3,4-diyl bis(2-methylpropanoate)

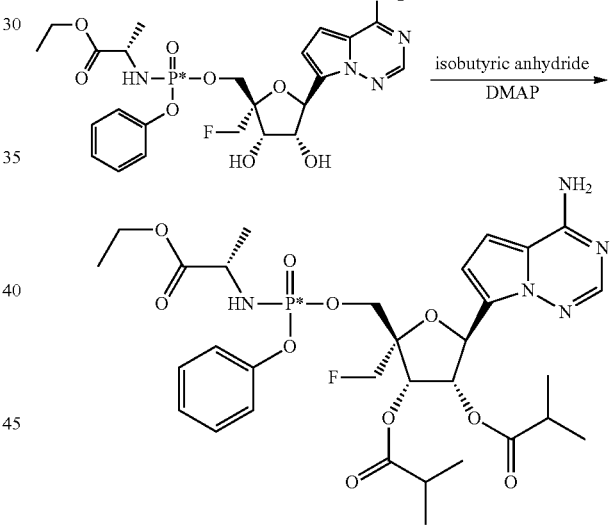

Example 13 (50 mg, 0.09 mmol) was dissolved in anhydrous tetrahydrofuran (2.0 mL) under argon. Isobutyric anhydride (30 mg, 0.19 mmol) and 4-dimethylaminopyridine (1 mg, 0.01 mmol) were added and the reaction mixture was stirred at rt. After 4 hours, the reaction mixture was diluted with ethyl acetate (10 mL) and washed twice with saturated aqueous sodium bicarbonate solution (10 mL) and once with brine (10 mL). The organic layer was dried over anhydrous sodium sulfate and concentrated under reduced pressure. The crude residue was purified by preparatory HPLC (Phenomenex Gemini 5 μm C18 110 Å 100×30 mm column) using gradient from 10-100% acetonitrile in water to afford the product, which was determined to be a single diastereomer by NMR spectroscopy. $^1$H NMR (400 MHz, DMSO-d$_6$) δ 7.85 (s, 1H), 7.79 (bs, 2H), 7.40-7.32 (m, 2H), 7.26-7.14 (m, 3H), 6.82 (d, J=4.5 Hz, 1H), 6.64 (d, J=4.5 Hz, 1H), 6.16 (dd, J=13.3, 10.1 Hz, 1H), 5.75 (dd, J=8.4, 5.5 Hz, 1H), 5.69 (d, J=5.5 Hz, 1H), 5.53 (d, J=8.3 Hz, 1H), 4.77-4.65 (m, 1H), 4.62-4.51 (m, 1H), 4.21-4.12 (m, 2H), 4.10-3.96 (m, 2H), 3.95-3.73 (m, 1H), 2.65 (hept, J=7.0 Hz, 1H), 2.41 (hept, J=7.0 Hz, 1H), 1.22 (d, J=7.0 Hz, 3H), 1.18-1.03 (m, 9H), 0.96 (dd, J=17.6, 7.0 Hz, 6H). $^{19}$F NMR (376 MHz, DMSO-$d_6$) δ-234.01 (t, J=46.7 Hz). $^{31}$P NMR (162 MHz, DMSO-$d_6$) δ 3.49. LCMS: MS m/z=694.42 [M+1], $t_R$=1.55 min; LC system: Thermo Accela 1250 UHPLC; MS system: Thermo LCQ Fleet; Column: Kinetex 2.6 µXB-C18 100A, 50×4.6 mm; Solvents: acetonitrile with 0.1% acetic acid, water with 0.1% acetic acid; Gradient: 0 min-0.2 min 2% acetonitrile, 0.2 min-1.5 min 2-100% acetonitrile, 1.5 min-2.2 min 100% acetonitrile, 2.2 min-2.4 min 100%-2% acetonitrile, 2.4 min-2.5 min 2% acetonitrile at 2 µl/min. HPLC: $t_R$=3.34 min; HPLC system: Agilent 1100 series; Column: Gemini 5 µC18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min. HPLC: $t_R$=5.70 min; HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 25. (2R,3S,4S,5S)-5-(4-aminopyrrolo[2,1-f][1,2,4]triazin-7-yl)-2-((((((S)-1-ethoxy-1-oxopropan-2-yl)amino)(Phenoxy)phosphoryl)oxy)methyl)-2-(fluoromethyl) tetrahydrofuran-3,4-diyl dipropionate

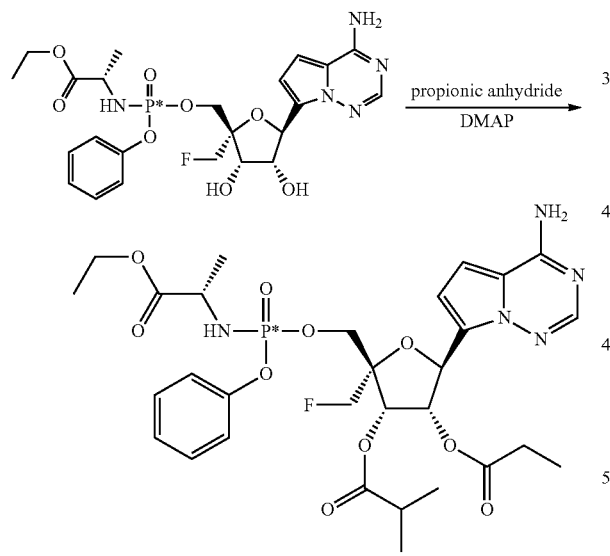

Example 13 (50 mg, 0.09 mmol) was dissolved in anhydrous tetrahydrofuran (2.0 mL) under argon. Propionic anhydride (25 mg, 0.19 mmol) and 4-dimethylaminopyridine (1 mg, 0.01 mmol) were added and the reaction mixture was stirred at rt. After 30 minutes, the reaction mixture was diluted with ethyl acetate (10 mL) and washed twice with saturated aqueous sodium bicarbonate solution (10 mL) and once with brine (10 mL). The organic layer was dried over anhydrous sodium sulfate and concentrated under reduced pressure. The crude residue was purified by preparatory HPLC (Phenomenex Gemini 5 µm C18 110 Å 100×30 mm column) using gradient from 10-100% acetonitrile in water to afford the product, which was determined to be a single diastereomer by NMR spectroscopy. $^1$H NMR (400 MHz, DMSO-$d_6$) δ 7.85 (s, 1H), 7.79 (bs, 2H), 7.41-7.31 (m, 2H), 7.27-7.14 (m, 3H), 6.83 (d, J=4.5 Hz, 1H), 6.66 (d, J=4.5 Hz, 1H), 6.16 (dd, J=13.3, 10.1 Hz, 1H), 5.78 (dd, J=8.6, 5.5 Hz, 1H), 5.69 (d, J=5.5 Hz, 1H), 5.53 (d, J=8.5 Hz, 1H), 4.73-4.62 (m, 1H), 4.61-4.49 (m, 1H), 4.21-4.11 (m, 2H), 4.09-3.98 (m, 2H), 3.91-3.74 (m, 1H), 2.46-2.37 (m, 2H), 2.29-2.12 (m, 2H), 1.22 (d, J=7.0 Hz, 3H), 1.14 (t, J=7.1 Hz, 3H), 1.07 (t, J=7.5 Hz, 3H), 0.93 (t, J=7.5 Hz, 3H). $^{19}$F NMR (376 MHz, DMSO-$d_6$) δ-234.52 (t, J=46.8 Hz). $^{31}$P NMR (162 MHz, DMSO-$d_6$) δ 3.45. LCMS: MS m/z=666.35 [M+1], $t_R$=1.43 min; LC system: Thermo Accela 1250 UHPLC; MS system: Thermo LCQ Fleet; Column: Kinetex 2.6 µXB-C18 100A, 50×4.6 mm; Solvents: acetonitrile with 0.1% acetic acid, water with 0.1% acetic acid; Gradient: 0 min-0.2 min 2% acetonitrile, 0.2 min-1.5 min 2-100% acetonitrile, 1.5 min-2.2 min 100% acetonitrile, 2.2 min-2.4 min 100%-2% acetonitrile, 2.4 min-2.5 min 2% acetonitrile at 2 µl/min. HPLC: $t_R$=3.11 min; HPLC system: Agilent 1100 series; Column: Gemini 5 µC18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min. HPLC: $t_R$=5.27 min; HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 26. 2-hydroxy-2-methylpropyl ((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate

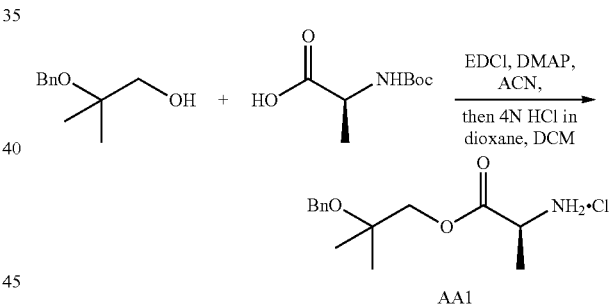

(S)-1-(2-(Benzyloxy)-2-methylpropoxy)-1-oxopropan-2-aminium chloride. To a mixture of Boc-L-alanine (1.26 g, 6.66 mmol), 2-benzyloxy-2-methylpropanol (1.0 g, 5.55 mmol), and EDCI (1.12 g, 7.21 mmol) in acetonitrile (20 mL) was added DMAP (2.04 g, 8.32 mmol). Then the mixture was stirred at room temperature for 2 h, then diluted with EtOAc, washed with brine, dried over sodium sulfate, and concentrated in vacuo. The obtained residue was purified by silica gel chromatography (EtOAc 0 to 60% in hexanes) to give a Boc-L-alanine propyl ester, which was dissolved in DCM (10 mL) and 4 N HCl in dioxane (5.5 mL, 22.19 mmol) was added at room temperature. The resulting mixture was stirred at room temperature for 2 h, concentrated in vacuo, re-dissolved in ACN (10 mL), lyophilized overnight to afford intermediate AA1 and used in next reaction. $^1$H NMR (400 MHz, Chloroform-d) δ 8.82 (s, 3H), 7.42-7.07 (m, 5H), 4.44 (s, 2H), 4.24 (m, 2H), 4.08 (d, J=11.2 Hz, 1H), 1.70 (d, J=7.0 Hz, 3H), 1.28 (d, J=2.4 Hz, 6H). LCMS m/z=251.97 [freebase M+1], $t_R$=0.85 min; LC system: Thermo Accela 1250 UHPLC; MS system: Thermo LCQ Fleet; Column: Phenomenex Kinetex 2.6 μXB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min

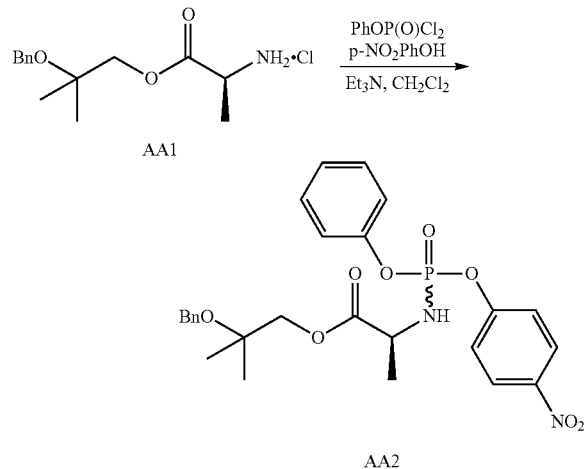

AA1

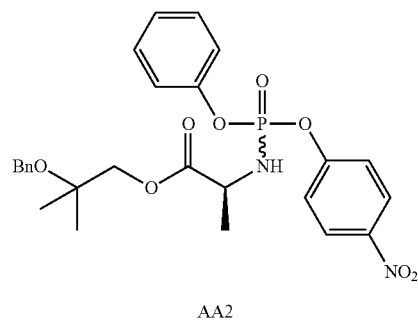

AA2

2-(benzyloxy)-2-methylpropyl ((4-nitrophenoxy)(phenoxy) phosphoryl)-L-alaninate. To a solution of intermediate AA1 (832 mg, 2.89 mmol) in DCM (20 mL) was added phenyl phosphorodichloridate (0.43 mL, 2.89 mmol) in one portion at −78° C. and triethylamine (0.80 mL, 5.76 mmol) was added dropwise over 5 min at −78° C. The resulting mixture was stirred for 30 min after removal of dry ice bath and cooled to −78° C. and p-nitrophenol (402 mg, 2.89 mmol) was added in one portion and triethylamine (0.40 mL, 2.89 mmol) was added over 5 min at −78° C. The resulting mixture was stirred for 50 min after removal of the dry ice bath, then diluted with DCM, washed with brine, concentrated in vacuo, and the resulting residue purified by silica gel column chromatography (EtOAc 0 to 60% in hexanes) to give intermediate AA2 (diastereomeric mixture). $^1$H NMR (400 MHz, Chloroform-d) δ 8.25-8.12 (m, 2H), 7.41-7.14 (m, 12H), 4.45 (m, 2H), 4.31-4.12 (m, 2H), 4.07 (m, 1H), 3.89 (m, 1H), 1.41 (m, 3H), 1.27 (m, 6H). $^{31}$P NMR (162 MHz, Chloroform-d) δ-3.10, −3.18. LCMS m/z=528.78 [M+1], $t_R$=1.70 min; LC system: Thermo Accela 1250 UHPLC; MS system: Thermo LCQ Fleet; Column: Phenomenex Kinetex 2.6 μXB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min -continued

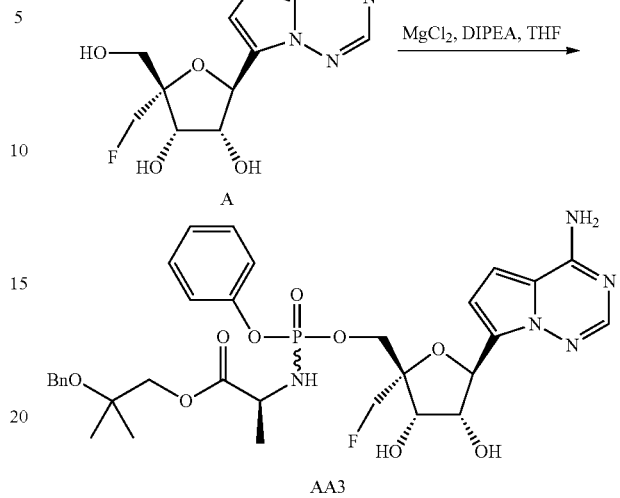

2-(benzyloxy)-2-methylpropyl ((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate. To a mixture of Intermediate 5 (0.04 g, 0.134 mmol), intermediate AA2 (0.081 g, 0.153 mmol), and magnesium chloride (0.064 g, 0.671 mmol) was added N,N-dimethylformamide (2 mL) at room temperature followed by the addition of N,N-diisopropylethylamine (0.07 mL, 0.402 mmol). The resulting mixture was stirred at 50° C. for 3 h. The reaction mixture was then purified by preparative HPLC (Phenominex Synergi 4u Hydro-RR 80 Å 150×30 mm column, 0-100% acetonitrile/water) to afford intermediate AA3. LCMS: MS m/z=688.18 [M+1], $t_R$=1.20 min (major isomer) and 1.22 min (minor isomer); LC system: Thermo Accela 1250 UHPLC; MS system: Thermo LCQ Fleet; Column: Phenomenex Kinetex 2.6 μXB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min.

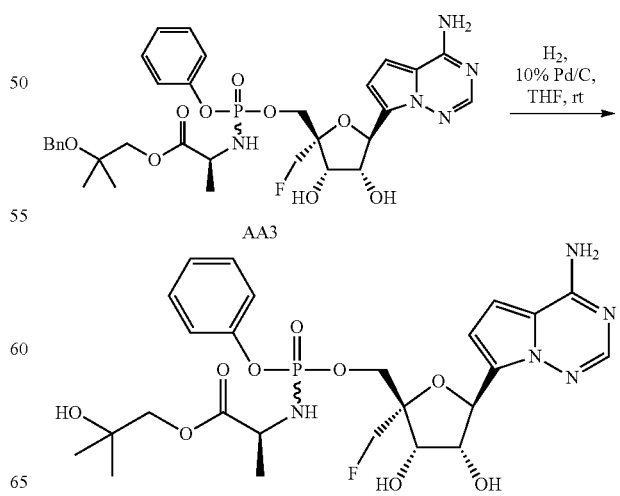

2-hydroxy-2-methylpropyl ((((2R,3S,4R,5S)-5-(4-amino-pyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate. To a solution of intermediate AA3 (14 mg, 0.02 mmol) in THF (2 mL) was added 10% Pd/C (11 mg, 0.01 mmol). The resulting mixture was stirred at room temperature for 15 h under $H_2$ gas and filtered. The filtrate was concentrated in vacuo, dissolved in ACN, and purified by prep. HPLC (Phenominex Gemini-NX 10u C18 110 250×30 mm column, ACN 10 to 100% in water) to give the product, as a diastereomeric mixture. $^1$H NMR (400 MHz, Methanol-$d_4$) δ 7.79 (s, 1H), 7.39-7.27 (m, 2H), 7.28-7.13 (m, 3H), 6.85 (dd, J=6.9, 4.5 Hz, 1H), 6.74 (dd, J=11.1, 4.5 Hz, 1H), 5.36 (dd, J=8.3, 5.9 Hz, 1H), 4.83-4.68 (m, 1H), 4.73-4.64 (m, 1H), 4.69-4.56 (m, 1H), 4.36 (dd, J=16.6, 5.2 Hz, 1H), 4.30-4.15 (m, 2H), 4.05-3.92 (m, 1H), 3.96-3.86 (m, 2H), 1.32 (ddd, J=19.2, 7.2, 1.1 Hz, 3H), 1.18-1.19 (m, 6H). $^{31}$P NMR (162 MHz, Methanol-$d_4$) δ 3.78, 3.54 $^{19}$F NMR (376 MHz, Methanol-$d_4$) −238.51-238.97 (m).

LCMS: MS m/z=598.05 [M+1], $t_R$=0.94 min; LC system: Thermo Accela 1250 UHPLC; MS system: Thermo LCQ Fleet; Column: Phenomenex Kinetex 2.6 μXB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=3.697 min (major isomer), 3.734 min (minor isomer); HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 27. (2R,3S,4S,5S)-5-(4-aminopyrrolo[2,1-f][1,2,4]triazin-7-yl)-2-(fluoromethyl)-2-((((((S)-1-(2-hydroxy-2-methylpropoxy)-1-oxopropan-2-yl)amino)(phenoxy) phosphoryl)oxy)methyl) tetrahydrofuran-3,4-diyl bis(2-methylpropanoate)

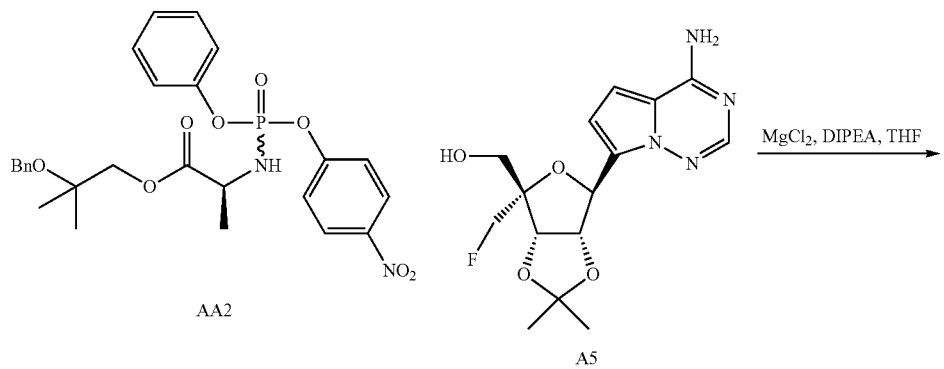

AA2

A5

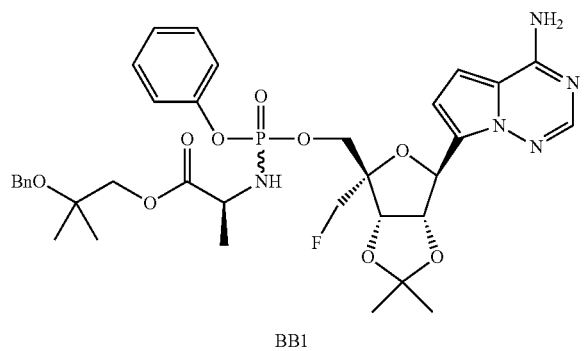

BB1

2-(benzyloxy)-2-methylpropyl ((((3aS,4R,6S,6aS)-6-(4-aminopyrrolo[2,1-f][1,2,4]triazin-7-yl)-4-(fluoromethyl)-2,2-dimethyltetrahydrofuro[3,4-d][1,3]dioxol-4-yl)methoxy)(phenoxy)phosphoryl)-L-alaninate. To a mixture of Intermediate 4 (0.2 g, 0.591 mmol), intermediate AA2 (0.375 g, 0.709 mmol), and magnesium chloride (0.112 g, 1.182 mmol) was added tetrahydrofuran (2.5 mL) at room temperature followed by the addition of N,N-diisopropylethylamine (0.258 mL, 1.478 mmol). The resulting mixture was stirred at 50° C. for 2 h. The reaction mixture was then then diluted with EtOAc, washed with brine, dried over sodium sulfate, and concentrated in vacuo. The obtained residue was purified by silica gel chromatography (EtOAc 0 to 100% in hexanes) to afford intermediate BB1 (diastereomeric mixture). LCMS: MS m/z=728.18 [M+1], $t_R$=1.39 min (minor isomer) and 1.42 min (major isomer); LC system: Thermo Accela 1250 UHPLC; MS system: Thermo LCQ Fleet; Column: Phenomenex Kinetex 2.6 μXB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min.

2-(benzyloxy)-2-methylpropyl ((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate. To an ice cold solution of intermediate BB1 (0.35 g, 0.481 mmol) in acetonitrile (14 mL) was added concentrated hydrochloric acid (0.35 mL, 9.6 mmol) dropwise. Reaction mixture was stirred at 0° C. for 4 h. The reaction mixture was then diluted with ice and neutralized with aqueous saturated sodium bicarbonate solution. The reaction mixture was extracted with ethyl acetate and the organic layer was separated, dried over sodium sulfate, filtered and concentrated. The obtained residue was purified by silica gel chromatography (0-20% methanol/dichloromethane) to afford intermediate BB2 (diastereomeric mixture). $^1$H NMR (400 MHz, Methanol-$d_4$) δ 7.78 (d, J=1.1 Hz, 1H), 7.38-7.12 (m, 10H), 6.88-6.81 (m, 1H), 6.74 (dd, J=8.3, 4.5 Hz, 1H), 5.36 (dd, J=8.3, 6.6 Hz, 1H), 4.82-4.67 (m, 1H), 4.71-4.63 (m, 1H), 4.67-4.55 (m, 1H), 4.45 (d, J=4.8 Hz, 2H), 4.34 (dd, J=16.4, 5.2 Hz, 1H), 4.29-4.12 (m, 3H), 4.10-3.90 (m, 2H), 1.35-1.21 (m, 9H). $^{19}$F NMR (376 MHz, Methanol-$d_4$) δ-238.39-238.76 (m). $^{31}$P NMR (162 MHz, Methanol-$d_4$) δ 3.69, 3.49. LCMS: MS m/z=688.10 [M+1]; $t_R$=1.20 min; LC system: Thermo Accela 1250 UHPLC; MS system: Thermo LCQ Fleet; Column: Phenomenex Kinetex 2.6 μXB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min.

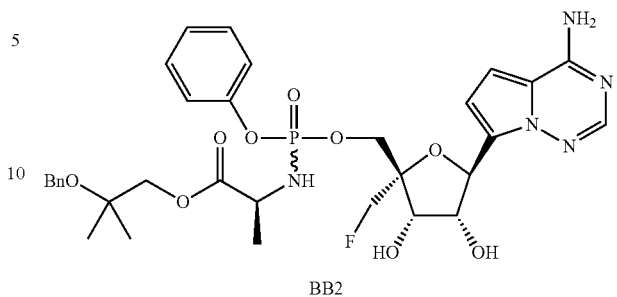

BB2

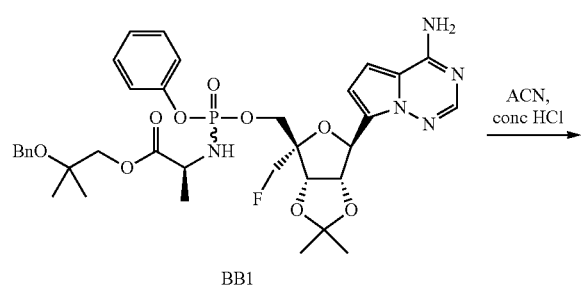

BB1

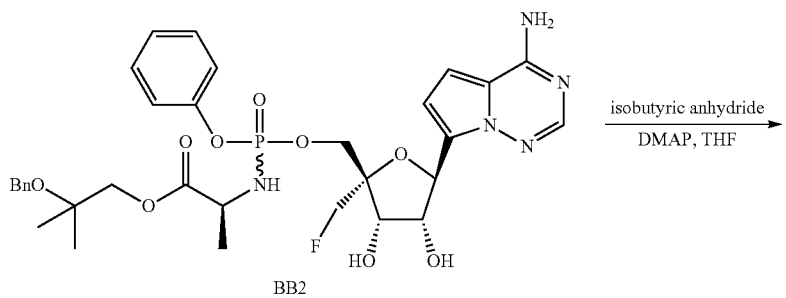

BB2

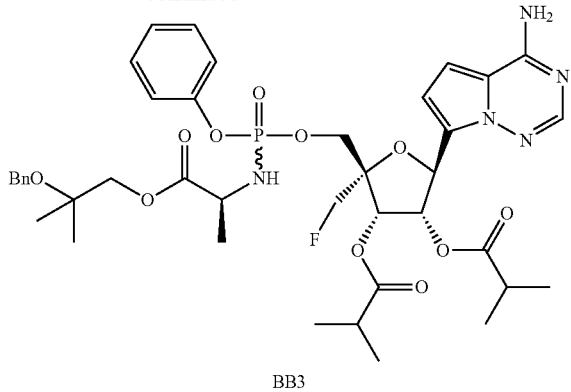

BB3

(2R,3S,4S,5S)-5-(4-Aminopyrrolo[2,1-f][1,2,4]triazin-7-yl)-2-((((((S)-1-(2-(benzyloxy)-2-methylpropoxy)-1-oxopropan-2-yl)amino)(phenoxy)phosphoryl)-oxy)methyl)-2-(fluoromethyl)tetrahydrofuran-3,4-diyl bis(2-methylpropanoate). To a solution of intermediate BB2 (0.05 g, 0.073 mmol) in THF (2 mL) was added isobutyric anhydride (0.072 mL, 0.436 mmol) and then DMAP (1.3 mg, 0.011 mmol) at room temperature. The resulting mixture was stirred for 30 min monitoring with LCMS, Reaction mixture was quenched with methanol and was concentrated. Residue obtained was purified by silica gel chromatography (0-15% methanol/dichloromethane) to afford intermediate BB3 (diastereomeric mixture). $^1$H NMR (400 MHz, Methanol-d$_4$) δ 7.79 (d, J=4.1 Hz, 1H), 7.36-7.12 (m, 10H), 6.87-6.73 (m, 1H), 6.60 (d, J=4.6 Hz, 1H), 5.87-5.76 (m, 2H), 5.59 (dd, J=7.8, 4.4 Hz, 1H), 4.76-4.63 (m, 1H), 4.65-4.51 (m, 1H), 4.46 (d, J=1.4 Hz, 2H), 4.35 (dt, J=9.1, 2.8 Hz, 1H), 4.26 (ddd, J=10.7, 5.4, 2.1 Hz, 1H), 4.18 (dd, J=11.5, 2.7 Hz, 1H), 4.13-3.93 (m, 2H), 2.73-2.59 (m, 1H), 2.53-2.39 (m, 1H), 1.34 (dd, J=7.1, 1.1 Hz, 2H), 1.31-1.18 (m, 13H), 1.01-1.09 (m, 6H). $^{19}$F NMR (376 MHz, Methanol-d$_4$) δ-235.36 (t, J=47.0 Hz), −235.91 (t, J=47.0 Hz). $^{31}$P NMR (162 MHz, Methanol-d$_4$) δ 3.45, 3.33. LCMS: MS m/z=828.21 [M+1]; t$_R$=1.60 min; LC system: Thermo Accela 1250 UHPLC; MS system: Thermo LCQ Fleet; Column: Phenomenex Kinetex 2.6 µXB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µL/min

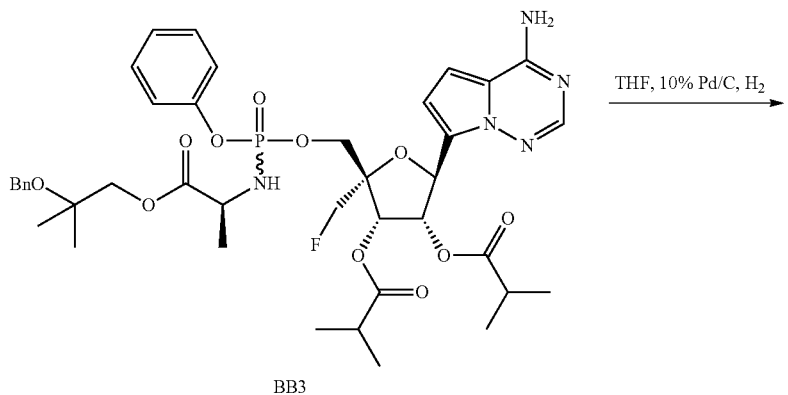

BB3

THF, 10% Pd/C, H$_2$

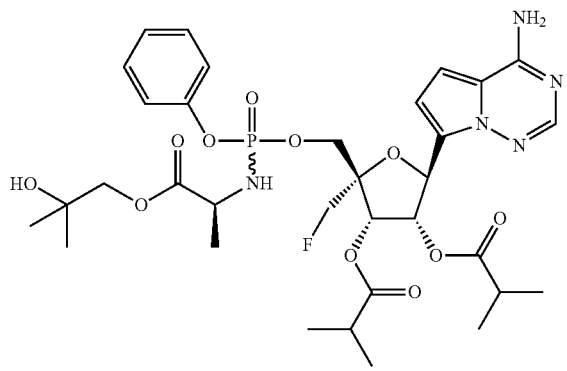

(2R,3S,4S,5S)-5-(4-aminopyrrolo[2,1-f][1,2,4]triazin-7-yl)-2-(fluoromethyl)-2-((((((S)-1-(2-hydroxy-2-methyl-propoxy)-1-oxopropan-2-yl)amino)(phenoxy) phosphoryl)oxy)methyl)tetrahydrofuran-3,4-diyl bis(2-methylpropanoate). To a solution of intermediate BB3 (40 mg, 0.048 mmol) in THF (2 mL) was added 10% Pd/C (26 mg, 0.024 mmol). The resulting mixture was stirred at room temperature for 15 h under $H_2$ gas and filtered. The filtrate was concentrated and the obtained residue was purified by silica gel chromatography (0-15% methanol/dichloromethane) to afford the product (diastereomeric mixture). $^1$H NMR (400 MHz, Methanol-$d_4$) δ 7.79 (d, J=4.2 Hz, 1H), 7.35-7.29 (m, 2H), 7.27-7.15 (m, 3H), 6.79 (d, J=4.6 Hz, 1H), 6.62 (d, J=4.6 Hz, 1H), 5.86-5.76 (m, 2H), 5.60-5.56 (m, 1H), 4.76-4.53 (m, 2H), 4.37-4.21 (m, 2H), 4.07-3.88 (m, 3H), 2.67 (p, J=6.9 Hz, 1H), 2.53-2.38 (m, 1H), 1.40-1.25 (m, 3H), 1.25-1.16 (m, 12H), 1.01-1.09 (m, 6H). $^{19}$F NMR (376 MHz, Methanol-$d_4$) δ-235.56 (t, J=46.9 Hz), −235.96 (t, J=46.9 Hz). $^{31}$P NMR (162 MHz, Methanol-$d_4$) δ 3.50, 3.45. LCMS: MS m/z=738.17 [M+1]; $t_R$=1.29 min; LC system: Thermo Accela 1250 UHPLC; MS system: Thermo LCQ Fleet; Column: Phenomenex Kinetex 2.6 μXB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μl/min. HPLC: $t_R$=5.31 min; HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Resolution of the Sp and Rp diastereomers. The diastereomers were isolated from each other by chiral preparatory SFC (SFC Chiralpak AD-H 5 μm, 21×250 mm; 30% isopropanol).

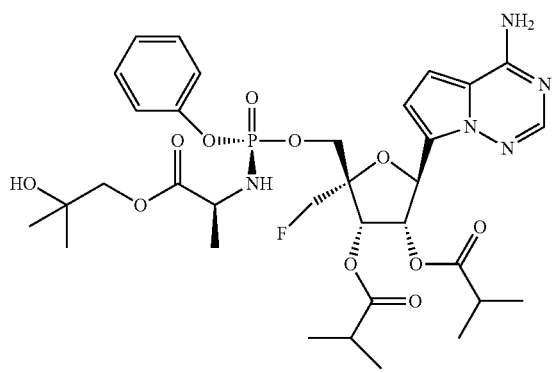

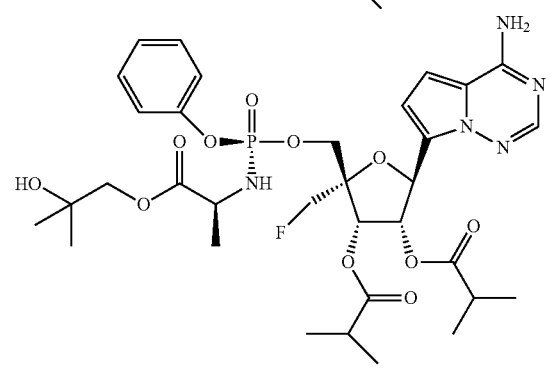

Example 28

First Eluting Diastereomer of Example 27: $^1$H NMR (400 MHz, Methanol-$d_4$) δ 7.80 (s, 1H), 7.36-7.27 (m, 2H), 7.25-7.12 (m, 3H), 6.85 (d, J=4.6 Hz, 1H), 6.76 (d, J=4.6 Hz, 1H), 5.92 (dd, J=7.6, 5.6 Hz, 1H), 5.84 (d, J=5.6 Hz, 1H), 5.59 (d, J=7.5 Hz, 1H), 4.72 (s, 1H), 4.61 (s, 1H), 4.34 (d, J=4.5 Hz, 2H), 4.04-3.87 (m, 3H), 2.73-2.58 (m, 1H), 2.48 (p, J=7.0 Hz, 1H), 1.30 (dd, J=7.2, 1.2 Hz, 3H), 1.25-1.16 (m, 12H), 1.03-1.10 m, (6H). $^{19}$F NMR (376 MHz, Methanol-$d_4$) δ-235.93 (t, J=47.0 Hz). $^{31}$P NMR (162 MHz, Methanol-$d_4$) δ 3.49. LCMS: MS m/z=738.16 [M+1]; $t_R$=1.31 min; LC system: Thermo Accela 1250 UHPLC; MS system: Thermo LCQ Fleet; Column: Phenomenex Kinetex 2.6 μXB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=5.282 min; HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 29

Second Eluting Diastereomer of Example 27: $^1$H NMR (400 MHz, Methanol-$d_4$) δ 7.79 (s, 1H), 7.37-7.28 (m, 2H), 7.25 (dt, J=8.7, 1.2 Hz, 2H), 7.18-7.20 (m, 1H), 6.79 (d, J=4.5 Hz, 1H), 6.62 (d, J=4.6 Hz, 1H), 5.88-5.77 (m, 2H), 5.59 (d, J=7.8 Hz, 1H), 4.78-4.65 (m, 1H), 4.66-4.53 (m, 1H), 4.34 (ddd, J=10.8, 4.8, 1.8 Hz, 1H), 4.27 (ddd, J=10.7, 5.6, 2.1 Hz, 1H), 4.09-3.92 (m, 2H), 3.91 (d, J=10.9 Hz, 1H), 2.67 (hept, J=7.0 Hz, 1H), 2.46 (hept, J=7.1 Hz, 1H), 1.37 (dd, J=7.1, 1.0 Hz, 3H), 1.26-1.10 (m, 12H), 1.02-1.08 (m, 6H). $^{19}$F NMR (376 MHz, Methanol-$d_4$) δ-235.54 (t, J=46.8 Hz). $^{31}$P NMR (162 MHz, Methanol-$d_4$) δ 3.44. LCMS: MS m/z=738.17 [M+1]; $t_R$=1.30 min; LC system: Thermo Accela 1250 UHPLC; MS system: Thermo LCQ Fleet; Column: Phenomenex Kinetex 2.6 μXB-$C_{18\ 100}$A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=5.277 min; HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 30. (S)-2-methoxypropyl ((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate

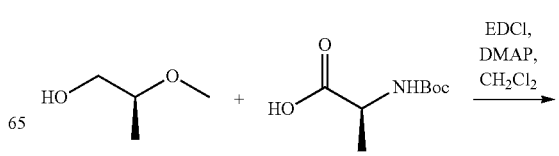

-continued

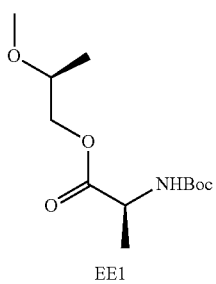

EE1

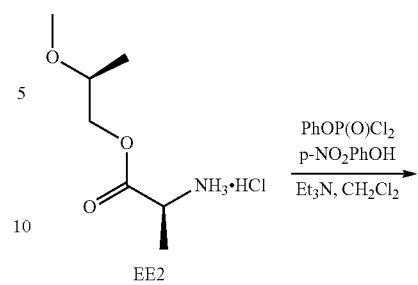

EE2

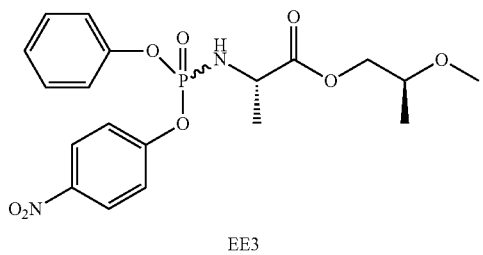

EE3

(S)-2-methoxypropyl (tert-butoxycarbonyl)-L-alaninate. (tert-butoxycarbonyl)-L-alanine (2.519 g, 0.013 mol) was taken up in acetonitrile (12 mL) and (S)-2-methoxypropan-1-ol (1 g, 0.011 mol) followed by EDCI (2.239 g, 0.014 mol) and DMAP (2.033 g, 0.017 mol) were added in one portion. The reaction was allowed to stir at room temperature for 4 h. The reaction was diluted with dichloromethane and water. The layers were split and the organic layer was dried over anhydrous sodium sulfate, filtered and then was concentrated under reduced pressure. Purification by silica gel chromatography 0-30% ethylacetate/hexane to afforded intermediate EE1. $^1$H NMR (400 MHz, DMSO-$d_6$) δ 7.31 (d, J=7.4 Hz, 1H), 4.10-3.92 (m, 3H), 3.50 (td, J=6.3, 4.2 Hz, 1H), 3.26 (s, 3H), 1.38 (s, 9H), 1.25 (d, J=7.4 Hz, 3H), 1.07 (d, J=6.4 Hz, 3H).

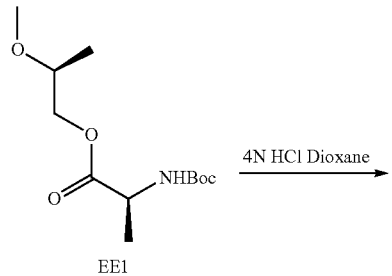

EE1

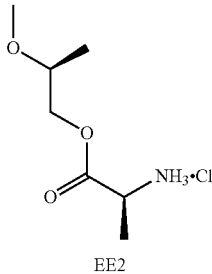

EE2

(S)-2-methoxypropyl)-L-alaninate hydrochloride. Intermediate EE1 (2.165 g, 0.008 mol) was taken up in anhydrous dichloromethane (22 mL) and 4 N HCl in dioxane (10.36 mL, 0.041 mol). The reaction was stirred at ambient temperature for 4 h. The reaction was concentrated under reduced pressure and co-evaporated with dichloromethane. The residue was placed under high vacuum overnight and intermediate EE2 was used as is without purification for the next step. $^1$H NMR (400 MHz, DMSO-$d_6$) δ 8.64 (s, 3H), 4.17-3.99 (m, 3H), 3.53 (m, 1H), 3.24 (s, 3H), 1.41 (d, J=7.2 Hz, 3H), 1.07 (d, J=6.4 Hz, 3H).

(S)-2-methoxypropyl ((4-nitrophenoxy)(phenoxy)phosphoryl)-L-alaninate. To a solution of intermediate EE2 (1.5 g, 7.589 mmol) and phenyl dichlorophosphate (1.129 mL, 7.589 mmol) in anhydrous dichloromethane (26 mL) was added triethylamine (2.34 mL, 16.66 mmol) at 0° C. under argon atmosphere. The resulting mixture was stirred for 1 h at 0° C. 4-Nitrophenol (1.056 g, 7.589 mmol) and triethylamine (1.17 mL, 8.33 mmol) were then added. After 1 h stirring at 0° C., the reaction mixture was diluted with Et$_2$O and the solids were filtered off. The crude was concentrated under reduced pressure and was purified by silica gel chromatography (80 g SiO$_2$ Combiflash HP Gold Column, 100% dichloromethane followed by 0-75% ethyl acetate/hexanes) to afford intermediate EE3 (diastereomeric mixture). $^1$H NMR (400 MHz, DMSO-$d_6$) δ 8.32-8.23 (m, 2H), 7.53-7.44 (m, 1H), 7.49-7.34 (m, 3H), 7.30-7.16 (m, 3H), 6.70 (ddd, J=13.6, 10.0, 7.9 Hz, 1H), 4.08-3.89 (m, 3H), 3.48-3.36 (m, 1H), 3.19 (d, J=1.0 Hz, 3H), 1.26-1.11 (m, 3H), 1.01 (dd, J=6.4, 1.5 Hz, 3H). $^{31}$P NMR (162 MHz, DMSO-$d_6$) δ-1.26, -1.47. LCMS: MS m/z=438.99 [M+1]; $t_R$=1.43 min; LC system: Thermo Accela 1250 UHPLC; MS system: Thermo LCQ Fleet; Column: Phenomenex Kinetex 2.6 μXB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min.

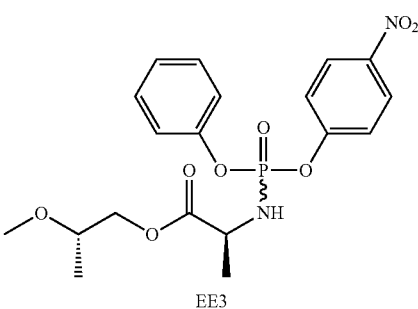

EE3

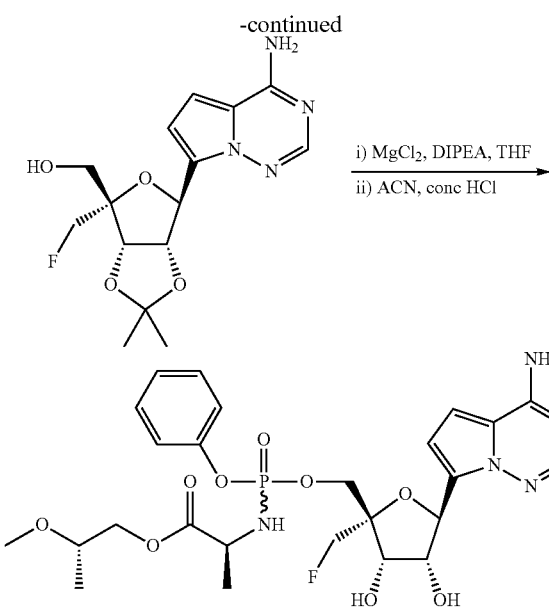

(S)-2-methoxypropyl ((((2R,3S,4R,5S)-5-(4-aminopyr-rolo[2,1-f][1,2,4]triazin-7-yl)-2-(fluoromethyl)-3,4-dihydroxytetrahydrofuran-2-yl)methoxy)(phenoxy)phosphoryl)-L-alaninate. To a mixture of Intermediate 4(0.15 g, 0.443 mmol), intermediate EE3 (0.214 g, 0.488 mmol), and magnesium chloride (0.063 g, 0.665 mmol) was added tetrahydrofuran (1.5 mL) at room temperature followed by the addition of N,N-diisopropylethylamine (0.193 mL, 1.108 mmol). The resulting mixture was stirred at 50° C. for 1.5 h. The reaction mixture was then concentrated under reduced pressure and the residue obtained was purified by preparative HPLC (Phenominex Synergi 4u Hydro-RR 80 Å 150× 30 mm column, 15%-85% acetonitrile/water. Pure fractions were combined and concentrated under reduced pressure. Residue obtained was dissolved in an anhydrous acetonitrile (3 mL) and was cooled in an ice bath followed by the dropwise addition of concentrated hydrochloric acid (0.2 mL, 2.4 mmol). The reaction mixture was stirred at room temperature for 1 h. After 1 h the reaction mixture was cooled in an ice bath and was diluted with ice followed by neutralized with aqueous sodium bicarbonate solution. The resulting mixture was purified by preparative HPLC (Phenominex Synergi 4u Hydro-RR 80 Å 150×30 mm column, 15%-85% acetonitrile/water gradient in 30 min run) to afford the product (diastereomeric mixture). $^1$H NMR (400 MHz, DMSO-$d_6$) δ 7.81 (d, J=2.4 Hz, 1H), 7.67 (s, 2H), 7.35 (dt, J=8.5, 6.9 Hz, 2H), 7.24-7.11 (m, 3H), 6.83 (dd, J=5.6, 4.5 Hz, 1H), 6.67 (dd, J=8.0, 4.5 Hz, 1H), 6.05 (td, J=13.9, 10.1 Hz, 1H), 5.30-5.18 (m, 2H), 5.10 (dd, J=7.3, 2.6 Hz, 1H), 4.67-4.55 (m, 1H), 4.50 (dd, J=14.2, 7.0 Hz, 2H), 4.18 (q, J=5.2 Hz, 1H), 3.96 (m, 4H), 3.83 (dd, J=10.5, 7.0 Hz, 1H), 3.49-3.40 (m, 1H), 3.20 (d, J=2.0 Hz, 3H), 1.20 (dd, J=15.3, 7.1 Hz, 3H), 1.02 (dd, J=6.3, 3.8 Hz, 3H). $^{19}$F NMR (376 MHz, DMSO-$d_6$) δ-236.33-236.84 (m). $^{31}$P NMR (162 MHz, DMSO-$d_6$) S 3.57, 3.44. LCMS: MS m/z=598.03 [M+1]; $t_R$=1.00 min (minor isomer) and 1.10 min (major isomer); LC system: Thermo Accela 1250 UHPLC; MS system: Thermo LCQ Fleet; Column: Phenomenex Kinetex 2.6 µXB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µl/min. HPLC: $t_R$=3.95 min (minor isomer), 4.018 min (major isomer); HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Resolution of the Sp and Rp diastereomers. The diastereomers were isolated from each other by chiral preparatory SFC (SFC Chiralpak AD-H 5 µm, 21×250 mm; 30% isopropanol).

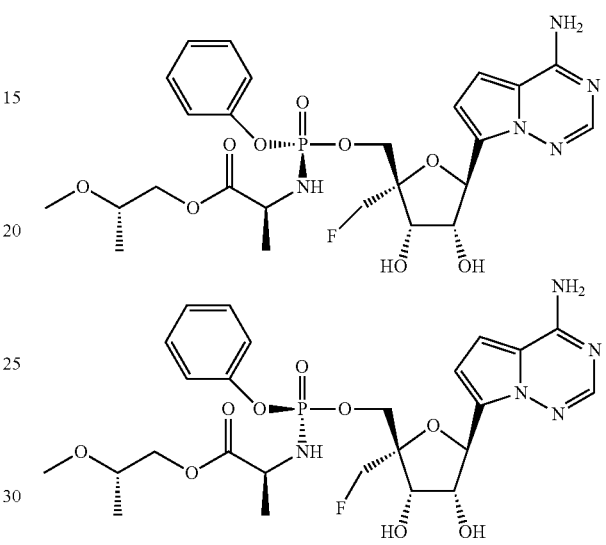

Example 31

First Eluting Diastereomer of Example 30: $^1$H NMR (400 MHz, Methanol-$d_4$) δ 7.78 (s, 1H), 7.33 (dd, J=8.5, 7.3 Hz, 2H), 7.24-7.13 (m, 3H), 6.86 (d, J=4.6 Hz, 1H), 6.75 (d, J=4.5 Hz, 1H), 5.37 (d, J=8.2 Hz, 1H), 4.82-4.71 (m, 1H), 4.71-4.59 (m, 2H), 4.38 (d, J=5.3 Hz, 1H), 4.26 (dd, J=5.2, 1.7 Hz, 2H), 4.07-3.99 (m, 2H), 3.98-3.85 (m, 1H), 3.58-3.49 (m, 1H), 3.32 (s, 3H), 1.26 (dd, J=7.2, 1.2 Hz, 3H), 1.11 (d, J=6.4 Hz, 3H). $^{19}$F NMR (376 MHz, Methanol-$d_4$) δ-238.62 (t, J=47.8 Hz). $^{31}$P NMR (162 MHz, Methanol-$d_4$) δ 3.69. LCMS: MS m/z=597.94 [M+1]; $t_R$=1.11 min; LC system: Thermo Accela 1250 UHPLC; MS system: Thermo LCQ Fleet; Column: Phenomenex Kinetex 2.6 µXB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µl/min. HPLC: $t_R$=3.939 min; HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 32

Second Eluting Diastereomer of Example 30: $^1$H NMR (400 MHz, Methanol-$d_4$) δ 7.79 (s, 1H), 7.39-7.29 (m, 2H), 7.27-7.14 (m, 3H), 6.85 (d, J=4.5 Hz, 1H), 6.73 (d, J=4.6 Hz, 1H), 5.36 (d, J=8.3 Hz, 1H), 4.82-4.55 (m, 3H), 4.33 (d, J=5.2 Hz, 1H), 4.21 (dt,J=5.8, 1.8 Hz, 2H), 4.04 (d, J=5.0 Hz, 2H), 3.93 (dq, J=9.8, 7.2 Hz, 1H), 3.59-3.48 (m, 1H), 3.31 (s, 3H), 1.31 (dd, J=7.1, 1.0 Hz, 3H), 1.10 (d, J=6.4 Hz, 3H). ¹⁹F NMR (376 MHz, Methanol-$d_4$) δ -238.78 (t, J=47.8 Hz). ³¹P NMR (162 MHz, Methanol-$d_4$) δ 3.44. LCMS: MS m/z=597.97 [M+1]; $t_R$=1.12 min; LC system: Thermo Accela 1250 UHPLC; MS system: Thermo LCQ Fleet; Column: Phenomenex Kinetex 2.6 μXB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=4.005 min; HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 33. (2R,3S,4S,5S)-5-(4-aminopyrrolo[2,1-f][1,2,4]triazin-7-yl)-2-(fluoromethyl)-2-(((((S)-1-methoxy-1-oxopropan-2-yl)amino)(phenoxy)phosphoryl)oxy) methyl)tetrahydrofuran-3,4-diyl dipropionate

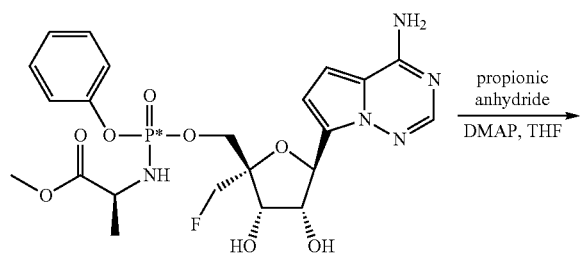

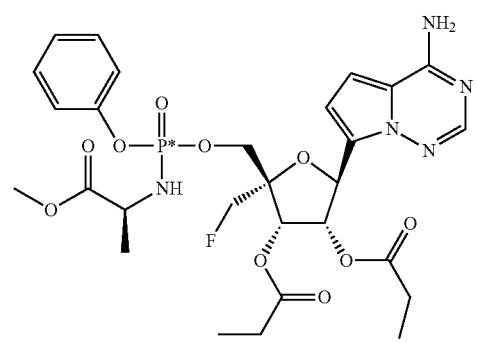

To a solution of Example 10 (0.057 g, 0.106 mmol) in THF (2 mL) were added propionic anhydride (0.041 mL, 0.317 mmol) and then DMAP (2.58 mg, 0.021 mmol) at room temperature. The resulting mixture was stirred for 10 min monitoring with LCMS, Reaction mixture was quenched with methanol and was diluted with ethyl acetate. The organic layer was washed with saturated aqueous sodium bicarbonate solution, separated, dried over sodium sulfate, filtered and concentrated. Residue obtained was purified by silica gel chromatography (0-15% methanol/dichloromethane) to afford the product, which was determined to be a single diastereomer by NMR spectroscopy. ¹H NMR (400 MHz, Methanol-$d_4$) δ 7.79 (s, 1H), 7.38-7.29 (m, 2H), 7.33-7.21 (m, 2H), 7.23-7.14 (m, 1H), 6.79 (d, J=4.5 Hz, 1H), 6.62 (d, J=4.6 Hz, 1H), 5.91-5.78 (m, 2H), 5.58 (d, J=7.9 Hz, 1H), 4.76-4.64 (m, 1H), 4.58 (q, J=10.0 Hz, 1H), 4.37-4.28 (m, 1H), 4.25 (ddd, J=10.5, 5.5, 2.1 Hz, 1H), 4.02-3.89 (m, 1H), 3.66 (s, 3H), 2.45 (qd, J=7.5, 1.0 Hz, 2H), 2.26 (qd, J=7.6, 3.2 Hz, 2H), 1.31 (dd, J=7.1, 1.0 Hz, 3H), 1.16 (t, J=7.6 Hz, 3H), 1.04 (t, J=7.5 Hz, 3H). ³¹P NMR (162 MHz, Methanol-$d_4$) δ 3.37. ¹⁹F NMR (376 MHz, Methanol-$d_4$) δ -236.42 (t, J=46.6 Hz). LCMS: MS m/z=652.09 [M+1]; $t_R$=1.23 min; LC system: Thermo Accela 1250 UHPLC; MS system: Thermo LCQ Fleet; Column: Phenomenex Kinetex 2.6 μXB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=4.994 min; HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 34. 2-ethylbutyl ((S)-(((2R,3S,4R,5S)-2-(fluoromethyl)-3,4-dihydroxy-5-(4-imino-3-((phosphonooxy)methyl)-3,4-dihydropyrrolo[2,1-f][1,2,4]triazin-7-yl)tetrahydrofuran-2-yl)methoxy)(phenoxy)phosphoryl)-L-alaninate

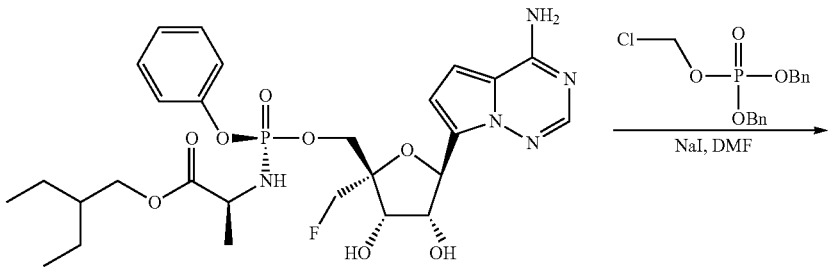

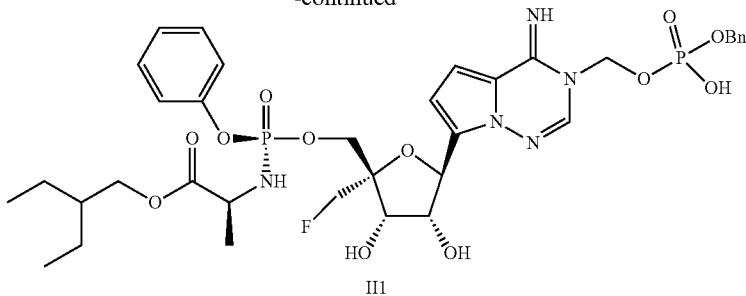

2-ethylbutyl ((S)-((((2R,3S,4R,5S)-5(3-((((benzyloxy) (hydroxy)phosphoryl)oxy)methyl)-4-imino-3,4-dihydropyr-rolo[2,1-f][1,2,4]triazin-7-yl)-2-(fluoromethyl)-3,4-dihydroxytetrahydrofuran-2-yl)methoxy)(phenoxy)phosphoryl)-L-alaninate. To a solution of Example 1 (0.125 g, 0.205 mmol) in DMF (2.25 mL) was added dibenzylchloromethyl phosphate and sodium iodide. Reaction mixture was stirred at room temperature for overnight and the resulting reaction mixture was purified by preparative HPLC (Phenominex Synergi 4u Hydro-RR 80 Å 150×30 mm column, 0-100% acetonitrile/water) to afford intermediate 111. $^1$H NMR (400 MHz, DMSO-$d_6$) δ 12.49 (s, 1H), 10.31 (d, J=10.5 Hz, 1H), 8.42 (s, 1H), 7.45 (dd, J=4.8, 2.3 Hz, 1H), 7.36 (t, J=7.9 Hz, 2H), 7.26 (d, J=4.3 Hz, 4H), 7.20 (dt, J=11.9, 6.6 Hz, 4H), 6.91 (d, J=4.7 Hz, 1H), 6.07 (dd, J=13.0, 10.1 Hz, 1H), 5.64 (d, J=10.8 Hz, 2H), 5.39 (d, J=4.7 Hz, 1H), 5.29 (s, 1H), 5.20 (d, J=8.7 Hz, 1H), 4.76 (d, J=6.9 Hz, 2H), 4.68-4.58 (m, 1H), 4.59-4.48 (m, 1H), 4.40 (s, 1H), 4.19 (t, J=3.8 Hz, 1H), 3.98 (ddd, J=19.0, 10.9, 5.6 Hz, 3H), 3.93-3.79 (m, 2H), 1.43 (h, J=6.3 Hz, 1H), 1.32-1.20 (m, 7H), 0.80 (t, J=7.4 Hz, 6H). $^{31}$P NMR (162 MHz, DMSO-$d_6$) δ 3.59, 0.13. $^{19}$F NMR (376 MHz, DMSO-$d_6$) δ-235.99 (t, J=47.6 Hz). LCMS: MS m/z=810.23 [M+1]; $t_R$=1.30 min; LC system: Thermo Accela 1250 UHPLC; MS system: Thermo LCQ Fleet; Column: Phenomenex Kinetex 2.6 μXB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min.

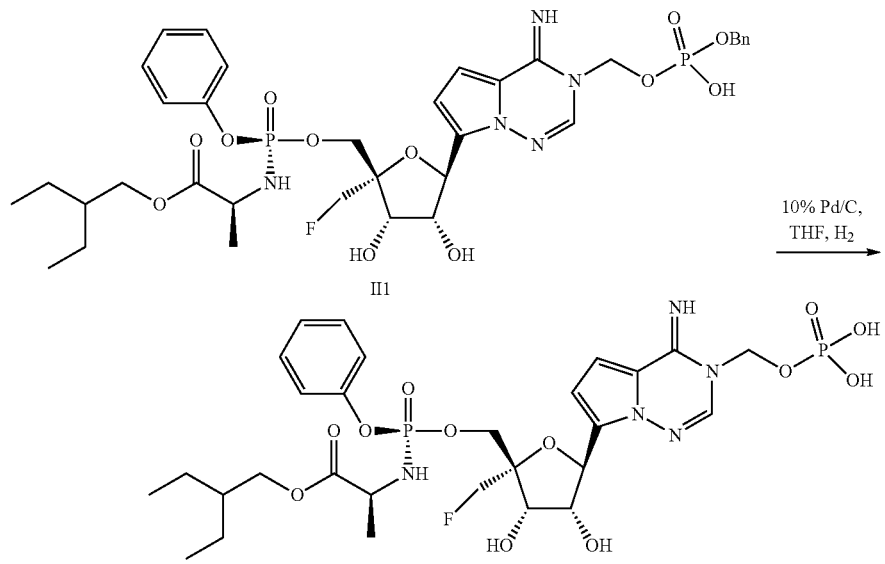

2-ethylbutyl ((S)-(((2R,3S,4R,5S)-2-(fluoromethyl)-3,4-dihydroxy-5-(4-imino-3-((phosphonooxy)methyl)-3,4-dihydropyrrolo[2,1-f][1,2,4]triazin-7-yl)tetrahydrofuran-2-yl) methoxy)(phenoxy)phosphoryl)-L-alaninate. To a solution of intermediate Ill (47 mg, 0.058 mmol) in THF (2 mL) was added 10% Pd/C (6.17 mg, 0.058 mmol). The resulting mixture was stirred at room temperature for 1.5 h under H$_2$ gas and filtered. The filtrate was concentrated and the obtained residue was purified by preparative HPLC (Phenominex Synergi 4u Hydro-RR 80 Å 150×30 mm column, 0-100% acetonitrile/water with TFA modifier) to afford the product, which was determined to be a single diastereomer by NMR spectroscopy. $^1$H NMR (400 MHz, DMSO-$d_6$) δ 10.33 (s, 1H), 8.42 (s, 1H), 7.48 (d, J=4.8 Hz, 1H), 7.40-7.30 (m, 2H), 7.24-7.13 (m, 3H), 6.90 (d, J=4.7 Hz, 1H), 6.07 (dd, J=13.1, 10.1 Hz, 1H), 5.67 (d, J=11.5 Hz, 2H), 5.41 (s, 1H), 5.19 (d, J=8.7 Hz, 1H), 4.63 (q, J=10.2 Hz, 1H), 4.57-4.44 (m, 1H), 4.39 (dd, J=8.8, 4.9 Hz, 1H), 4.18 (d, J=4.9 Hz, 1H), 4.06-3.77 (m, 5H), 1.42 (h, J=6.2 Hz, 1H), 1.33-1.19 (m, 7H), 0.80 (t, J=7.5 Hz, 6H). $^{19}$F NMR (376 MHz, DMSO-$d_6$) δ-74.19 (s), -236.54 (t, J=47.9 Hz). $^{31}$P NMR (162 MHz, DMSO-$d_6$) δ 3.59, 0.12. LCMS: MS m/z=720.16 [M+1]; $t_R$=1.21 min; LC system: Thermo Accela 1250 UHPLC; MS system: Thermo LCQ Fleet; Column: Phenomenex Kinetex 2.6 μXB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µL/min. HPLC: $t_R$=4.854 min; HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 35. (R)-1-methylpyrrolidin-3-yl ((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy) (phenoxy)phosphoryl)-L-alaninate

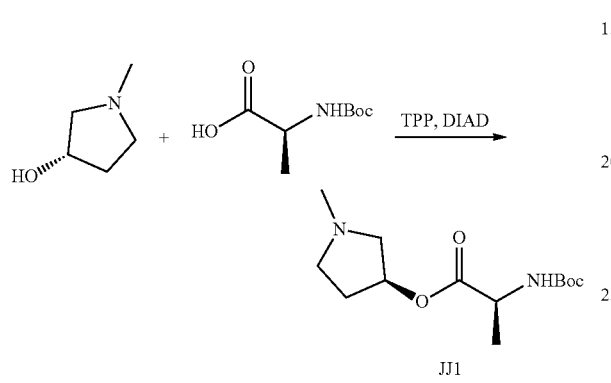

R-1-methylpyrrolidin-3-yl tert-butoxycarbonyl-L-alaninate. To a solution of (S)-1-methylpyrrolidin-3-ol (1.0 g, 0.01 mol) and (tert-butoxycarbonyl)-L-alanine (2.058 g, 0.011 mol) in THF (20 mL) was added triphenylphosphine (3.63 g, 0.014 mol) in one portion. To the resulting reaction mixture was added diisopropyl azodicarboxylate (2.53 mL, 0.013 mol) and reaction mixture was stirred at room temperature for 2 h. Diluted reaction with EtOAc and washed with saturated aqueous sodium bicarbonate solution followed by 5% aqueous citric acid solution. Washed citric acid extract with EtOAc (2×). Basified acid extract with 2 N aqueous NaOH solution to give pH of 9 and extracted with EtOAc (2×). Organic layer separated, dried over anhydrous sodium sulfate, filtered and concentrated under reduced pressure to afford intermediate JJ1. $^1$H NMR (400 MHz, Chloroform-d) δ 5.29-5.18 (m, 1H), 5.02 (s, 1H), 4.28 (t, J=7.6 Hz, 1H), 2.80 (dd, J=9.6, 5.4 Hz, 1H), 2.69 (d, J=3.6 Hz, 2H), 2.42-2.19 (m, 5H), 1.89-1.72 (m, 1H), 1.43 (s, 9H), 1.36 (d, J=7.2 Hz, 3H).

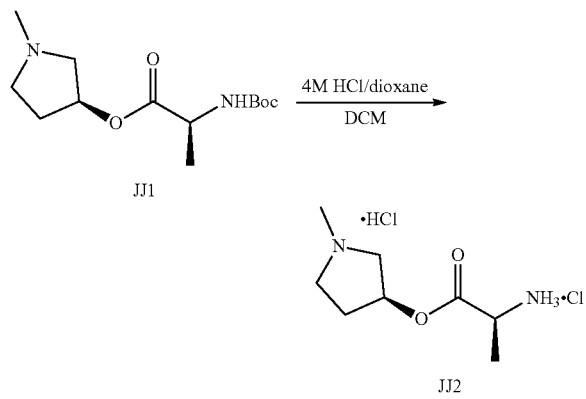

(R)-1-methylpyrrolidin-3-yl-L-alaninate dihydrochloride. Intermediate JJ1 (2.27 g, 0.008 mol) was taken up in anhydrous dichloromethane (20 mL) and 4 N HCl in dioxane (14.59 mL, 0.058 mol) was added. Stirred at ambient temperature for 4 h. Concentrated under reduced pressure and co-evaporated with dichloromethane. Placed under high vacuum overnight and intermediate JJ2 was used as is in the next step. H NMR (400 MHz, DMSO-$d_6$) δ 11.34 (s, 1H), 8.81 (s, 3H), 5.38 (s, 1H), 4.06 (q, J=7.1 Hz, 1H), 3.44 (d, J=78.6 Hz, 5H), 2.84 (s, 3H), 2.12 (s, 1H), 1.43 (d, J=7.1 Hz, 3H).

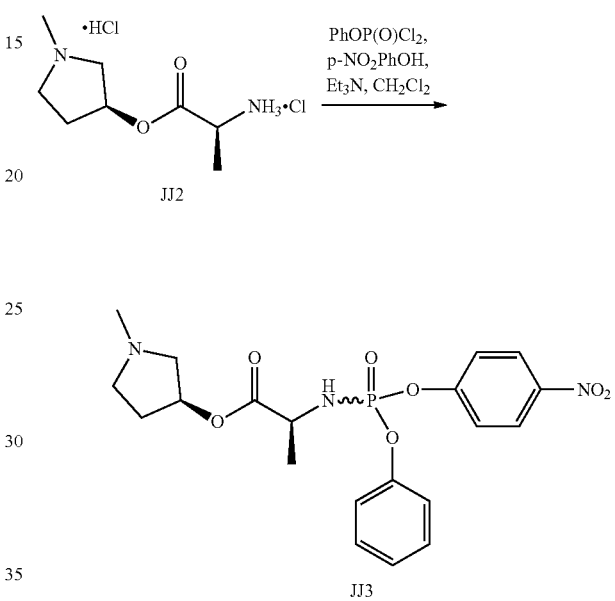

(R)-1-methylpyrrolidin-3-yl ((4-nitrophenoxy)(phenoxy)phosphoryl)-L-alaninate. To a solution of intermediate JJ2 (1.5 g, 4.079 mmol) and phenyl dichlorophosphate (0.607 mL, 4.079 mmol) in anhydrous dichloromethane (19 mL) was added triethylamine (1.848 mL, 13.155 mmol) at 0° C. under argon atmosphere. The resulting mixture was stirred for 1 h at 0° C. 4-Nitrophenol (0.567 g, 4.079 mmol) and triethylamine (0.616 mL, 4.385 mmol) were then added. After 1 h stirring at 0° C., the reaction mixture was diluted with Et$_2$O and the solids were filtered off. The crude was concentrated under reduced pressure and was purified by silica gel chromatography (80 g SiO$_2$ Combiflash HP Gold Column, 0-10% methanol/dichloromethane) to afford intermediate JJ3 (diastereomeric mixture). $^1$H NMR (400 MHz, Chloroform-d) δ 8.26-8.18 (m, 2H), 7.44-7.30 (m, 4H), 7.26-7.15 (m, 3H), 5.20 (d, J=8.5 Hz, 1H), 4.24-3.89 (m, 1H), 3.80 (dd, J=11.5, 8.8 Hz, 1H), 2.97-2.80 (m, 1H), 2.75 (d, J=21.6 Hz, 1H), 2.68-2.58 (m, 1H), 2.39-2.18 (m, 5H), 1.78 (dd, J=14.6, 7.8 Hz, 1H), 1.45-1.34 (m, 3H). LCMS: MS m/z=450.23 [M+1]; $t_R$=1.07 min; LC system: Thermo Accela 1250 UHPLC; MS system: Thermo LCQ Fleet; Column: Phenomenex Kinetex 2.6 µXB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µL/min.

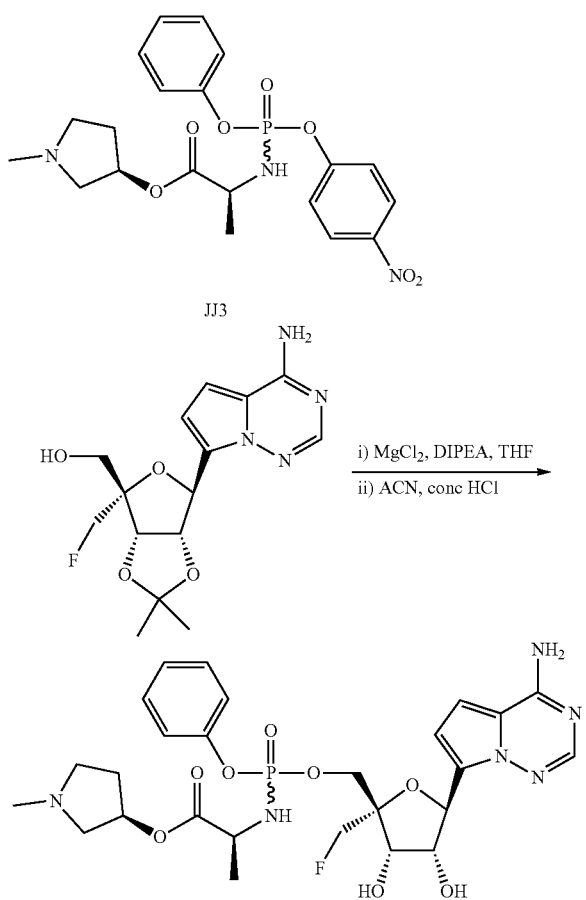

(R)-1-methylpyrrolidin-3-yl ((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy) (phenoxy)phosphoryl)-L-alaninate. To a mixture of Intermediate 4 (0.1 g, 0.296 mmol), intermediate JJ3 (0.5 g, 1.113 mmol), and magnesium chloride (0.141 g, 1.478 mmol) was added tetrahydrofuran (3 mL) at room temperature followed by the addition of N,N-diisopropylethylamine (0.129 mL, 0.739 mmol). The resulting mixture was stirred at 50° C. for 2 h. The reaction mixture was then concentrated under reduced pressure and the residue obtained was diluted with saturated sodium chloride solution and ethyl acetate. The layers were split and the organic layer was dried over anhydrous sodium sulfate, filtered and was concentrated under reduced pressure. The residue obtained and was purified by silica gel chromatography using 0-10% methanol/dichloromethane. Pure fractions obtained were combined and concentrated. The residue obtained was dissolved in an anhydrous acetonitrile (3 mL) and was cooled in an ice bath followed by the dropwise addition of concentrated hydrochloric acid (0.257 mL, 3.086 mmol). The reaction mixture was stirred at room temperature for 1 h and concentrated. The residue obtained was purified by preparative HPLC (Phenominex Synergi 4u Hydro-RR 80 Å 150×30 mm column, 0-100% acetonitrile/water with TFA modifier). Pure fractions were combined and concentrated under reduced pressure. The residue obtained was diluted with water and neutralized with aqueous saturated sodium bicarbonate solution. Aqueous layer was extracted with ethyl acetate. Organic layer was separated, dried over sodium sulfate, filtered and concentrated. Dissolved the residue in acetonitrile and water and lyophilized to afford the product (diastereomeric mixture). $^1$H NMR (400 MHz, Methanol-$d_4$) δ 7.79 (d, J=0.7 Hz, 1H), 7.40-7.29 (m, 2H), 7.28-7.15 (m, 3H), 6.86 (dd, J=6.7, 4.5 Hz, 1H), 6.75 (dd, J=13.6, 4.6 Hz, 1H), 5.41-5.32 (m, 1H), 5.14 (ddt, J=8.1, 5.4, 2.6 Hz, 1H), 4.82-4.55 (m, 3H), 4.36 (dd, J=14.7, 5.3 Hz, 1H), 4.28-4.18 (m, 2H), 3.97-3.79 (m, 1H), 2.87-2.76 (m, 1H), 2.76-2.59 (m, 2H), 2.34 (s, 3H), 2.40-2.19 (m, 2H), 1.79 (ddt, J=14.5, 7.6, 3.9 Hz, 1H), 1.28 (ddd, J=17.1, 7.1, 1.1 Hz, 3H). $^{19}$F NMR (376 MHz, Methanol-$d_4$) δ -238.41-238.79 (m). $^{31}$P NMR (162 MHz, Methanol-$d_4$) δ 3.72, 3.44. LCMS: MS m/z=609.20 [M+1]; $t_R$=0.80 min; LC system: Thermo Accela 1250 UHPLC; MS system: Thermo LCQ Fleet; Column: Phenomenex Kinetex 2.6 µXB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µL/min HPLC: $t_R$=3.113 min (major isomer) and 3.168 min (minor isomer); HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 36. (2R,3S,4S,5S)-5-(4-aminopyrrolo[2,1-f][1,2,4]triazin-7-yl)-2-(fluoromethyl)-2-(((((S)-1-(((R)-1-methylpyrrolidin-3-yl)oxy)-1-oxopropan-2-yl)amino)(phenoxy) phosphoryl)oxy)methyl) tetrahydrofuran-3,4-diyl bis(2-methylpropanoate)

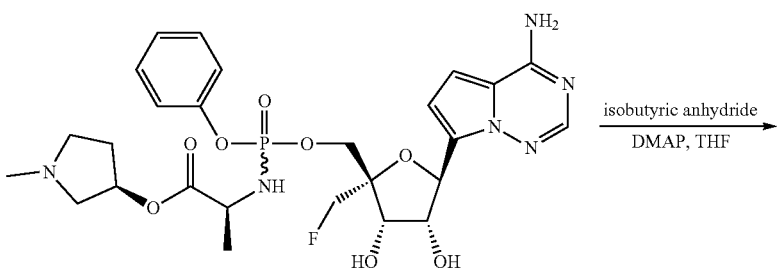

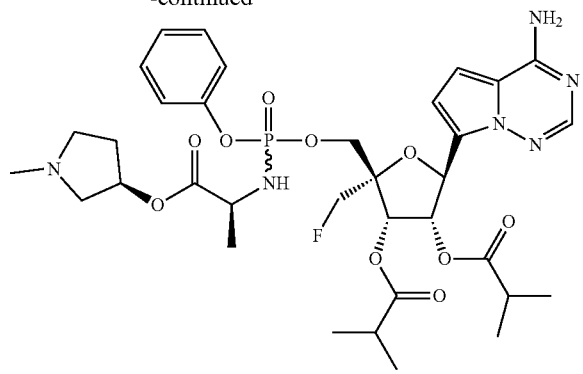

To a solution of Example 35 (0.045 g, 0.074 mmol) in THF (2 mL) were added isobutyric anhydride (0.074 mL, 0.444 mmol) and then DMAP (1.3 mg, 0.011 mmol) at room temperature. The resulting mixture was stirred for 30 min monitoring with LCMS, Reaction mixture was quenched with methanol and was concentrated. Residue obtained was purified by preparative HPLC (Phenominex Synergi 4u Hydro-RR 80 Å 150×30 mm column, 0-100% acetonitrile/water with TFA modifier) to afford the product (diastereomeric mixture). $^1$H NMR (400 MHz, Methanol-$d_4$) δ 7.80 (d, J=3.4 Hz, 1H), 7.33 (dd, J=8.4, 7.4 Hz, 2H), 7.28-7.15 (m, 3H), 6.87-6.58 (m, 2H), 5.96-5.71 (m, 2H), 5.59 (dd, J=7.9, 2.7 Hz, 1H), 5.20 (d, J=5.2 Hz, 1H), 4.77-4.49 (m, 2H), 4.40-4.22 (m, 2H), 4.02-3.83 (m, 1H), 2.94-2.62 (m, 3H), 2.54-2.35 (m, 5H), 2.25 (dq, J=22.6, 7.4 Hz, 2H), 1.89-1.72 (m, 1H), 1.32 (dd, J=7.1, 1.1 Hz, 3H), 1.22 (dd, J=7.0, 1.1 Hz, 6H), 1.06 (ddd, J=18.6, 7.0, 4.7 Hz, 6H). $^{19}$F NMR (376 MHz, Methanol-$d_4$) δ-235.33 (t, J=46.8 Hz), -235.86 (t, J=46.7 Hz). $^{31}$P NMR (162 MHz, Methanol-$d_4$) δ 3.38. LCMS: MS m/z=749.24 [M+1]; $t_R$=1.13 min; LC system: Thermo Accela 1250 UHPLC; MS system: Thermo LCQ Fleet; Column: Phenomenex Kinetex 2.6 µXB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µL/min.

Resolution of the Sp and Rp diastereomers. The diastereomers were isolated from each other by chiral preparatory SFC (SFC Chiralpak IA 5 µm, 25×250 mm; 25% isopropanol).

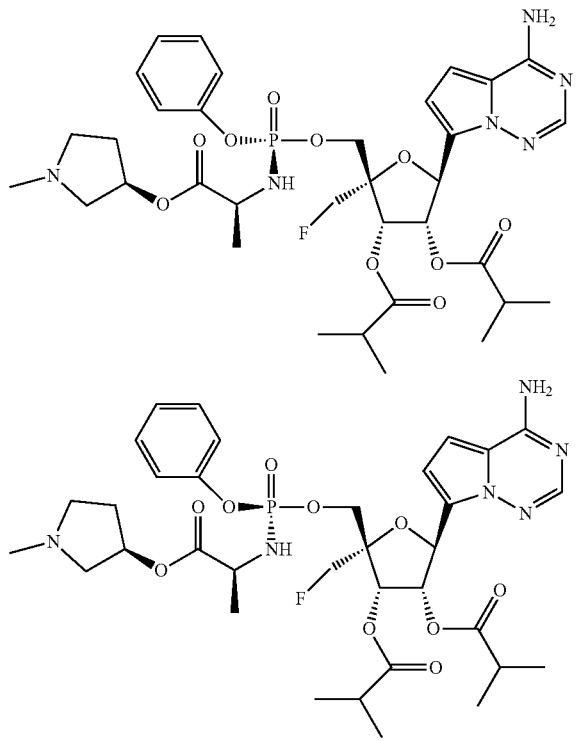

Example 37

First Eluting Diastereomer of Example 36: $^1$H NMR (400 MHz, Methanol-$d_4$) δ 7.81 (s, 1H), 7.38-7.29 (m, 2H), 7.27-7.14 (m, 3H), 6.84 (d, J=4.5 Hz, 1H), 6.76 (d, J=4.5 Hz, 1H), 5.96-5.79 (m, 2H), 5.59 (d, J=7.8 Hz, 1H), 5.22 (dq, J=6.8, 3.6 Hz, 1H), 4.73 (s, 1H), 4.61 (s, 1H), 4.42-4.26 (m, 2H), 3.99-3.85 (m, 1H), 3.14-2.92 (m, 3H), 2.68 (dt, J=14.0, 7.0 Hz, 2H), 2.58-2.42 (m, 4H), 2.32 (dq, J=14.7, 7.4 Hz, 1H), 2.04-1.83 (m, 1H), 1.25 (ddd, J=20.9, 7.1, 1.1 Hz, 9H), 1.06 (dd, J=17.9, 7.0 Hz, 6H). $^{19}$F NMR (376 MHz, Methanol-d$_4$) δ -235.85 (t, J=46.7 Hz). $^{31}$P NMR (162 MHz, Methanol-d$_4$) δ 3.43 LCMS: MS m/z=749.24 [M+1]; t$_R$=1.16 min; LC system: Thermo Accela 1250 UHPLC; MS system: Thermo LCQ Fleet; Column: Phenomenex Kinetex 2.6 μXB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μl/min HPLC: t$_R$=4.614 min; HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 38

Second Eluting Diastereomer of Example 36: $^1$H NMR (400 MHz, Methanol-d$_4$) δ 7.80 (s, 1H), 7.38-7.28 (m, 2H), 7.26-7.16 (m, 3H), 6.80 (d, J=4.6 Hz, 1H), 6.63 (d, J=4.6 Hz, 1H), 5.89-5.75 (m, 2H), 5.59 (d, J=7.9 Hz, 1H), 5.19 (ddt, J=8.0, 5.4, 2.7 Hz, 1H), 4.79-4.51 (m, 2H), 4.42-4.19 (m, 2H), 3.95 (dq, J=9.8, 7.1 Hz, 1H), 2.96-2.60 (m, 4H), 2.53-2.37 (m, 5H), 2.32-2.17 (m, 1H), 1.82 (dtd, J=14.3, 7.2, 2.6 Hz, 1H), 1.33 (dd, J=7.1, 1.1 Hz, 3H), 1.22 (dd, J=7.0, 1.2 Hz, 6H), 1.05 (dd, J=18.3, 7.0 Hz, 6H). $^{19}$F NMR (376 MHz, Methanol-d$_4$) δ -235.32 (t, J=46.8 Hz). $^{31}$P NMR (162 MHz, Methanol-d$_4$) δ 3.37. LCMS: MS m/z=749.23 [M+1]; t$_R$=1.13 min; LC system: Thermo Accela 1250 UHPLC; MS system: Thermo LCQ Fleet; Column: Phenomenex Kinetex 2.6 μXB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μl/min. HPLC: t$_R$=4.553 min; HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 39. (R)-2-methoxypropyl ((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate

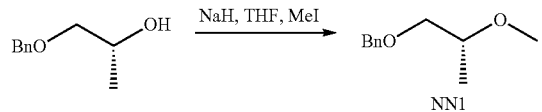

(R)-((2-met oxypropoxy methyl) benzene. To an ice co solution of (R)-(−)-1-Benzyloxy-2-propanol (3.0 g, 0.018 mol) in THF (20 mL) was added sodium hydride (0.866 g, 0.036 mol) portion-wise. Reaction mixture was stirred at 0° C. for 30 min followed by the addition of methyl iodide (2.247 mL, 0.036 mol). Reaction mixture was stirred at 0° C. for 1 h and was diluted with ice cold water and ethyl acetate. Organic layer was separated, dried over sodium sulfate, filtered and concentrated. The residue obtained was purified by silica gel chromatography using 0-40% ethyl acetate/hexanes to afford intermediate NN1. $^1$H NMR (400 MHz, Chloroform-d) δ 7.37 (d, J=4.3 Hz, 4H), 7.31 (dd, J=10.5, 6.1 Hz, 1H), 4.66-4.53 (m, 2H), 3.64-3.38 (m, 3H), 3.42 (s, 3H), 1.18 (d, J=6.3 Hz, 3H).

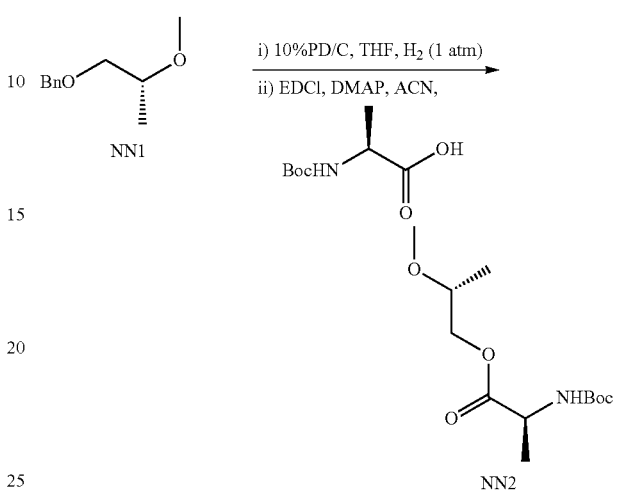

(R)-2-methoxypropyl (tert-butoxycarbonyl)-L-alaninate. To a degassed solution of intermediate NN1 (2.0 g, 0.011 mol) in THF (20 mL) was added 10% Pd/C (0.3 g, 0.003 mol) and the reaction mixture was stirred under hydrogen overnight. The reaction mixture was filtered and to the filtrate was added (tert-butoxycarbonyl)-L-alanine (2.519 g, 0.013 mol), acetonitrile (10 mL), EDCI (2.5 g, 0.016 mol) and DMAP (2.169 g, 0.018 mol) in one portion. The reaction mixture was allowed to stir at room temperature overnight and diluted with ethylacetate and water. The layers were split and the organic layer was dried over anhydrous sodium sulfate, filtered and was concentrated under reduced pressure. Purification by silica gel chromatography 0-30% ethylacetate/hexane to afford intermediate NN2. $^1$H NMR (400 MHz, DMSO-d$_6$) δ 7.26 (d, J=7.4 Hz, 1H), 4.10-3.93 (m, 2H), 3.91 (dd, J=11.4, 5.7 Hz, 1H), 3.46 (td, J=6.2, 4.2 Hz, 1H), 3.23 (s, 3H), 1.35 (s, 9H), 1.25-1.10 (m, 3H), 1.05 (d, J=6.4 Hz, 3H).

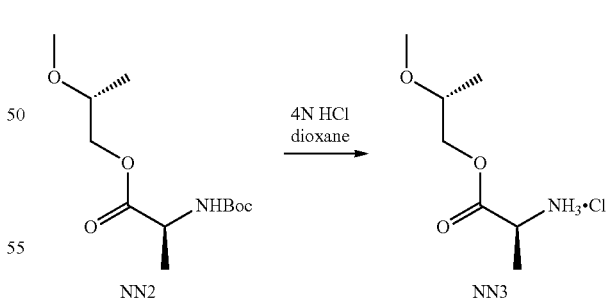

(R)-2-methoxypropyl)-L-alaninate hydrochloride. Intermediate NN2 (2.5 g, 0.010 mol) was dissolved in anhydrous dichloromethane (25 mL) and 4 N HCl in dioxane (11.96 mL, 0.048 mol). The resulting solution was stirred at ambient temperature for 4 h. The reaction was concentrated under reduced pressure and co-evaporated with dichloromethane. Resulting residue was placed under high vacuum overnight and intermediate NN3 was used as is in the next step. $^1$H NMR (400 MHz, DMSO-d$_6$) δ 8.63 (s, 3H), 4.19 (dd, J=11.4, 3.8 Hz, 1H), 4.10-3.96 (m, 2H), 3.59-3.46 (m, 1H), 3.24 (s, 3H), 1.41 (d, J=7.2 Hz, 3H), 1.08 (d, J=6.4 Hz, 3H).

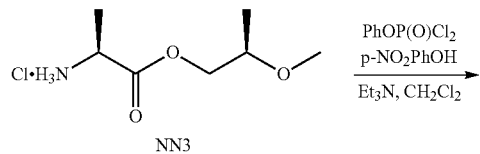

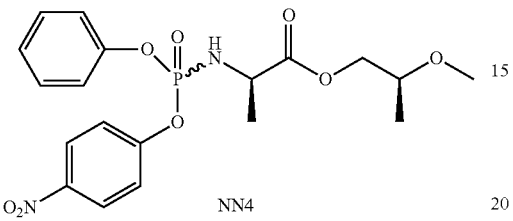

(R)-2-methoxypropyl ((4-nitrophenoxy)(phenoxy)phosphoryl)-L-alaninate. To a solution of intermediate NN3 (1.95 g, 9.865 mmol) and phenyl dichlorophosphate (1.468 mL, 9.865 mmol) in anhydrous dichloromethane (34 mL) was added triethylamine (3.05 mL, 21.71 mmol) at 0° C. under argon atmosphere. The resulting mixture was stirred for 1 h at 0° C. 4-Nitrophenol (1.372 g, 9.865 mmol) and triethylamine (1.525 mL, 10.85 mmol) were then added. After 1 h stirring at 0° C., the reaction mixture was diluted with Et$_2$O and the solids were filtered off. The crude was concentrated under reduced pressure and was purified by silica gel chromatography (80 g SiO$_2$ Combiflash HP Gold Column, 100% dichloromethane followed by 0-100% ethyl acetate/hexanes) to afford intermediate NN4 (diastereomeric mixture). $^1$H NMR (400 MHz, DMSO-d$_6$) δ 8.33-8.23 (m, 2H), 7.54-7.44 (m, 1H), 7.49-7.33 (m, 3H), 7.23 (m, 3H), 6.70 (ddd, J=13.7, 9.9, 8.3 Hz, 1H), 4.09-3.94 (m, 2H), 3.92 (ddd, J=11.4, 5.7, 1.4 Hz, 1H), 3.48-3.36 (m, 1H), 3.20 (d, J=1.5 Hz, 3H), 1.23 (ddd, J=7.2, 4.0, 1.2 Hz, 3H), 1.01 (dd, J=6.4, 1.1 Hz, 3H). $^{31}$P NMR (162 MHz, DMSO-d$_6$) δ-1.26, -1.48. LCMS: MS m/z=439.00 [M+1]; t$_R$=1.43 min; LC system: Thermo Accela 1250 UHPLC; MS system: Thermo LCQ Fleet; Column: Phenomenex Kinetex 2.6 μXB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min

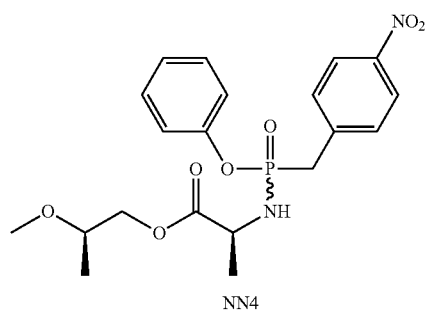

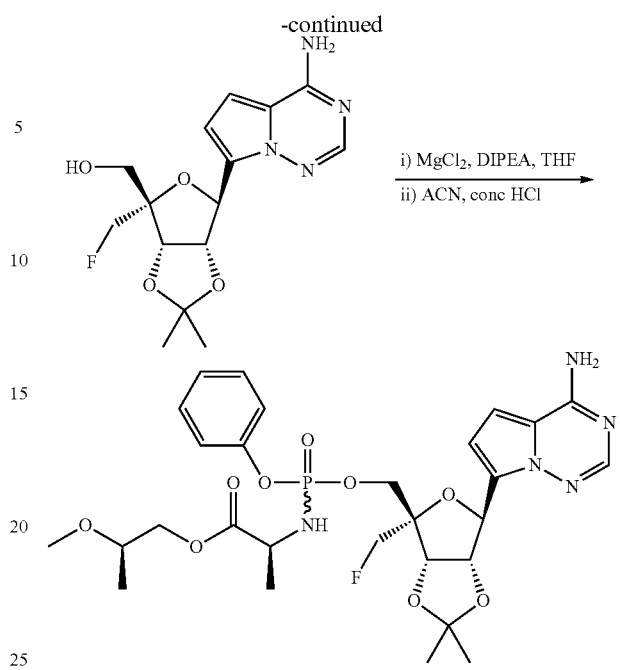

(R)-2-methoxypropyl (((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate. To a mixture of Intermediate 4 (0.15 g, 0.443 mmol), intermediate NN4 (0.214 g, 0.488 mmol), and magnesium chloride (0.063 g, 0.665 mmol) was added tetrahydrofuran (1.5 mL) at room temperature followed by the addition of N,N-diisopropylethylamine (0.193 mL, 1.108 mmol). The resulting mixture was stirred at 50° C. for 1.5 h. The reaction mixture was then concentrated under reduced pressure and the residue obtained was purified by preparative HPLC (Phenominex Synergi 4u Hydro-RR 80 Å 150× 30 mm column, 0-100% acetonitrile/water). Pure fractions were combined and concentrated under reduced pressure. Residue obtained was dissolved in an anhydrous acetonitrile (3 mL) and was cooled in an ice bath followed by the dropwise addition of concentrated hydrochloric acid (0.2 mL, 2.4 mmol). The reaction mixture was stirred at room temperature for 1 h. After 1 h the reaction mixture was cooled in an ice bath and was diluted with ice followed by neutralization with aqueous sodium bicarbonate solution. The resulting mixture was purified by preparative HPLC (Phenominex Synergi 4u Hydro-RR 80 Å 150×30 mm column, 0-100% acetonitrile/water) to afford the product (diastereomeric mixture). $^1$H NMR (400 MHz, Methanol-d$_4$) δ 7.78 (d, J=1.1 Hz, 1H), 7.33 (q, J=7.8 Hz, 2H), 7.27-7.13 (m, 3H), 6.85 (dd, J=6.2, 4.6 Hz, 1H), 6.74 (dd, J=10.6, 4.6 Hz, 1H), 5.36 (dd, J=8.3, 6.1 Hz, 1H), 4.82-4.55 (m, 3H), 4.35 (dd, J=17.4, 5.3 Hz, 1H), 4.29-4.15 (m, 2H), 4.10 (ddd, J=11.5, 4.0, 2.6 Hz, 1H), 4.06-3.86 (m, 2H), 3.53 (ddt, J=9.8, 6.3, 3.5 Hz, 1H), 3.31 (s, 3H), 1.29 (ddd, J=19.7, 7.2, 1.1 Hz, 3H), 1.11 (dd, J=6.4, 2.3 Hz, 3H). $^{19}$F NMR (376 MHz, Methanol-d$_4$) δ-238.52-238.94 (m). $^{31}$P NMR (162 MHz, Methanol-d$_4$) δ 3.70, 3.41. LCMS: MS m/z=598.04 [M+1]; t$_R$=0.99 min; LC system: Thermo Accela 1250 UHPLC; MS system: Thermo LCQ Fleet; Column: Phenomenex Kinetex 2.6 μXB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min HPLC: $t_R$=3.947 min (minor isomer), 4.011 min (major isomer); HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Resolution of the Sp and Rp diastereomers. The diastereomers were isolated from each other by chiral preparatory SFC (SFC Chiralpak AD-H 5 μm, 21×250 mm; 30% isopropanol):

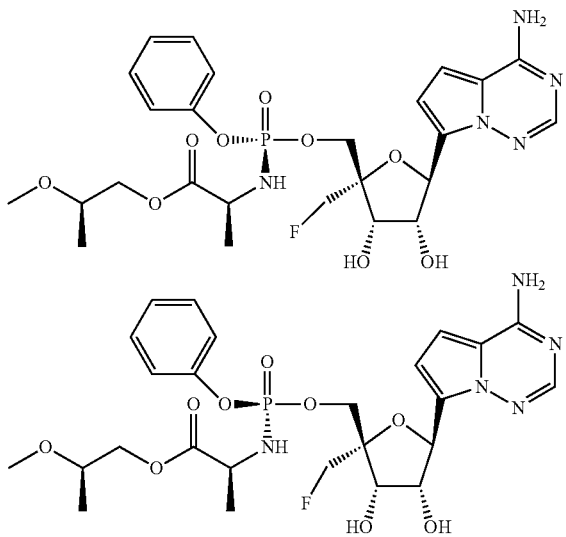

Example 40

First Eluting Diastereomer of Example 39: $^1$H NMR (400 MHz, Methanol-$d_4$) δ 7.78 (s, 1H), 7.37-7.28 (m, 2H), 7.24-7.13 (m, 3H), 6.86 (d, J=4.5 Hz, 1H), 6.76 (d, J=4.5 Hz, 1H), 5.37 (d, J=8.2 Hz, 1H), 4.83-4.71 (m, 1H), 4.71-4.59 (m, 2H), 4.37 (d, J=5.3 Hz, 1H), 4.26 (dd, J=5.0, 1.7 Hz, 2H), 4.09 (dd, J=11.5, 4.0 Hz, 1H), 4.06-3.86 (m, 2H), 3.60-3.48 (m, 1H), 3.31 (s, 3H), 1.26 (dd, J=7.2, 1.2 Hz, 3H), 1.12 (d, J=6.4 Hz, 3H). $^{19}$F NMR (376 MHz, Methanol-$d_4$) δ-238.68 (t, J=47.9 Hz). $^{31}$P NMR (162 MHz, Methanol-$d_4$) δ 3.71. LCMS: MS m/z=598.08 [M+1]; $t_R$=0.96 min; LC system: Thermo Accela 1250 UHPLC; MS system: Thermo LCQ Fleet; Column: Phenomenex Kinetex 2.6 μXB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μl/min. HPLC: $t_R$=3.938 min; HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 41

Second Eluting Diastereomer of Example 39: 1H NMR (400 MHz, Methanol-$d_4$) δ 7.78 (s, 1H), 7.39-7.29 (m, 2H), 7.27-7.14 (m, 3H), 6.84 (d, J=4.5 Hz, 1H), 6.73 (d, J=4.5 Hz, 1H), 5.36 (d, J=8.4 Hz, 1H), 4.82-4.56 (m, 3H), 4.33 (d, J=5.2 Hz, 1H), 4.21 (tt, J=6.0, 3.6 Hz, 2H), 4.10 (dd, J=11.5, 3.9 Hz, 1H), 4.03-3.88 (m, 2H), 3.53 (pd, J=6.3, 4.0 Hz, 1H), 1.31 (dd, J=7.2, 1.0 Hz, 3H), 1.11 (d, J=6.4 Hz, 3H). $^{19}$F NMR (376 MHz, Methanol-$d_4$) δ-238.81 (t, J=47.6 Hz). $^{31}$P NMR (162 MHz, Methanol-$d_4$) δ 3.42 LCMS: MS m/z=598.05 [M+1]; $t_R$=0.99 min; LC system: Thermo Accela 1250 UHPLC; MS system: Thermo LCQ Fleet; Column: Phenomenex Kinetex 2.6 μXB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=4.004 min; HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 42. 2-butoxyethyl (((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate

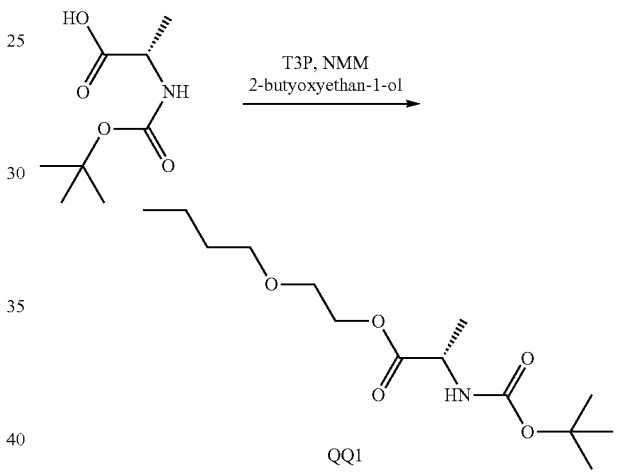

2-butoxyethyl (tert-butoxycarbonyl)-L-alaninate. To a stirred solution of (tert-butoxycarbonyl)-L-alanine (10.57 g, 56 mmol) and 2-butoxyethan-1-ol (6.00 g, 51 mmol) in dry dichloromethane (100 mL) were added N-methylmorpholine (16.75 mL, 152 mmol), 4-(dimethylamino)pyridine (0.12 g, 1 mmol) and tri-propylphosphonic acid cyclic anhydride (36.27 mL, 61 mmol, 50% in ethyl acetate) at 0° C. under an atmosphere of argon. The reaction mixture was then stirred at room temperature for 2 hours. The reaction mixture was washed with water (50 mL), twice with 10% solution of citric acid (2×40 mL), twice with saturated aqueous sodium bicarbonate solution (2×40 mL) and once with brine (50 mL), dried over sodium sulfate, filtered through a 3 cm layer of silica gel which was washed with additional dichloromethane. The combined organics were concentrated down under reduced pressure, co-distilled with dichloromethane and dried under high vacuum overnight to afford intermediate QQ1. $^1$H NMR (400 MHz, DMSO-$d_6$) δ 7.27 (d, J=7.4 Hz, 1H), 4.26-4.14 (m, 1H), 4.14-4.06 (m, 1H), 4.05-3.93 (m, 1H), 3.58-3.49 (m, 2H), 3.39 (t, J=6.5 Hz, 2H), 1.50-1.42 (m, 2H), 1.38 (s, 9H), 1.35-1.27 (m, 2H), 1.23 (d, J=7.4 Hz, 3H), 0.87 (t, J=7.4 Hz, 3H).

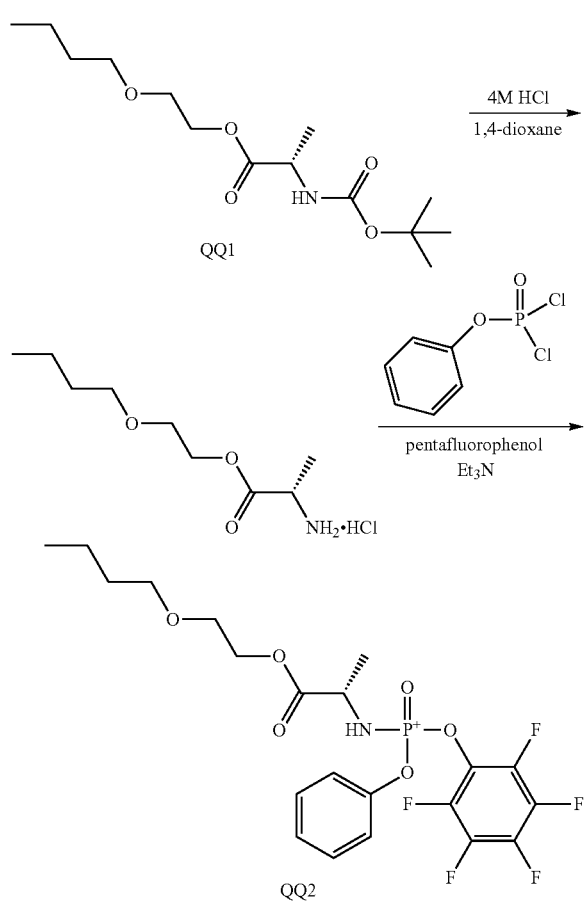

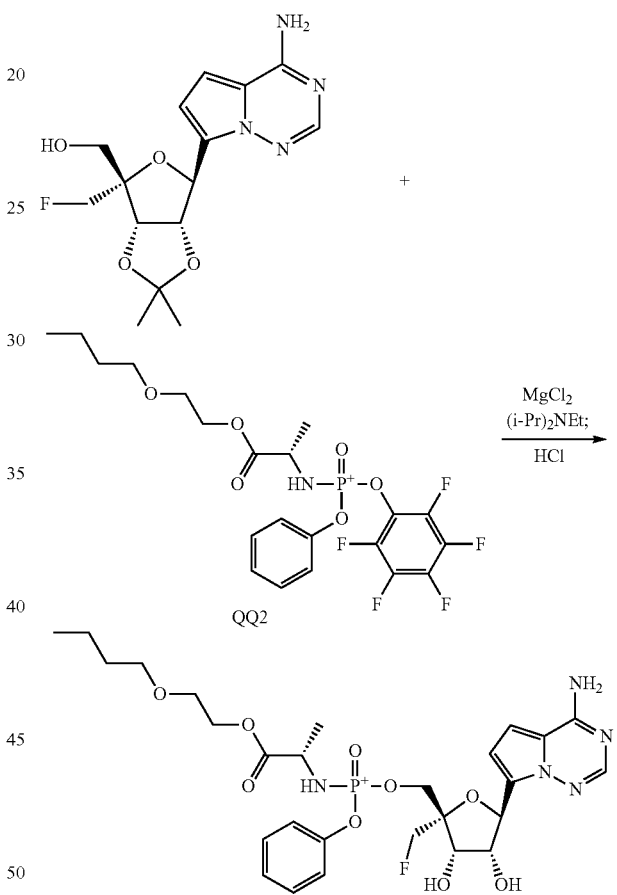

2-butoxyethyl ((perfluorophenoxy)(phenoxy)phosphoryl)-L-alaninate. The intermediate QQ1 (14.2 g, 49.07 mmol) was dissolved in 50 mL of 4 M HCl in 1,4-dioxane and the reaction mixture was stirred at room temperature for 2 hours, concentrated under reduced pressure and co-distilled with toluene to give the pure solid which was dried under high vacuum for 1 hour. The solids were suspended in dichloromethane (200 mL) and phenyl dichlorophosphate (8.03 mL, 53.98 mmol) and triethylamine (14.96 mL, 107.96 mmol) were sequentially added at −78° C. and the resulting mixture was stirred at room temperature for 2 hours. The reaction mixture was cooled down to 0° C. and pentafluorophenol (9.03 g, 49.07 mmol) and triethylamine (8.84 mL, 63.79 mmol) were then sequentially added and the resulting mixture was then allowed to warm to room temperature. After 3 hours, the reaction mixture was cooled down to 0° C. and solids were filtered off, the filtrate was washed with saturated ammonium chloride water solution (100 mL), water (100 mL) and brine (50 mL). The organics were dried over sodium sulfate and filtered through a 3 cm layer of silica gel which was washed with 1:5 ethyl acetate and dichloromethane mixture (100 mL). Combined organics were concentrated down under reduced pressure to afford 22.5 g of solid crude product as a mixture of both isomers on phosphorus based on the NMR. The solids were dissolved in boiling mixture of diisopropyl ether (6 mL) and hexane (200 mL) and the mixture was vigorously stirred at room temperature overnight. The solid product was isolated by filtration and washed with hexane (3×40 mL) to afford intermediate QQ2. Intermediate QQ2 was determined to be a single diastereomer by NMR spectroscopy. $^{1}$H NMR (400 MHz, DMSO-d$_6$) δ 7.47-7.35 (m, 2H), 7.31-7.16 (m, 3H), 6.93 (dd, J=14.2, 9.9 Hz, 1H), 4.23-4.08 (m, 2H), 4.07-3.90 (m, 1H), 3.52 (t, J=4.8 Hz, 2H), 3.35 (t, J=6.5 Hz, 2H), 1.46-1.37 (m, 2H), 1.36-1.18 (m, 5H), 0.84 (t, J=7.4 Hz, 3H). $^{19}$F NMR (376 MHz, DMSO-d$_6$) δ-154.25 (d, J=21.6 Hz, 2F), −160.87 (td, J=23.3, 3.2 Hz, 1F), −163.70 (td, J=24.0, 4.2 Hz, 2F). $^{31}$P NMR (162 MHz, DMSO-d$_6$) δ 0.42. LCMS: MS m/z=511.95 [M+1], t$_R$=1.70 min; LC system: Thermo Accela 1250 UHPLC; MS system: Thermo LCQ Fleet; Column: Kinetex 2.6 μXB-C18 100A, 50×4.6 mm; Solvents: acetonitrile with 0.1% acetic acid, water with 0.1% acetic acid; Gradient: 0 min-0.2 min 2% acetonitrile, 0.2 min-1.5 min 2-100% acetonitrile, 1.5 min-2.2 min 100% acetonitrile, 2.2 min-2.4 min 100%-2% acetonitrile, 2.4 min-2.5 min 2% acetonitrile at 2 μL/min.

2-butoxyethyl (((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate. Tetrahydrofuran (0.7 mL) was added to a mixture of Intermediate 4 (100 mg, 0.296 mmol), intermediate QQ2 (196 mg, 0.384 mmol), and magnesium chloride (42 mg, 0.443 mmol) at room temperature. The mixture was heated to 40° C. for 10 min, and N,N-diisopropylethylamine (0.129 mL, 0.739 mmol) was added. After stirring for 2 hours at 40° C., the reaction mixture was allowed to cool to room temperature, and was concentrated down under reduced pressure. The crude residue was dissolved in ethyl acetate (20 mL) and the resulting mixture was washed with water (20 mL) and brine (20 mL). The organic layer was separated, dried over anhydrous sodium sulfate and concentrated under reduced pressure. The crude residue was dissolved in acetonitrile (5 mL) and concentrated aqueous hydrochloric acid solution (0.246 mL) was added dropwise at 0° C. After 4 hours at 0° C., the reaction mixture was diluted with ethyl acetate (30 mL) and water (20 mL) at 0° C. and the resulting mixture was washed with saturated aqueous sodium bicarbonate solution (20 mL) and brine (20 mL). The organic layer was dried over anhydrous sodium sulfate and concentrated under reduced pressure. The crude residue was purified by preparatory HPLC (Phenomenex Gemini 5 μm $C_{18\ 110}$Å 100×30 mm column) using gradient from 10-100% acetonitrile in water to afford the product, which was determined to be a single diastereomer by NMR spectroscopy. $^1$H NMR (400 MHz, DMSO-$d_6$) δ 8.10-7.75 (m, 3H), 7.43-7.33 (m, 2H), 7.27-7.15 (m, 3H), 6.91 (d, J=4.4 Hz, 1H), 6.71 (d, J=4.5 Hz, 1H), 6.11 (dd, J=13.3, 10.1 Hz, 1H), 5.43-5.10 (m, 3H), 4.70-4.57 (m, 1H), 4.58-4.44 (m, 2H), 4.23-4.12 (m, 2H), 4.13-4.02 (m, 1H), 3.99 (d, J=5.3 Hz, 2H), 3.93-3.78 (m, 1H), 3.55-3.49 (m, 2H), 3.35-3.33 (m, 2H), 1.47-1.37 (m, 2H), 1.34-1.17 (m, 5H), 0.84 (t, J=7.4 Hz, 3H). $^{19}$F NMR (376 MHz, DMSO-$d_6$) δ-236.74 (t, J=47.9 Hz). $^{31}$P NMR (162 MHz, DMSO-$d_6$) δ 3.44. LCMS: MS m/z=626.03 [M+1], $t_R$=1.26 min; LC system: Thermo Accela 1250 UHPLC; MS system: Thermo LCQ Fleet; Column: Kinetex 2.6 μXB-C18 100A, 50×4.6 mm; Solvents: acetonitrile with 0.1% acetic acid, water with 0.1% acetic acid; Gradient: 0 min-0.2 min 2% acetonitrile, 0.2 min-1.5 min 2-100% acetonitrile, 1.5 min-2.2 min 100% acetonitrile, 2.2 min-2.4 min 100%-2% acetonitrile, 2.4 min-2.5 min 2% acetonitrile at 2 μl/min. HPLC: $t_R$=2.78 min; HPLC system: Agilent 1100 series; Column: Gemini 5 μC18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min. HPLC: $t_R$=4.68 min; HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 43. 2-methoxy-2-methylpropyl ((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate

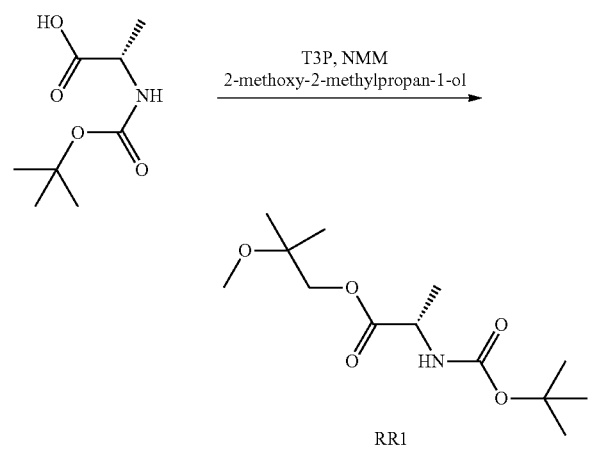

2-methoxy-2-methylpropyl (tert-butoxycarbonyl)-L-alaninate. To a stirred solution of (tert-butoxycarbonyl)-L-alanine (4.00 g, 21 mmol) and 2-methoxy-2-methylpropan-1-ol (2.00 g, 19 mmol) in dry dichloromethane (50 mL) were added N-methylmorpholine (6.33 mL, 58 mmol), 4-(dimethylamino)pyridine (0.05 g, 0.4 mmol) and tri-propylphosphonic acid cyclic anhydride (13.72 mL, 23 mmol, 50% in ethyl acetate) at 0° C. under an atmosphere of argon. The reaction mixture was then stirred at room temperature for 2 hours. The reaction mixture was washed with water (30 mL), twice with 10% solution of citric acid (2×20 mL), twice with saturated aqueous sodium bicarbonate solution (2×20 mL) and once with brine (20 mL), dried over sodium sulfate, filtered through a 3 cm layer of silica gel which was washed with 3:1 mixture of dichloromethane and ethyl acetate. The combined organics were concentrated down under reduced pressure, co-distilled with dichloromethane and dried under high vacuum overnight to afford intermediate RR1. $^1$H NMR (400 MHz, DMSO-$d_6$) δ 7.30 (d, J=7.4 Hz, 1H), 4.10-3.77 (m, 3H), 3.11 (s, 3H), 1.37 (s, 9H), 1.24 (d, J=7.4 Hz, 3H), 1.10 (s, 6H).

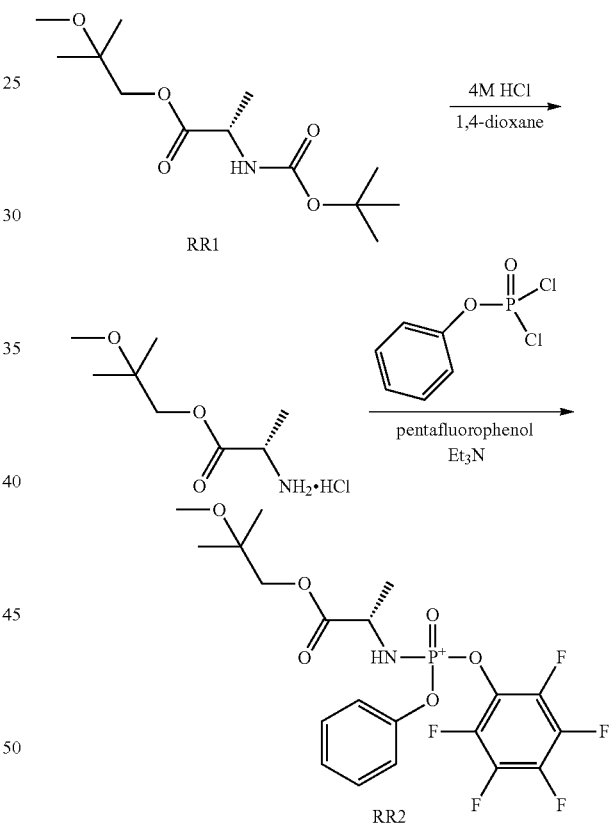

2-methoxy-2-methylpropyl ((perfluorophenoxy)(phenoxy)-phosphoryl)-L-alaninate. The intermediate RR1 (5.1 g, 18.52 mmol) was dissolved in 15 mL of 4 M HCl in 1,4-dioxane and the reaction mixture was stirred at room temperature for 2 hours, concentrated under reduced pressure and co-distilled with toluene to give the pure solid which was dried under high vacuum for 1 hour. The solids were suspended in dichloromethane (100 mL) and phenyl dichlorophosphate (3.03 mL, 20.37 mmol) and triethylamine (5.65 mL, 40.75 mmol) were sequentially added at −78° C. and the resulting mixture was stirred at room temperature for 2 hours. The reaction mixture was cooled down to 0° C. and pentafluorophenol (3.41 g, 18.52 mmol) and triethylamine (3.59 mL, 25.93 mmol) were then sequentially added and the resulting mixture was then allowed to warm to room temperature. After 3 hours, the reaction mixture was cooled down to 0° C. and solids were filtered off, the filtrate was washed with saturated ammonium chloride water solution (100 mL), water (100 mL) and brine (50 mL). The organics were dried over sodium sulfate and filtered through a 3 cm layer of silica gel which was washed with 1:3 ethyl acetate and dichloromethane mixture (100 mL). Combined organics were concentrated down under reduced pressure to afford 6.23 g of the crude product as a mixture of both isomers on phosphorus based on the NMR. The solids were dissolved in boiling diisopropyl ether (50 mL) and the mixture was vigorously stirred at room temperature overnight. The solid product was filtered off and washed with cold diisopropyl ether (2×10 mL) and hexane (3×20 mL) to afford intermediate RR2. Intermediate RR2 was determined to be a single diastereomer by NMR spectroscopy. $^1$H NMR (400 MHz, DMSO-$d_6$) δ 7.46-7.36 (m, 2H), 7.29-7.16 (m, 3H), 6.92 (dd, J=14.2, 9.9 Hz, 1H), 4.12-3.86 (m, 3H), 3.09 (s, 3H), 1.31 (d, J=7.1 Hz, 3H), 1.09 (s, 6H). $^{19}$F NMR (376 MHz, DMSO-$d_6$) δ-154.22 (d, J=21.4 Hz, 2F), −160.89 (td, J=23.4, 3.2 Hz, 1F), −163.69 (td, J=23.4, 4.0 Hz, 2F). $^{31}$P NMR (162 MHz, DMSO-$d_6$) δ 0.43. LCMS: MS m/z=497.86 [M+1], $t_R$=1.65 min; LC system: Thermo Accela 1250 UHPLC; MS system: Thermo LCQ Fleet; Column: Kinetex 2.6 μXB-C18 100A, 50×4.6 mm; Solvents: acetonitrile with 0.1% acetic acid, water with 0.1% acetic acid; Gradient: 0 min-0.2 min 2% acetonitrile, 0.2 min-1.5 min 2-100% acetonitrile, 1.5 min-2.2 min 100% acetonitrile, 2.2 min-2.4 min 100%-2% acetonitrile, 2.4 min-2.5 min 2% acetonitrile at 2 μL/min.

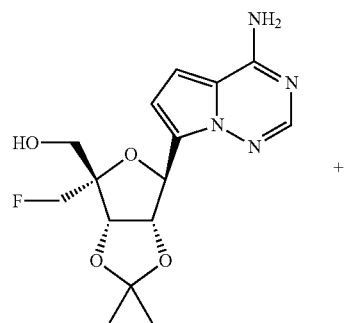

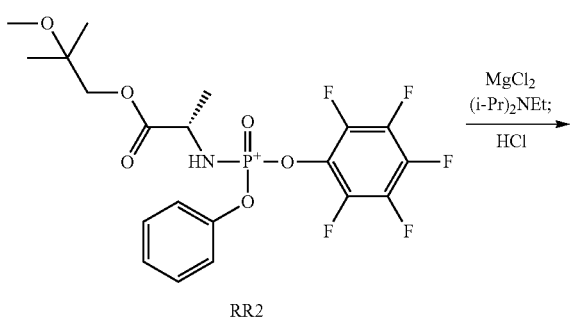

RR2

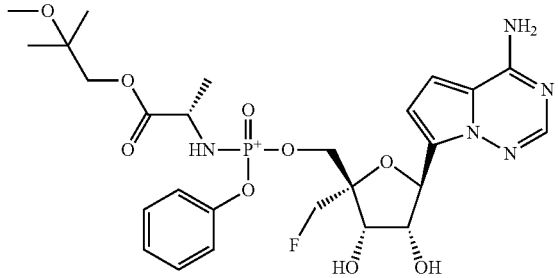

2-methoxy-2-methylpropyl ((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate. Tetrahydrofuran (0.7 mL) was added to a mixture of Intermediate 4 (100 mg, 0.296 mmol), intermediate RR2 (191 mg, 0.384 mmol), and magnesium chloride (42 mg, 0.443 mmol) at room temperature. The mixture was heated to 40° C. for 10 min, and N,N-diisopropylethylamine (0.129 mL, 0.739 mmol) was added. After stirring for 2 hours at 40° C., the reaction mixture was allowed to cool to room temperature, and was concentrated down under reduced pressure. The crude residue was dissolved in ethyl acetate (20 mL) and the resulting mixture was washed with water (20 mL) and brine (20 mL). The organic layer was separated, dried over anhydrous sodium sulfate and concentrated under reduced pressure. The crude residue was dissolved in acetonitrile (5 mL) and concentrated aqueous hydrochloric acid solution (0.246 mL) was added dropwise at 0° C. After 4 hours at 0° C., the reaction mixture was diluted with ethyl acetate (30 mL) and water (20 mL) at 0° C. and the resulting mixture was washed with saturated aqueous sodium bicarbonate solution (20 mL) and brine (20 mL). The organic layer was dried over anhydrous sodium sulfate and concentrated under reduced pressure. The crude residue was purified by preparatory HPLC (Phenomenex Gemini 5 μm C18 110 Å 100×30 mm column) using gradient from 10-100% acetonitrile in water to afford the product, which was determined to be a single diastereomer by NMR spectroscopy. $^1$H NMR (400 MHz, DMSO-$d_6$) δ 7.83 (s, 1H), 7.70 (bs, 2H), 7.44-7.30 (m, 2H), 7.26-7.14 (m, 3H), 6.84 (d, J=4.4 Hz, 1H), 6.68 (d, J=4.4 Hz, 1H), 6.10 (dd, J=13.1, 10.1 Hz, 1H), 5.29-5.21 (m, 2H), 5.13 (d, J=7.3 Hz, 1H), 4.72-4.43 (m, 3H), 4.25-4.15 (m, 1H), 4.03-3.95 (m, 3H), 3.95-3.82 (m, 2H), 3.08 (s, 3H), 1.26 (d, J=7.2 Hz, 3H), 1.09 (s, 6H). $^{19}$F NMR (376 MHz, DMSO-$d_6$) δ-236.71 (t, J=48.1 Hz). $^{31}$P NMR (162 MHz, DMSO-$d_6$) δ 3.47. LCMS: MS m/z=612.03 [M+1], $t_R$=1.16 min; LC system: Thermo Accela 1250 UHPLC; MS system: Thermo LCQ Fleet; Column: Kinetex 2.6 μXB-C18 100A, 50×4.6 mm; Solvents: acetonitrile with 0.1% acetic acid, water with 0.1% acetic acid; Gradient: 0 min-0.2 min 2% acetonitrile, 0.2 min-1.5 min 2-100% acetonitrile, 1.5 min-2.2 min 100% acetonitrile, 2.2 min-2.4 min 100%-2% acetonitrile, 2.4 min-2.5 min 2% acetonitrile at 2 μl/min. HPLC: $t_R$=2.47 min; HPLC system: Agilent 1100 series; Column: Gemini 5 μC18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

Example 44. ethyl ((((2R,3S,4R,5S)-5-(4-aminopyr-rolo[2,1-f][1,2,4]triazin-7-yl)-2-(fluoromethyl)-3,4-dihydroxytetrahydrofuran-2-yl)methoxy)(naphtha-len-1-yloxy)phosphoryl)-L-alaninate

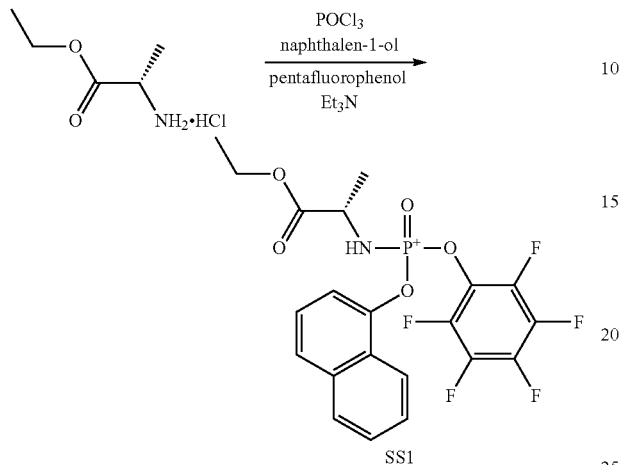

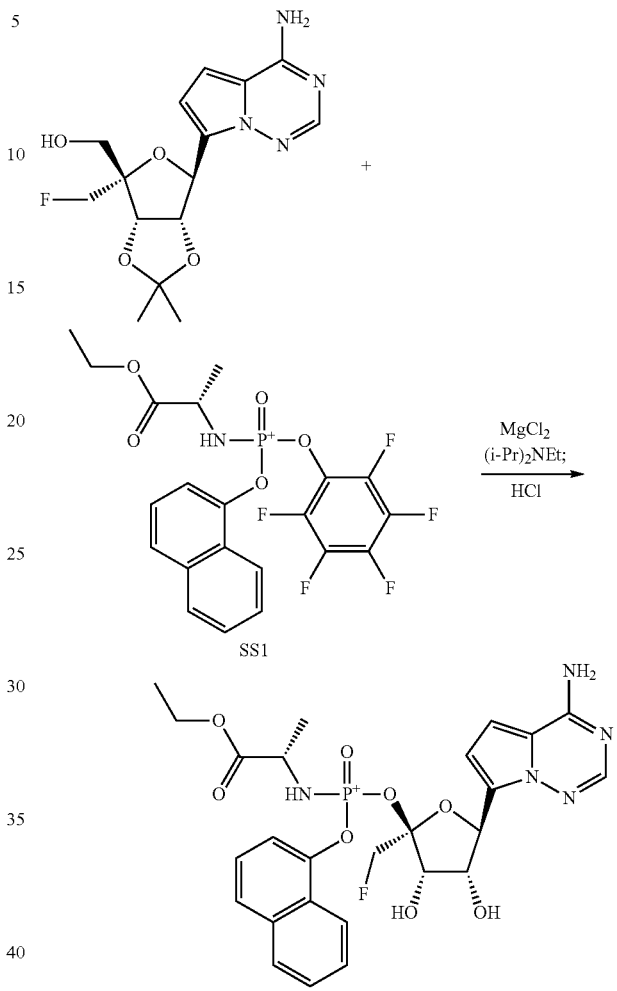

ethyl ((naphthalen-1-yloxy)(perfluorophenoxy)phospho-ryl)-L-alaninate. To a solution of phosphoryl trichloride (3.00 g, 19.57 mmol) in dry tetrahydrofuran (50 mL) at −78° C. under argon was added naphthalen-1-ol (2.82 g, 19.57 mmol). Triethylamine (6.00 mL, 43.05 mmol) was added dropwise. After 15 minutes, the reaction was allowed to warm to 0° C. After 30 minutes, the reaction was cooled again to −78° C. and ethyl L-alaninate hydrochloride (3.01 g, 19.57 mmol) was added followed by triethylamine (2.73 mL, 19.57 mmol). The reaction was allowed to warm to room temperature and stirred for 3 hours. The reaction was cooled to 0° C. and pentafluorophenol (3.60 g, 19.57 mmol) was added followed by a dropwise addition of triethylamine (3.00 mL, 21.52 mmol). The reaction mixture was allowed to warm to room temperature and stirred for 2 hours, diluted with ethyl acetate (100 mL) and washed with saturated ammonium chloride water solution (100 mL), water (100 mL) and brine (100 mL). The organics were dried over sodium sulfate, filtered and were concentrated down under reduced pressure. The crude residue was purified by silica gel column chromatography suing gradient from 0 to 35% ethyl acetate in hexane to afford 4.9 g of the crude product as a mixture of diastereomers. The solids were dissolved in boiling diisopropyl ether (70 mL) and the mixture was vigorously stirred at room temperature overnight. The solid product was filtered off and washed with cold diisopropyl ether (2×10 mL) and hexane (3×20 mL) to afford interme-diate SS1. Intermediate SS1 was determined to be a single diastereomer by NMR spectroscopy. $^1$H NMR (400 MHz, DMSO-$d_6$) δ 8.14-8.08 (m, 1H), 8.03-7.98 (m, 1H), 7.82 (d, J=7.7 Hz, 1H), 7.67-7.44 (m, 4H), 7.11 (dd, J=14.3, 9.9 Hz, 1H), 4.15-3.92 (m, 3H), 1.33 (d, J=7.1 Hz, 3H), 1.09 (t, J=7.1 Hz, 3H). $^{19}$F NMR (376 MHz, DMSO-$d_6$) δ-154.19 (d, J=21.6 Hz, 2F), −160.70 (t, J=23.4 Hz, 1F), −163.61 (t, J=21.9 Hz, 2F). $^{31}$P NMR (162 MHz, DMSO-$d_6$) δ 0.68. LCMS: MS m/z=489.95 [M+1], $t_R$=1.76 min; LC system: Thermo Accela 1250 UHPLC; MS system: Thermo LCQ Fleet; Column: Kinetex 2.6 μXB-C18 100A, 50×4.6 mm; Solvents: acetonitrile with 0.1% acetic acid, water with 0.1% acetic acid; Gradient: 0 min-0.2 min 2% acetonitrile, 0.2 min-1.5 min 2-100% acetonitrile, 1.5 min-2.2 min 100% acetonitrile, 2.2 min-2.4 min 100%-2% acetonitrile, 2.4 min-2.5 min 2% acetonitrile at 2 μL/min.

ethyl ((((2R,3S,4R,5S)-5-(4-aminopyrrolo[2,1-f][1,2,4] triazin-7-yl)-2-(fluoromethyl)-3,4-dihydroxytetrahydro-furan-2-yl)methoxy)(naphthalen-1-yloxy)phosphoryl)-L-al-aninate. Tetrahydrofuran (0.4 mL) was added to a mixture of Intermediate 4 (50 mg, 0.148 mmol), intermediate SS1 (94 mg, 0.192 mmol), and magnesium chloride (21 mg, 0.222 mmol) at room temperature. The mixture was heated to 40° C. for 10 min, and N,N-diisopropylethylamine (0.064 mL, 0.369 mmol) was added. After stirring for 2 hours at 40° C., the reaction mixture was allowed to cool to room tempera-ture, and was concentrated down under reduced pressure. The crude residue was dissolved in ethyl acetate (20 mL) and the resulting mixture was washed with water (20 mL) and brine (20 mL). The organic layer was separated, dried over anhydrous sodium sulfate and concentrated under reduced pressure. The crude residue was dissolved in acetonitrile (5 mL) and concentrated aqueous hydrochloric acid solution (0.123 mL) was added dropwise at 0° C. After 4 hours at 0° C., the reaction mixture was diluted with ethyl acetate (30 mL) and water (20 mL) at 0° C. and the resulting mixture was washed with saturated aqueous sodium bicar-bonate solution (20 mL) and brine (20 mL). The organic layer was dried over anhydrous sodium sulfate and concen-trated under reduced pressure. The crude residue was purified by preparatory HPLC (Phenomenex Gemini 5 μm C$_{18}$ 110Å 100×30 mm column) using gradient from 10-100% acetonitrile in water to afford the product, which was determined to be a single diastereomer by NMR spectroscopy. $^1$H NMR (400 MHz, DMSO-d$_6$) δ 8.19-8.10 (m, 1H), 8.02-7.93 (m, 1H), 7.87 (s, 1H), 7.80-7.72 (m, 1H), 7.62-7.55 (m, 2H), 7.52-7.43 (m, 2H), 6.91 (d, J=4.4 Hz, 1H), 6.67 (d, J=4.5 Hz, 1H), 6.26 (dd, J=13.0, 10.1 Hz, 1H), 5.38-5.11 (m, 3H), 4.74-4.46 (m, 3H), 4.22 (d, J=4.9 Hz, 1H), 4.13-3.99 (m, 4H), 3.95-3.86 (m, 1H), 1.22 (d, J=7.1 Hz, 3H), 1.12 (t, J=7.1 Hz, 3H). $^{19}$F NMR (376 MHz, DMSO-d$_6$) δ -236.51 (t, J=47.7 Hz). $^{31}$P NMR (162 MHz, DMSO-d$_6$) δ 3.98. LCMS: MS m/z=604.02 [M+1], t$_R$=1.21 min; LC system: Thermo Accela 1250 UHPLC; MS system: Thermo LCQ Fleet; Column: Kinetex 2.6 μXB-C18 100A, 50×4.6 mm; Solvents: acetonitrile with 0.1% acetic acid, water with 0.1% acetic acid; Gradient: 0 min-0.2 min 2% acetonitrile, 0.2 min-1.5 min 2-100% acetonitrile, 1.5 min-2.2 min 100% acetonitrile, 2.2 min-2.4 min 100%-2% acetonitrile, 2.4 min-2.5 min 2% acetonitrile at 2 μL/min. HPLC: t$_R$=2.69 min; HPLC system: Agilent 1100 series; Column: Gemini 5 μC18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min. HPLC: t$_R$=4.51 min; HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 45. 2-(2-ethoxyethoxy)ethyl ((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate

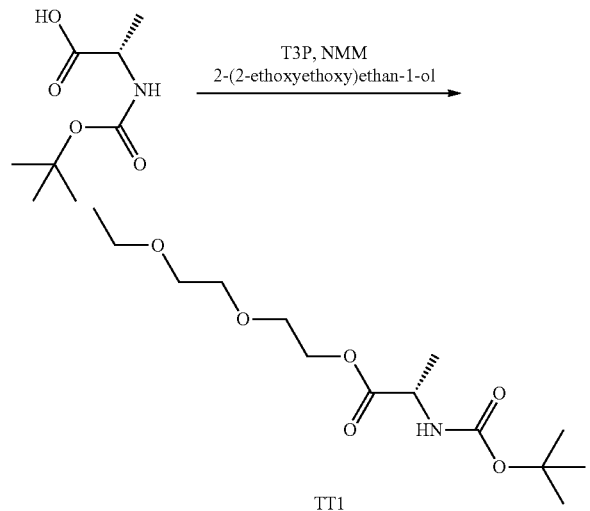

2-(2-ethoxyethoxy)ethyl (tert-butoxycarbonyl)-L-alaninate. To a stirred solution of (tert-butoxycarbonyl)-L-alanine (12.41 g, 66 mmol) and 2-(2-ethoxyethoxy)ethan-1-ol (8.00 g, 60 mmol) in dry dichloromethane (100 mL) were added N-methylmorpholine (19.67 mL, 179 mmol), 4-(dimethylamino)pyridine (0.15 g, 1.2 mmol) and tri-propylphosphonic acid cyclic anhydride (42.6 mL, 72 mmol, 50% in ethyl acetate) at 0° C. under an atmosphere of argon. The reaction mixture was then stirred at room temperature for 2 hours. The reaction mixture was washed with water (50 mL), twice with 10% solution of citric acid (2×40 mL), twice with saturated aqueous sodium bicarbonate solution (2×40 mL) and once with brine (50 mL), dried over sodium sulfate, filtered through a 3 cm layer of silica gel which was washed with additional dichloromethane. The combined organics were concentrated down under reduced pressure, co-distilled with dichloromethane and dried under high vacuum overnight to afford intermediate TT1. $^1$H NMR (400 MHz, DMSO-d$_6$) δ 7.27 (d, J=7.4 Hz, 1H), 4.23-4.14 (m, 1H), 4.14-4.06 (m, 1H), 4.05-3.94 (m, 1H), 3.64-3.56 (m, 2H), 3.55-3.49 (m, 2H), 3.49-3.39 (m, 4H), 1.38 (s, 9H), 1.23 (d, J=7.4 Hz, 3H), 1.09 (t, J=7.0 Hz, 3H).

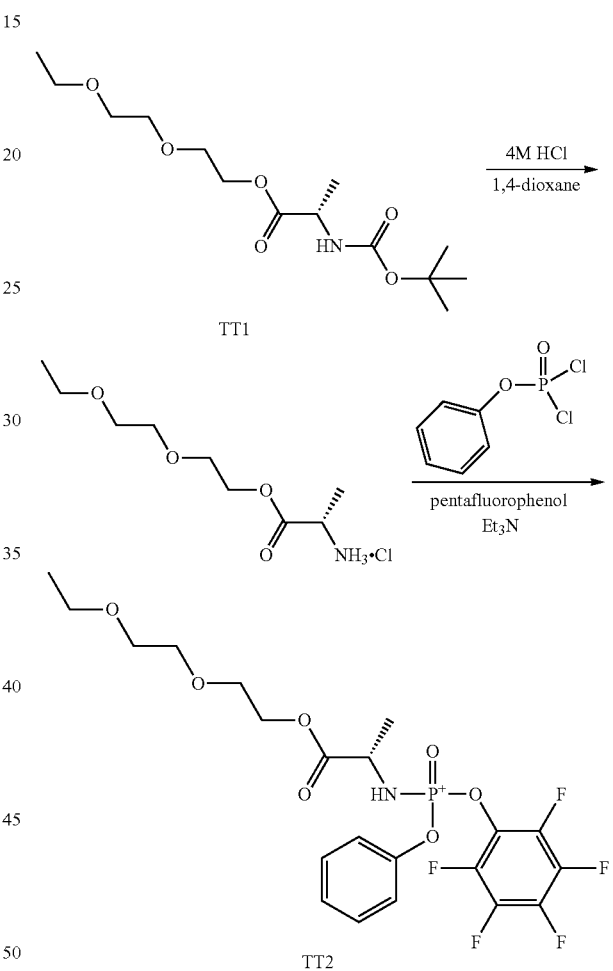

2-(2-ethoxyethoxy)ethyl ((perfluorophenoxy)(phenoxy)phosphoryl)-L-alaninate. The intermediate TT1 (18.3 g, 59.93 mmol) was dissolved in 50 mL of 4 M HCl in 1,4-dioxane and the reaction mixture was stirred at room temperature for 2 hours, concentrated under reduced pressure and co-distilled with toluene to give the crude product which was dried under high vacuum for 1 hour. The resulting solids were suspended in dichloromethane (100 mL) and phenyl dichlorophosphate (9.81 mL, 65.92 mmol) and triethylamine (18.28 mL, 131.84 mmol) were sequentially added at -78° C. and the resulting mixture was stirred at room temperature for 2 hours. The reaction mixture was cooled down to 0° C. and pentafluorophenol (11.03 g, 59.93 mmol) and triethylamine (10.80 mL, 78.05 mmol) were then sequentially added and the resulting mixture was then allowed to warm to room temperature. After 3 hours, the reaction mixture was cooled down to 0° C. and solids were filtered off, the filtrate was washed with saturated ammonium chloride water solution (100 mL), water (100 mL) and brine (50 mL). The organics were dried over sodium sulfate and filtered through a 3 cm layer of silica gel which was washed with 1:1 ethyl acetate and dichloromethane mixture (100 mL). Combined organics were concentrated down under reduced pressure to afford 21.7 g of the crude product as a mixture of diastereomers. The solids were dissolved in minimum amount of boiling diisopropyl ether and the mixture was vigorously stirred at room temperature overnight. The solid product was filtered off and washed with cold diisopropyl ether (2×20 mL) and hexane (3×40 mL) to afford intermediate TT2. Intermediate TT2 was determined to be a single diastereomer by NMR spectroscopy. $^1$H NMR (400 MHz, DMSO-d$_6$) δ 7.47-7.36 (m, 2H), 7.30-7.20 (m, 3H), 6.92 (dd, J=14.2, 9.9 Hz, 1H), 4.21-4.08 (m, 2H), 4.07-3.92 (m, 1H), 3.62-3.56 (m, 2H), 3.53-3.47 (m, 2H), 3.45-3.36 (m, 4H), 1.29 (d, J=7.1 Hz, 3H), 1.07 (t, J=7.0 Hz, 3H). $^{19}$F NMR (376 MHz, DMSO-d$_6$) δ-154.24 (d, J=21.5 Hz, 2F), −160.86 (t, J=23.1 Hz, 1F), −163.68 (t, J=21.7 Hz, 2F). $^{31}$P NMR (162 MHz, DMSO-d$_6$) δ 0.40. LCMS: MS m/z=528.06 [M+1], t$_R$-1.64 min; LC system: Thermo Accela 1250 UHPLC; MS system: Thermo LCQ Fleet; Column: Kinetex 2.6 μXB-C18 100A, 50×4.6 mm; Solvents: acetonitrile with 0.1% acetic acid, water with 0.1% acetic acid; Gradient: 0 min-0.2 min 2% acetonitrile, 0.2 min-1.5 min 2-100% acetonitrile, 1.5 min-2.2 min 100% acetonitrile, 2.2 min-2.4 min 100%-2% acetonitrile, 2.4 min-2.5 min 2% acetonitrile at 2 μL/min.

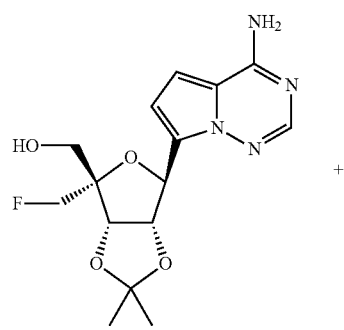

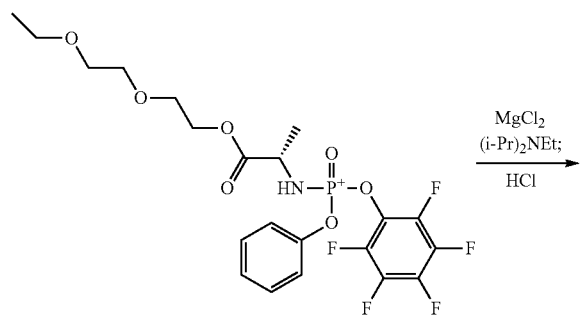

TT2

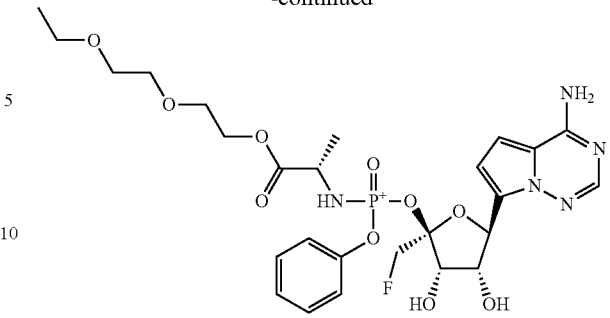

2-(2-ethoxyethoxy)ethyl ((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate. Tetrahydrofuran (0.7 mL) was added to a mixture of Intermediate 4 (100 mg, 0.295 mmol), intermediate TT2 (203 mg, 0.384 mmol), and magnesium chloride (42 mg, 0.443 mmol) at room temperature. The mixture was heated to 40° C. for 10 min, and N,N-diisopropylethylamine (0.129 mL, 0.739 mmol) was added. After stirring for 2 hours at 40° C., the reaction mixture was allowed to cool to room temperature, and was concentrated down under reduced pressure. The crude residue was dissolved in ethyl acetate (20 mL) and the resulting mixture was washed with water (20 mL) and brine (20 mL). The organic layer was separated, dried over anhydrous sodium sulfate and concentrated under reduced pressure. The crude residue was dissolved in acetonitrile (5 mL) and concentrated aqueous hydrochloric acid solution (0.246 mL) was added dropwise at 0° C. After 4 hours at 0° C., the reaction mixture was diluted with ethyl acetate (30 mL) and water (20 mL) at 0° C. and the resulting mixture was washed with saturated aqueous sodium bicarbonate solution (20 mL) and brine (20 mL). The organic layer was dried over anhydrous sodium sulfate and concentrated under reduced pressure. The crude residue was purified by preparatory HPLC (Phenomenex Gemini 5 μm C18 110 Å 100×30 mm column) using gradient from 10-100% acetonitrile in water to afford the product, which was determined to be a single diastereomer by NMR spectroscopy. $^1$H NMR (400 MHz, DMSO-d$_6$) δ 7.84 (s, 1H), 7.77 (bs, 2H), 7.42-7.34 (m, 2H), 7.28-7.13 (m, 3H), 6.86 (d, J=4.5 Hz, 1H), 6.69 (d, J=4.5 Hz, 1H), 6.11 (dd, J=13.3, 10.1 Hz, 1H), 5.37-5.22 (m, 2H), 5.20-5.10 (m, 1H), 4.64 (q, J=10.2 Hz, 1H), 4.57-4.43 (m, 2H), 4.24-4.14 (m, 2H), 4.12-4.05 (m, 1H), 4.03-3.97 (m, 2H), 3.92-3.79 (m, 1H), 3.59-3.54 (m, 2H), 3.51-3.45 (m, 2H), 3.43-3.38 (m, 4H), 1.24 (d, J=7.1 Hz, 3H), 1.07 (t, J=7.0 Hz, 3H). $^{19}$F NMR (376 MHz, DMSO-d$_6$) δ-236.74 (t, J=48.1 Hz). $^{31}$P NMR (162 MHz, DMSO-d$_6$) δ 3.43. LCMS: MS m/z=642.08 [M+1], t$_R$=1.13 min; LC system: Thermo Accela 1250 UHPLC; MS system: Thermo LCQ Fleet; Column: Kinetex 2.6 μXB-C18 100A, 50×4.6 mm; Solvents: acetonitrile with 0.1% acetic acid, water with 0.1% acetic acid; Gradient: 0 min-0.2 min 2% acetonitrile, 0.2 min-1.5 min 2-100% acetonitrile, 1.5 min-2.2 min 100% acetonitrile, 2.2 min-2.4 min 100%-2% acetonitrile, 2.4 min-2.5 min 2% acetonitrile at 2 μl/min. HPLC: t$_R$=2.43 min; HPLC system: Agilent 1100 series; Column: Gemini 5 μC18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min. HPLC: t$_R$=4.05 min; HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 46. butyl ((S)-(((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate

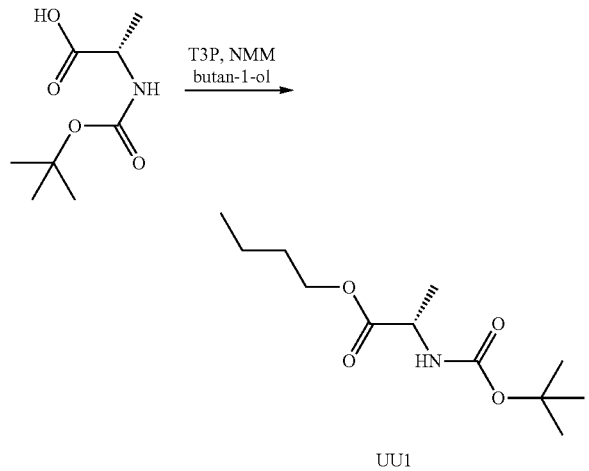

butyl (tert-butoxycarbonyl)-L-alaninate. To a stirred solution of (tert-butoxycarbonyl)-L-alanine (14.04 g, 74 mmol) and butan-1-ol (5.00 g, 67 mmol) in dry dichloromethane (100 mL) were added N-methylmorpholine (22.25 mL, 202 mmol), 4-(dimethylamino)pyridine (0.17 g, 1.4 mmol) and tri-propylphosphonic acid cyclic anhydride (48.19 mL, 81 mmol, 50% in ethyl acetate) at 0° C. under an atmosphere of argon. The reaction mixture was then stirred at room temperature for 2 hours. The reaction mixture was washed with water (50 mL), twice with 10% solution of citric acid (2×40 mL), twice with saturated aqueous sodium bicarbonate solution (2×40 mL) and once with brine (50 mL), dried over sodium sulfate, filtered through a 3 cm layer of silica gel which was washed with additional dichloromethane. The combined organics were concentrated down under reduced pressure, co-distilled with dichloromethane and dried under high vacuum overnight to afford intermediate UU1. $^1$H NMR (400 MHz, DMSO-$d_6$) δ 7.27 (d, J=7.4 Hz, 1H), 4.19-3.89 (m, 3H), 1.60-1.48 (m, 2H), 1.42-1.28 (m, 11H), 1.22 (d, J=7.4 Hz, 3H), 0.88 (t, J=7.4 Hz, 3H).

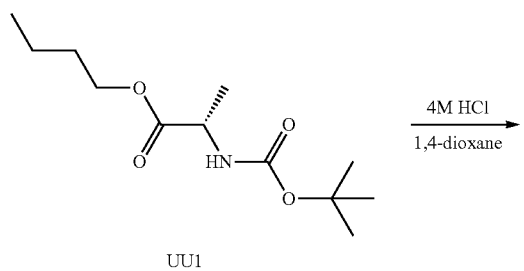

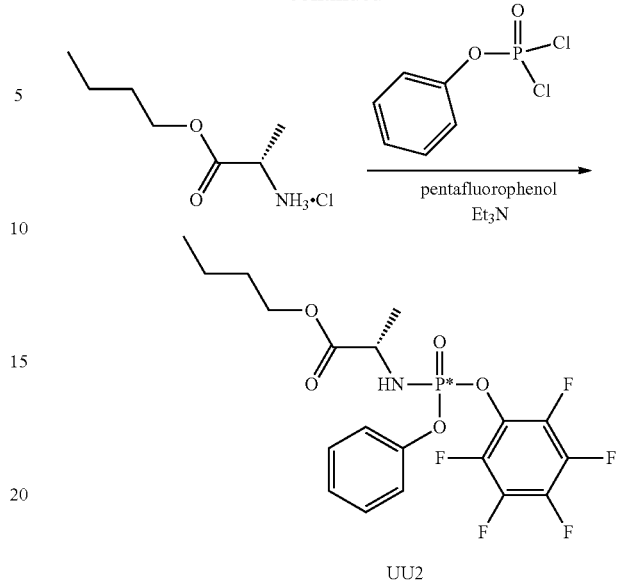

butyl ((perfluorophenoxy)(phenoxy)phosphoryl)-L-alaninate. The intermediate UU1 (6.75 g, 27.5 mmol) was dissolved in 30 mL of 4 M HCl in 1,4-dioxane and the reaction mixture was stirred at room temperature for 2 hours, concentrated under reduced pressure and co-distilled with toluene to give the cure solid which was dried under high vacuum for 1 hour. The solids were suspended in dichloromethane (30 mL) and phenyl dichlorophosphate (4.51 mL, 30.3 mmol) and triethylamine (8.39 mL, 60.6 mmol) were sequentially added at −78° C. and the resulting mixture was stirred at room temperature for 2 hours. The reaction mixture was cooled down to 0° C. and pentafluorophenol (5.07 g, 27.5 mmol) and triethylamine (4.20 mL, 30.0 mmol) were then sequentially added and the resulting mixture was then allowed to warm to room temperature. After 3 hours, the reaction mixture was cooled down to 0° C. and solids were filtered off, the filtrate was washed with saturated ammonium chloride water solution (50 mL), water (50 mL) and brine (20 mL). The organics were dried over sodium sulfate and filtered through a 3 cm layer of silica gel which was washed with additional dichloromethane (50 mL). Combined organics were concentrated down under reduced pressure to afford 12.2 g of the crude product as a mixture of diastereomers. The solids were dissolved in boiling hexane (120 mL) and the mixture was vigorously stirred at room temperature overnight. The solid product was filtered off and washed with hexane (3×30 mL) to afford intermediate UU2. Intermediate UU2 was determined to be a single diastereomer by NMR spectroscopy. $^1$H NMR (400 MHz, DMSO-$d_6$) δ 7.47-7.36 (m, 2H), 7.30-7.17 (m, 3H), 6.89 (dd, J=14.2, 9.9 Hz, 1H), 4.12-3.91 (m, 3H), 1.59-1.45 (m, 2H), 1.38-1.19 (m, 5H), 0.85 (t, J=7.3 Hz, 3H). $^{19}$F NMR (376 MHz, DMSO-$d_6$) δ-154.24 (d, J=20.7 Hz, 2F), −160.88 (t, J=23.1 Hz, 1F), −163.70 (t, J=21.6 Hz, 2F). $^{31}$P NMR (162 MHz, DMSO-$d_6$) δ 0.48. LCMS: MS m/z=467.92 [M+1], $t_R$=1.86 min; LC system: Thermo Accela 1250 UHPLC; MS system: Thermo LCQ Fleet; Column: Kinetex 2.6 µXB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% acetonitrile at 2 µL/min.

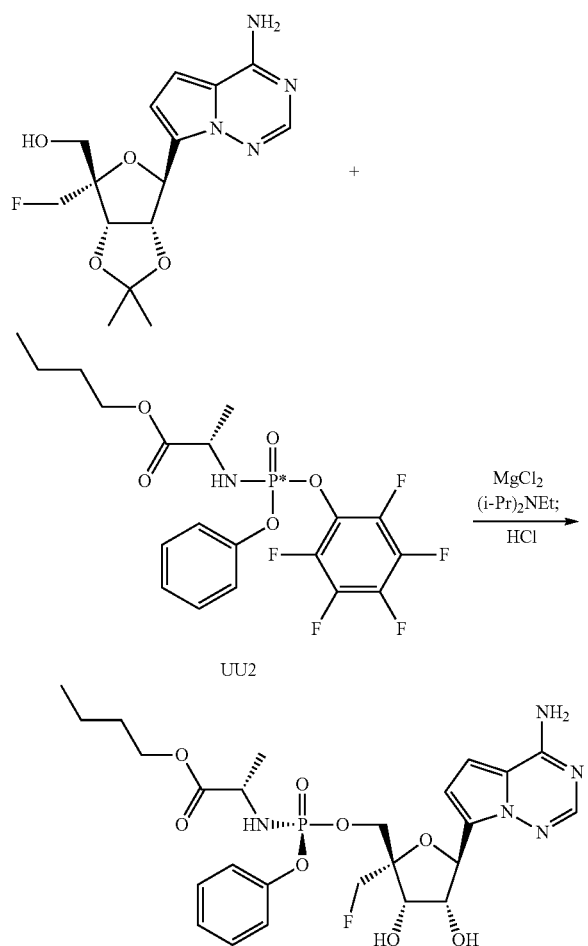

UU2 butyl ((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate. Tetrahydrofuran (0.5 mL) was added to a mixture of Intermediate 4 (70 mg, 0.207 mmol), intermediate UU2 (126 mg, 0.269 mmol), and magnesium chloride (30 mg, 0.310 mmol) at room temperature. The mixture was heated to 40° C. for 10 min, and N,N-diisopropylethylamine (0.090 mL, 0.517 mmol) was added. After stirring for 2 hours at 40° C., the reaction mixture was allowed to cool to room temperature, and was concentrated down under reduced pressure. The crude residue was dissolved in ethyl acetate (20 mL) and the resulting mixture was washed with water (20 mL) and brine (20 mL). The organic layer was separated, dried over anhydrous sodium sulfate and concentrated under reduced pressure. The crude residue was dissolved in acetonitrile (2 mL) and concentrated aqueous hydrochloric acid solution (0.172 mL) was added dropwise at 0° C. After 4 hours at 0° C., the reaction mixture was diluted with ethyl acetate (30 mL) and water (20 mL) at 0° C. and the resulting mixture was washed with saturated aqueous sodium bicarbonate solution (20 mL) and brine (20 mL). The organic layer was dried over anhydrous sodium sulfate and concentrated under reduced pressure. The crude residue was purified by preparatory HPLC (Phenomenex Gemini 5 μm C18 110 Å 100×30 mm column) using gradient from 10-100% acetonitrile in water to afford the product, which was determined to be a single diastereomer by NMR spectroscopy. $^1$H NMR (400 MHz, DMSO-$d_6$) δ 7.83 (s, 1H), 7.73 (bs, 2H), 7.43-7.32 (m, 2H), 7.25-7.13 (m, 3H), 6.85 (d, J=4.5 Hz, 1H), 6.69 (d, J=4.5 Hz, 1H), 6.08 (dd, J=13.2, 10.2 Hz, 1H), 5.34-5.21 (m, 2H), 5.20-5.07 (m, 1H), 4.71-4.58 (m, 1H), 4.57-4.41 (m, 2H), 4.29-4.15 (m, 1H), 4.10-3.94 (m, 4H), 3.93-3.74 (m, 1H), 1.60-1.42 (m, 2H), 1.36-1.13 (m, 5H), 0.84 (t, J=7.4 Hz, 3H). $^{19}$F NMR (376 MHz, DMSO-$d_6$) δ-236.73 (t, J=47.8 Hz). $^{31}$P NMR (162 MHz, DMSO-$d_6$) δ 3.49. LCMS: MS m/z=582.02 [M+1], $t_R$=1.22 min; LC system: Thermo Accela 1250 UHPLC; MS system: Thermo LCQ Fleet; Column: Kinetex 2.6 μXB-C18 100A, 50×4.6 mm; Solvents: acetonitrile with 0.1% acetic acid, water with 0.1% acetic acid; Gradient: 0 min-0.2 min 2% acetonitrile, 0.2 min-1.5 min 2-100% acetonitrile, 1.5 min-2.2 min 100% acetonitrile, 2.2 min-2.4 min 100%-2% acetonitrile, 2.4 min-2.5 min 2% acetonitrile at 2 μl/min. HPLC: $t_R$=2.75 min; HPLC system: Agilent 1100 series; Column: Gemini 5 μC18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min. HPLC: $t_R$=4.60 min; HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 47. ethyl ((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(4-(tert-butyl)phenoxy)phosphoryl)-L-alaninate

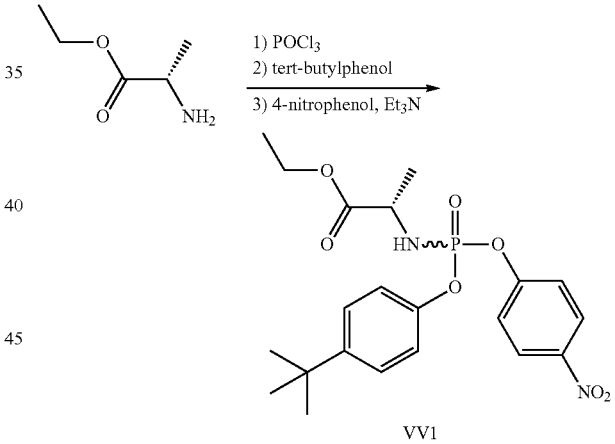

VV1 ethyl ((4-(tert-butyl)phenoxy)(4-nitrophenoxy)phosphoryl)-L-alaninate. To a solution of phosphorus(V) oxychloride (0.61 mL, 6.52 mmol) in dichloromethane (20 mL) at −78° C. under an atmosphere of argon was added L-alanine ethyl ester (1.00 g, 6.52 mmol). Triethylamine (2.00 mL, 14.35 mmol) was added dropwise slowly. After 15 minutes, the reaction was allowed to warm to 0° C. After 30 minutes, the reaction was cooled to −78° C. and 4-tert-butylphenol (0.98 g, 6.52 mmol) was added. Triethylamine (0.91 mL, 6.52 mmol) was added. The reaction was allowed to warm to room temperature and stirred for 3 h. The reaction was cooled to 0° C. 4-Nitrophenol (0.91 g, 6.52 mmol) was added followed by a dropwise addition of triethylamine (0.91 mL, 6.52 mmol). The reaction was allowed to warm to room temperature and stirred for 2 h. The reaction was diluted with ethyl acetate and washed with ammonium chloride, water, brine. The organics were dried over sodium sulfate, filtered and wereconcentrated. Intermediate VV1 (diastereomeric mixture) was isolated as an oil by silica gel chromatography (using a gradient from 0-50% ethyl acetate in hexanes). $^1$H NMR (400 MHz, DMSO-d$_6$) δ 8.31 (d, J=8.8 Hz, 2H), 7.57-7.36 (m, 4H), 7.24-7.09 (m, 2H), 6.76-6.57 (m, 1H), 4.12-3.77 (m, 3H), 1.30-1.21 (m, 12H), 1.11 (t, J=7.1 Hz, 3H). $^{31}$P NMR (162 MHz, DMSO-d$_6$) δ-1.16, −1.24. LCMS: MS m/z=451.00 [M+1], t$_R$=1.84 min; LC system: Thermo Accela 1250 UHPLC; MS system: Thermo LCQ Fleet; Column: Kinetex 2.6p XB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 L/min.

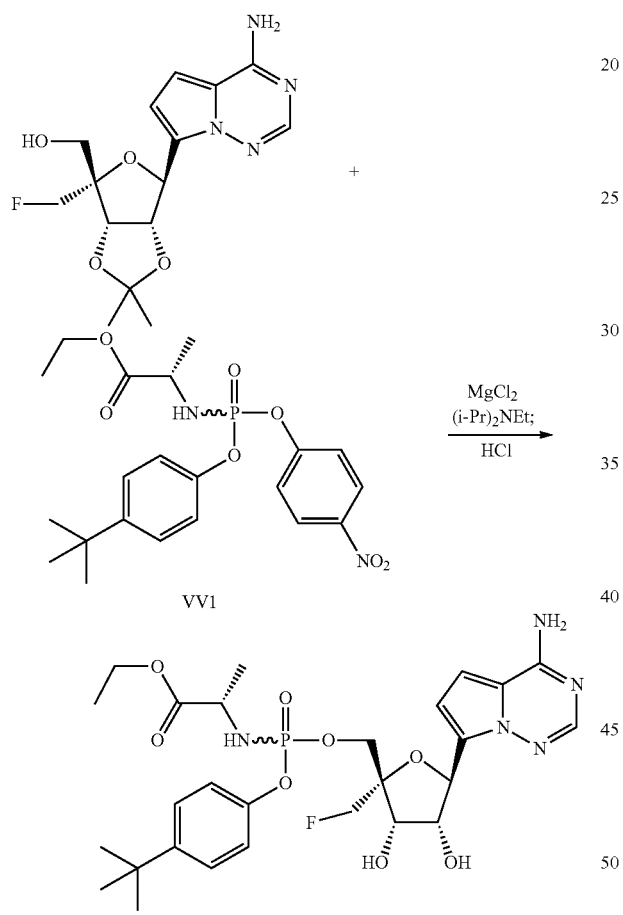

ethyl ((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(4-(tert-butyl)phenoxy)phosphoryl)-L-alaninate. Tetrahydrofuran (0.5 mL) was added to a mixture of Intermediate 4 (40 mg, 0.12 mmol), intermediate VV1 (71 mg, 0.16 mmol), and magnesium chloride (17 mg, 0.18 mmol) at room temperature. The mixture was stirred at room temperature for 20 minutes. N,N-diisopropylethylamine (52 µL, 0.30 mmol) was added. The reaction was heated to 50° C. for 2 h. The reaction mixture was allowed to cool to room temperature, and diluted with ethyl acetate (2 mL). The organics were washed with water (2 mL), dried over sodium sulfate, filtered and were concentrated. To a solution of the residue in acetonitrile (2 mL) at was added aqueous hydrochloric acid solution (0.3 mL, 3.6 mmol, 12 M) dropwise at 0° C. After 1 h, the reaction mixture was diluted with ethyl acetate (5 mL) and the resulting mixture was washed with saturated aqueous sodium carbonate solution (5 mL) and brine (5 mL). The organic layer was dried over anhydrous sodium sulfate and concentrated under reduced pressure. The residue was purified by HPLC chromatography (Phenomenex Gemini 5 µm C$_{18\ 110}$ Å, 100×30 mm, gradient from 5-100% acetonitrile in water) to afford example VV (diastereomeric mixture). LCMS: MS m/z=609.96 [M+1], t$_R$=1.42 min (minor), 1.44 min (major); LC system: Thermo Accela 1250 UHPLC; MS system: Thermo LCQ Fleet; Column: Kinetex 2.6 µXB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 µL/min Resolution of the Sp and Rp diastereomers. The diastereomers were isolated from each other by chiral preparatory SFC (SFC chiralpack AD-H 5 µm, 250×21 mm; methanol 25%):

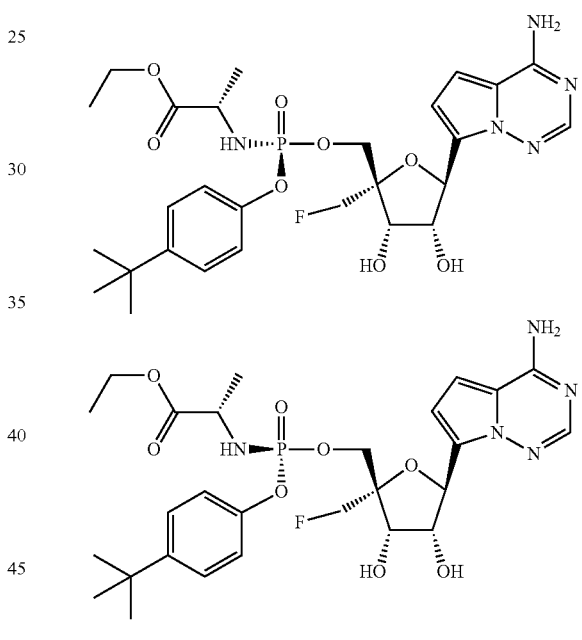

Example 48

First Eluting Diastereomer of Example 47: $^1$H NMR (400 MHz, Methanol-d$_4$) δ 8.00 (s, 1H), 7.40-7.33 (m, 3H), 7.16-7.09 (m, 2H), 6.99 (d, J=4.8 Hz, 1H), 5.40 (d, J=8.1 Hz, 1H), 4.82-4.72 (m, 1H), 4.70-4.57 (m, 2H), 4.39 (d, J=5.2 Hz, 1H), 4.34-4.20 (m, 2H), 4.12 (q, J=7.1 Hz, 2H), 3.96-3.83 (m, 1H), 1.33-1.26 (m, 12H), 1.22 (t, J=7.1 Hz, 3H). $^{31}$P NMR (162 MHz, Methanol-d$_4$) δ 3.93. $^{19}$F NMR (376 MHz, Methanol-d$_4$) δ-238.56 (t, J=47.8 Hz). LCMS: MS m/z=609.96 [M+1], t$_R$=1.42 min; LC system: Thermo Accela 1250 UHPLC; MS system: Thermo LCQ Fleet; Column: Kinetex 2.6 µXB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 µL/min. HPLC: t$_R$=2.91 min; HPLC system: Agilent 1290

Example 49

Second Eluting Diastereomer of Example 47: $^1$H NMR (400 MHz, Methanol-$d_4$) δ 7.99 (s, 1H), 7.43-7.35 (m, 2H), 7.35-7.30 (m, 1H), 7.20-7.13 (m, 2H), 6.96 (d, J=4.7 Hz, 1H), 5.39 (d, J=8.4 Hz, 1H), 4.82-4.69 (m, 1H), 4.69-4.53 (m, 2H), 4.35 (d, J=5.2 Hz, 1H), 4.28-4.15 (m, 2H), 4.15-4.07 (m, 2H), 3.99-3.84 (m, 1H), 1.35-1.26 (m, 12H), 1.22 (t, J=7.1 Hz, 3H). $^{31}$P NMR (162 MHz, Methanol-$d_4$) δ 3.78. $^{19}$F NMR (376 MHz, Methanol-$d_4$) δ-238.79 (t, J=47.8 Hz). LCMS: MS m/z=609.96 [M+1], $t_R$=1.45 min; LC system: Thermo Accela 1250 UHPLC; MS system: Thermo LCQ Fleet; Column: Kinetex 2.6 μXB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=2.94 min; Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 50. (1-methylcyclopropyl)methyl ((((2R, 3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate

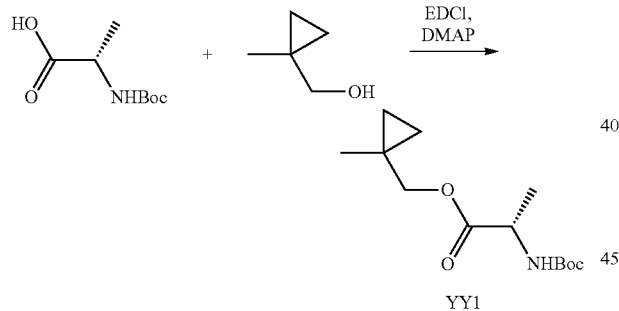

(1-methylcyclopropyl)methyl (tert-butoxycarbonyl)-L-alaninate. 1-(3-Dimethylaminopropyl)-3-ethylcarbodiimide hydrochloride (1.22 g, 6.36 mmol) was added to a solution of (tert-butoxycarbonyl)-alanine (1.00 g, 5.29 mmol) in 10 mL of acetonitrile under an atmosphere of argon. After 15 minutes, 4-(dimethylamino)-pyridine (0.71 g, 5.81 mmol) then (1-methylcyclopropyl)methanol (0.51 ml, 5.29 mmol) was added. The reaction was stirred for 2 h at room temperature. The reaction was diluted with ethyl acetate (20 mL) and washed with a 5% citric acid solution in water (2×10 mL). The organics were washed with saturated aqueous sodium bicarbonate (10 mL), water (5 mL) then brine (10 mL). The organics were dried over sodium sulfate, filtered and were concentrated. The residue was purified by silica gel chromatography (using a gradient from 0-10% ethyl acetate in hexanes) to afford intermediate YY1. $^1$H NMR (400 MHz, DMSO-$d_6$) δ 7.26 (d, J=7.4 Hz, 1H), 4.09-3.69 (m, 3H), 1.38 (s, 9H), 1.25 (d, J=7.5 Hz, 3H), 1.06 (s, 3H), 0.56-0.39 (m, 2H), 0.38-0.24 (m, 2H).

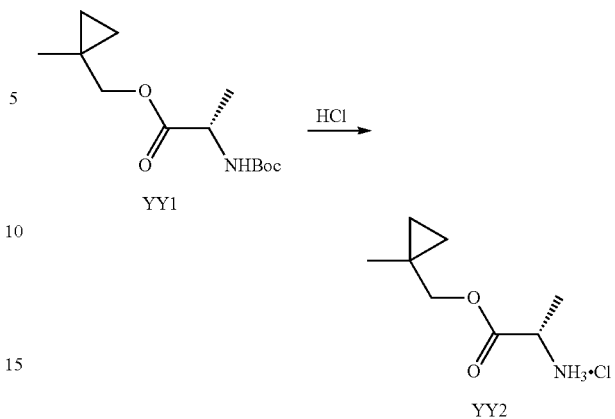

(1-methylcyclopropyl)methyl L-alaninate hydrochloride. Hydrogen chloride, 4 M in 1,4-dioxane, (3.7 mL, 14.80 mmol) was added to a solution of intermediate YY1 (1.85 g, 7.19 mmol) in dichloromethane (10 mL) at 0° C. After 1 h, the reaction was concentrated. The residue was taken up in dichloromethane (10 mL) and concentrated. The previous step was repeated. Intermediate YY2 was taken on to the next reaction without further purification. $^1$H NMR (400 MHz, DMSO-$d_6$) δ 8.41 (s, 3H), 4.13 (q, J=7.2 Hz, 1H), 4.07-3.91 (m, 2H), 1.43 (d, J=7.2 Hz, 3H), 1.10 (s, 3H), 0.56-0.47 (m, 2H), 0.39-0.33 (m, 2H).

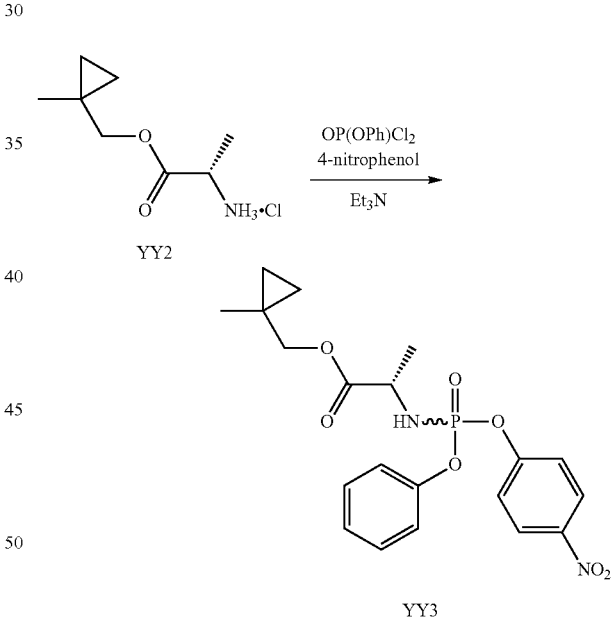

(1-methylcyclopropyl)methyl ((4-nitrophenoxy)(phenoxy)phosphoryl)-L-alaninate. Phenyl dichlorophosphate (0.82 mL, 5.45 mmol) and triethylamine (1.58 mL, 11.36 mmol) were sequentially added to a suspension intermediate YY2 (880 mg, 4.54 mmol) in dichloromethane (15 mL) at 0° C. After 1 h, 4-nitrophenol (0.63 g, 4.54 mmol) and triethylamine (0.79 mL, 5.8 mmol) were then sequentially added at 0° C., and the resulting mixture was then allowed to warm to room temperature. After 2.5 h, the reaction mixture was diluted with dichloromethane (50 mL), washed with saturated aqueous sodium bicarbonate solution (50 mL) and brine (50 mL), dried over anhydrous sodium sulfate, and concentrated under reduced pressure. The crude residue was purified by silica gel chromatography eluting with 0-100% ethyl acetate in hexanes to afford intermediate YY3 (diastereomeric mixture). $^1$H NMR (400 MHz, DMSO-$d_6$) δ 8.34-8.27 (m, 2H), 7.55-7.37 (m, 4H), 7.31-7.17 (m, 3H), 6.78-6.65 (m, 1H), 4.13-3.97 (m, 1H), 3.89-3.76 (m, 2H), 1.31-1.21 (m, 3H), 1.02 (d, J=1.5 Hz, 3H), 0.49-0.37 (m, 2H), 0.35-0.23 (m, 2H). $^{31}$P NMR (162 MHz, DMSO-$d_6$) δ-1.25,-1.44. LCMS: MS m/z=433.02 [M−1], $t_R$=1.75 min (minor), 1.77 (major); LC system: Thermo Accela 1250 UHPLC; MS system: Thermo LCQ Fleet; Column: Kinetex 2.6 μXB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min.

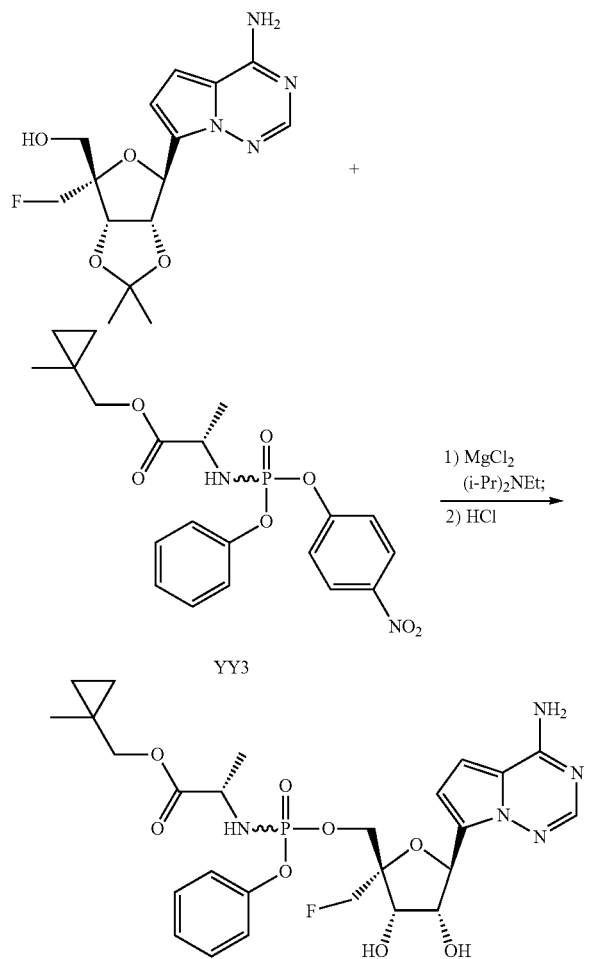

YY3

(1-methylcyclopropyl)methyl ((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate. Tetrahydrofuran (0.5 mL) was added to a mixture of Intermediate 4 (40 mg, 0.12 mmol), intermediate YY3 (67 mg, 0.15 mmol), and magnesium chloride (17 mg, 0.18 mmol) at room temperature. The mixture was stirred at room temperature for 20 minutes. N,N-diisopropylethylamine (52 μL, 0.30 mmol) was added. The reaction was heated to 50° C. for 2 h. The reaction mixture was allowed to cool to room temperature, and diluted with ethyl acetate (2 mL). The organics were washed with water (2 mL), dried over sodium sulfate, filtered and were concentrated. To a solution of the residue in acetonitrile (2 mL) at was added aqueous hydrochloric acid solution (0.3 mL, 3.60 mmol, 12 M) dropwise at 0° C. After 1 h, the reaction mixture was diluted with ethyl acetate (5 mL) and the resulting mixture was washed with saturated aqueous sodium bicarbonate solution (5 mL) and brine (5 mL). The organic layer was dried over anhydrous sodium sulfate and concentrated under reduced pressure. The residue was purified by HPLC chromatography (Phenomenex Gemini 5 μm $C_{18}$ 110 Å, 100×30 mm, 5-100% acetonitrile in water) to afford the product (diastereomeric mixture). LCMS: MS m/z=593.95 [M+1], $t_R$=1.33 min (minor), 1.35 min (major); LC system: Thermo Accela 1250 UHPLC; MS system: Thermo LCQ Fleet; Column: Kinetex 2.6 μXB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min Resolution of the Sp and Rp diastereomers. The diastereomers were isolated from each other by chiral preparatory HPLC (Chiralpak IA 5 μm, 250×22 mm; ethanol 100%):

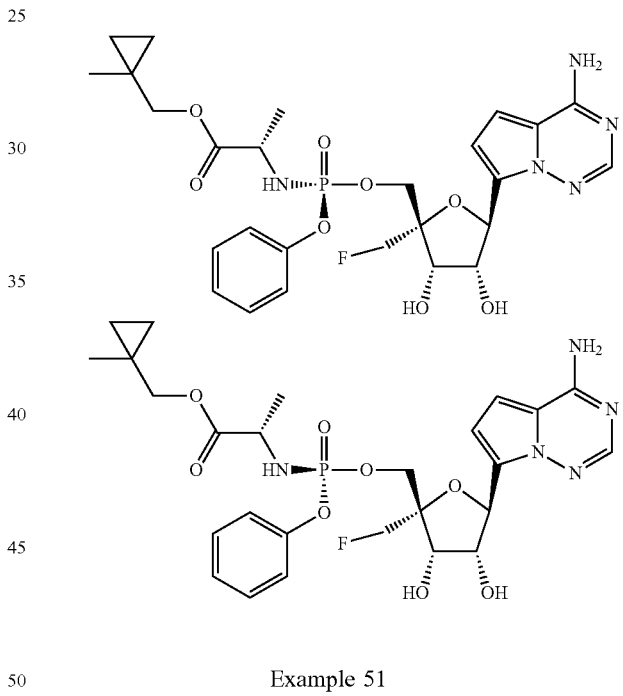

Example 51

First Eluting Diastereomer of Example 50: $^1$H NMR (400 MHz, Methanol-$d_4$) δ 7.87 (s, 1H), 7.36-7.29 (m, 2H), 7.25-7.15 (m, 3H), 7.07 (d, J=4.6 Hz, 1H), 6.86 (d, J=4.6 Hz, 1H), 5.38 (d, J=8.2 Hz, 1H), 4.81-4.73 (m, 1H), 4.70-4.59 (m, 2H), 4.38 (d, J=5.3 Hz, 1H), 4.33-4.23 (m, 2H), 4.00-3.86 (m, 3H), 1.34-1.28 (m, 3H), 1.10 (s, 3H), 0.51-0.47 (m, 2H), 0.38-0.33 (m, 2H). $^{31}$P NMR (162 MHz, Methanol-$d_4$) δ 3.75. $^{19}$F NMR (376 MHz, Methanol-$d_4$) δ-238.49 (t, J=48.0 Hz). LCMS: MS m/z=594.00 [M+1], $t_R$=1.33 min; LC system: Thermo Accela 1250 UHPLC; MS system: Thermo LCQ Fleet; Column: Kinetex 2.6p XB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=2.70 min; HPLC system:

Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 52

Second Eluting Diastereomer of Example 50: $^1$H NMR (400 MHz, Methanol-d$_4$) δ 7.99 (s, 1H), 7.42-7.31 (m, 3H), 7.29-7.15 (m, 3H), 6.93 (d, J=4.7 Hz, 1H), 5.38 (d, J=8.4 Hz, 1H), 4.80-4.69 (m, 1H), 4.69-4.53 (m, 2H), 4.33 (d, J=5.2 Hz, 1H), 4.29-4.15 (m, 2H), 4.03-3.90 (m, 2H), 3.85 (d, J=11.1 Hz, 1H), 1.38-1.32 (m, 3H), 1.10 (s, 3H), 0.52-0.43 (m, 2H), 0.39-0.32 (m, 2H). $^{31}$P NMR (162 MHz, Methanol-d$_4$) δ 3.60. $^{19}$F NMR (376 MHz, Methanol-d$_4$) δ-238.78 (t, J=47.7 Hz). LCMS: MS m/z=594.00 [M+1], t$_R$=1.35 min; LC system: Thermo Accela 1250 UHPLC; MS system: Thermo LCQ Fleet; Column: Kinetex 2.6 µXB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 µL/min. HPLC: t$_R$=2.76 min; Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 53. 3,3,3-trifluoro-2,2-dimethylpropyl ((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate

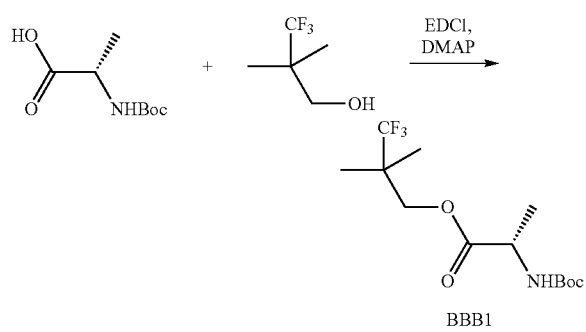

3,3,3-trifluoro-2,2-dimethylpropyl (tert-butoxycarbonyl)-L-alaninate. 1-(3-Dimethylaminopropyl)-3-ethylcarbodiimide hydrochloride (2.43 g, 12.69 mmol) was added to a solution of (tert-butoxy carbonyl)-L-alanine (2.00 g, 10.57 mmol) in 10 mL of acetonitrile under an atmosphere of argon. After 15 minutes, 4-(dimethylamino)-pyridine (1.42 g, 11.62 mmol) then 3,3,3-trifluoro-2,2-dimethylpropan-1-ol (1.69 ml, 10.55 mmol) was added. The reaction was stirred for 2 h at room temperature. The reaction was diluted with ethyl acetate (20 mL) and washed with a 5% citric acid solution in water (2×10 mL). The organics were washed with saturated aqueous sodium bicarbonate (10 mL), water (5 mL) then brine (10 mL). The organics were dried over sodium sulfate, filtered and were concentrated. The residue was purified by silica gel chromatography (using a gradient from 0-10% ethyl acetate in hexanes) to afford intermediate BBB1. $^1$H NMR (400 MHz, DMSO-d$_6$) δ 7.32 (d, J=7.3 Hz, 1H), 4.15 (d, J=11.6 Hz, 1H), 4.08-3.95 (m, 2H), 1.37 (s, 9H), 1.25 (d, J=7.3 Hz, 3H), 1.13-1.09 (m, 6H).

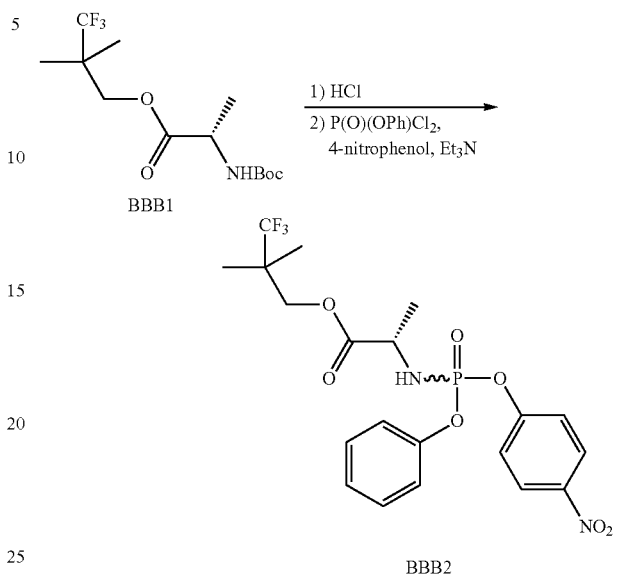

3,3,3-trifluoro-2,2-dimethylpropyl ((4-nitrophenoxy)(phenoxy) phosphoryl)-L-alaninate. 4 M hydrogen chloride in 1,4-dioxane (10 mL, 40.00 mmol) was added to a solution of intermediate BBB1 (1.88 g, 6.00 mmol) in dichloromethane (5 mL). After 1 h, the reaction was concentrated. The residue was dissolved in dichloromethane (15 mL) and cooled to 0° C. (Phenyl dichlorophosphate (1.07 mL, 7.21 mmol) and triethylamine (1.83 mL, 13.22 mmol) were added sequentially. After 1 h, 4-nitrophenol (0.836 g, 6.00 mmol) and triethylamine (0.92 mL, 7.00 mmol) were then sequentially added at 0° C., and the resulting mixture was then allowed to warm to room temperature. After 2.5 h, the reaction mixture was diluted with dichloromethane (50 mL), washed with saturated aqueous sodium bicarbonate solution (50 mL) and brine (50 mL), dried over anhydrous sodium sulfate, and concentrated under reduced pressure. The crude residue was purified by silica gel chromatography eluting with 0-100% ethyl acetate in hexanes to afford intermediate BBB2 (diastereomeric mixture). $^1$H NMR (400 MHz, DMSO-d$_6$) δ 8.30 (d, J=8.9 Hz, 2H), 7.56-7.36 (m, 4H), 7.35-7.16 (m, 3H), 6.85-6.64 (m, 1H), 4.18-3.94 (m, 3H), 1.30-1.23 (m, 3H), 1.10 (s, 6H). $^{31}$P NMR (162 MHz, DMSO-d$_4$) δ-1.29, −1.46. $^{19}$F NMR (376 MHz, DMSO-d$_6$) δ-76.19, −76.19.

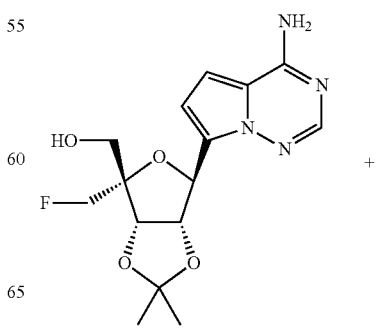

161

-continued

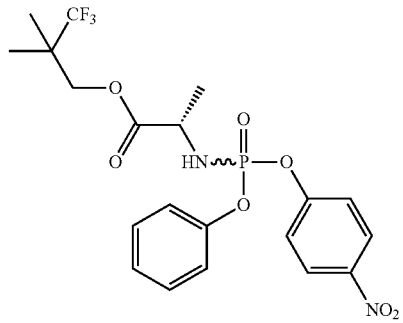

BBB2

1) MgCl₂
(i-Pr)₂NEt;
2) HCl

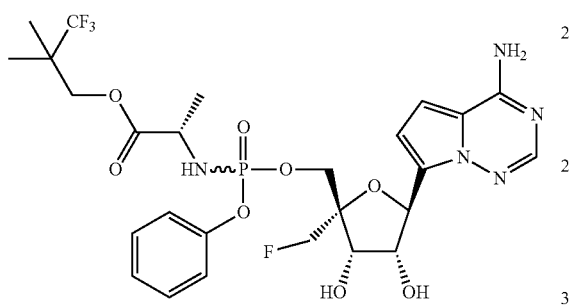

3,3,3-trifluoro-2,2-dimethylpropyl ((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate. Tetrahydrofuran (0.5 mL) was added to a mixture of Intermediate 4 (40 mg, 0.12 mmol), BBB2 (73 mg, 0.15 mmol), and magnesium chloride (17 mg, 0.18 mmol) at room temperature. The mixture was stirred at room temperature for 20 minutes. N,N-diisopropylethylamine (52 μL, 0.30 mmol) was added. The reaction was heated to 50° C. for 2 h. The reaction mixture was allowed to cool to room temperature, and diluted with ethyl acetate (2 mL). The organics were washed with water (2 mL), dried over sodium sulfate, filtered and were concentrated. To a solution of the residue in acetonitrile (2 mL) was added aqueous hydrochloric acid solution (0.3 mL, 3.60 mmol, 12 M) dropwise at 0° C. After 1 h, the reaction mixture was diluted with ethyl acetate (5 mL) and the resulting mixture was washed with saturated aqueous sodium bicarbonate solution (5 mL) and brine (5 mL). The organic layer was dried over anhydrous sodium sulfate and concentrated under reduced pressure. The residue was purified by HPLC chromatography (Phenomenex Gemini 5 μm C18 110 Å, 100×30 mm, 5-100 acetonitrile in water) to afford the product. LCMS: MS m/z=649.97 [M+1], $t_R$=1.38 min (minor), 1.40 min (major); LC system: Thermo Accela 1250 UHPLCz; MS system: Thermo LCQ Fleet; Column: Kinetex 2.6 μXB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min Resolution of the Sp and Rp diastereomers. The diastereomers were isolated from each other by chiral preparatory SFC (SFC chiralpack AD-H 5 μm, 250×21 mm; isopropanol 30%):

162

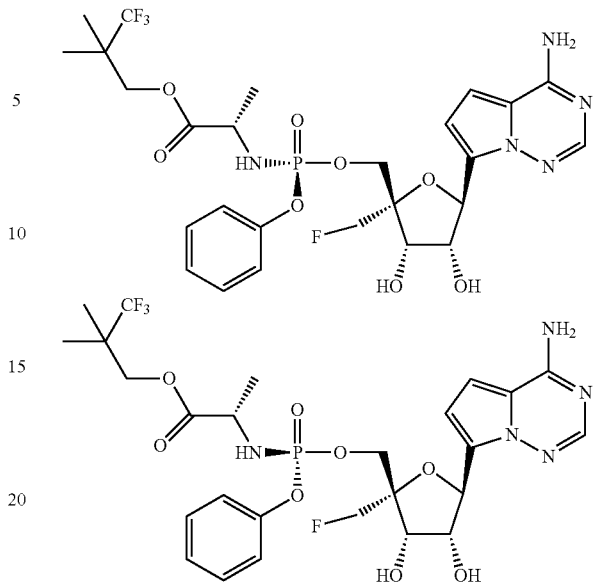

Example 54

First Eluting Diastereomer of Example 53: ¹H NMR (400 MHz, Methanol-d₄) δ 7.84 (s, 1H), 7.38-7.30 (m, 2H), 7.24-7.15 (m, 3H), 7.00 (d, J=4.6 Hz, 1H), 6.82 (d, J=4.6 Hz, 1H), 5.38 (d, J=8.2 Hz, 1H), 4.82-4.73 (m, 1H), 4.70-4.62 (m, 2H), 4.38 (d, J=5.3 Hz, 1H), 4.31-4.24 (m, 2H), 4.17 (d, J=11.5 Hz, 1H), 4.09-4.03 (m, 1H), 4.01-3.93 (m, 1H), 1.37-1.26 (m, 3H), 1.19-1.12 (m, 6H). ³¹P NMR (162 MHz, Methanol-d₄) δ 3.69. ¹H decoupled ¹⁹F NMR (376 MHz, Methanol-d₄) δ-78.76 (s), −238.55 (t, J=47.8 Hz). LCMS: MS m/z=649.97 [M+1], $t_R$=1.38 min; LC system: Thermo Accela 1250 UHPLC; MS system: Thermo LCQ Fleet; Column: Kinetex 2.6 μXB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=2.88 min; HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 55

Second Eluting Diastereomer of Example 53: 1H NMR (400 MHz, Methanol-d₄) δ 7.89 (s, 1H), 7.40-7.32 (m, 2H), 7.28-7.17 (m, 3H), 7.10 (d, J=4.6 Hz, 1H), 6.83 (d, J=4.6 Hz, 1H), 5.38 (d, J=8.3 Hz, 1H), 4.81-4.70 (m, 1H), 4.70-4.57 (m, 2H), 4.33 (d, J=5.2 Hz, 1H), 4.29-4.14 (m, 3H), 4.07-3.91 (m, 2H), 1.34 (dd, J=7.2, 1.0 Hz, 3H), 1.17-1.11 (m, 6H). ³¹P NMR (162 MHz, Methanol-d₄) δ 3.50. ¹⁹F NMR (376 MHz, Methanol-d₄) δ-78.77 (s), −238.67 (t, J=47.8 Hz). LCMS: MS m/z=649.97 [Mz+1], $t_R$=1.40 min; LC system: Thermo Accela 1250 UHPLC; MS system: Thermo LCQ Fleet; Column: Kinetex 2.6 μXB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2

μL/min. HPLC: $t_R$=2.89 min; Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 56. propyl (((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate

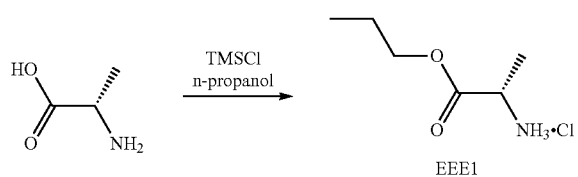

propyl L-alaninate hydrochloride. To a mixture of L-alanine (20.00 g, 224.48 mmol) and 1-propanol (200 mL) was added chlorotrimethylsilane (30 mL, 272.68 mmol). The resulting mixture was stirred at 70° C. in a sealed vessel for 15 h. The reaction was concentrated under reduced pressure. The solids were crushed, taken up in a mixture of ethyl acetate/hexanes (100 mL, 50:50) and filtered. The filter cake was washed with ethyl acetate/hexanes (20 mL, 50:50) and dried under high vacuum to give intermediate EEE1. $^1$H NMR (400 MHz, DMSO-$d_6$) δ 8.63 (s, 3H), 4.20-3.95 (m, 3H), 1.69-1.54 (m, 2H), 1.41 (d, J=7.2 Hz, 3H), 0.88 (t, J=7.4 Hz, 3H).

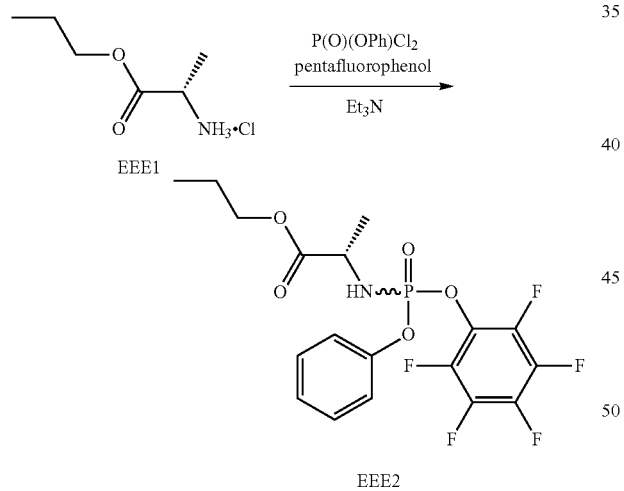

propyl ((perfluorophenoxy)(phenoxy)phosphoryl)-L-alaninate. Phenyl dichlorophosphate (4.88 mL, 32.81 mmol) and triethylamine (9.12 mL, 65.62 mmol) were sequentially added to a suspension EEE1 (5.00 g, 29.83 mmol) in dichloromethane (50 mL) at 0° C. After 1 h, pentafluorophenol (5.49 g, 29.83 mmol) and triethylamine (4.55 mL, 32.81 mmol) were sequentially added at 0° C., and the resulting mixture was then allowed to warm to room temperature. After 2.5 h, the reaction mixture was diluted with dichloromethane (100 mL), washed with saturated aqueous sodium bicarbonate solution (100 mL) and brine (100 mL), dried over anhydrous sodium sulfate, and concentrated under reduced pressure. The crude residue was purified by silica gel chromatography (using a gradient from 0-30% ethyl acetate in hexanes) to afford intermediate EEE2 (diastereomeric mixture). $^1$H NMR (400 MHz, DMSO-$d_6$) δ 7.46-7.38 (m, 2H), 7.30-7.18 (m, 3H), 6.89 (dd, J=14.1, 9.9 Hz, 1H), 4.03-3.92 (m, 3H), 1.62-1.48 (m, 2H), 1.29 (d, J=6.8 Hz, 3H), 0.85 (t, J=7.4 Hz, 3H). $^{19}$F NMR (376 MHz, DMSO-$d_6$) δ -154.11-154.32 (m), -160.60-161.00 (m), -163.56-163.91 (m). $^{31}$P NMR (162 MHz, DMSO-$d_6$) δ 0.48. LCMS: MS m/z=453.9 [M+1], $t_R$=1.81 min; LC system: Thermo Accela 1250 UHPLC; MS system: Thermo LCQ Fleet; Column: Kinetex 2.6 μXB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min.

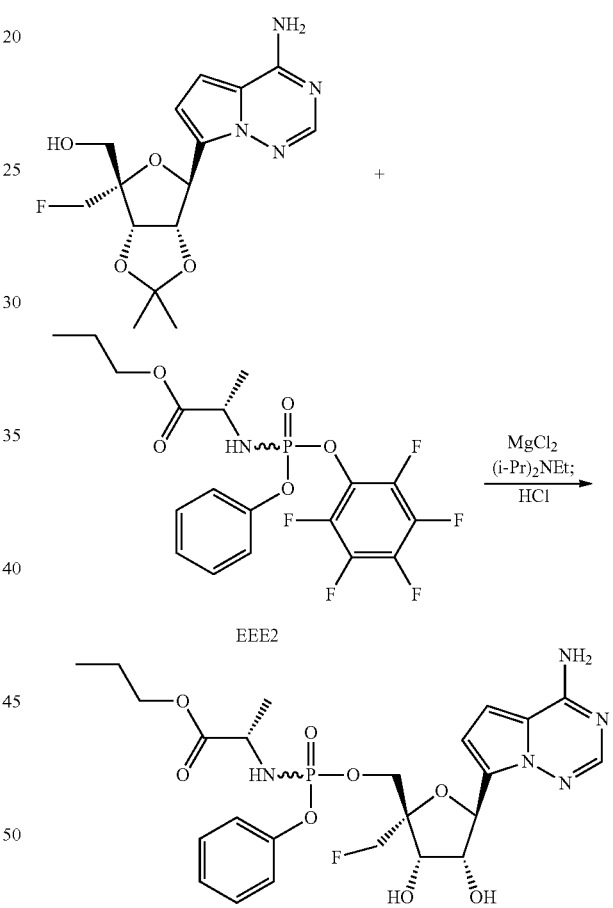

propyl (((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate. Tetrahydrofuran (0.5 mL) was added to a mixture of Intermediate 4 (40 mg, 0.12 mmol), intermediate EEE2 (63 mg, 0.15 mmol), and magnesium chloride (17 mg, 0.18 mmol) at room temperature. The mixture was stirred at room temperature for 20 minutes. N,N-diisopropylethylamine (52 μL, 0.30 mmol) was added. The reaction was heated to 50° C. for 2 h. The reaction mixture was allowed to cool to room temperature, and diluted with ethyl acetate (2 mL). The organics were washed with water (2 mL), dried over sodium sulfate, filtered and were concentrated. To a solution of the residue in acetonitrile (2 mL) was added aqueous hydrochloric acid solution (0.3 mL, 3.60 mmol, 12 M) dropwise at 0° C. After 1 h, the reaction mixture was diluted with ethyl acetate (5 mL) and the resulting mixture was washed with saturated aqueous sodium bicarbonate solution (5 mL) and brine (5 mL). The organic layer was dried over anhydrous sodium sulfate and concentrated under reduced pressure. The residue was purified by HPLC chromatography (Phenomenex Gemini 5 μm $C_{18}$ 110 Å, 100×30 mm, 5-100% acetonitrile in water) to afford example EEE (diastereomeric mixture). LCMS: MS m/z=567.94 [M+1], $t_R$=1.24 min (minor), 1.26 min (major); LC system: Thermo Accela 1250 UHPLC; MS system: Thermo LCQ Fleet; Column: Kinetex 2.6 μXB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min Resolution of the Sp and Rp diastereomers. The diastereomers were isolated from each other by chiral preparatory SFC (SFC chiralpack AD-H 5 μm, 250×21 mm; ethanol 35%):

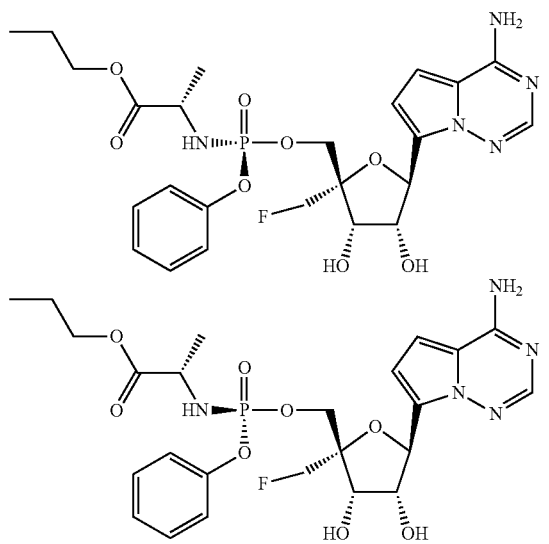

Example 57

First Eluting Diastereomer of Example 56: $^1$H NMR (400 MHz, Methanol-$d_4$) δ 7.96 (s, 1H), 7.36-7.28 (m, 2H), 7.25 (d, J=4.7 Hz, 1H), 7.22-7.14 (m, 3H), 6.94 (d, J=4.7 Hz, 1H), 5.39 (d, J=8.2 Hz, 1H), 4.81-4.73 (m, 1H), 4.70-4.60 (m, 2H), 4.38 (d, J=5.2 Hz, 1H), 4.33-4.21 (m, 2H), 4.11-3.99 (m, 2H), 3.97-3.87 (m, 1H), 1.70-1.57 (m, 2H), 1.33-1.27 (m, 3H), 0.93 (t, J=7.4 Hz, 3H). $^{31}$P NMR (162 MHz, Methanol-$d_4$) δ 3.59. $^{19}$F NMR (376 MHz, Methanol-$d_4$) δ-236.94 (t, J=47.7 Hz). LCMS: MS m/z=567.94 [M], $t_R$=1.24 min; LC system: Thermo Accela 1250 UHPLC; MS system: Thermo LCQ Fleet; Column: Kinetex 2.6 μXB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μl/min. HPLC: $t_R$=2.53 min; HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 58

Second Eluting Diastereomer of Example 56: $^1$H NMR (400 MHz, Methanol-$d_4$) δ 7.90 (s, 1H), 7.41-7.33 (m, 2H), 7.28-7.17 (m, 3H), 7.12 (d, J=4.6 Hz, 1H), 6.85 (d, J=4.7 Hz, 1H), 5.38 (d, J=8.4 Hz, 1H), 4.80-4.70 (m, 1H), 4.70-4.57 (m, 2H), 4.34 (d, J=5.2 Hz, 1H), 4.27-4.17 (m, 2H), 4.11-3.98 (m, 2H), 3.97-3.85 (m, 1H), 1.71-1.55 (m, 2H), 1.36-1.29 (m, 3H), 0.92 (t, J=7.4 Hz, 3H). $^{31}$P NMR (162 MHz, Methanol-$d_4$) δ 3.59. $^{19}$F NMR (376 MHz, Methanol-$d_4$) δ-237.39 (t, J=47.7 Hz). LCMS: MS m/z=567.94 [M+1], $t_R$-1.26 min; LC system: Thermo Accela 1250 UHPLC; MS system: Thermo LCQ Fleet; Column: Kinetex 2.6 μXB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μl/min. HPLC: $t_R$=2.57 min; Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 59. pentyl ((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate

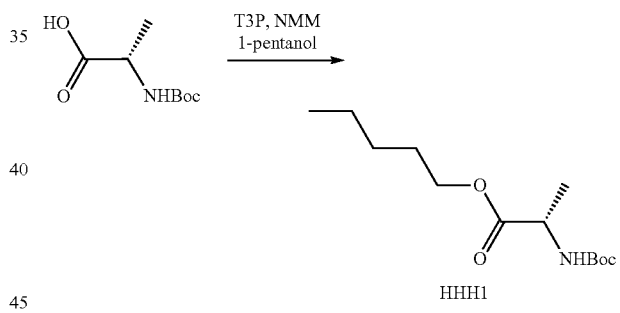

pentyl (tert-butoxycarbonyl)-L-alaninate. To a stirred solution of (tert-butoxycarbonyl)-L-alanine (5.00 g, 26 mmol) and 1-pentanol (2.12 g, 24.05 mmol) in 100 mL of dry dichloromethane were added 4-methylmorpholine (7.93 mL, 72.15 mmol), 4-(dimethylamino)pyridine (59 mg, 0.48 mmol) and tri-propylphosphonic acid cyclic anhydride (17.18 mL, 28.86 mmol, 50% in ethyl acetate) at 0° C. under an atmosphere of argon. The reaction mixture was then stirred at room temperature for 2 h. The reaction mixture was washed with 2×10% solution of citric acid in water (20 mL), 2× with saturated aqueous solution of sodium bicarbonate (20 mL) and once with brine (50 mL). The combined organics were dried over sodium sulfate, filtered through a 3 cm layer of silica gel which was washed with additional dichloromethane (200 mL). The organics were concentrated under reduced pressure, co-distilled with DCM and dried under high vacuum overnight. No further purification was done and intermediate HHH1 was carried on to the next step. $^1$H NMR (400 MHz, DMSO-$d_6$) δ 7.26 (d, J=7.4 Hz, 1H), 4.25-3.80 (m, 3H), 1.65-1.48 (m, 2H), 1.41-1.18 (m, 16H), 1.00-0.74 (m, 3H).

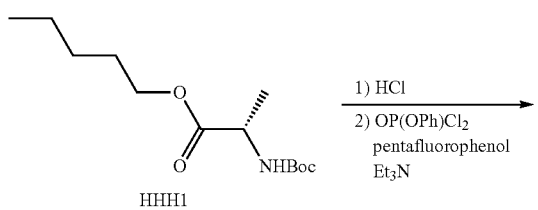

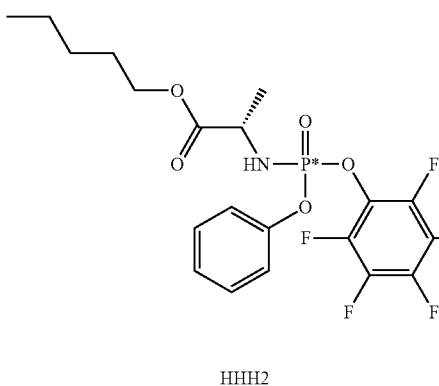

HHH2

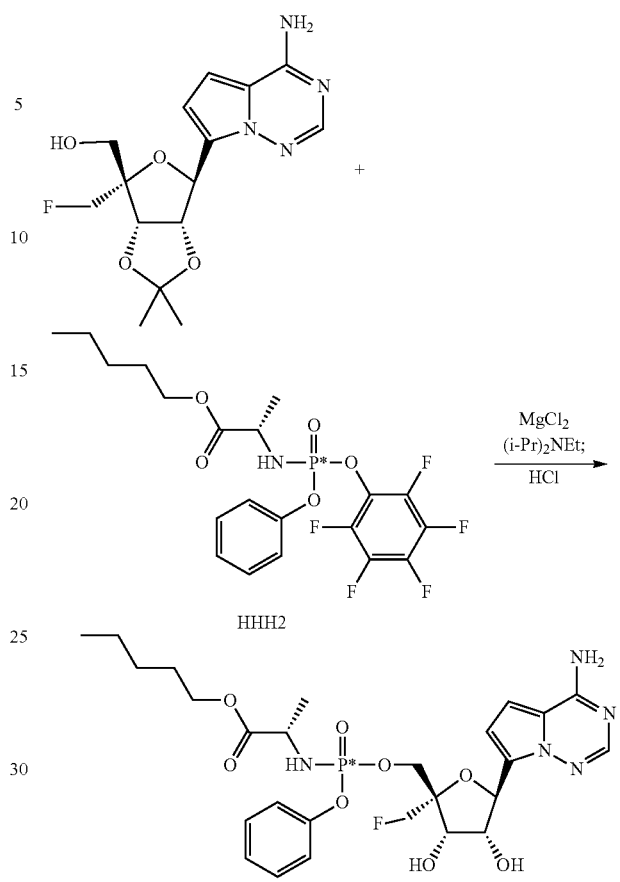

pentyl ((perfluorophenoxy)(phenoxy)phosphoryl)-L-alaninate. Intermediate HHH1 (6.11 g, 22.3 mmol) was taken up in dichloromethane (20 mL) and cooled to 0° C. Hydrogen chloride (30.00 L, 120.00 mmol, 4 N in dioxane) was added. After 2 h, the reaction was concentrated under reduced pressure. The residue was dissolved in dichloromethane (30 mL) and cooled to 0° C. Phenyl dichlorophosphate (3.65 mL, 24.53 mmol) and triethylamine (6.80 mL, 49.06 mmol) were sequentially added. After 1 h, pentafluorophenol (4.0 g, 22.30 mmol) and triethylamine (3.40 mL, 24.53 mmol) were then sequentially added at 0° C., and the resulting mixture was then allowed to warm to room temperature. After 2.5 h, the reaction mixture was diluted with dichloromethane (50 mL), washed with a saturated aqueous sodium bicarbonate solution (50 mL), brine (50 mL), dried over anhydrous sodium sulfate, and filtered through 3 cm of silica gel. The pad was washed with additional dichloromethane (200 mL). The organics were concentrated under reduced pressure. The residue was dissolved in hot hexanes (30 mL) and then diluted with hexanes (120 mL). The reaction was allowed to stir for 2 h and intermediate HHH2 was isolated by filtration. Intermediate HHH2 was determined to be a single diastereomer by NMR spectroscopy. $^1$H NMR (400 MHz, DMSO-$d_6$) δ 7.46-7.37 (m, 2H), 7.30-7.19 (m, 3H), 6.90 (dd, J=14.3, 9.9 Hz, 1H), 4.07-3.93 (m, 3H), 1.58-1.48 (m, 2H), 1.33-1.20 (m, 7H), 0.88-0.77 (m, 3H). $^{19}$F NMR (376 MHz, DMSO-$d_6$) δ -154.24 (d, J=21.5 Hz), -160.86 (t, J=23.1 Hz), -163.69 (dd, J=24.2, 20.4 Hz). $^{31}$P NMR (162 MHz, DMSO-$d_6$) δ 0.47. LCMS: MS m/z=481.8 [M+1], $t_R$=1.91 min; LC system: Thermo Accela 1250 UHPLC; MS system: Thermo LCQ Fleet; Column: Kinetex 2.6 µXB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 µL/min.

pentyl ((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate. Tetrahydrofuran (0.5 mL) was added to a mixture of Intermediate 4 (40 mg, 0.12 mmol), intermediate HHH2 (74 mg, 0.15 mmol), and magnesium chloride (17 mg, 0.18 mmol) at room temperature. The mixture was stirred at room temperature for 20 minutes. N,N-diisopropylethylamine (52 µL, 0.30 mmol) was added. The reaction was heated to 50° C. for 2 h. The reaction mixture was allowed to cool to room temperature, and diluted with ethyl acetate (2 mL). The organics were washed with water (2 mL), dried over sodium sulfate, filtered and were concentrated. To a solution of the residue in acetonitrile (2 mL) was added an aqueous hydrochloric acid solution (0.3 mL, 3.60 mmol, 12 M) dropwise at 0° C. After 1 h, the reaction mixture was diluted with ethyl acetate (5 mL) and the resulting mixture was washed with a saturated aqueous sodium bicarbonate solution (5 mL) and brine (5 mL). The organic layer was dried over anhydrous sodium sulfate and concentrated under reduced pressure. The residue was purified by HPLC chromatography (Phenomenex Gemini 5 µm $C_{18}$ 110 Å, 100×30 mm, 5-100 acetonitrile in water) to afford the product, which was determined to be a single diastereomer by NMR spectroscopy. $^1$H NMR (400 MHz, Methanol-$d_4$) δ 7.80 (s, 1H), 7.39-7.31 (m, 2H), 7.29-7.15 (m, 3H), 6.87 (d, J=4.6 Hz, 1H), 6.75 (d, J=4.5 Hz, 1H), 5.36 (d, J=8.3 Hz, 1H), 4.81-4.57 (m, 3H), 4.34 (d, J=5.2 Hz, 1H), 4.21 (d, J=5.3 Hz, 2H), 4.14-4.00 (m, 2H), 3.95-3.86 (m, 1H), 1.66-1.52 (m, 2H), 1.36-1.25 (m, 7H), 0.93-0.85 (m, 3H). $^{31}$P NMR (162 MHz, Methanol-$d_4$) δ 3.59. $^{19}$F NMR (376 MHz, Methanol-d$_4$) δ-238.85 (t, J=47.7 Hz). LCMS: MS m/z=595.97 [M+1], t$_R$=1.43 min; LC system: Thermo Accela 1250 UHPLC; MS system: Thermo LCQ Fleet; Column: Kinetex 2.6 µXB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 µL/min HPLC: t$_R$=2.87 min; Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 60. (2R,3S,4S,5S)-5-(4-aminopyrrolo[2,1-f][1,2,4]triazin-7-yl)-2-(((((S)-(((S)-1-(2-ethylbutoxy)-1-oxopropan-2-yl)amino)(Phenoxy)phosphoryl)oxy)methyl)-2-(fluoromethyl)tetrahydrofuran-3,4-diyl diacetate

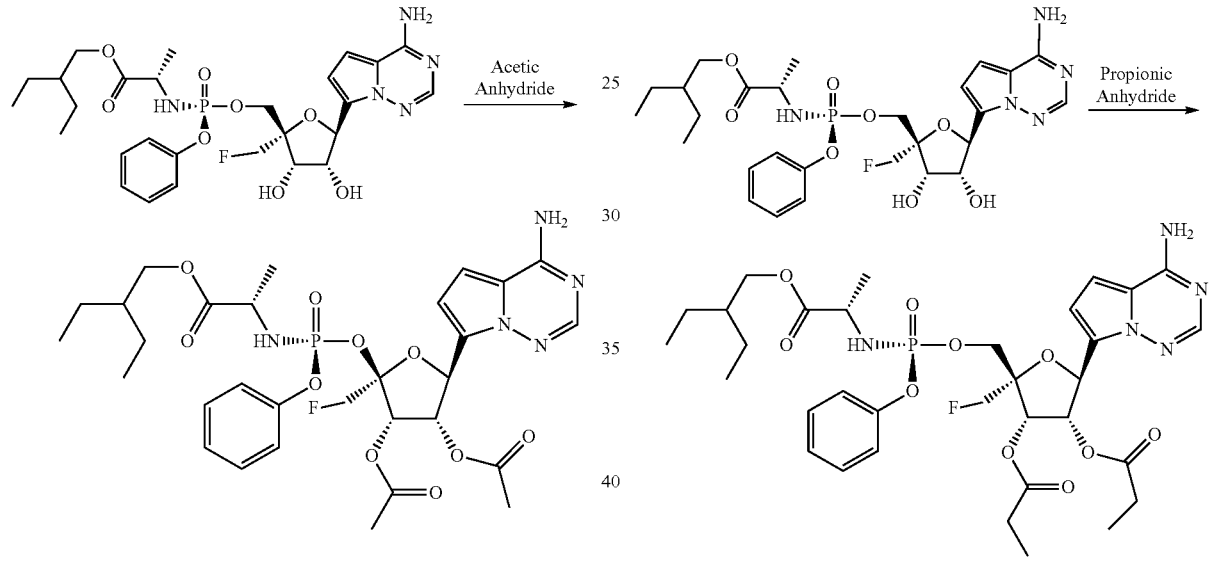

Acetic anhydride (11 mg, 0.11 mmol) and Example 1 (33 mg, 0.05 mmol) were dissolved in anhydrous tetrahydrofuran (1.0 mL) under argon and the mixture was stirred at room temperature for 5 minutes. 4-Dimethylaminopyridine (0.7 mg, 0.005 mmol) was added and the reaction mixture was stirred at room temperature. After 2 hours, methanol (0.5 mL) was added and the mixture was stirred for 20 minutes, then diluted with ethyl acetate (10 mL) and washed twice with a saturated aqueous sodium bicarbonate solution (10 mL) and once with brine (10 mL). The organic layer was dried over anhydrous sodium sulfate and concentrated under reduced pressure. The crude residue was purified by preparatory HPLC (Phenomenex Gemini 5 µm C18 110 Å 100×30 mm column) using gradient from 10-100% acetonitrile in water to afford the product, which was determined to be a single diastereomer by NMR spectroscopy. $^1$H NMR (400 MHz, Methanol-d$_4$) δ 7.82 (s, 1H), 7.38-7.31 (m, 2H), 7.28-7.23 (m, 2H), 7.22-7.17 (m, 1H), 6.86 (d, J=4.6 Hz, 1H), 6.66 (d, J=4.6 Hz, 1H), 5.89-5.82 (m, 1H), 5.80 (d, J=5.5 Hz, 1H), 5.59 (d, J=7.9 Hz, 1H), 4.76-4.68 (m, 1H), 4.65-4.54 (m, 1H), 4.36-4.30 (m, 1H), 4.30-4.24 (m, 1H), 4.10-3.91 (m, 3H), 2.14 (s, 3H), 1.98 (s, 3H), 1.57-1.43 (m, 1H), 1.41-1.28 (m, 7H), 0.88 (t, J=7.5 Hz, 6H). $^{31}$P NMR (162 MHz, Methanol-d$_4$) δ 3.40. $^{19}$F NMR (376 MHz, Methanol-d$_4$) δ-236.51 (t, J=46.9 Hz). LCMS: MS m/z=694.1 [M+1], t$_R$=1.67 min; LC system: Thermo Accela 1250 UHPLC; MS system: Thermo LCQ Fleet; Column: Kinetex 2.6 µXB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 µL/min HPLC: t$_R$=3.32 min; Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 61. (2R,3S,4S,5S)-5-(4-aminopyrrolo[2,1-f][1,2,4]triazin-7-yl)-2-(((((S)-(((S)-1-(2-ethylbutoxy)-1-oxopropan-2-yl)amino)(Phenoxy)phosphoryl)oxy)methyl)-2-(fluoromethyl)tetrahydrofuran-3,4-diyl dipropionate

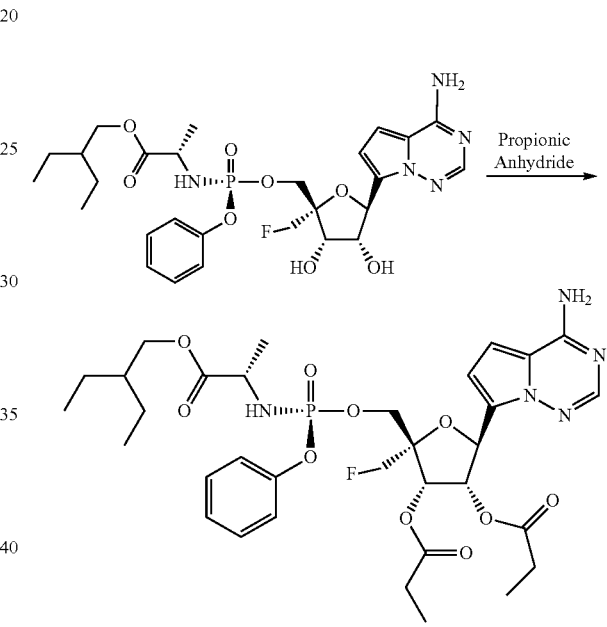

Propionic anhydride (14 mg, 0.11 mmol) and Example 1 (33 mg, 0.05 mmol) were dissolved in anhydrous tetrahydrofuran (1.0 mL) under argon and the mixture was stirred at room temperature for 5 minutes. 4-Dimethylaminopyridine (0.7 mg, 0.005 mmol) was added and the reaction mixture was stirred at room temperature. After 2 h, methanol (0.5 mL) was added and the mixture was stirred for 20 minutes, then diluted with ethyl acetate (10 mL) and washed twice with a saturated aqueous sodium bicarbonate solution (10 mL) and once with brine (10 mL). The organic layer was dried over anhydrous sodium sulfate and concentrated under reduced pressure. The crude residue was purified by preparatory HPLC (Phenomenex Gemini 5 µm C18 110 Å 100×30 mm column) using gradient from 10-100% acetonitrile in water to afford the product, which was determined to be a single diastereomer by NMR spectroscopy. $^1$H NMR (400 MHz, Methanol-d$_4$) δ 7.83 (s, 1H), 7.41-7.29 (m, 2H), 7.29-7.23 (m, 2H), 7.23-7.16 (m, 1H), 6.89 (d, J=4.6 Hz, 1H), 6.67 (d, J=4.6 Hz, 1H), 5.92-5.79 (m, 2H), 5.59 (d, J=7.7 Hz, 1H), 4.76-4.67 (m, 1H), 4.65-4.54 (m, 1H), 4.37-4.31 (m, 1H), 4.29-4.24 (m, 1H), 4.09-4.04 (m, 1H), 4.03-3.94 (m, 2H), 2.49-2.42 (m, 2H), 2.31-2.23 (m, 2H), 1.54-1.46 (m, 1H), 1.40-1.31 (m, 7H), 1.17 (t, J=7.6 Hz, 3H), 1.05 (t, J=7.5 Hz, 3H), 0.88 (t, J=7.5 Hz, 6H). $^{31}$P NMR (162 MHz, Methanol-d$_4$) δ 3.41. $^{19}$F NMR (376 MHz, Methanol-d$_4$) δ-236.30 (t, J=46.9 Hz). LCMS: MS m/z=722.0 [M+1], t$_R$=1.78 min; LC system: Thermo Accela 1250 UHPLC; MS system: Thermo LCQ Fleet; Column: Kinetex 2.6p XB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 µL/min HPLC: t$_R$=3.54 min; Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 62. (2R,3S,4S,5S)-5-(4-aminopyrrolo[2,1-f][1,2,4]triazin-7-yl)-2-(((((S)-(((S)-1-(2-ethylbutoxy)-1-oxopropan-2-yl)amino)(Phenoxy)phosphoryl)oxy)methyl)-2-(fluoromethyl)tetrahydrofuran-3,4-diyl bis(2-methylpropanoate)

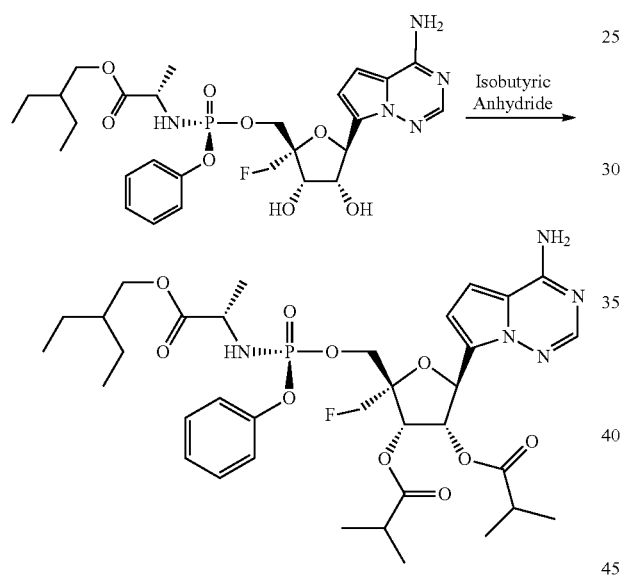

Isobutyric anhydride (18 mg, 0.11 mmol) and Example 1 (34 mg, 0.06 mmol) were dissolved in anhydrous tetrahydrofuran (1.0 mL) under argon and the mixture was stirred at room temperature for 5 minutes. 4-Dimethylaminopyridine (0.7 mg, 0.006 mmol) was added and the reaction mixture was stirred at room temperature. After 2 hours, methanol (0.5 mL) was added and the mixture was stirred for 20 minutes, then diluted with ethyl acetate (10 mL) and washed twice with a saturated aqueous sodium bicarbonate solution (10 mL) and once with brine (10 mL). The organic layer was dried over anhydrous sodium sulfate and concentrated under reduced pressure. The crude residue was purified by preparatory HPLC (Phenomenex Gemini 5 µm C18 110 Å 100×30 mm column) using gradient from 10-100% acetonitrile in water to afford the product, which was determined to be a single diastereomer by NMR spectroscopy. $^1$H NMR (400 MHz, Methanol-d$_4$) δ 7.88 (s, 1H), 7.37-7.28 (m, 2H), 7.28-7.21 (m, 2H), 7.21-7.16 (m, 1H), 6.99 (d, J=4.6 Hz, 1H), 6.69 (d, J=4.6 Hz, 1H), 5.88-5.75 (m, 2H), 5.66-5.53 (m, 1H), 4.78-4.67 (m, 1H), 4.63-4.54 (m, 1H), 4.40-4.31 (m, 1H), 4.31-4.23 (m, 1H), 4.10-4.02 (m, 1H), 4.02-3.89 (m, 2H), 2.68 (hep, J=7.0 Hz, 1H), 2.47 (hep, J=7.0 Hz, 1H), 1.58-1.43 (m, 1H), 1.39-1.30 (m, 7H), 1.25-1.18 (m, 6H), 1.08 (d, J=7.0 Hz, 3H), 1.03 (d, J=7.0 Hz, 3H), 0.87 (t, J=7.5 Hz, 6H). $^{31}$P NMR (162 MHz, Methanol-d$_4$) δ 3.44. $^{19}$F NMR (376 MHz, Methanol-d$_4$) δ-235.60 (t, J=46.8 Hz). LCMS: MS m/z=750.1 [M+1], t$_R$=1.88 min; LC system: Thermo Accela 1250 UHPLC; MS system: Thermo LCQ Fleet; Column: Kinetex 2.6 µXB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 µL/min HPLC: t$_R$=3.73 min; Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 63. (2R,3S,4S,5S)-5-(4-aminopyrrolo[2,1-f][1,2,4]triazin-7-yl)-2-((((((S)-1-(cyclohexyloxy)-1-oxopropan-2-yl)amino)(Phenoxy)phosphoryl)oxy)methyl)-2-(fluoromethyl)tetrahydrofuran-3,4-diyl bis(2-methylpropanoate)

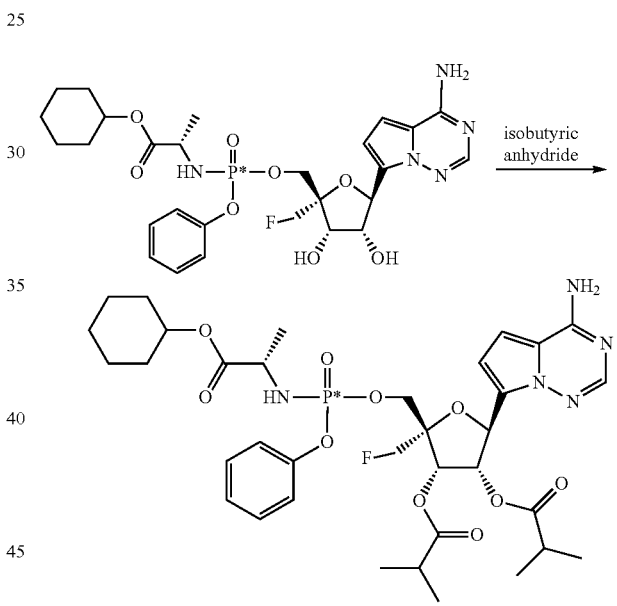

Proprionic anhydride (17 mg, 0.13 mmol) and Example 14(40 mg, 0.07 mmol) were dissolved in anhydrous tetrahydrofuran (1.0 mL) under argon and the mixture was stirred at room temperature for 5 minutes. 4-Dimethylaminopyridine (8 mg, 0.07 mmol) was added and the reaction mixture was stirred at room temperature. After 2 hours, methanol (0.5 mL) was added and the mixture was stirred for 20 minutes, then diluted with ethyl acetate (10 mL) and washed twice with a saturated aqueous sodium bicarbonate solution (10 mL) and once with brine (10 mL). The organic layer was dried over anhydrous sodium sulfate and concentrated under reduced pressure. The crude residue was purified by preparatory HPLC (Phenomenex Gemini 5 µm C18 110 Å 100×30 mm column) using gradient from 10-100% acetonitrile in water to afford the product, which was determined to be a single diastereomer by NMR spectroscopy. $^1$H NMR (400 MHz, Methanol-d$_4$) δ 7.83 (s, 1H), 7.37-7.30 (m, 2H), 7.29-7.23 (m, 2H), 7.23-7.16 (m, 1H), 6.87 (d, J=4.6 Hz, 1H), 6.65 (d, J=4.6 Hz, 1H), 5.88-5.79 (m, 2H), 5.59 (d, J=7.6 Hz, 1H), 4.79-4.66 (m, 2H), 4.66-4.55 (m, 1H), 4.39-4.32 (m, 1H), 4.31-4.25 (m, 1H), 3.98-3.88 (m, 1H), 2.68 (hep, J=7.0, 1H), 2.47 (hep, J=7.0, 1H), 1.85-1.76 (m, 2H), 1.75-1.67 (m, 2H), 1.58-1.49 (m, 1H), 1.47-1.28 (m, 8H), 1.24-1.21 (m, 6H), 1.08 (d, J=7.0 Hz, 3H), 1.04 (d, J=6.9 Hz, 3H). $^{31}$P NMR (162 MHz, Methanol-$d_4$) δ 3.45. $^{19}$F NMR (376 MHz, Methanol-$d_4$) δ-235.50 (t, J=46.9 Hz). LCMS: MS m/z=748.1 [M+1], $t_R$=1.85 min; LC system: Thermo Accela 1250 UHPLC; MS system: Thermo LCQ Fleet; Column: Kinetex 2.6 μXB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min HPLC: $t_R$=3.64 min; Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 64. tetrahydro-2H-pyran-4-yl ((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate

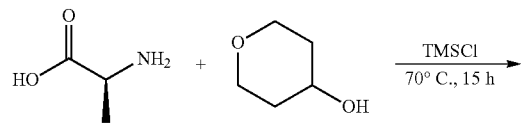

(S)-tetrahydro-2H-pyran-4-yl 2-aminopropanoate hydrochloride. To a mixture of L-alanine (500 mg, 5.61 mmol) and tetrahydro-2H-pyran-4-ol (5 g, 49.0 mmol) was added TMSCl (2 mL). The resulting mixture was stirred at 70° C. for 15 h and concentrated in vacuo and the resulting solids were extracted with 5% EtOAc in hexanes, filtered, and washed with 5% EtOAc in hexanes several times. The resulting solid was dried under high vacuum for 15 h to give intermediate MMM1. Due to the hygroscopic nature of the solid it was used as is in subsequent reactions.

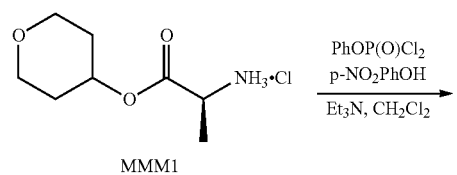

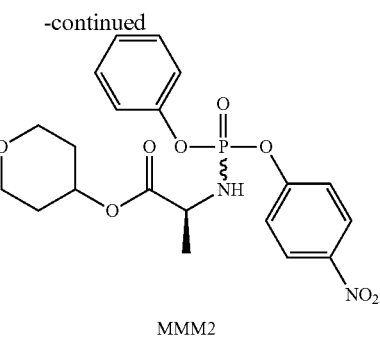

(2S)-tetrahydro-2H-pyran-4-yl 2-(((4-nitrophenoxy)(phenoxy) phosphoryl)amino)propanoate. Intermediate MMM1 (1.33 g, 6.34 mmol) was dissolved in methylene chloride (15 mL), cooled to −78° C., and phenyl dichlorophosphate (1.137 mL, 7.61 mmol) added quickly. Triethylamine (2.2 mL, 15.2 mmol) was added over 30 min at −78° C. and the resulting mixture was stirred for 30 min at −78° C. 4-nitrophenol (882 mg, 6.34 mmol) was then added in one portion and triethylamine (1.1 mL, 7.61 mmol) was added over 30 min at −78° C. The mixture was stirred for 30 min at −78° C., washed with water (2×), brine, and dried over sodium sulfate. The sodium sulfate was removed by filtration and the filtrated was concentrated in vacuo. The residue was purified by silica gel column chromatography (EtOAc 0 to 70% in hexanes) to give intermediate MMM2 (diastereomeric mixture). $^1$H NMR (400 MHz, Chloroform-d) δ 8.22 (m, 2H), 7.49-7.06 (m, 7H), 4.95 (m, 1H), 4.14 (m, 1H), 4.07-3.80 (m, 3H), 3.52 (m, 2H), 1.95-1.81 (m, 2H), 1.64 m, 2H), 1.42 (m, 3H). $^{31}$P NMR (162 MHz, Chloroform-d) δ-3.09, −3.13.

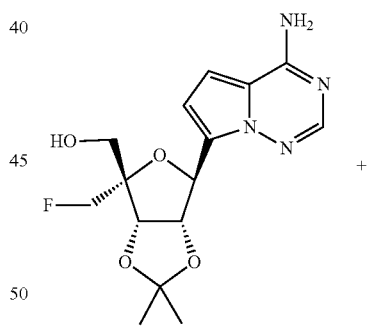

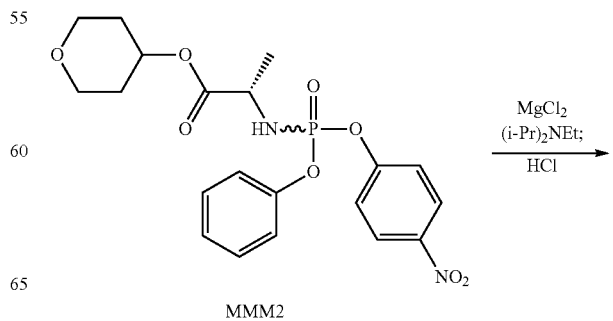

-continued

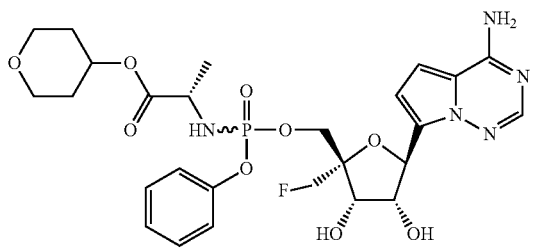

tetrahydro-2H-pyran-4-yl (((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate. Tetrahydrofuran (5 mL) was added to a mixture of Intermediate 4 (250 mg, 0.74 mmol), intermediate MMM2 (433 mg, 0.96 mmol), and magnesium chloride (106 mg, 1.11 mmol) at room temperature. The mixture was stirred at room temperature for 20 minutes. N,N-diisopropylethylamine (322 µL, 1.85 mmol) was added. The reaction was heated to 50° C. for 2 h. The reaction mixture was allowed to cool to room temperature, and diluted with ethyl acetate (20 mL). The organics were washed with water (10 mL), dried over sodium sulfate, filtered and were concentrated. To a solution of the residue in acetonitrile (5 mL) at was added aqueous hydrochloric acid solution (0.6 mL, 7.39 mmol, 12 M) dropwise at 0° C. After 1 h, the reaction mixture was diluted with ethyl acetate (20 mL) and the resulting mixture was washed with a saturated aqueous sodium bicarbonate solution (10 mL) and brine (10 mL). The organic layer was dried over anhydrous sodium sulfate and concentrated under reduced pressure. The residue was purified by HPLC chromatography (Phenomenex Gemini 5 µm C18 110 Å, 100×30 mm, 5-100% acetonitrile in water) to afford the product (diastereomeric mixture). $^1$H NMR (400 MHz, Methanol-$d_4$) δ 7.86-7.82 (m, 1H), 7.40-7.30 (m, 2H), 7.28-7.15 (m, 3H), 6.99-6.93 (m, 1H), 6.83-6.77 (m, 1H), 5.40-5.35 (m, 1H), 4.95-4.88 (m, 1H), 4.81-4.58 (m, 3H), 4.40-4.31 (m, 1H), 4.29-4.18 (m, 2H), 3.97-3.78 (m, 3H), 3.56-3.46 (m, 2H), 1.92-1.82 (m, 2H), 1.66-1.55 (m, 2H), 1.34-1.25 (m, 3H). $^{31}$P NMR (162 MHz, Methanol-$d_4$) δ 3.75, 3.56. $^{19}$F NMR (376 MHz, Methanol-$d_4$) δ-238.53, −238.74. LCMS: MS m/z=610.01 [M+1], $t_R$=1.16 min (minor), 1.18 min (major); LC system: Thermo Accela 1250 UHPLC; MS system: Thermo LCQ Fleet; Column: Kinetex 2.6 µXB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 µL/min HPLC: $t_R$=2.32 min (minor), 2.37 (major); Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 65. (2R,3S,4S,5S)-5-(4-aminopyrrolo[2,1-f][1,2,4]triazin-7-yl)-2-(fluoromethyl)-2-((((((S)-1-oxo-1-((tetrahydro-2H-pyran-4-yl)oxy)propan-2-yl)amino)(phenoxy)phosphoryl)oxy)methyl)tetrahydrofuran-3,4-diyl bis(2-methylpropanoate)

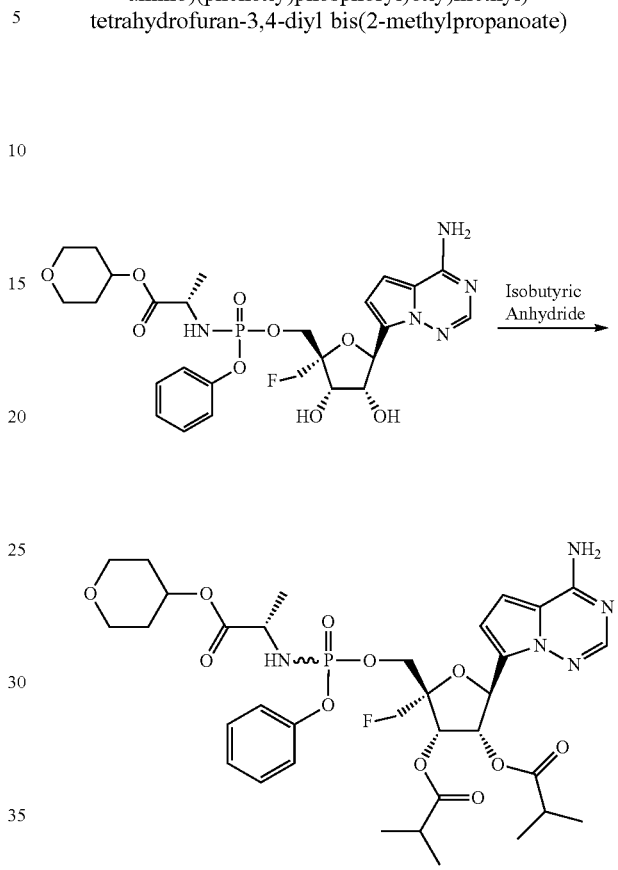

Isobutyric anhydride (26 mg, 0.16 mmol) and Example 64(50 mg, 0.08 mmol) were dissolved in anhydrous tetrahydrofuran (1.0 mL) under argon and the mixture was stirred at room temperature for 5 minutes. 4-Dimethylaminopyridine (8 mg, 0.07 mmol) was added and the reaction mixture was stirred at room temperature. After 2 hours, methanol (0.5 mL) was added and the mixture was stirred for 20 minutes, then diluted with ethyl acetate (10 mL) and washed twice with a saturated aqueous sodium bicarbonate solution (10 mL) and once with brine (10 mL). The organic layer was dried over anhydrous sodium sulfate and concentrated under reduced pressure. The crude residue was purified by preparatory HPLC (Phenomenex Gemini 5 µm C18 110 Å 100×30 mm column) using gradient from 10-100% acetonitrile in water to afford the product (diastereomeric mixture). LCMS: MS m/z=750.1 [M+1], $t_R$=1.62 min (major), 1.65(minor); LC system: Thermo Accela 1250 UHPLC; MS system: Thermo LCQ Fleet; Column: Kinetex 2.6 µXB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 µL/min.

Resolution of the Sp and Rp diastereomers. The diastereomers were isolated from each other by chiral preparatory SFC (SFC chiralpack 1 Å 5 µm, 250×21 mm; isopropanol 30%):

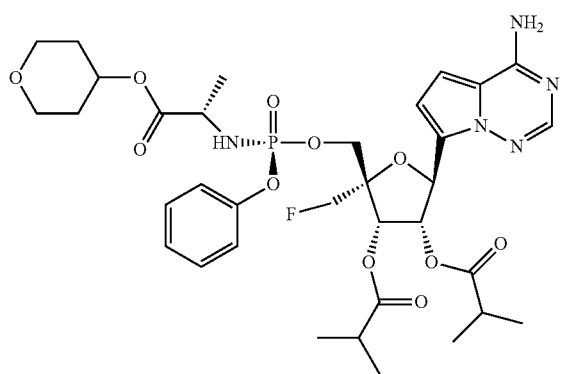

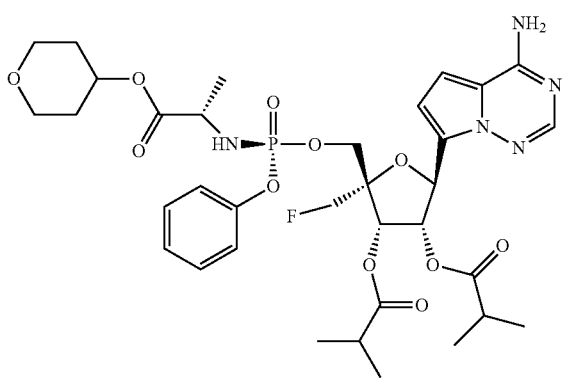

Example 66

First Eluting Diastereomer of Example 65: $^1$H NMR (400 MHz, Methanol-d$_4$) δ 7.81 (s, 1H), 7.39-7.30 (m, 2H), 7.26-7.16 (m, 3H), 6.85 (d, J=4.4 Hz, 1H), 6.77 (d, J=4.6 Hz, 1H), 5.96-5.90 (m, 1H), 5.85 (d, J=5.6 Hz, 1H), 5.60 (d, J=7.7 Hz, 1H), 4.95-4.89 (m, 2H), 4.73 (s, 1H), 4.62 (s, 1H), 4.38-4.29 (m, 2H), 3.96-3.80 (m, 2H), 3.56-3.46 (m, 2H), 2.73-2.64 (m, 1H), 2.53-2.44 (m, 1H), 1.91-1.83 (m, 2H), 1.67-1.56 (m, 2H), 1.35-1.20 (m, 9H), 1.09 (d, J=7.0 Hz, 3H), 1.05 (d, J=7.0 Hz, 3H). $^{31}$P NMR (162 MHz, Methanol-d$_4$) δ 3.50. $^1$H decoupled $^{19}$F NMR (376 MHz, Methanol-d$_4$) δ-235.96. LCMS: MS m/z=750.08 [M+1], t$_R$=1.62 min; LC system: Thermo Accela 1250 UHPLC; MS system: Thermo LCQ Fleet; Column: Kinetex 2.6 μXB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min HPLC: t$_R$=3.23 min; Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 67

Second Eluting Diastereomer of Example 65: $^1$H NMR (400 MHz, Methanol-d$_4$) δ 7.80 (s, 1H), 7.38-7.30 (m, 2H), 7.29-7.23 (m, 2H), 7.22-7.17 (m, 1H), 6.80 (d, J=4.5 Hz, 1H), 6.61 (d, J=4.5 Hz, 1H), 5.87-5.79 (m, 2H), 5.60 (d, J=7.8 Hz, 1H), 4.99-4.91 (m, 1H), 4.78-4.66 (m, 1H), 4.66-4.54 (m, 1H), 4.40-4.32 (m, 1H), 4.32-4.25 (m, 1H), 4.02-3.92 (m, 1H), 3.90-3.82 (m, 2H), 3.57-3.46 (m, 2H), 2.74-2.64 (m, 1H), 2.51-2.42 (m, 1H), 1.95-1.83 (m, 2H), 1.69-1.56 (m, 2H), 1.37-1.28 (m, 3H), 1.23 (d, J=7.0 Hz, 6H), 1.08 (d, J=7.0 Hz, 3H), 1.03 (d, J=7.0 Hz, 3H). $^{31}$P NMR (162 MHz, Methanol-d$_4$) δ 3.40. $^1$H decoupled $^{19}$F NMR (376 MHz, Methanol-d$_4$) δ-235.32. LCMS: MS m/z=750.07 [M+1], t$_R$=1.65 min; LC system: Thermo Accela 1250 UHPLC; MS system: Thermo LCQ Fleet; Column: Kinetex 2.6 μXB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min HPLC: t$_R$=3.24 min; Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 68. 2-propylpentyl ((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate

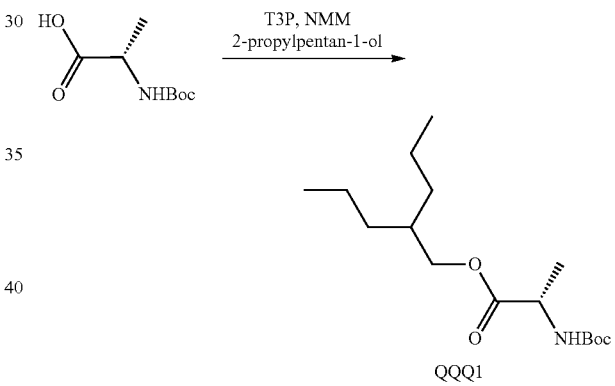

2-Propylpentyl (tert-butoxycarbonyl)-L-alaninate. To a stirred solution of (tert-butoxycarbonyl)-L-alanine (5.00 g, 26.42 mmol) and 2-propylpentan-1-ol (3.13 g, 24.02 mmol) in 100 mL of dry dichloromethane were added 4-methylmorpholine (7.92 mL, 72.07 mmol), 4-(dimethylamino)pyridine (59 mg, 0.48 mmol) and tri-propylphosphonic acid cyclic anhydride (17.16 mL, 28.83 mmol, 50% in ethyl acetate) at 0° C. under an atmosphere of argon. The reaction mixture was then stirred at room temperature for 2 h. The reaction mixture was washed with 2×10% solution of citric acid in water (20 mL), 2× with saturated aqueous solution of sodium bicarbonate (20 mL) and once with brine (50 mL). The combined organics were dried over sodium sulfate, filtered through a 3 cm layer of silica gel which was washed with additional dichloromethane (200 mL). The organics were concentrated under reduced pressure, co-distilled with DCM and dried under high vacuum overnight. No further purification was done and intermediate QQQ1 was carried on to the next step. $^1$H NMR (400 MHz, DMSO-d$_6$) δ 7.27 (d, J=7.5 Hz, 1H), 4.06-3.86 (m, 3H), 1.67-1.56 (m, 1H), 1.43-1.10 (m, 20H), 0.93-0.79 (m, 6H).

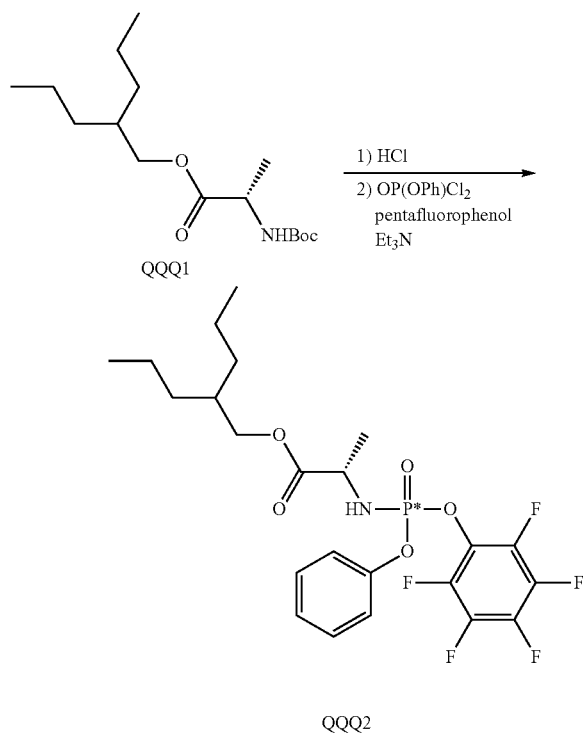

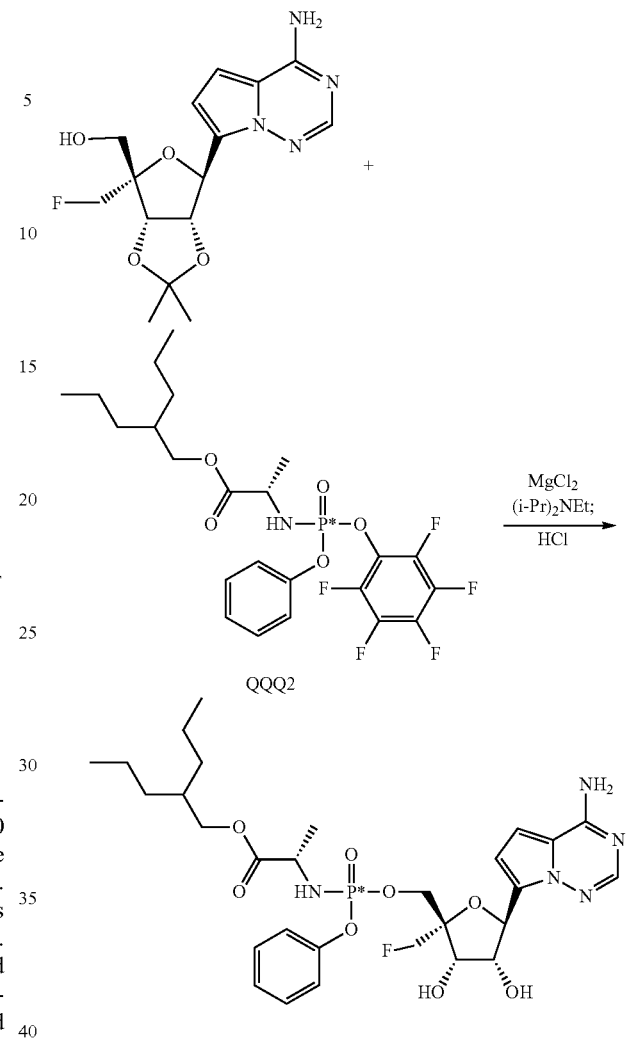

2-propylpentyl ((perfluorophenoxy)(phenoxy)phosphoryl)-L-alaninate. 4 M hydrogen chloride in 1,4-dioxane (10 mL, 40.00 mmol) was added to a solution of intermediate QQQ1 (5.70 g, 18.93 mmol) in dichloromethane (5 mL). After 1 h, the reaction was concentrated. The residue was dissolved in dichloromethane (15 mL) and cooled to 0° C. (Phenyl dichlorophosphate (3.10 mL, 20.82 mmol) and triethylamine (5.77 mL, 41.64 mmol) were added sequentially. After 1 h, pentafluorophenol (3.48 g, 18.93 mmol) and triethylamine (2.89 mL, 20.82 mmol) were then sequentially added at 0° C., and the resulting mixture was then allowed to warm to room temperature. After 2.5 h, the reaction mixture was diluted with dichloromethane (50 mL), washed with saturated aqueous sodium bicarbonate solution (50 mL) and brine (50 mL), dried over anhydrous sodium sulfate, and filtered through 3 cm of silica gel. The silica gel cake was washed with additional dichloromethane (100 mL). The organics were concentrated. The residue was dissolved in 30 mL of hot hexanes and then diluted with 120 mL of hexanes. The reaction was allowed to stir for 5 h then filtered to isolate intermediate QQQ2. Intermediate QQQ2 was determined to be a single diastereomer by NMR spectroscopy. $^1$H NMR (400 MHz, DMSO-$d_6$) δ 7.44-7.37 (m, 2H), 7.48-7.36 (m, 1H), 6.94-6.85 (m, 1H), 4.06-3.90 (m, 3H), 1.66-1.55 (m, 1H), 1.32-1.18 (m, 11H), 0.85-0.79 (m, 6H). $^{19}$F NMR (376 MHz, DMSO-$d_6$) δ-154.23 (d, J=22.6 Hz), −160.88 (t, J=23.5 Hz), −163.71 (t, J=22.0 Hz). $^{31}$P NMR (162 MHz, DMSO-$d_6$) δ 0.44. LCMS: MS m/z=523.78 [M+1], $t_R$=2.04 min; LC system: Thermo Accela 1250 UHPLC; MS system: Thermo LCQ Fleet; Column: Kinetex 2.6 μXB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μl/min.

2-propylpentyl ((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate. Tetrahydrofuran (0.5 mL) was added to a mixture of Intermediate 4 (40 mg, 0.12 mmol), intermediate QQQ2 (80 mg, 0.15 mmol), and magnesium chloride (17 mg, 0.18 mmol) at room temperature. The mixture was stirred at room temperature for 20 minutes. N,N-diisopropylethylamine (52 μL, 0.30 mmol) was added. The reaction was heated to 50° C. for 2 h. The reaction mixture was allowed to cool to room temperature, and diluted with ethyl acetate (2 mL). The organics were washed with water (2 mL), dried over sodium sulfate, filtered and were concentrated. To a solution of the residue in acetonitrile (2 mL) at was added aqueous hydrochloric acid solution (0.3 mL, 12 M) dropwise at 0° C. After 1 h, the reaction mixture was diluted with ethyl acetate (5 mL) and the resulting mixture was washed with saturated aqueous sodium bicarbonate solution (5 mL) and brine (5 mL). The organic layer was dried over anhydrous sodium sulfate and concentrated under reduced pressure. The residue was purified by HPLC chromatography (Phenomenex Gemini 5 μm $C_{18\ 110}$ Å, 100×30 mm, 5-100% acetonitrile in water) to afford the product, which was determined to be a single diastereomer by NMR spectroscopy. $^1$H NMR (400 MHz, Methanol-$d_4$) δ 7.81 (s, 1H), 7.39-7.31 (m, 2H), 7.28-7.16 (m, 3H), 6.88 (d, J=4.5 Hz, 1H), 6.75 (d, J=4.5 Hz, 1H), 5.36 (d, J=8.3 Hz, 1H), 4.81-4.57 (m, 3H), 4.34 (d, J=5.2 Hz, 1H), 4.26-4.17 (m, 2H), 4.07-4.01 (m, 1H), 3.98-3.88 (m, 2H), 1.69-1.61 (m, 1H), 1.38-1.20 (m, 11H), 0.94-0.83 (m, 6H). $^{31}$P NMR (162 MHz, Methanol-$d_4$) δ 3.55. $^1$H decoupled $^{19}$F NMR (376 MHz, Methanol-$d_4$) δ -238.83. LCMS: MS m/z=638.03 [M+1], $t_R$=1.58 min; LC system: Thermo Accela 1250 UHPLC; MS system: Thermo LCQ Fleet; Column: Kinetex 2.6 μXB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=3.29 min; Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 69. ethyl (((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-valinate

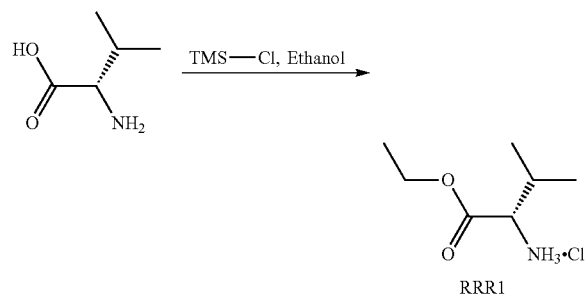

ethyl L-valinate hydrochloride. Chlorotrimethylsilane (4.58 ml, 36 mmol) was added to as solution of L-valine (5.0 g, 43 mmol) in ethanol (20 mL). The reaction was heated for 18 h at 70° C. The reaction was concentrated under reduced pressure. No further purification was done and intermediate RRR1 was taken on to the next step -1 NMR (400 MHz, DMSO-$d_6$) δ 8.58 (s, 3H), 4.31-4.14 (m, 2H), 3.87-3.80 (m, 1H), 2.24-2.13 (m, 1H), 1.24 (t, J=7.1 Hz, 3H), 0.99 (d, J=7.0 Hz, 3H), 0.95 (d, J=6.9 Hz, 3H).

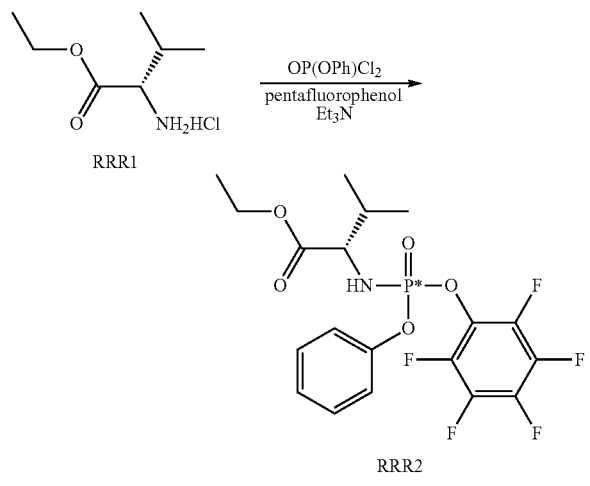

ethyl ((perfluorophenoxy)(phenoxy)phosphoryl)-L-valinate. Intermediate RRR1 (7.40 g, 40.74 mmol) was dissolved in dichloromethane (15 mL) and cooled to 0° C. Phenyl dichlorophosphate (6.67 mL, 44.81 mmol) and triethylamine (12.42 mL, 89.62 mmol) were added sequentially. After 1 h, pentafluorophenol (7.50 g, 40.74 mmol) and triethylamine (6.21 mL, 44.81 mmol) were then sequentially added at 0° C., and the resulting mixture was then allowed to warm to room temperature. After 2.5 h, the reaction mixture was diluted with dichloromethane (50 mL), washed with a saturated aqueous sodium bicarbonate solution (50 mL) and brine (50 mL), dried over anhydrous sodium sulfate, and filtered through 3 cm of silica gel. The silica gel cake was washed with additional dichloromethane (100 mL). The organics were concentrated. The residue was dissolved in 30 mL of hot hexanes and then diluted with 120 mL of hexanes. The reaction was allowed to stir for 5 h then filtered to isolate intermediate RRR2. Intermediate RRR2 was determined to be a single diastereomer by NMR spectroscopy. $^1$H NMR (400 MHz, DMSO-$d_6$) δ 7.48-7.34 (m, 2H), 7.28-7.18 (m, 3H), 6.81-6.71 (m, 1H), 4.07 (q, J=7.1 Hz, 2H), 3.69-3.58 (m, 1H), 2.01-1.88 (m, 1H), 1.16 (t, J=7.1 Hz, 3H), 0.80 (d, J=6.8 Hz, 3H), 0.76 (d, J=6.8 Hz, 3H). $^{19}$F NMR (376 MHz, DMSO-$d_6$) δ-154.30 (d, J=21.4 Hz), -161.10 (t, J=23.3 Hz), -163.77 (dd, J=24.0, 20.1 Hz). $^{31}$P NMR (162 MHz, DMSO-$d_6$) δ 1.95. LCMS: MS m/z=467.87 [M+1], $t_R$=1.85 min; LC system: Thermo Accela 1250 UHPLC; MS system: Thermo LCQ Fleet; Column: Kinetex 2.6 μXB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min.

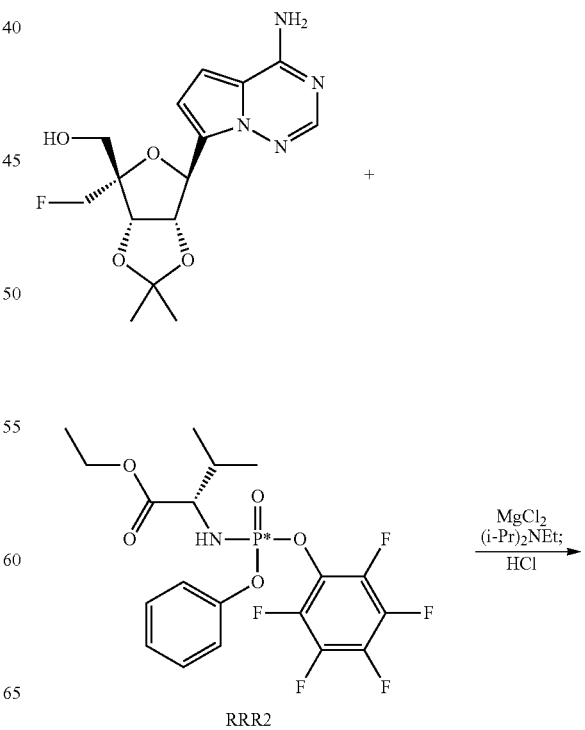

-continued

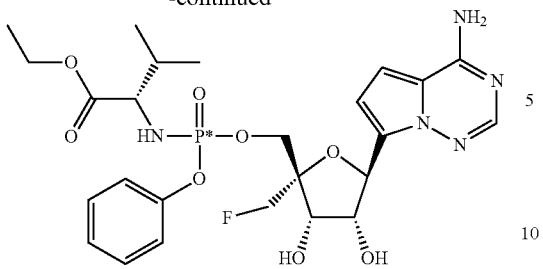

ethyl ((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-valinate. Tetrahydrofuran (0.5 mL) was added to a mixture of Intermediate 4 (40 mg, 0.12 mmol), intermediate RRR2 (72 mg, 0.15 mmol), and magnesium chloride (17 mg, 0.18 mmol) at room temperature. The mixture was stirred at room temperature for 20 minutes. N,N-diisopropylethylamine (52 µL, 0.30 mmol) was added. The reaction was heated to 50° C. for 2 h. The reaction mixture was allowed to cool to room temperature, and diluted with ethyl acetate (2 mL). The organics were washed with water (2 mL), dried over sodium sulfate, filtered and were concentrated. To a solution of the residue in acetonitrile (2 mL) at was added aqueous hydrochloric acid solution (0.3 mL, 12 M) dropwise at 0° C. After 1 h, the reaction mixture was diluted with ethyl acetate (5 mL) and the resulting mixture was washed with a saturated aqueous sodium bicarbonate solution (5 mL) and brine (5 mL). The organic layer was dried over anhydrous sodium sulfate and concentrated under reduced pressure. The residue was purified by HPLC chromatography (Phenomenex Gemini 5 µm C18 110 Å, 100×30 mm, 5-100% acetonitrile in water) to afford the product, which was determined to be a single diastereomer by NMR spectroscopy. $^1$H NMR (400 MHz, Methanol-$d_4$) δ 7.84 (s, 1H), 7.40-7.31 (m, 2H), 7.27-7.15 (m, 3H), 6.97 (d, J=4.5 Hz, 1H), 6.79 (d, J=4.5 Hz, 1H), 5.36 (d, J=8.4 Hz, 1H), 4.81-4.71 (m, 1H), 4.70-4.59 (m, 2H), 4.35 (d, J=5.1 Hz, 1H), 4.26-4.20 (m, 2H), 4.16-4.05 (m, 2H), 3.64 (dd, J=9.9, 6.2 Hz, 1H), 2.05-1.95 (m, 1H), 1.21 (t, J=7.2 Hz, 3H), 0.93 (t, J=7.7 Hz, 6H). $^{31}$P NMR (162 MHz, Methanol-$d_4$) δ 4.41. $^1$H decoupled $^{19}$F NMR (376 MHz, Methanol-$d_4$) δ-238.95. LCMS: MS m/z=581.94 [M+1], $t_R$=1.30 min; LC system: Thermo Accela 1250 UHPLC; MS system: Thermo LCQ Fleet; Column: Kinetex 2.6 µXB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 µl/min HPLC: $t_R$=2.64 min; Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 70. isobutyl ((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate

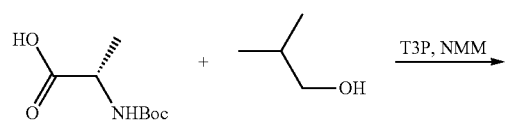

-continued

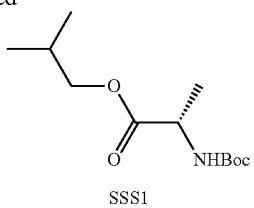

SSS1 isobutyl (tert-butoxycarbonyl)-L-alaninate. To a stirred solution of (tert-butoxycarbonyl)-L-alanine (1.00 g, 5.29 mmol) and 1-methylpropan-1-ol (0.60 mL, 6.34 mmol) in 10 mL of dry dichloromethane were added 4-methylmorpholine (1.74 mL, 15.86 mmol), 4-(dimethylamino)pyridine (13 mg, 0.11 mmol) and tri-propylphosphonic acid cyclic anhydride (3.78 mL, 6.34 mmol, 50% in ethyl acetate) at 0° C. under an atmosphere of argon. The reaction mixture was then stirred at room temperature for 2 h. The reaction mixture was washed with 2×10% solution of citric acid in water (20 mL), 2× with saturated aqueous solution of sodium bicarbonate (20 mL) and once with brine (50 mL). The combined organics were dried over sodium sulfate, filtered through a 3 cm layer of silica gel which was washed with additional dichloromethane (200 mL). The organics were concentrated under reduced pressure, co-distilled with DCM and dried under high vacuum overnight. No further purification was done and intermediate SSS1 was carried on to the next step. $^1$H NMR (400 MHz, DMSO-$d_6$) δ 7.26 (d, J=7.4 Hz, 1H), 4.08-3.94 (m, 1H), 3.93-3.72 (m, 2H), 1.93-1.78 (m, 1H), 1.44-1.29 (m, 9H), 1.24 (d, J=7.4 Hz, 3H), 0.88 (d, J=6.7 Hz, 6H).

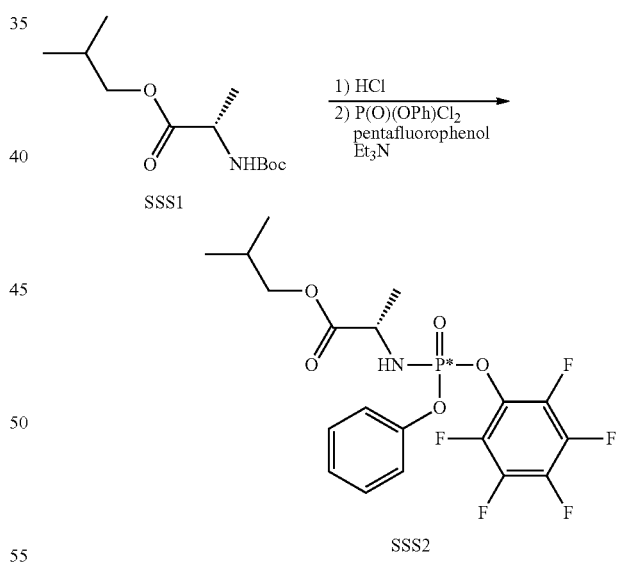

isobutyl ((perfluorophenoxy)(phenoxy)phosphoryl)-L-alaninate. 4 M hydrogen chloride in 1,4-dioxane (10 mL, 40.00 mmol) was added to a solution of intermediate SSS1 (12.15 g, 49.54 mmol) in dichloromethane (5 mL). After 1 h, the reaction was concentrated. The residue was dissolved in dichloromethane (15 mL) and cooled to 0° C. Phenyl dichlorophosphate (8.11 mL, 54.50 mmol) and triethylamine (15.11 mL, 108.99 mmol) were added sequentially. After 1 h, pentafluorophenol (9.12 g, 49.54 mmol) and triethylamine (7.55 mL, 54.50 mmol) were then sequentially added at 0° C., and the resulting mixture was then allowed to warm to room temperature. After 2.5 h, the reaction mixture was diluted with dichloromethane (50 mL), washed with saturated aqueous sodium bicarbonate solution (50 mL) and brine (50 mL), dried over anhydrous sodium sulfate, and filtered through 3 cm of silica gel. The silica gel cake was washed with additional dichloromethane (100 mL). The organics were concentrated. The residue was dissolved in 30 mL of hot hexanes and then diluted with 120 mL of hexanes. The reaction was allowed to stir for 5 h then intermediate SSS2 was isolated by filtration. Intermediate SSS2 was determined to be a single diastereomer by NMR spectroscopy. H NMR (400 MHz, DMSO-$d_6$) δ 7.45-7.38 (m, 2H), 7.23 (dd, J=11.2, 7.8 Hz, 3H), 6.91 (dd, J=14.2, 10.0 Hz, 1H), 4.07-3.94 (m, 1H), 3.81 (d, J=6.6 Hz, 2H), 1.89-1.79 (m, 1H), 1.29 (d, J=7.1 Hz, 3H), 0.86 (d, J=6.7 Hz, 6H). $^{31}$P NMR (162 MHz, DMSO-$d_6$) δ 0.49. $^{19}$F NMR (376 MHz, DMSO-$d_6$) δ-154.25 (d, J=21.3 Hz), −160.86 (t, J=23.3 Hz), −163.55-163.79 (m). LCMS: MS m/z=467.8 [M+1], $t_R$=1.88 min; LC system: Thermo Accela 1250 UHPLC; MS system: Thermo LCQ Fleet; Column: Kinetex 2.6 μXB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min.

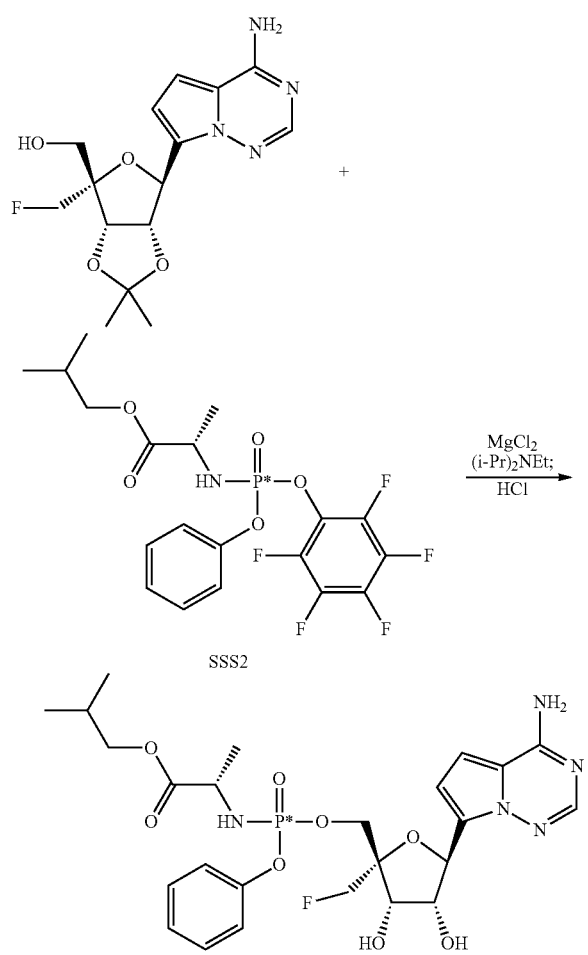

isobutyl (((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate.

Tetrahydrofuran (0.5 mL) was added to a mixture of Intermediate 4 (40 mg, 0.12 mmol), intermediate SSS2 (72 mg, 0.15 mmol), and magnesium chloride (17 mg, 0.18 mmol) at room temperature. The mixture was stirred at room temperature for 20 minutes. NN-diisopropylethylamine (52 μL, 0.30 mmol) was added. The reaction was heated to 50° C. for 2 h. The reaction mixture was allowed to cool to room temperature, and diluted with ethyl acetate (2 mL). The organics were washed with water (2 mL), dried over sodium sulfate, filtered and were concentrated. To a solution of the residue in acetonitrile (2 mL) at was added an aqueous hydrochloric acid solution (0.3 mL, 12 M) dropwise at 0° C. After 1 h, the reaction mixture was diluted with ethyl acetate (5 mL) and the resulting mixture was washed with a saturated aqueous sodium bicarbonate solution (5 mL) and brine (5 mL). The organic layer was dried over anhydrous sodium sulfate and concentrated under reduced pressure. The residue was purified by HPLC chromatography (Phenomenex Gemini 5 μm C18 110 Å, 100×30 mm, 5-100% acetonitrile in water) to afford the product, which was determined to be a single diastereomer by NMR spectroscopy. $^1$H NMR (400 MHz, Methanol-$d_4$) δ 7.84 (s, 1H), 7.39-7.32 (m, 2H), 7.27-7.17 (m, 3H), 6.96 (d, J=4.6 Hz, 1H), 6.79 (d, J=4.6 Hz, 1H), 5.37 (d, J=8.3 Hz, 1H), 4.81-4.70 (m, 1H), 4.70-4.58 (m, 2H), 4.34 (d, J=5.1 Hz, 1H), 4.25-4.17 (m, 2H), 3.98-3.80 (m, 3H), 1.95-1.85 (m, 1H), 1.32 (d, J=7.1 Hz, 3H), 0.91 (d, J=6.7 Hz, 6H). $^{31}$P NMR (162 MHz, Methanol-$d_4$) δ 3.57. $^1$H decoupled $^{19}$F NMR (376 MHz, Methanol-$d_4$) δ-238.78. LCMS: MS m/z=581.97 [M+1], $t_R$=1.35 min; LC system: Thermo Accela 1250 UHPLC; MS system: Thermo LCQ Fleet; Column: Kinetex 2.6 μXB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min HPLC: $t_R$=2.73 min; Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 71. cyclobutyl ((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate

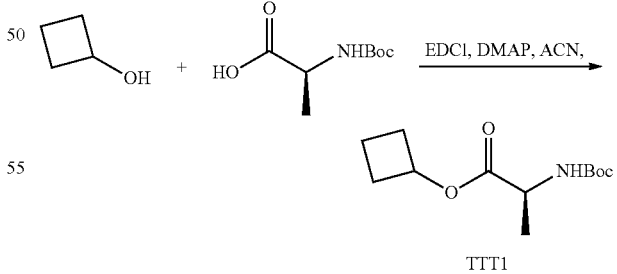

cyclobutyl (tert-butoxycarbonyl)-L-alaninate. (tert-butoxycarbonyl)-L-alanine (9.447 g, 0.05 mol) was taken up in acetonitrile (36 mL) and cyclobutanol (3 g, 0.042 mol) followed by EDCI (8.396 g, 0.054 mol) and DMAP (7.624 g, 0.062 mol) were added in one portion. The reaction was allowed to stir at room temperature for 4 h. The reaction was diluted with dichloromethane and water. The layers were split and the organic layer was dried over anhydrous sodium sulfate, filtered and then was concentrated under reduced pressure. Purification was conducted by silica gel chromatography 0-30% ethylacetate/hexane to afforded intermediate TT1. $^1$H NMR (400 MHz, DMSO-d$_6$) δ 7.21 (d, J=7.3 Hz, 1H), 4.87 (p, J=7.4 Hz, 1H), 3.91 (h, J=7.3 Hz, 1H), 2.20-2.28 (m, 2H), 2.10-1.85 (m, 2H), 1.78-1.65 (m, 1H), 1.58 (m, 1H), 1.36 (s, 9H), 1.19 (d, J=7.4 Hz, 3H).

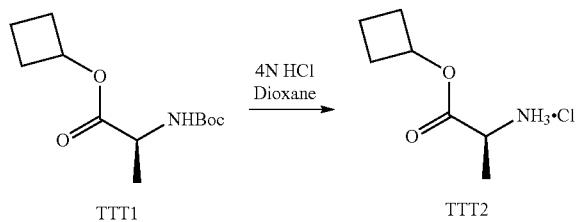

cyclobutyl-L-alaninate hydrochloride. Intermediate TTT1 (8 g, 0.033 mol) was taken up in anhydrous dichloromethane (88 mL) and 4 N HCl in dioxane (41.1 mL, 0.164 mol). The reaction was stirred at ambient temperature for 4 h. The reaction was concentrated under reduced pressure and co-evaporated with dichloromethane. The residue was placed under high vacuum overnight and intermediate TTT2 was used as is without purification for the next step. $^1$H NMR (400 MHz, DMSO-d$_6$) δ 8.65 (s, 3H), 5.03-4.90 (m, 1H), 3.97 (q, J=7.2 Hz, 1H), 2.34-2.21 (m, 2H), 2.04 (m, 2H), 1.82-1.68 (m, 1H), 1.68-1.51 (m, 1H), 1.39 (d, J=7.2 Hz, 3H).

cyclobutyl ((perfluorophenoxy)(phenoxy)-phosphoryl)-L-alaninate. To a solution of intermediate TTT2 (5.67 g, 31.56 mmol) and phenyl dichlorophosphate (4.696 mL, 31.56 mmol) in anhydrous dichloromethane (100 mL) was added triethylamine (9.76 mL, 69.44 mmol) at 0° C. under argon atmosphere. The resulting mixture was stirred for 1 h at 0° C. Pentafluorophenol (5.81 g, 31.56 mmol) and triethylamine (4.88 mL, 34.72 mmol) were then added. After 1 h of stirring at 0° C., the reaction mixture was diluted with Et$_2$O and the solids were filtered off. The crude was concentrated under reduced pressure and was purified by silica gel chromatography using an eluent ramp of 0-100% ethyl acetate/hexanes to afford the desired compound as a diastereomeric mixture. The compound obtained was dried under high vacuum, causing solidification. Diisopropyl ether was added to the solidified material and was sonicated to obtain a fine solid. The solids were isolated by filtration. Another round of sonication with diisopropyl ether and filtration afforded intermediate TTT3. Intermediate TTT3 was determined to be a single diastereomer by NMR spectroscopy. $^1$H NMR (400 MHz, DMSO-d$_6$) δ 7.40 (dd, J=8.8, 7.0 Hz, 2H), 7.27-7.16 (m, 3H), 6.85 (dd, J=14.1, 9.9 Hz, 1H), 4.91-4.78 (m, 1H), 4.00-3.82 (m, 1H), 2.28-2.15 (m, 2H), 1.99-1.84 (m, 2H), 1.76-1.63 (m, 1H), 1.56 (m, 1H), 1.25 (dd, J=7.1, 1.2 Hz, 3H). $^{19}$F NMR (376 MHz, DMSO-d$_6$) δ-154.11-154.31 (m), −160.88 (t, J=23.3 Hz), −163.67 (t, J=23.6 Hz). $^{31}$P NMR (162 MHz, DMSO-d$_6$) δ 0.45. LCMS: MS m/z=465.94 [M+1]; t$_R$=1.67 min; LC system: Thermo Accela 1250 UHPLC; MS system: Thermo LCQ Fleet; Column: Phenomenex Kinetex 2.6 μXB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min.

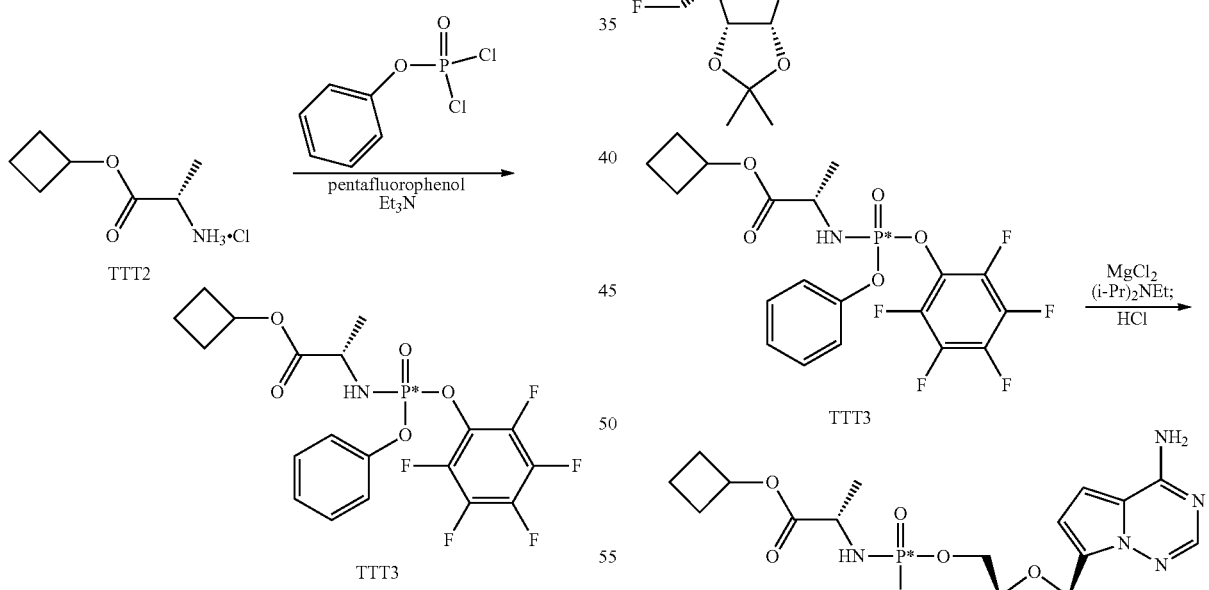

cyclobutyl ((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate. To a mixture of Intermediate 4 (0.1 g, 0.296 mmol), intermediate TTT3 (0.151 g, 0.325 mmol), and magnesium chloride (0.042 g, 0.0.443 mmol) was added tetrahydrofuran (1.5 mL) at room temperature followed by the addition of N,N-diisopropylethylamine (0.129 mL, 0.739 mmol). The resulting mixture was stirred at 50° C. for 1.5 h. The reaction mixture was then concentrated under reduced pressure and the residue obtained was diluted with a saturated sodium chloride solution and ethyl acetate. The layers were split and the organic layer was dried over anhydrous sodium sulfate, filtered and was concentrated under reduced pressure. The residue obtained was purified using preparative HPLC (Phenominex Synergi 4u Hydro-RR 80 Å 150×30 mm column, 15%-85% acetonitrile/water). Fractions were combined and concentrated under reduced pressure. The residue obtained was dissolved in anhydrous acetonitrile (3 mL) and was cooled in an ice bath followed by the dropwise addition of concentrated hydrochloric acid (0.133 mL, 1.6 mmol). The reaction mixture was stirred at room temperature for 1 h. After 1 h the reaction mixture was cooled in an ice bath and was neutralized with saturated aqueous sodium bicarbonate solution. The solids that separated were isolated by filtration, washed with water and purified by silica gel chromatography by 0-20% methanol/dichloromethane to afford the product, which was determined to be a single diastereomer by NMR spectroscopy. $^1$H NMR (400 MHz, Methanol-$d_4$) δ 7.78 (s, 1H), 7.39-7.30 (m, 2H), 7.27-7.14 (m, 3H), 6.84 (d, J=4.5 Hz, 1H), 6.73 (d, J=4.5 Hz, 1H), 5.36 (d, J=8.3 Hz, 1H), 4.99-4.86 (m, 1H), 4.82-4.56 (m, 3H), 4.34 (d, J=5.2 Hz, 1H), 4.24-4.15 (m, 2H), 3.87 (m, 1H), 2.35-2.22 (m, 2H), 2.02 (m, 2H), 1.82-1.68 (m, 1H), 1.69-1.53 (m, 1H), 1.28 (dd, J=7.1, 1.0 Hz, 3H). $^{19}$F NMR (376 MHz, Methanol-$d_4$) δ-238.78 (dd, J=48.6, 46.9 Hz). $^{31}$P NMR (162 MHz, Methanol-$d_4$) δ 3.52. LCMS: MS m/z=580.05 [M+1]; $t_R$=1.08 min; LC system: Thermo Accela 1250 UHPLC; MS system: Thermo LCQ Fleet; Column: Phenomenex Kinetex 2.6 μXB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=4.415 min; HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 72. oxetan-3-yl ((S)-(((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate

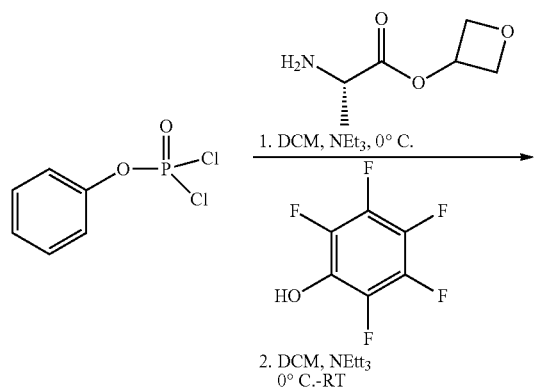

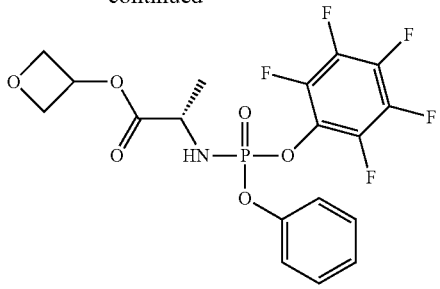

Oxetan-3-yl ((perfluorophenoxy)(phenoxy)phosphoryl)-L-alaninate. To a solution of oxetan-3-yl L-alaninate (1.98 g, 9.55 mmol) in DCM (50 ml) was added phenyl phosphorodichloridate (2.01 g, 9.55 mmol) in one portion. The resulting mixture was cooled to 0° C. and triehylamine (0.97 g, 9.55 mmol) was added drop wise. The resulting mixture was stirred for 30 min after removal of ice bath and cooled to 0° C. and 2,3,4,5,6-pentafluorophenol (1.76 g, 9.55 mmol) was added in one portion and triethylammine (0.97 g, 9.55 mmol) was added drop wise. The resulting mixture was stirred for 30 min after removal of ice bath, diluted with EtOAc, washed with water and brine, the organic solvent was concentrated in vacuum, and the resulting residue was purified by silica gel column chromatography eluting with 0-100% ethyl acetate in hexanes to afford the intermediate. $^1$H NMR (400 MHz, Chloroform-d) δ 7.38-7.34 (m, 2H), 7.28-7.19 (m, 3H), 5.49-5.43 (m, 1H), 4.91-4.85 (m, 2H), 4.63-4.56 (m, 2H), 4.27-4.22 (m, 1H), 4.06-4.02 (m, 1H), 1.51-1.48 (m, 3H). $^{31}$P NMR (162 MHz, Chloroform-d) δ 0.38, 0.22. LCMS: MS m/z=468.01 [M+1], $t_R$=1.63 min; LC system: Thermo Accela 1250 UHPLC; MS system: Thermo LCQ Fleet; Column: Kinetex 2.6 μXB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μl/min. HPLC: $t_R$=3.15 min; HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

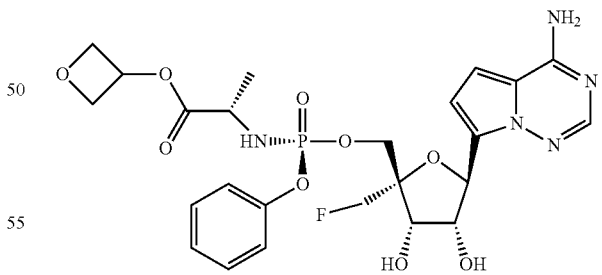

To a mixture of Intermediate 4 (0.0345 g, 0.103 mmol), oxetan-3-yl ((perfluorophenoxy)(phenoxy)phosphoryl)-L-alaninate (0.626 g, 0.134 mmol), and magnesium chloride (0.015 g, 0.155 mmol) was added tetrahydrofuran (1.0 mL) at room temperature followed by the addition of N,N-diisopropylethylamine (0.063 mL, 0.361 mmol). The resulting mixture was stirred at 50° C. for 1.5 h. The reaction mixture was then concentrated under reduced pressure and the residue obtained was diluted with a saturated sodium chloride solution and ethyl acetate. The layers were split and the organic layer was dried over anhydrous sodium sulfate, filtered and was concentrated under reduced pressure. The residue obtained was purified using preparative HPLC (Phenominex Synergi 4u Hydro-RR 80 Å 150×30 mm column, 15%-85% acetonitrile/water). Fractions were combined and concentrated under reduced pressure. LCMS: MS m/z=581.97 [M];]; $t_R$=1.12 min; LC system: Thermo Accela 1250 UHPLC; MS system: Thermo LCQ Fleet; Column: Phenomenex Kinetex 2.6 µXB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% acetonitrile at 1800 µl/min. HPLC: $t_R$=3.37 min; Agilent Infinity 129011; Column: Phenomenex Kinetex 2.8 µC$_{18\ 100}$A, 100×4.6 mm; Solvents: acetonitrile with 0.1% trifluoroacetic acid, water with 0.1% trifluoroacetic acid; Gradient: 0-0.55 min 2% acetonitrile, 0.55-8.55 min 2-98% acetonitrile, 8.55-9.25 min 98% acetonitrile at 1500 µl/min Example 73. (2R,3S,4S,5S)-5-(4-aminopyrrolo[2,1-f][1,2,4]triazin-7-yl)-2-(fluoromethyl)-2-((((S)-(((S)-1-(oxetan-3-yloxy)-1-oxopropan-2-yl)amino)(phenoxy)phosphoryl)oxy)methyl)tetrahydrofuran-3,4-diyl bis(2-methylpropanoate)

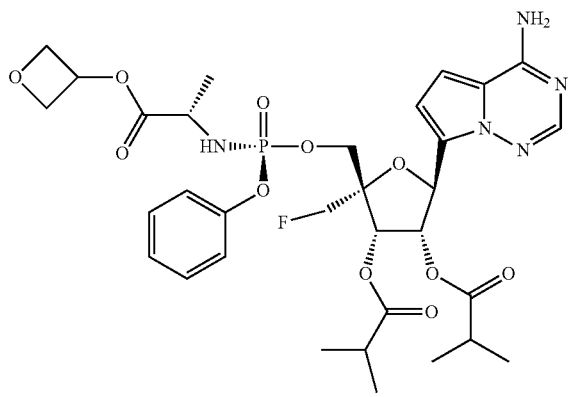 [SMILES: CC(C)C(=O)O[C@H]1[C@H](c2ccc3c(N)ncnn23)O[C@](CF)(CO[P@@](=O)(N[C@@H](C)C(=O)OC2COC2)Oc2ccccc2)[C@H]1OC(=O)C(C)C]

Isobutyric anhydride (8.2 mg, 0.05 mmol) and Example 72 (15 mg, 0.03 mmol) were dissolved in anhydrous tetrahydrofuran (1.0 mL) under argon and the mixture was stirred at room temperature for 5 minutes. 4-Dimethylaminopyridine (0.3 mg, 0.003 mmol) was added and the reaction mixture was stirred at room temperature. After 2 hours, methanol (0.5 mL) was added and the mixture was stirred for 20 minutes, then diluted with ethyl acetate (10 mL) and washed twice with a saturated aqueous sodium bicarbonate solution (10 mL) and once with brine (10 mL). The organic layer was dried over anhydrous sodium sulfate and concentrated under reduced pressure. The crude residue was purified by preparatory HPLC (Phenomenex Gemini 5 µm C18 110 Å 100×30 mm column) using gradient from 10-100% acetonitrile in water to afford the product, which was determined to be a single diastereomer by NMR spectroscopy. $^1$H NMR (400 MHz, Methanol-$d_4$) δ 8.14 (s, 2H), 7.37 (t, J=7.8 Hz, 1H), 7.31-7.18 (m, 4H), 6.98 (d, J=4.6 Hz, 2H), 6.84 (dd, J=36.1, 4.5 Hz, 1H), 5.45 (d, J=5.7 Hz, 2H), 5.21 (t, J=6.1 Hz, 2H), 4.97 (d, J=6.4 Hz, 2H), 4.89-4.82 (m, 1H), 4.71 (d, J=47.0 Hz, 1H), 4.62-4.54 (m, 1H), 4.37 (d, J=4.7 Hz, 1H), 3.78 (d, J=11.4 Hz, 2H), 3.67 (d, J=11.4 Hz, 2H), 2.71 (p, J=7.0 Hz, 1H), 2.52 (p, J=7.0 Hz, 1H), 1.33-1.29 (m, 3H), 1.25 (d, J=7.0 Hz, 6H), 1.12 (d, J=7.0 Hz, 3H), 1.08 (d, J=7.0 Hz, 3H). $^{31}$P NMR (162 MHz, Methanol-$d_4$) δ 3.50. Decoupled $^{19}$F NMR (376 MHz, Methanol-$d_4$) δ-235.96 (s). LCMS: MS m/z=722.1 [M+1], $t_R$=1.56 min; LC system: Thermo Accela 1250 UHPLC; MS system: Thermo LCQ Fleet; Column: Kinetex 2.6 µXB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 µl/min.

Example 74. 2-ethylbutyl ((S)-(((2R,3S,4R,5S)-5-(4-butyramidopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate

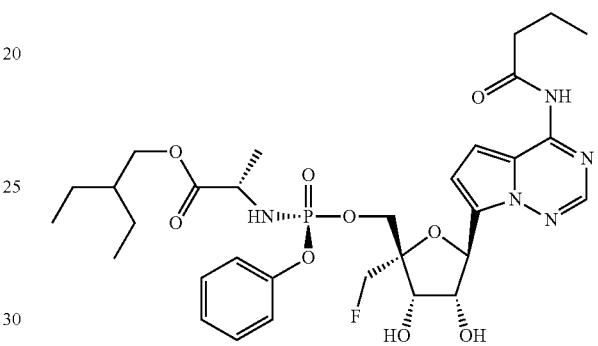

To a solution of Intermediate 6 (150 mg, 0.231 mmol) in anhydrous pyridine (1 mL) was added butanoyl chloride (0.026 mL, 0.254 mmol) dropwise under argon atmosphere at room temperature. After 30 min., the reaction mixture was purified by preparatory HPLC (Phenomenex Gemini 5 µm C18 110 Å 100×30 mm column) using gradient from 20-100% acetonitrile in water to afford the compound. LCMS: MS m/z=720.27 [M+1];]; $t_R$=1.76 min; LC system:: Dionex Ultimate 3000 UHPLC; Column: Phenomenex Kinetex 2.6 µC18 100A, 50×3.0 mm; Solvents: acetonitrile with 0.1% formic acid, water with 0.1% formic acid; Gradient: 0 min-0.2 min 40% acetonitrile, 0.2 min-1.55 min 40%-100% acetonitrile, 1.55 min-2.80 min 100% acetonitrile, 2.80-2.81 min 100%-40% acetonitrile at 1100p/min. The compound obtained was taken up in acetonitrile (4 mL) and conc HCl (0.4 mL) was added dropwise at 0° C. The reaction was stirred at ambient temperature for 1 h. After 1 h the reaction mixture was cooled in an ice bath and was neutralized with aqueous sodium bicarbonate solution. The resulting mixture was purified by preparative HPLC (Phenomenex Gemini 5 µm C$_{18\ 110}$Å 100×30 mm column) using gradient from 20-100% acetonitrile in water to afford the compound. $^1$H NMR (400 MHz, DMSO-$d_6$) δ 10.73 (s, 1H), 8.25 (s, 1H), 7.40-7.31 (m, 2H), 7.24-7.13 (m, 4H), 6.93-6.92 (m, 1H), 6.08-6.02 (m, 1H), 5.34-5.32 (m, 1H), 5.19 (s, 2H), 4.65-4.63 (m, 1H), 4.58-4.45 (m, 2H), 4.21-4.20 (m, 1H), 4.03-3.92 (m, 3H), 3.93-3.76 (m, 2H), 2.69-2.65 (m, 2H), 1.65-1.60 (m, 2H), 1.44-1.41 (m, 1H), 1.32-1.18 (m, 7H), 0.94-0.91 (m, 3H), 0.79-0.77 (m, 6H). $^{31}$P NMR (162 MHz, DMSO-$d_6$) δ 3.54. $^{19}$F NMR (376 MHz, DMSO-$d_6$) δ-236.50 (t, J=47.9 Hz). LCMS: MS m/z=680.22 [M+1];]; $t_R$=1.37 min; LC system::Dionex Ultimate 3000 UHPLC; Column: Phenomenex Kinetex 2.6 µC18 100A, 50×3.0 mm; Solvents: acetonitrile with 0.1% formic acid, water with 0.1% formic acid; Gradient: 0 min-0.2 min 40% acetonitrile, 0.2 min-1.55 min 40%-100% acetonitrile, 1.55 min-2.80 min 100% acetonitrile, 2.80-2.81 min 100%-40% acetonitrile at 1100 µl/min.

Example 75. 2-ethylbutyl ((S)-(((2R,3S,4R,5S)-5-(4-benzamidopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate

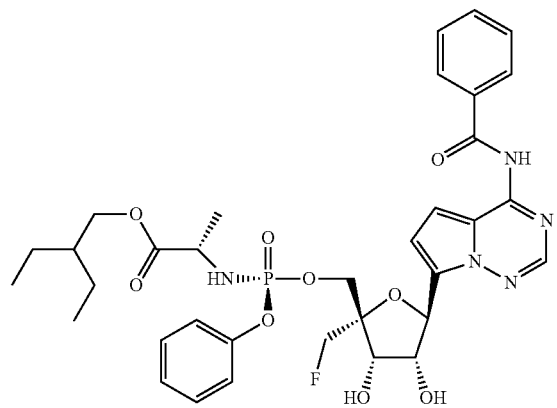 [SMILES: CCC(CC)COC(=O)[C@H](C)N[P@](=O)(OC[C@@]1(CF)O[C@@H](c2ccc3c(NC(=O)c4ccccc4)ncnn23)[C@H](O)[C@@H]1O)Oc1ccccc1]

To a solution of Intermediate 6 (100 mg, 0.154 mmol) in anhydrous pyridine (1 mL) was added benzoyl chloride (0.018 mL, 0.154 mmol) dropwise under argon atmosphere at room temperature. After 30 min., the reaction mixture was purified by preparatory HPLC (Phenomenex Gemini 5 µm C18 110 Å 100×30 mm column) using gradient from 20-100% acetonitrile in water to afford the compound. LCMS: MS m/z=754.26 [M+1];]; $t_R$=1.88 min; LC system: Dionex Ultimate 3000 UHPLC; Column: Phenomenex Kinetex 2.6 µC18 100A, 50×3.0 mm; Solvents: acetonitrile with 0.1% formic acid, water with 0.1% formic acid; Gradient: 0 min-0.2 min 40% acetonitrile, 0.2 min-1.55 min 40%-100% acetonitrile, 1.55 min-2.80 min 100% acetonitrile, 2.80-2.81 min 100%-40% acetonitrile at 1100p/min. The compound obtained was taken up in acetonitrile (3 mL) and conc HCl (0.3 mL) was added dropwise at 0° C. The reaction was stirred at ambient temperature for 1 h. After 1 h the reaction mixture was cooled in an ice bath and was neutralized with aqueous sodium bicarbonate solution. The resulting mixture was purified by preparative HPLC (Phenomenex Gemini 5 µm C18 110 Å 100×30 mm column) using gradient from 20-100% acetonitrile in water to afford the compound. $^1$H NMR (400 MHz, DMSO-$d_6$) δ 13.15 (s, 0.3H), 11.21 (s, 0.7H), 8.33-7.99 (m, 3H), 7.62-7.48 (m, 3H), 7.38-7.34 (m, 2H), 7.23-6.97 (m, 5H), 6.09-6.03 (m, 1H), 5.33-5.32 (m, 2H), 5.23-5.21 (m, 1H), 4.69-4.63 (m, 1H), 4.57-4.49 (m, 2H), 4.22-4.20 (m, 1H), 4.02-3.79 (m, 5H), 1.46-1.40 (m, 1H), 1.32-1.19 (m, 7H), 0.79-0.77 (m, 6H). $^{31}$P NMR (162 MHz, DMSO-$d_6$) δ 3.55. LCMS: MS m/z=714.27 [M+1];]; $t_R$=1.85 min; LC system: Dionex Ultimate 3000 UHPLC; MS system: Thermo LCQ Fleet; Column: Phenomenex Kinetex 2.6 µC18 100A, 50×3.0 mm; Solvents: acetonitrile with 0.1% formic acid, water with 0.1% formic acid; Gradient: 0 min-1.6 min 2-100% acetonitrile, 1.6 min-1.8 min 100% acetonitrile, 1.80 min-1.90 min 100%-2% acetonitrile, 1.90 min-2.20 min 2% acetonitrile at 1100p/min.

Example 76. 2-ethylbutyl ((S)-(((2R,3S,4R,5S)-5-(4-(2-cyclohexylacetamido)pyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate

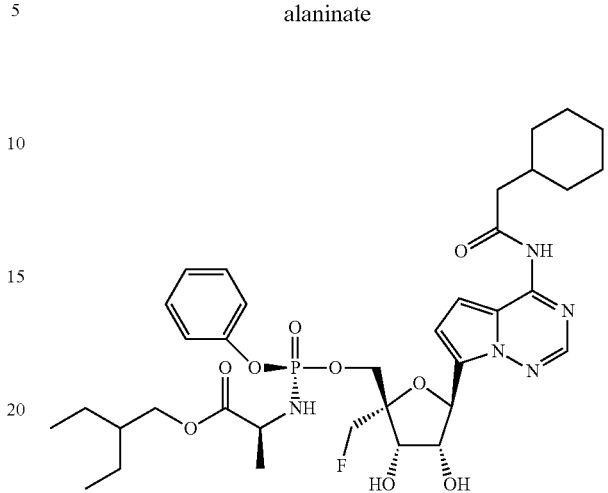

To a solution of Intermediate 6 (150 mg, 0.231 mmol) in anhydrous pyridine (1 mL) was added cyclohexylacetyl chloride (0.039 mL, 0.254 mmol) dropwise under argon atmosphere at room temperature. After 30 min., the reaction mixture was purified by preparatory HPLC (Phenomenex Gemini 5 µm C18 110 Å 100×30 mm column) using gradient from 20-100% acetonitrile in water to afford the compound. LCMS: MS m/z=774.45 [M+1];]; $t_R$=1.98 min; LC system: Thermo Accela 1250 UHPLC; MS system: Dionex Ultimate 3000 UHPLC; Column: Phenomenex Kinetex 2.6 µC18 100A, 50×3.0 mm; Solvents: acetonitrile with 0.1% formic acid, water with 0.1% formic acid; Gradient: 0 min-0.2 min 40% acetonitrile, 0.2 min-1.55 min 40%-100% acetonitrile, 1.55 min-2.80 min 100% acetonitrile, 2.80-2.81 min 100%-40% acetonitrile at 1100 µl/min. The compound obtained was taken up in acetonitrile (4 mL) and conc HCl (0.4 mL) was added dropwise at 0° C. The reaction was stirred at ambient temperature for 1 h. After 1 h the reaction mixture was cooled in an ice bath and was neutralized with aqueous sodium bicarbonate solution. The resulting mixture was purified by preparative HPLC (Phenomenex Gemini 5 µm C18 110 Å 100×30 mm column) using gradient from 20-100% acetonitrile in water to afford the compound. $^1$H NMR (400 MHz, DMSO-$d_6$) δ 10.71 (s, 1H), 8.25 (s, 1H), 7.37-7.34 (m, 2H), 7.23-7.13 (m, 4H), 6.94-6.93 (m, 1H), 6.08-6.02 (m, 1H), 5.34-5.30 (m, 2H), 5.19 (s, 1H), 4.68-4.48 (m, 3H), 4.20-4.19 (m, 1H), 4.00-3.78 (m, 5H), 2.55-2.53 (m, 2H), 1.87-1.56 (m, 5H), 1.45-1.38 (m, 1H), 1.31-1.07 (m, 11H), 1.04-0.92 (m, 2H), 0.81-0.77 (m, 6H). $^{31}$P NMR (162 MHz, DMSO-$d_6$) δ 3.54. $^{19}$F NMR (376 MHz, DMSO-$d_6$) δ-236.47 (t, J=48.1 Hz). LCMS: MS m/z=734.20 [M+1];]; $t_R$=1.23 min; LC system: Dionex Ultimate 3000 UHPLC; MS system: Thermo LCQ Fleet; Column: Phenomenex Kinetex 2.6 µC18 100A, 50×3.0 mm; Solvents: acetonitrile with 0.1% formic acid, water with 0.1% formic acid; Gradient: 0 min-1.6 min 2-100% acetonitrile, 1.6 min-1.8 min 100% acetonitrile, 1.80 min-1.90 min 100%-2% acetonitrile, 1.90 min-2.20 min 2% acetonitrile at 1100 µl/min.

Example 77. Cyclopropylmethyl (((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate

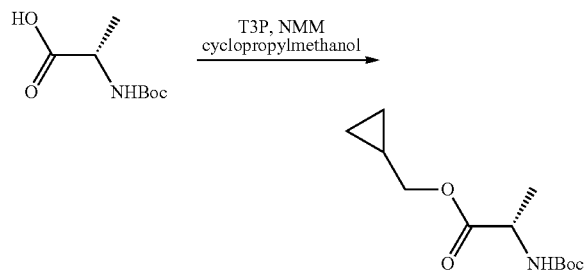

Cyclopropylmethyl (tert-butoxycarbonyl)-L-alaninate. To a stirred solution of boc-L-alanine (7.00 g, 37.00 mmol) and cyclopropanemethanol (3.20 g, 44.39 mmol) in 50 mL of dry dichloromethane were added tinder argon, N-methylmorpholine (12.20 mL, 110.99 mmol), 4-(dimethylamino)pyridine (0.094 g, 0.74 mmol) and tri-propylphosphonic acid cyclic anhydride (26.43 ml, 44.39 mmol, 50% in ethyl acetate) at 0° C. The reaction mixture was then stirred at room temperature for 2 hours (difficult to monitor the conversion by TLC or LCMS). The reaction mixture was washed with water (20 mL) 2×10% solution of citric acid (20 mL), 2× with a sat. aqueous solution of NaHCO₃ (20 mL) and once with brine (20 mL) The organics were dried over Na₂SO₄, filtered through a 3 cm layer of silica gel which was washed with additional dichloromethane. Organics were concentrated down under reduced pressure, co-distilled with dichloromethane and dried under high vacuum overnight to afford the intermediate. $^1$H NMR (400 MHz, DMSO-$d_6$) δ 7.25 (d, J=7.3 Hz, 1H), 4.12-3.77 (m, 3H), 1.38 (s, 9H), 1.24 (d, J=7.4 Hz, 3H), 1.12-0.99 (m, 1H), 0.57-0.42 (m, 2H), 0.31-0.19 (m, 2H).

nyl)-L-alaninate (8.26 g, 33.96 mmol) was taken up in dichloromethane (20 mL) and cooled to 0° C. Hydrogen chloride (30.00 mL, 120.00 mmol, 4 N in dioxane) was added. After 2 h, the reaction was concentrated under reduced pressure. The residue was dissolved in dichloromethane (30 mL) and cooled to 0° C. Phenyl dichlorophosphate (5.56 mL, 37.35 mmol) and triethylamine (10.36 mL, 74.70 mmol) were sequentially added. After 1 h, pentafluorophenol (6.25 g, 33.96 mmol) and triethylamine (5.18 mL, 37.35 mmol) were then sequentially added at 0° C., and the resulting mixture was then allowed to warm to room temperature. After 2.5 h, the reaction mixture was diluted with dichloromethane (50 mL), washed with saturated aqueous sodium bicarbonate solution (50 mL), brine (50 mL), dried over anhydrous sodium sulfate, and filtered through 3 cm of silica gel. The pad was washed with additional dichloromethane (200 mL). The organics were concentrated under reduced pressure. The residue was dissolved in warm tert-butyl methyl ether (100 mL) then diluted with 100 mL of hexanes. The reaction was allowed to stir for 2 h and the intermediate was isolated by filtration. The intermediate was determined to be a single diastereomer by NMR spectroscopy. $^1$H NMR (400 MHz, DMSO-$d_6$) δ 7.47-7.38 (m, 2H), 7.30-7.18 (m, 3H), 6.98-6.82 (m, 1H), 4.06-3.93 (m, 1H), 3.87 (d, J=7.2 Hz, 2H), 1.30 (d, J=6.9 Hz, 3H), 1.12-0.98 (m, 1H), 0.53-0.43 (m, 2H), 0.27-0.20 (m, 2H). $^{19}$F NMR (376 MHz, DMSO-$d_6$) δ-154.22 (d, J=21.9 Hz), −160.88 (t, J=22.4 Hz), −163.70 (t, J=21.8 Hz). $^{31}$P NMR (162 MHz, DMSO-$d_6$) δ 0.47 (t, J=12.5 Hz). LCMS: MS m/z=465.8 [M+1], $t_R$=1.80 min; LC system: Thermo Accela 1250 UHPLC; MS system: Thermo LCQ Fleet; Column: Kinetex 2.6 μXB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μl/min.

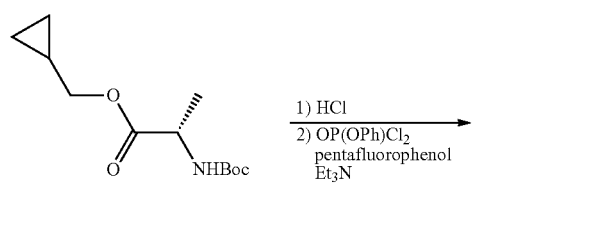

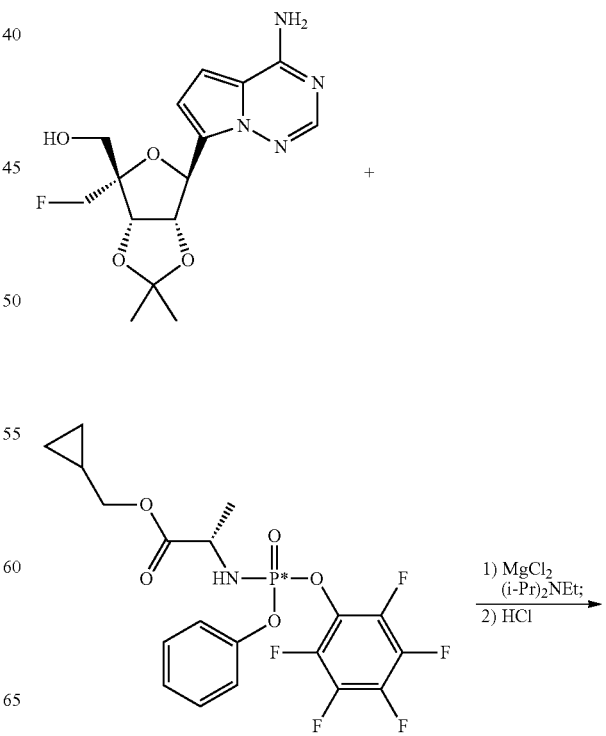

Cyclopropylmethyl ((perfluorophenoxy)(phenoxy)phosphoryl)-L-alaninate. Cyclopropylmethyl (tert-butoxycarbo- 197
-continued

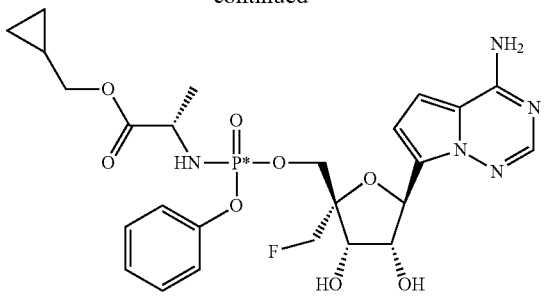

Cyclopropylmethyl (((((2R,3S,4R,5S)-5-(4-aminopyrrolo[2,1-f][1,2,4]triazin-7-yl)-2-(fluoromethyl)-3,4-dihydroxytetrahydrofuran-2-yl)methoxy)(phenoxy)phosphoryl)-L-alaninate. Tetrahydrofuran (0.5 mL) was added to a mixture of Intermediate 4 (10 mg, 0.03 mmol), cyclopropylmethyl ((perfluorophenoxy)(phenoxy)phosphoryl)-L-alaninate (15 mg, 0.03 mmol), and magnesium chloride (4 mg, 0.4 mmol) at room temperature. The mixture was stirred at room temperature for 20 minutes. N,N-diisopropylethylamine (15 µL, 0.09 mmol) was added. The reaction was heated to 50° C. for 2 h. The reaction mixture was allowed to cool to room temperature, and diluted with ethyl acetate (2 mL). The organics were washed with water (2 mL), dried over sodium sulfate, filtered and were concentrated. To a solution of the residue in acetonitrile (2 mL) at was added aqueous hydrochloric acid solution (0.3 mL, 3.60 mmol, 12 M) dropwise at 0° C. After 1 h, the reaction mixture was diluted with ethyl acetate (5 mL) and the resulting mixture was washed with saturated aqueous sodium bicarbonate carbonate solution (5 mL) and brine (5 mL). The organic layer was dried over anhydrous sodium sulfate and concentrated under reduced pressure. The residue was purified by HPLC chromatography (Phenomenex Gemini 5 µm C18 110 Å, 100×30 mm, 5-100 acetonitrile in water) to afford the product, which was determined to be a single diastereomer by NMR spectroscopy. $^1$H NMR (400 MHz, Methanol-$d_4$) δ 7.91 (s, 1H), 7.40-7.33 (m, 2H), 7.30-7.17 (m, 3H), 7.14 (d, J=4.7 Hz, 1H), 6.86 (d, J=4.7 Hz, 1H), 5.37 (d, J=8.4 Hz, 1H), 4.81-4.69 (m, 1H), 4.68-4.57 (m, 2H), 4.34 (d, J=5.2 Hz, 1H), 4.29-4.16 (m, 2H), 3.99-3.85 (m, 3H), 1.32 (d, J=7.1 Hz, 3H), 1.17-1.04 (m, 1H), 0.56-0.48 (m, 2H), 0.29-0.22 (m, 2H). $^{31}$P NMR (162 MHz, Methanol-$d_4$) δ 3.53. $^{19}$F NMR (376 MHz, Methanol-$d_4$) δ-238.80 (t, J=48.0 Hz). LCMS: MS m/z=579.89 [M+1], $t_R$=1.28 min; LC system: Thermo Accela 1250 UHPLC; MS system: Thermo LCQ Fleet; Column: Kinetex 2.6 µXB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 µl/min. HPLC: $t_R$=2.62 min; Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

C. Biological Examples

Example 78. Expression and Purification of Dengue NS5 Proteins

The genes coding for full-length NS5 sequence of Dengue serotype 2 (strain New Guinea C) was synthesized and cloned into NheI/XhoI sites of vector pET28b, resulting in N-terminal HIS-tagged NS5. The sequence confirmed plasmid was transformed into *E. coli* BL21 (DE3) and the cells were grown in LB medium until OD$_{600}$ reached 0.5. The protein expression was induced by addition of 0.5 mM IPTG and the culture was continued shaking at 250 rpm overnight at 16° C. After centrifugation, the cell pellet from 1 L bacterial culture was resuspended in buffer A containing 50 mM HEPES (pH 7.6), 500 mM NaCl, 10% Glycerol, 0.5% TritonX100, 2 mM TCEP, supplemented with two tablets of EDTA free Complete Protease Inhibitor Cocktail (Roche Diagnostics, Risch-Rotkreuz, Switzerland). Cells were lysed using microfluidizer followed by centrifugation. The clarified supernatant was purified through 5 mL Ni-NTA column (GE Healthcare) equilibrated in Buffer B [25 mM HEPES 7.5, 500 mM NaCl, 10% Gly, 0.1% CHAPS and 1 mM TCEP]. The column was washed with Buffer B containing 40 mM imidazole and NHIS-NS5 was eluted with a gradient of Buffer B containing 500 mM imidazole. Fractions containing NHIS-NS5 were pooled and further purified by size exclusion chromatography using a 120 mL Superdex 200 column (GE Healthcare) equilibrated in Buffer C [25 mM HEPES 7.2, 200 mM NaCl, 10% Glycerol, 0.1% CHAPS, 2 mM DTT]. The mass and purity of the NHIS-NS5 protein was confirmed by mass spectrometry analysis.

Alternatively, the Ni-NTA purified NHIS-NS5 was used to remove N-terminal NHIS-tag by adding Thrombin protease and incubated overnight with dialysis against buffer B at 4° C. The tag-removed NS5 protein was separated from others on a second Ni-NTA column, and further purified by size exclusion chromatography using a 120 mL Superdex 200 column (GE Healthcare) equilibrated in Buffer C [25 mM HEPES 7.2, 200 mM NaCl, 10% Glycerol, 0.1% CHAPS, 2 mM DTT]. The mass and purity of the NS5 protein was confirmed by mass spectrometry analysis.

Example 79. DENV Pol IC50

A 244 nucleotide secondary structureless heteropolymeric RNA (sshRNA) with sequence 5'-(UCAG)20(UCCAAG)14(UCAG)20-3' (SEQ ID NO: 1) is used as the template with 5'-CUG-3' primer in the DENV2-NS5 polymerase assay. Six two-fold dilutions of compounds starting from 200 nM and no inhibitor control are plated in 96-well plates. 100 nM DENV2 NS5 is preincubated for 5 minutes at room temperature in a reaction mixture containing 40 mM Tris-HCl (pH 7.5), 10 mM NaCl, 3 mM DTT, 0.2 unit/µL RNasin Plus RNase Inhibitor, 200 ng/µL sshRNA, 20 µM CUG and 2 mM MgCl$_2$. Enzyme mix is added to compound dilutions and reactions initiated by the addition of a mixture containing 20 µM of three natural NTP plus 2 µM of analog:base matched competing natural NTP containing 1:100 α-33P-NTP. After 90 minutes at 30° C., 5 µL of the reaction mixtures are spotted on DE81 anion exchange paper. Filter papers are washed three times with Na$_2$HPO$_4$ (125 mM, pH 9) for 5 minutes, rinsed with water and ethanol, then air-dried and exposed to phosphorimager. Synthesized RNA is quantified using Typhoon Trio Imager and Image Quant TL Software and reaction rates are calculated by linear regression using GraphPad Prism 5.0. IC$_{50}$ values are calculated in Prism by non-linear regression analysis using the dose-response (variable slope) equation (four-parameter logistic equation): Y=Bottom+(Top-Bottom)/(1+10^((Log IC$_{50}$_X)*HillSlope)).

Example 80. RSV RNP Preparation

RSV ribonucleoprotein (RNP) complexes were prepared from a method modified from Mason et al. (1). HEp-2 cells were plated at a density of 7.1×10⁴ cells/cm² in MEM+10% fetal bovine serum (FBS) and allowed to attach overnight at 37° C. (5% $CO_2$). Following attachment, the cells were infected with RSV A2 (MOI=5) in 35 mL MEM+2% FBS. At 20 hours post-infection, the media was replaced with MEM+2% FBS supplemented with 2 µg/mL actinomycin D and returned to 37° C. for one hour. The cells were then washed once with PBS and treated with 35 mL of PBS+250 µg/mL lyso-lecithin for one minute, after which all liquid was aspirated. The cells were harvested by scrapping them into 1.2 mL of buffer A [50 mM TRIS acetate (pH 8.0), 100 mM potassium acetate, 1 mM DTT and 2 [µg/mL actinomycin D] and lysed by repeated passage through an 18 gauge needle (10 times). The cell lysate was placed in ice for 10 minutes and then centrifuged at 2400 g for 10 minutes at 4° C. The supernatant (S1) was removed and the pellet (P1) was disrupted in 600 uL of Buffer B [10 mM TRIS acetate (pH 8.0), 10 mM potassium acetate and 1.5 mM $MgCl_2$] supplemented with 1% Triton X-100 by repeated passage through an 18 gauge needle (10 times). The resuspended pellet was placed in ice for 10 minutes and then centrifuged at 2400 g for 10 minutes at 4° C. The supernatant (S2) was removed and the pellet (P2) was disrupted in 600 uL of Buffer B supplemented with 0.5% deoxycholate and 0.1% Tween 40. The resuspended pellet was placed in ice for 10 minutes and then centrifuged at 2400 g for 10 minutes at 4° C. The supernatant (S3) fraction, containing the enriched RSV RNP complexes, was collected and the protein concentration determined by UV absorbance at 280 nm. Aliquoted RSV RNP S3 fractions were stored at −80° C.

Example 81. RSV RNP Assay

Transcription reactions contained 25 µg of crude RSV RNP complexes in 30 µL of reaction buffer [50 mM TRIS-acetate (pH 8.0), 120 mM potassium acetate, 5% glycerol, 4.5 mM $MgCl_2$, 3 mM DTT, 2 mM ethyleneglycol-bis(2-aminoethylether)-tetraacetic acid (EGTA), 50 µg/mL BSA, 2.5 U RNasin (Promega), ATP, GTP, UTP, CTP and 1.5 uCi [α-32P] NTP (3000 Ci/mmol)]. The radiolabeled nucleotide used in the transcription assay was selected to match the nucleotide analog being evaluated for inhibition of RSV RNP transcription. Cold, competitive NTP was added at a final concentration of one-half its Km (ATP=20 µM, GTP=12.5 µM, UTP=6 µM and CTP=2 µM). The three remaining nucleotides were added at a final concentration of 100 µM.

To determine whether nucleotide analogs inhibited RSV RNP transcription, compounds were added using a 6 step serial dilution in 5-fold increments. Following a 90 minute incubation at 30° C., the RNP reactions were stopped with 350 µL of Qiagen RLT lysis buffer and the RNA was purified using a Qiagen RNeasy 96 kit. Purified RNA was denatured in RNA sample loading buffer (Sigma) at 65° C. for 10 minutes and run on a 1.2% agarose/MOPS gel containing 2 M formaldehyde. The agarose gel was dried and exposed to a Storm phosphorimager screen and developed using a Storm phosphorimager (GE Healthcare). The concentration of compound that reduced total radiolabeled transcripts by 50% ($IC_{50}$) was calculated by non-linear regression analysis of two replicates.

Example 82. DENV-2 moDC EC50

Human monocyte-derived dendritic cells (moDCs) were derived from CD14+ monocytes (AllCells) cultured in Human Mo-DC Differentiation medium containing GM-CSF and IL-4 (Miltenyi Biotec). On day 7, moDCs were harvested by mechanical disruption, washed and suspended in serum-free RPMI. moDCs were infected with Vero-derived Dengue 2, New Guinea strain (NGC) at a MOI=0.1 for two hours in serum-free RPMI with gentle agitation at 37° C. Cells were washed and resuspended in 10% serum-containing RPMI (Gibco, supplemented with sodium pyruvate, NEAA, Penicillin-Streptomycin). 10≡cells were plated in triplicate in 96-well plates with compounds dispensed at graded doses (Hewlett-Packard D300 Digital Dispenser). All wells were normalized to 0.25% DMSO. At 48 hours, cells were washed with 1×PBS and all supernatants removed. Total RNA was extracted using RNEasy 96 plates (Qiagen) and used to generate first-strand cDNA using XLT cDNA 5× Supermix (QuantaBio). cDNA was used as a template in a Taqman qPCR duplex reaction specific to DENV2 viral and GAPDH gene expression. $EC_{50}$ values were determined using Prism Graphpad software, with normalization to a positive control and no compound negative control wells.

Example 83. moDC CC50

Human monocyte-derived dendritic cells (moDCs) were derived from CD14+ monocytes (AllCells) cultured in Human Mo-DC Differentiation medium containing GM-CSF and IL-4 (Miltenyi Biotec). On day 7, moDCs were harvested by mechanical disruption, washed and cultured in triplicate at 1×10^5-5×10^4 cells/well in 96-well plates with compounds dispensed at graded doses (Hewlett-Packard D300 Digital Dispenser). All wells were normalized to 0.25% DMSO. After 48 hours, CellTiter Glo (Promega) was added and incubated for 10 minutes at room temp before reading on a luminometer. % viability curves were calculated against no compound and no cell control wells. $CC_{50}$ values were determined using Prism Graphpad software.

Example 84. DENV-2 Huh-7 EC50

Huh7 (Human hepatocarcinoma 7) cells were maintained in 10% FCS-containing DMEM complete media. On the day of the assay, cells were trypsinized (0.1% Trypsin-EDTA), washed and infected for 2 hours in serum-free DMEM with Dengue serotype 2 New Guinea C (NGC) strain at MOI=0.1 with gentle agitation at 37° C. After 2 hours, cells were washed with serum-free media and suspended in 10% FCS-containing DMEM (Gibco, supplemented with sodium pyruvate, NEAA, Penicillin-Streptomycin). 10^5 cells were plated in triplicate in 96-well plates with compounds dispensed at graded doses (Hewlett-Packard D300 Digital Dispenser). All wells were normalized to 0.25% DMSO. At 48 hours, cells were washed with 1× PBS and all supernatants removed. Total RNA was extracted using RNEasy 96 plates (Qiagen) and used to generate first-strand cDNA using XLT cDNA 5× Supermix (QuantaBio). cDNA was used as a template in a Taqman qPCR duplex reaction specific to DENV2 viral and GAPDH gene expression. $EC_{50}$ values were determined using Prism Graphpad software, with normalization to a positive control and no compound negative control wells.

Example 85. Huh-7 CC50

Human hepatocarcinoma 7 (Huh7) cells were maintained in 10% FCS-containing complete DMEM. On day of assay, cells were trypsinized with 0.1% Trypsin-EDTA, washed and cultured in triplicate at 1-2×10^4 cells/well in 96-well plates with compounds dispensed at graded doses (Hewlett- Packard D300 Digital Dispenser). All wells were normalized to 0.25% DMSO. After 48 hours, CellTiter Glo (Promega) was added and incubated for 10 minutes at room temp before reading on a luminometer. % viability curves were calculated against no compound and no cell control wells. $CC_{50}$ values were determined using Prism Graphpad software.

Example 86. RSV HEp-2 EC50

Antiviral activity against RSV is determined using an infectious cytopathic cell protection assay in HEp-2 cells. In this assay, compounds inhibiting viral infection and/or replication produce a cytoprotective effect against the virus-induced cell killing that can be quantified using a cell viability reagent. The techniques used here are novel adaptations of methods described in published literature (Chapman et al., Antimicrob Agents Chemother. 2007, 51(9): 3346-53.)

HEp-2 cells are obtained from ATCC (Manassas, VI) and maintained in MEM media supplemented with 10% fetal bovine serum and penicillin/streptomycin. Cells are passaged twice a week and kept at subconfluent stage. Commercial stock of RSV strain A2 (Advanced Biotechnologies, Columbia, MD) is titered before compound testing to determine the appropriate dilution of the virus stock that generates desirable cytopathic effect in HEp-2 cells.

For antiviral tests, HEp-2 cells are grown in large cell culture flasks to near confluency but not fully so. The compounds to be tested are prediluted in DMSO in 384-well compound dilution plates, either in an 8 or 40 sample per plate standardized dose response format. 3-fold serial dilution increments of each test compound are prepared in the plates and test samples are transferred via acoustic transfer apparatus (Echo, Labcyte) at 100 nL per well into cell culture assay 384-well plates. Each compound dilution is transferred in single or quadruplicate samples into dry assay plates, which are stored until assay is ready to go. The positive and negative controls are laid out in opposite on ends of the plate in vertical blocks (1 column).

Subsequently, an infectious mixture is prepared using an appropriate dilution of virus stock previously determined by titration with cells at a density of 50,000/mL and 20 uL/well is added to test plates w/compounds via automation (uFlow, Biotek). Each plate includes negative and positive controls (16 replicates each) to create 0% and 100% virus inhibition standards, respectively. Following the infection with RSV, testing plates are incubated for 4 days in a 37° C. cell culture incubator. After the incubation, a cell viability reagent, Cell TiterGlo (Promega, Madison, WI) is added to the assay plates, which are incubated briefly, and a luminescent readout is measured (Envision, Perkin Elmer) in all the assay plates. The RSV-induced cytopathic effect, percentage inhibition, is determined from the levels of remaining cell viability. These numbers are calculated for each tested concentration relative to the 0% and 100% inhibition controls, and the $EC_{50}$ value for each compound is determined by non-linear regression as a concentration inhibiting the RSV-induced cytopathic effect by 50%. Various potent anti-RSV tool compounds are used as positive controls for antiviral activity.

Example 87. HEp-2 CC50

Cytotoxicity of tested compounds is determined in uninfected HEp-2 cells in parallel with the antiviral activity using the cell viability reagent in a similar fashion as described before for other cell types (Cihlar et al., Antimicrob Agents Chemother. 2008, 52(2):655-65). The same protocol as for the determination of antiviral activity is used for the measurement of compound cytotoxicity except that the cells are not infected with RSV. Instead, an uninfected cell mixture at the same density is added at 20 uL/well to plates containing prediluted compounds, also at 100 nL/sample. Assay plates are then incubated for 4 days followed by a cell viability test using the same CellTiter Glo reagent addition and measurement of luminescent readouts. Untreated cell and cells treated at 2 µM puromycin (Sigma, St. Louis, MO) serve as 100% and 0% cell viability control, respectively. The percent of cell viability is calculated for each tested compound concentration relative to the 0% and 100% controls and the $CC_{50}$ value is determined by non-linear regression as a compound concentration reducing the cell viability by 50%.

Example 88. RSV NHBE EC50

Normal human bronchial epithelial (NHBE) cells were purchased from Lonza (Walkersville, MD, Cat #CC-2540) and cultured in Bronchial Epithelial Growth Media (BEGM) (Lonza, Walkersville, MID, Cat 9 CC-3170). The cells were passaged 1-2 times per week to maintain<80% confluency. The NHBE cells were discarded after 6 passages in culture.

To conduct the RSV A2 antiviral assay, NHBE cells were plated in 96-well plates at a density of 7,500 cells per well in BEGM and allowed to attach overnight at 37° C. Following attachment, 100 µL of cell culture media was removed and 3-fold serially diluted compound was added using a Hewlett-Packard D300 Digital Dispenser. The final concentration of DMSO was normalized to 0.05%. Following compound addition, the NHBE cells were infected by the addition of 100 µL of RSV A2 at a titer of $1\times10^{4.5}$ tissue culture infectious doses/mL in BEGM and then incubated at 37° C. for 4 days. The NHBE cells were then allowed to equilibrate to 25° C. and cell viability was determined by removing 100 µL of culture medium and adding 100 µL of Cell-Titer Glo viability reagent. The mixtures were incubated for 10 minutes at 25° C., and the luminescence signal was quantified on an Envision luminescence plate reader.

TABLE 3

| | Activity Data | | | | | |
|---|---|---|---|---|---|---|
| Example No. | DENV-2 moDC EC50 (nM) | moDC CC50 (nM) | DENV-2 Huh-7 EC50 (nM) | Huh-7 CC50 (nM) | RSV Hep-2 EC50 (nM) | Hep-2 CC50 (nM) |
| Intermediate 5 | | | | | >50000 | >50000 |
| 1 | 117 | >5885.49 | 151 | 18003 | 119 | >50000 |
| Comp. Ex. 1 | | | 2333 | | | |
| 3 | 156 | >11076.8 | 92 | >25000 | 77 | >100000 |
| 4 | 58 | 4776 | 132 | 17783 | 29 | >100000 |
| 5 | | | 381 | 12232 | 575 | >50000 |

TABLE 3-continued

Activity Data

| Example No. | DENV-2 moDC EC50 (nM) | moDC CC50 (nM) | DENV-2 Huh-7 EC50 (nM) | Huh-7 CC50 (nM) | RSV Hep-2 EC50 (nM) | Hep-2 CC50 (nM) |
|---|---|---|---|---|---|---|
| 6 | | | 157 | 7079 | 92 | >50000 |
| 7 | 40 | 6693 | 159 | >25000 | 24 | >100000 |
| 8 | 45 | 6401 | 191 | >25000 | 259 | >50000 |
| 9 | 128 | 4880 | 191 | >25000 | 179 | >50000 |
| 10 | 679 | >19512.1 | 843 | >25000 | 909 | >50000 |
| 11 | 380 | 16092 | 586 | >18791.5 | 2042 | 12641 |
| 12 | 753 | >25000 | 453 | >25000 | 1367 | >100000 |
| 13 | 274 | >10206.4 | 487 | >25000 | 844 | >89407 |
| 14 | 165 | >7759.4 | 205 | >25000 | 187 | >100000 |
| 15 | | | 1626 | >25000 | 1459 | >50000 |
| 16 | 214 | 3804 | 736 | 13441 | 1105 | 32973 |
| 17 | | | 510 | >25000 | 516 | >100000 |
| 18 | 264 | >10465.2 | 384 | >25000 | 1298 | >100000 |
| 19 | 212 | 10913 | 416 | >25000 | 722 | >97053 |
| 20 | | | 2571 | >25000 | 3183 | >100000 |
| 21 | 1039 | >17257.6 | 3063 | >25000 | 1777 | >100000 |
| 22 | 735 | >23603.2 | 1026 | >25000 | 2360 | 71734 |
| 23 | 387 | 10908 | 1803 | >23226.5 | 4317 | 26334 |
| 24 | 257 | 18557 | 1556 | 16005 | 1833 | 16618 |
| 25 | 213 | 12186 | 291 | >25000 | 919 | 69982 |
| 26 | | | >24014.3 | >25000 | 39293 | >100000 |
| 28 | >5000 | >25000 | 1429 | >21902.1 | | |
| 29 | 951 | >16922.7 | 1457 | >20891.5 | 1750 | 21568 |
| 30 | | | | | 4133 | >100000 |
| 31 | | | 951 | >25000 | 1899 | >100000 |
| 32 | | | 2596 | >25000 | 3729 | >100000 |
| 33 | | | 811 | >25000 | 1224 | 43266 |
| 34 | 334 | 7655 | 165 | 6470 | | |
| 35 | | | >25000 | >25000 | 42773 | >100000 |
| 37 | >5000 | >25000 | 2700 | >25000 | | |
| 38 | 422 | 12170 | 2553 | >24563.7 | | |
| 39 | | | | | 2472 | >100000 |
| 40 | 1596 | >25000 | 519 | >25000 | 3435 | >100000 |
| 41 | 814 | >21826.3 | 1458 | >25000 | 1995 | >100000 |
| 42 | 258 | 5330 | 667 | 21054 | 860 | >100000 |
| 43 | 626 | 17947 | 1199 | >25000 | 2155 | >100000 |
| 44 | | | 191 | 17120 | 148 | 26465 |
| 45 | >5000 | >25000 | 4575 | >25000 | 21760 | >100000 |
| 46 | 158 | 3354 | 386 | 10249 | 236 | 37099 |
| 47 | | | 650 | 21429 | 389 | 65855 |
| 48 | | | 390 | 15405 | 215 | 30186 |
| 49 | | | 334 | >25000 | 225 | >100000 |
| 51 | 131 | 4582 | 326 | >25000 | 524 | >100000 |
| 52 | 71 | 7853 | 381 | >15630.9 | | |
| 53 | | | 419 | 19747 | 565 | >100000 |
| 54 | 241 | 3255 | 409 | >25000 | 180 | >100000 |
| 55 | 103 | 4185 | 611 | >25000 | 150 | >100000 |
| 57 | 393 | 4121 | 626 | >25000 | | |
| 58 | 124 | 2038 | 499 | >20310.5 | | |
| 59 | 62 | 7039 | 153 | 11337 | 298 | 45067 |
| 60 | | | 1208 | >24810 | 1105 | 36218 |
| 61 | | | 568 | 15027 | 855 | 19095 |
| 62 | | | 662 | 8085 | 10097 | 16781 |
| 63 | 321 | 5600 | 602 | 10677 | 2424 | 19101 |
| 64 | | | 1995 | >25000 | | |
| 66 | | | 802 | >25000 | 1413 | 16778 |
| 67 | | | 947 | >25000 | 2999 | 17426 |
| 68 | 169 | 6257 | 278 | >25000 | 141 | >100000 |
| 69 | | | >25000 | >25000 | >50000 | >50000 |
| 70 | 190 | 3567 | 245 | 10615 | 212 | 69409 |
| 71 | 143 | 8798 | 298 | 13017 | 290 | >100000 |
| 72 | | | 12374 | >25000 | 15627 | >50000 |
| 73 | | | 302 | 9337 | | |
| 75 | | | 175 | | | |

TABLE 4

| | Activity Data | |
|---|---|---|
| Example No. | RSV NHBE EC50 (nM) | DENV Pol IC50 (nM) |
| Intermediate 5 | >4832.18 | |
| 1 | 595 | |
| Comp. Ex. 2 | | 7093 |
| 2 | | 737 |
| 10 | 2108 | |
| 11 | 367 | |

Comparative Example 1. 2-ethylbutyl ((((2R,3S,4R,5S)-5-(4-aminopyrrolo[2,1-f][1,2,4]triazin-7-yl)-2-(chloromethyl)-3,4-dihydroxytetrahydrofuran-2-yl)methoxy)(phenoxy)phosphoryl)-L-alaninate

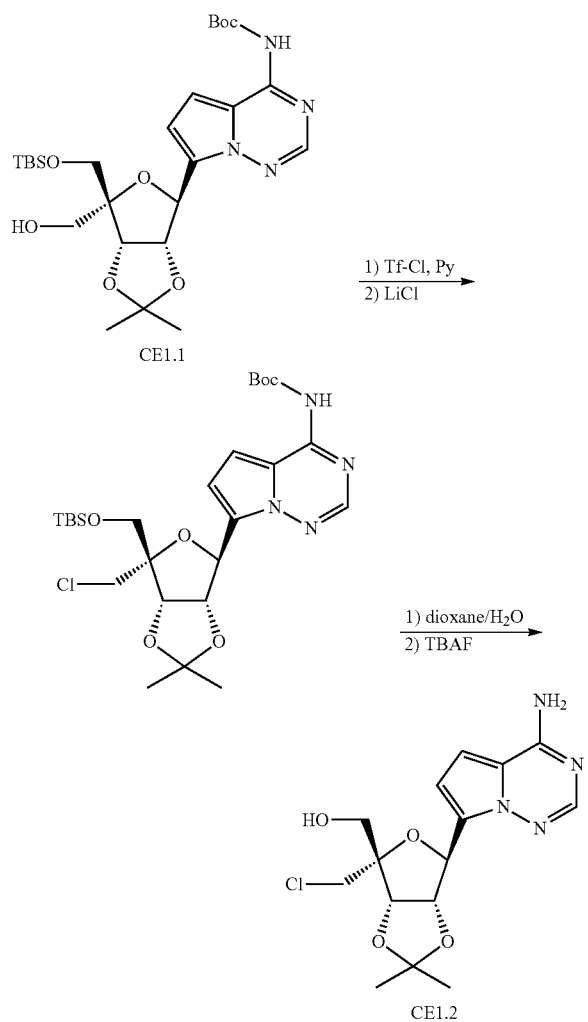

((3aS,4R,6S,6aS)-6-(4-aminopyrrolo[2,1-f][1,2,4]triazin-7-yl)-4-(chloromethyl)-2,2-dimethyltetrahydrofuro[3,4-d][1,3]dioxol-4-yl)methanol. CE1.1 (Intermediate 14j from WO 2015/069939; 200 mg, 0.363 mmol) was dissolved in 5 mL of anhydrous pyridine. Trifluoromethane sulfonyl chloride (58 uL, 0.545 mmol) was added in one portion and stirred for 60 mins. More Trifluoromethane sulfonyl chloride (58 uL, 0.545 mmol) was added and stirred for 30 mins. Trifluoromethane sulfonyl chloride (100 uL) was added and stirred for 30 mins. Reaction was concentrated under reduced pressure. Residue was dissolved in 5 mL anhydrous DMF, and lithium chloride (308 mg, 7.26 mmol) was added in one portion. Reaction was stirred for 16 hrs.

Reaction was diluted with EtOAc (15 mL) and washed with brine (3×10 mL). Organic extract was dried over anhydrous sodium sulfate and concentrated under reduced pressure. The crude residue was purified via SiO$_2$ column chromatography (12 g SiO$_2$ Combiflash HP Gold Column, 0-20% ethyl acetate/hexanes). Fractions were combined and concentrated under reduced pressure. Residue was dissolved in dioxane (8 mL) and water (2 mL) and stirred at 120° C. for 2 hrs. Reaction was concentrated under reduced pressure.

Residue was dissolved in THF (5 mL). Tetrabutylammonium fluoride trihydrate (97 mg, 0.307 mmol) was added, and the reaction was stirred for 1 hr. Reaction was diluted with EtOAc (15 mL) and washed with brine (5×5 mL). Organic extract was dried over anhydrous sodium sulfate and concentrated under reduced pressure. The crude residue was purified via SiO$_2$ column chromatography (4 g SiO$_2$ Combiflash HP Gold Column, 0-100% ethyl acetate/hexanes). Fractions were combined and concentrated under reduced pressure to afford the intermediate CE1.2. $^1$H NMR (400 MHz, chloroform-d) δ 7.87 (s, 1H), 6.65 (d, J=4.5 Hz, 1H), 6.54 (d, J=4.5 Hz, 1H), 6.12 (bs, 2H), 5.33 (dd, J=6.9, 5.9 Hz, 1H), 5.14 (d, J=6.9 Hz, 1H), 5.05 (d, J=5.9 Hz, 1H), 3.98-3.71 (m, 4H), 1.63 (s, 3H), 1.36 (s, 3H). LCMS: MS m/z=355.3 [M+1], 353.4 [M−1], t$_R$=1.04 min; LC system: Thermo Dionex Ultimate 3000 UHPLC; Column: Phenomenex Kinetex 2.6 μC18 100A, 50×3 mm; Solvents: A: Water with 0.1% acetic acid, B: Acetonitrile with 0.1% acetic acid; Gradient: 0 min-0.3 min 5% B, 0.3 min-1.5 min 5-100% B, 1.5 min-2 min 100% B, 2 min-2.2 min 100-5% B at 2 mL/min. HPLC: t$_R$=2.15 min; HPLC system: Agilent 1100 series; Column: Phenomenex Gemini 5 μC18 110A, 50×4.6 mm; Solvent: A: Water with 0.1% TFA, B: Acetonitrile with 0.1% TFA; Gradient: 2-98% B in 5 min at 2 mL/min.

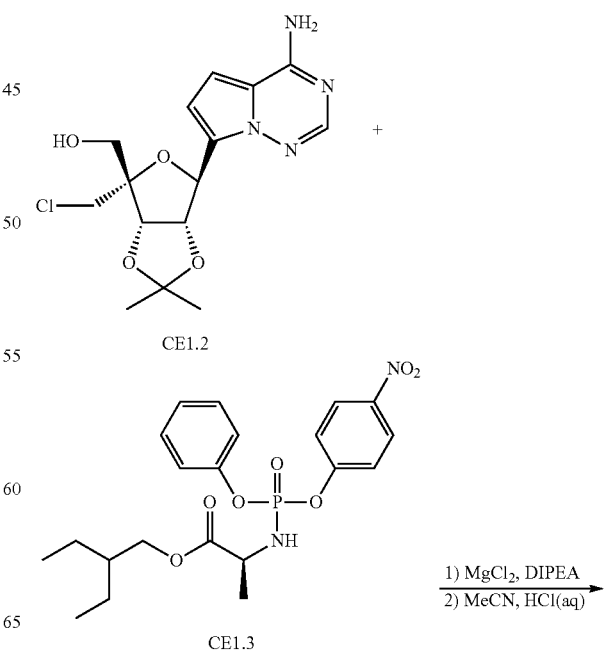

-continued

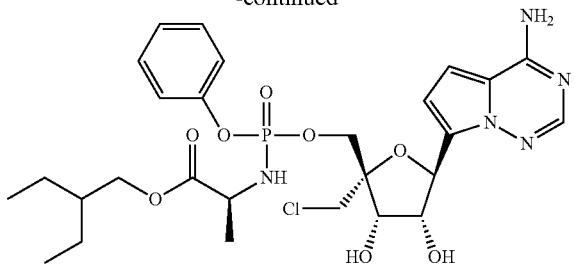

2-ethylbutyl ((((2R,3S,4R,5S)-5-(4-aminopyrrolo[2,1-f][1,2,4]triazin-7-yl)-2-(chloromethyl)-3,4-dihydroxytetrahydrofuran-2-yl)methoxy) (phenoxy)phosphoryl)-L-alaninate. CE1.2 (47 mg, 0.132 mmol) and CE1.3 (72 mg, 0.159 mmol) were mixed and dissolved in 2 mL of anhydrous THF. Magnesium chloride (38 mg, 0.396 mmol) was added in one portion. DIPEA (57 uL, 0.33 mmol) was added, and the reaction was stirred at 40° C. for 16 hrs. Reaction was diluted with EtOAc (15 mL) and washed with water (5×10 mL) and then with brine (5 mL). Organic extract was dried over anhydrous sodium sulfate and concentrated under reduced pressure. Residue was dissolved in MeCN (5 mL) and stirred in an ice bath. Concentrate aqueous hydrochloric acid (250 uL) was added dropwise. Reaction was stirred in an ice bath for 2 hrs. 1 M triethylammonium bicarbonate solution was added to the reaction to give pH of 8, and the reaction was then concentrated under reduced pressure. Crude residue was purified with prep HPLC under neutral condition (5-100% MeCN/water). Fractions were combined and concentrated under reduced pressure. Residue was dissolved in MeCN and water and freeze-dried to afford the product. $^1$H NMR (400 MHz, methanol-$d_4$) δ 7.77 (m, 1H), 7.39-7.09 (m, 5H), 6.84 (m, 1H), 6.74 (m, 1H), 5.36 (m, 1H), 4.72 (m, 1H), 4.41-4.23 (m, 3H), 4.07-3.84 (m, 5H), 1.53-1.40 (m, 1H), 1.38-1.25 (m, 7H), 0.89-0.81 (m, 6H). $^{31}$P NMR (162 MHz, methanol-$d_4$) δ 3.46, 3.59. LCMS: MS m/z=626.2 [M+1], 624.6 [M−1], $t_R$=1.30 min; LC system: Thermo Dionex Ultimate 3000 UHPLC; Column: Phenomenex Kinetex 2.6 μC18 100A, 50×3 mm; Solvents: A: Water with 0.1% acetic acid, B: Acetonitrile with 0.1% acetic acid; Gradient: 0 min-0.3 min 5% B, 0.3 min-1.5 min 5-100% B, 1.5 min-2 min 100% B, 2 min-2.2 min 100-5% B at 2 mL/min. HPLC: $t_R$=3.14 min; HPLC system: Agilent 1100 series; Column: Phenomenex Gemini 5 μC18 110A, 50×4.6 mm; Solvent: A: Water with 0.1% TFA, B: Acetonitrile with 0.1% TFA; Gradient: 2-98% B in 5 min at 2 mL/min. HPLC: $t_R$=5.247, 5.327 min; HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Comparative Example 2. ((2R,3S,4R,5S)-5-(4-aminopyrrolo[2,1-f][1,2,4]triazin-7-yl)-2-(chloromethyl)-3,4-dihydroxytetrahydrofuran-2-yl)methyl tetrahydrogen triphosphate

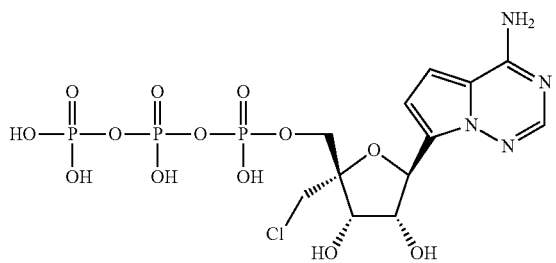 [SMILES: Nc1ncnn2c([C@@H]3O[C@](CCl)(COP(=O)(O)OP(=O)(O)OP(=O)(O)O)[C@@H](O)[C@H]3O)ccc12]

See compound TP13 (Example 33) in WO 2015/069939.

Although the foregoing invention has been described in some detail by way of illustrations and Examples for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound of Formula (I):

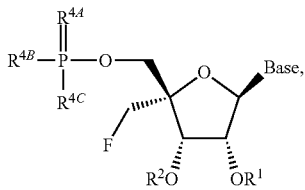

Formula (I)

or a pharmaceutically acceptable salt thereof, wherein:
Base is

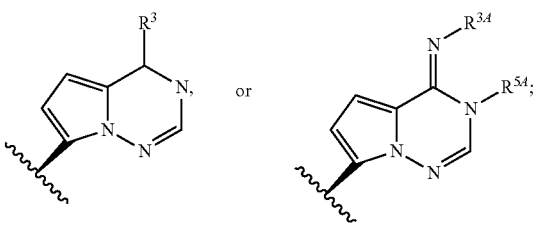

$R^1$ and $R^2$ are each independently H or —C(O)$R^{1A}$, wherein $R^{1A}$ is $C_{1-6}$ alkyl;
$R^3$ is —N(H)$R^{3A}$;
$R^{3A}$ is H, —CH$_2$OP(O)(OH)$_2$, or —C(O)$R^{3D}$, wherein $R^{3D}$ is $C_{6-12}$ aryl or $C_{1-6}$ alkyl optionally substituted with a $C_{3-6}$ cycloalkyl;
$R^{4A}$ is O;
$R^{4B}$ and $R^{4C}$ are each independently:
(A) —OH;
(B) —OR$^{4B1}$, wherein $R^{4B1}$ is $C_{6-12}$ aryl;
(C)

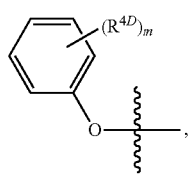

wherein
subscript m is 0, 1, 2, 3, 4, or 5; and
each $R^{4D}$ is independently $C_{1-6}$ alkyl;
(D)

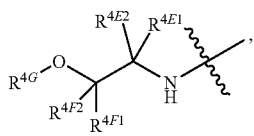

wherein
$R^{4E1}$ and $R^{4E2}$ are each independently H or $C_{1-6}$ alkyl;
$R^{4F1}$ and $R^{4F2}$ together are oxo;
$R^{4G}$ is $C_{1-8}$ alkyl optionally substituted with 1 to 3 $R^{4G1}$, $C_{3-8}$ cycloalkyl, or a 3 to 8 membered heterocyclyl having 1 to 3 heteroatoms selected from N, O and S, optionally substituted with 1 to 3 $R^{4G3}$;
each $R^{4G1}$ is independently —OH, $C_{1-6}$ alkoxy, —(CH$_2$OCH$_2$)$_{1-5}$—CH$_3$, $C_{1-3}$ haloalkyl, or $C_{3-8}$ cycloalkyl optionally substituted with 1 to 3 $R^{4G9}$;
each $R^{4G3}$ and $R^{4G9}$ is independently $C_{1-6}$ alkyl; or
(E) —(OP(O)(OH))$_{1-2}$—OH; and
$R^{5A}$ is $C_{1-6}$ alkyl substituted with —OP(O)(OH)$_2$.

2. The compound of claim 1, or a pharmaceutically acceptable salt thereof, wherein $R^1$ and $R^2$ are each H.

3. The compound of claim 1, or a pharmaceutically acceptable salt thereof, wherein $R^1$ and $R^2$ are each —C(O)$R^{1A}$; and
$R^{1A}$ is methyl, ethyl, n-propyl, iso-propyl, n-butyl, iso-butyl, sec-butyl or t-butyl.

4. The compound of claim 1, or a pharmaceutically acceptable salt thereof, wherein
$R^1$ and $R^2$ are each —C(O)$R^{1A}$; and
$R^{1A}$ is methyl, ethyl, or iso-propyl.

5. The compound of claim 1, or a pharmaceutically acceptable salt thereof, having the formula:

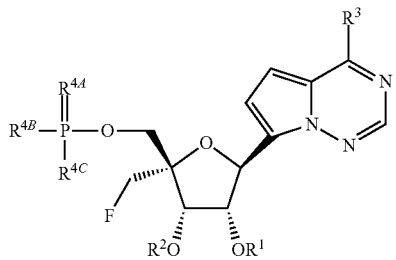

wherein
$R^3$ is —N(H)$R^{3A}$;
$R^{3A}$ is H or —C(O)$R^{3D}$; and
$R^{3D}$ is phenyl or $C_{1-3}$ alkyl optionally substituted with a $C_{3-6}$ cycloalkyl.

6. The compound of claim 1, or a pharmaceutically acceptable salt thereof, wherein
$R^3$ is —NH$_2$.

7. The compound of claim 1, or a pharmaceutically acceptable salt thereof, wherein
$R^{4B}$ and $R^{4C}$ are each independently:
(A) —OH;
(B) —OR$^{4B1}$, wherein $R^{4B1}$ is naphthyl;

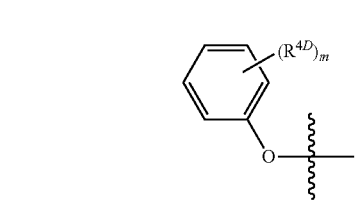

(C), wherein
subscript m is 0 or 1; and
$R^{4D}$ is $C_{1-6}$ alkyl;

(D)

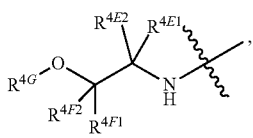

wherein $R^{4E1}$ is $C_{1-3}$ alkyl;

$R^{4E2}$ is H;

$R^{4F1}$ and $R^{4F2}$ together are oxo;

$R^{4G}$ is $C_{1-8}$ alkyl optionally substituted with 1 $R^{4G1}$, $C_{4-6}$ cycloalkyl, or a 4 to 6 membered heterocyclyl having 1 heteroatom selected from N and O, optionally substituted with 1 $R^{4G3}$;

each $R^{4G1}$ is independently —OH, $C_{1-4}$ alkoxy, —(CH$_2$OCH$_2$)$_{1-2}$-CH$_3$, $C_{1-3}$ haloalkyl, or $C_{3-6}$ cycloalkyl optionally substituted with 1 $R^{4G9}$;

each $R^{4G3}$ and $R^{4G9}$ is independently $C_{1-3}$ alkyl; or (E) —(OP(O)(OH))$_{1-2}$—OH.

8. The compound of claim 1, or a pharmaceutically acceptable salt thereof, wherein $R^{4B}$ is:

(B) —OR$^{4B1}$, wherein R$^{4B1}$ is naphthyl; or (C)

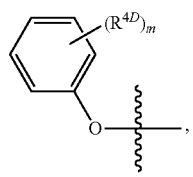

wherein subscript m is 0 or 1; and $R^{4D}$ is t-butyl; or (E) —(OP(O)(OH))$_{1-2}$—OH.

9. The compound of claim 1, or a pharmaceutically acceptable salt thereof, wherein $R^{4C}$ is:

(A) —OH; or (D)

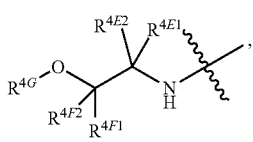

wherein $R^{4E1}$ is methyl;

$R^{4E2}$ is H;

$R^{4F1}$ and $R^{4F2}$ together are oxo; and $R^{4G}$ is methyl, ethyl, n-propyl, iso-propyl, n-butyl, iso-butyl, sec-butyl, tert-butyl, n-pentyl, neopentyl, n-hexane, 2,2-dimethyl-butyl, 3,3-dimethyl-butyl, 2-ethyl-butyl, or 2-n-propyl-pentyl, each optionally substituted with OH, methoxy, ethoxy, propoxy, butoxy, CF$_3$, Me(CH$_2$OCH$_2$)$_2$—, cyclopropyl or 1-methylcyclopropyl, cyclobutyl, cyclopentyl, or cyclohexyl, pyrrolidinyl, oxetanyl, or tetrahydropyranyl, each optionally substituted with methyl, ethyl, n-propyl or iso-propyl.

10. The compound of claim 1, or a pharmaceutically acceptable salt thereof, wherein $R^{5A}$ is —CH$_2$OP(O)(OH)$_2$.

11. The compound of claim 1, or a pharmaceutically acceptable salt thereof, having the Formula (Ib):

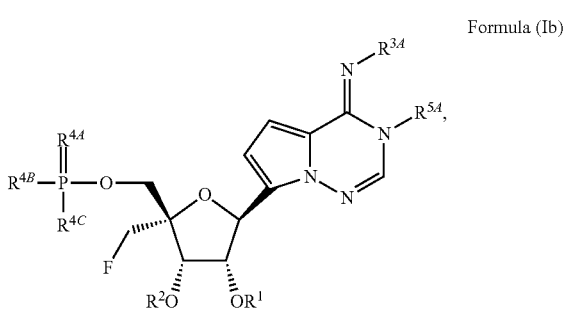

Formula (Ib)

wherein $R^{3A}$ is H; and $R^{5A}$ is —CH$_2$OP(O)(OH)$_2$.

12. The compound of claim 1, or a pharmaceutically acceptable salt thereof, having the Formula (Id):

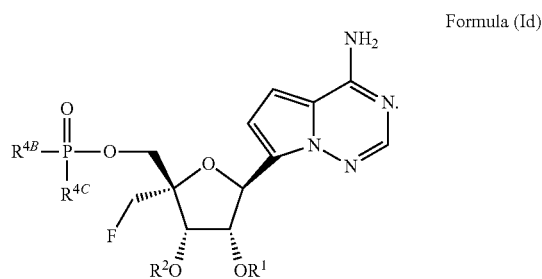

Formula (Id)

13. The compound of claim 1, or a pharmaceutically acceptable salt thereof, having the Formula (Ie):

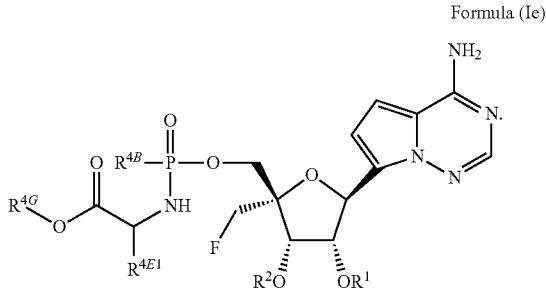

Formula (Ie)

14. The compound of claim 1, or a pharmaceutically acceptable salt thereof, having the Formula (If):

Formula (If)

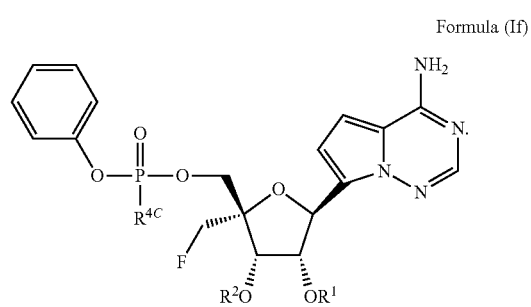

15. The compound of claim 1, or a pharmaceutically acceptable salt thereof, having the Formula (Ig):

Formula (Ig)

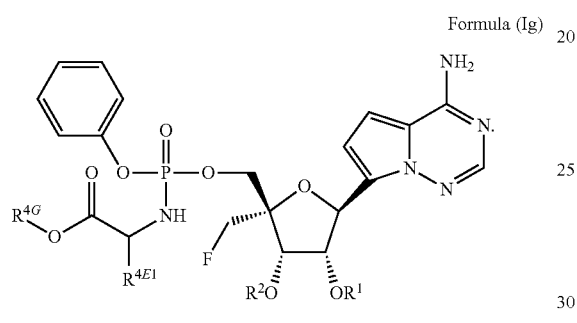

16. The compound of claim 1, or a pharmaceutically acceptable salt thereof, having the Formula (Ih):

Formula (Ih)

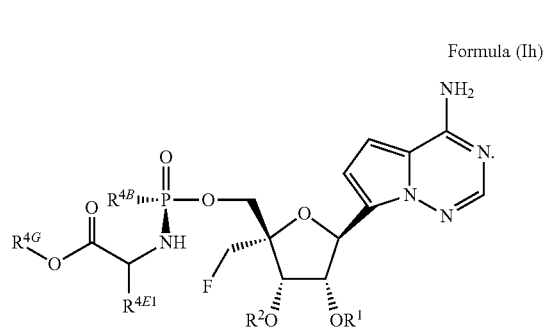

17. The compound of claim 1, or a pharmaceutically acceptable salt thereof, having the Formula (Ij):

Formula (Ij)

18. The compound of claim 1, or a pharmaceutically acceptable salt thereof, having the Formula (Ik):

Formula (Ik)

19. The compound of claim 1, or a pharmaceutically acceptable salt thereof, having the Formula (Im):

Formula (Im)

20. The compound of claim 1, or a pharmaceutically acceptable salt thereof, wherein $R^{4C}$ is:

21. The compound of claim 1, or a pharmaceutically acceptable salt thereof, wherein $R^{4C}$ is:

22. The compound of claim 1, or a pharmaceutically acceptable salt thereof, wherein
 $R^{4G}$ is
  methyl, ethyl, n-propyl, iso-propyl, n-butyl, iso-butyl, sec-butyl, tert-butyl, n-pentyl, neopentyl, n-hexane, 2,2-dimethyl-butyl, 3,3-dimethyl-butyl, 2-ethyl-butyl, or 2-n-propyl-pentyl, each optionally substituted with OH, methoxy, ethoxy, propoxy, butoxy, $CF_3$, $Me(CH_2OCH_2)_2$—, cyclopropyl or 1-methyl-cyclopropyl,
  cyclobutyl, cyclopentyl, or cyclohexyl,
  pyrrolidinyl, oxetanyl, or tetrahydropyranyl, each optionally substituted with methyl, ethyl, n-propyl or iso-propyl.

23. The compound of claim 1, or a pharmaceutically acceptable salt thereof, wherein
$R^{4G}$ is
methyl optionally substituted with Me(CH$_2$OCH$_2$)$_2$—, cyclopropyl or 1-methylcyclopropyl,
ethyl optionally substituted with butoxy,
n-propyl optionally substituted with methoxy,
iso-propyl, n-butyl,
iso-butyl optionally substituted with OH, methoxy or CF$_3$,
n-pentyl, neopentyl, n-hexane, 2,2-dimethyl-butyl, 3,3-dimethyl-butyl, 2-ethyl-butyl, 2-n-propyl-pentyl,
cyclobutyl, cyclohexyl,
N-methyl-pyrrolidinyl, oxetanyl, or tetrahydropyranyl.

24. The compound of claim 1, or a pharmaceutically acceptable salt thereof, wherein
$R^1$ and $R^2$ are both H or —C(O)R$^{1A}$, wherein R$^{1A}$ is methyl, ethyl or iso-propyl;
$R^3$ is —NH$_2$;
$R^{4B}$ is:
OPh; and
$R^{4C}$ is:

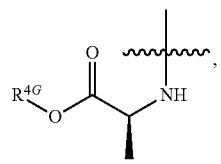

wherein
$R^{4G}$ is
methyl, ethyl, n-propyl, iso-propyl, n-butyl, iso-butyl, sec-butyl, tert-butyl, n-pentyl, neopentyl, n-hexane, 2,2-dimethyl-butyl, 3,3-dimethyl-butyl, 2-ethyl-butyl, or 2-n-propyl-pentyl, each optionally substituted with OH, methoxy, ethoxy, propoxy, butoxy, CF$_3$, Me(CH$_2$OCH$_2$)$_2$—, cyclopropyl or 1-methylcyclopropyl,
cyclobutyl, cyclopentyl, or cyclohexyl,
pyrrolidinyl, oxetanyl, or tetrahydropyranyl, each optionally substituted with methyl, ethyl, n-propyl or iso-propyl.

25. The compound of claim 1, or a pharmaceutically acceptable salt thereof, having Formula (In):

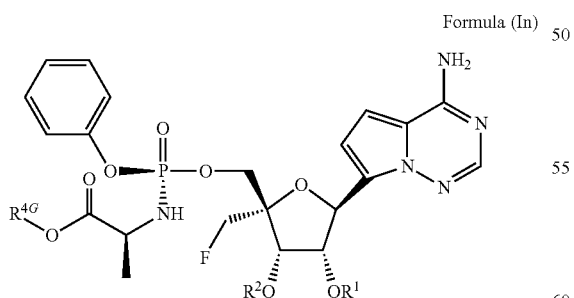

Formula (In)

wherein
$R^1$ and $R^2$ are both H or —C(O)R$^{1A}$, wherein R$^{1A}$ is methyl, ethyl or iso-propyl; and
$R^{4G}$ is
methyl, ethyl, n-propyl, iso-propyl, n-butyl, iso-butyl, sec-butyl, tert-butyl, n-pentyl, neopentyl, n-hexane, 2,2-dimethyl-butyl, 3,3-dimethyl-butyl, 2-ethyl-butyl, or 2-n-propyl-pentyl, each optionally substituted with OH, methoxy, ethoxy, propoxy, butoxy, CF$_3$, Me(CH$_2$OCH$_2$)$_2$—, cyclopropyl or 1-methylcyclopropyl,
cyclobutyl, cyclopentyl, or cyclohexyl,
pyrrolidinyl, oxetanyl, or tetrahydropyranyl, each optionally substituted with methyl, ethyl, n-propyl or iso-propyl.

26. The compound of claim 1, or a pharmaceutically acceptable salt thereof, selected from the group consisting of

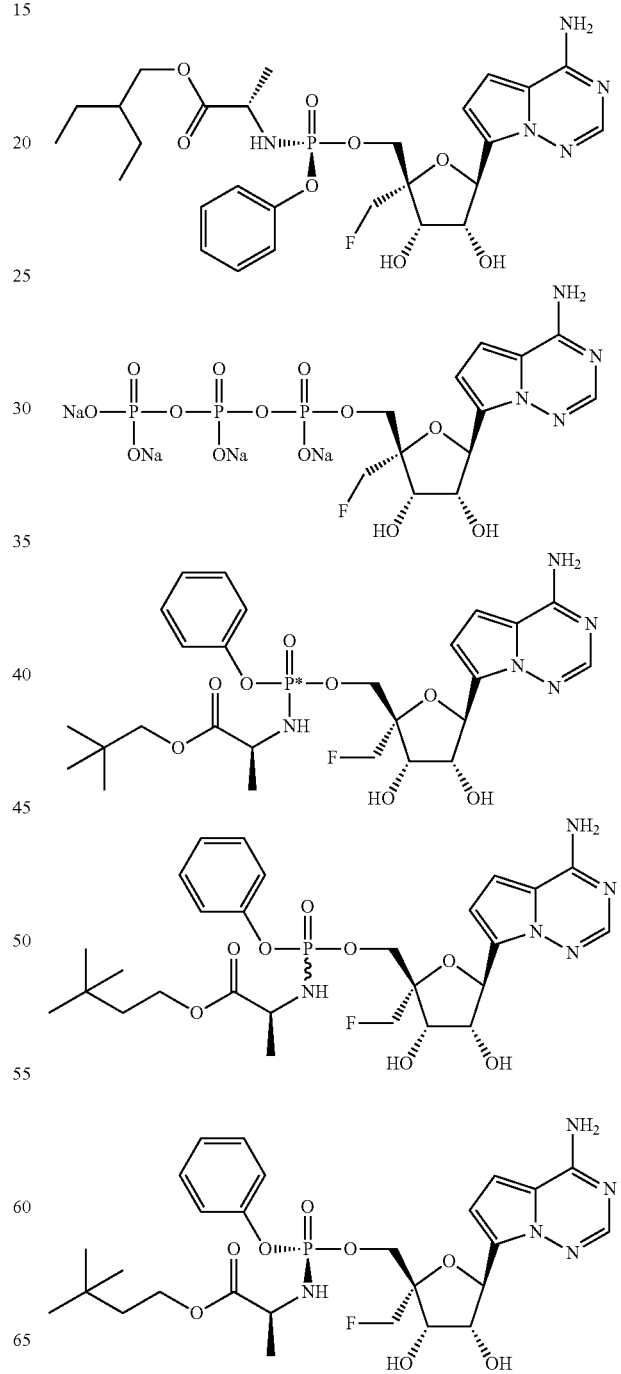

217
-continued
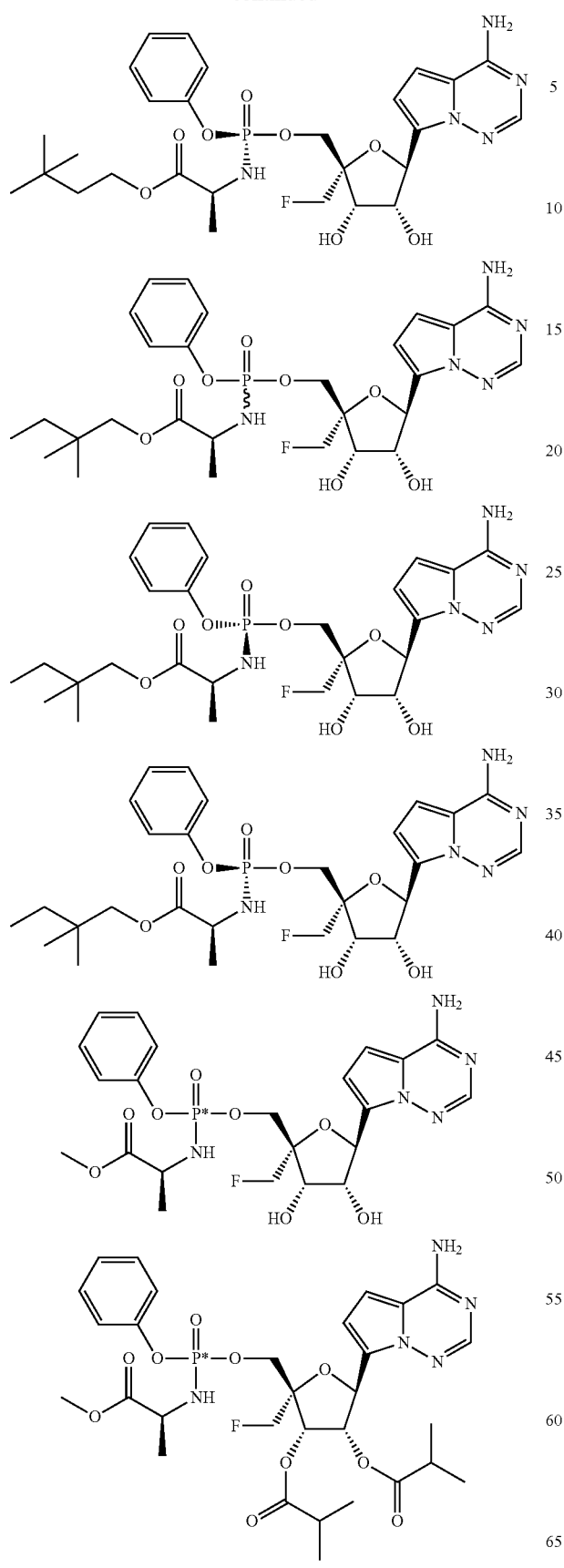
218
-continued
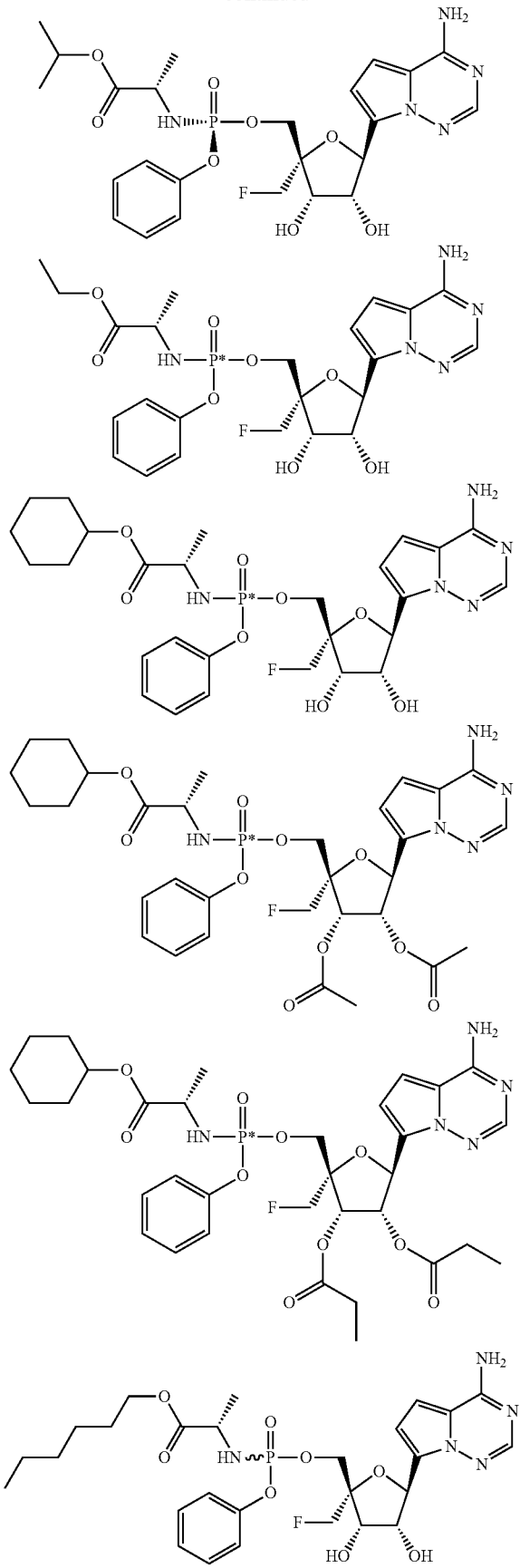

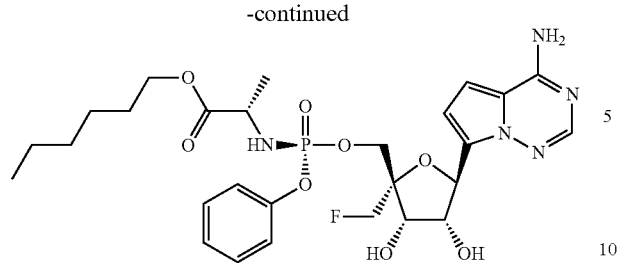
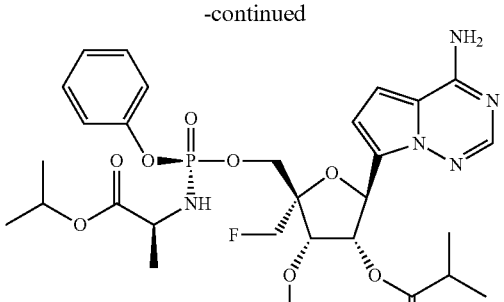

221
-continued
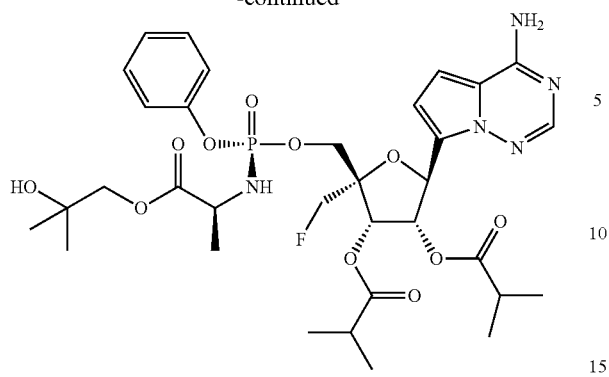
222
-continued
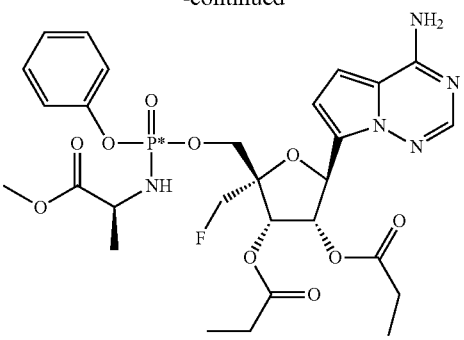
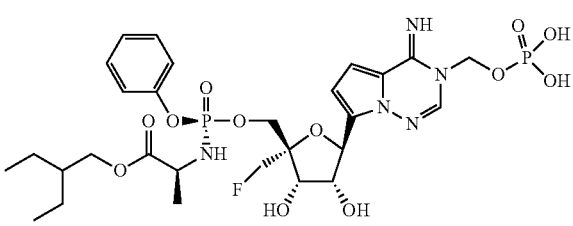
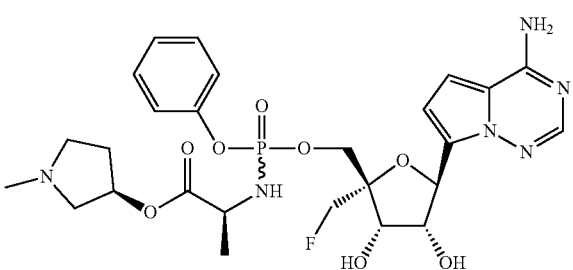
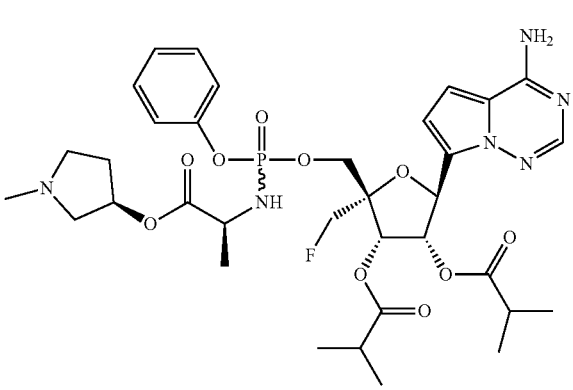
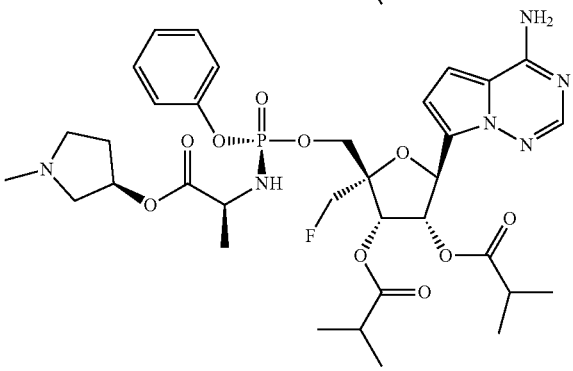

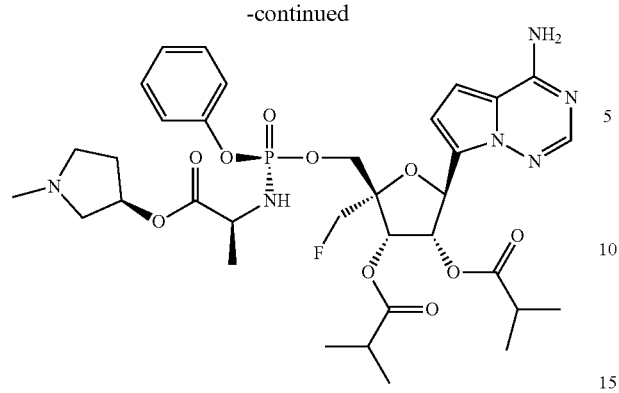
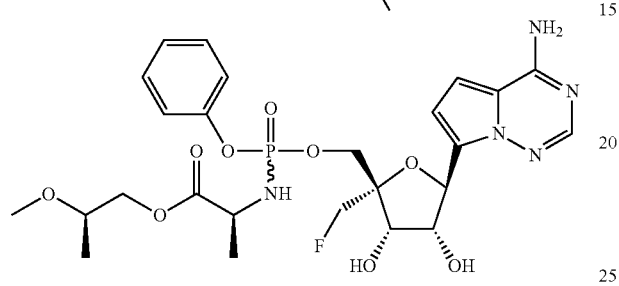
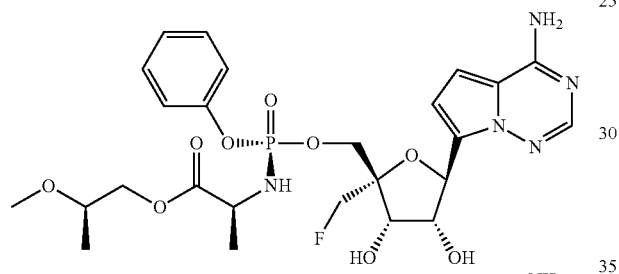
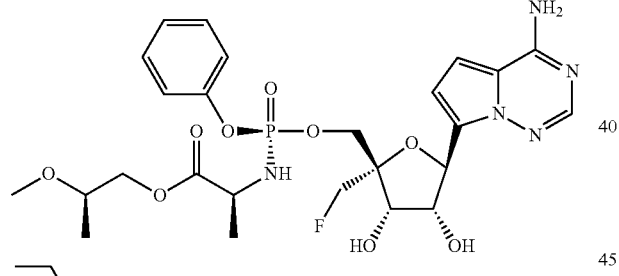
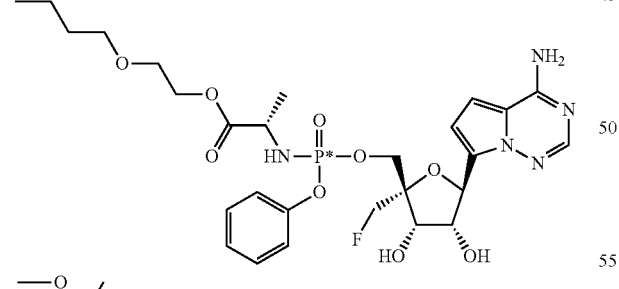
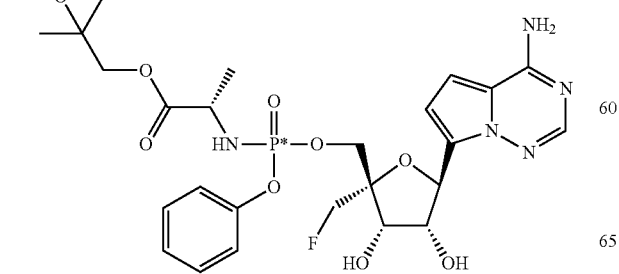
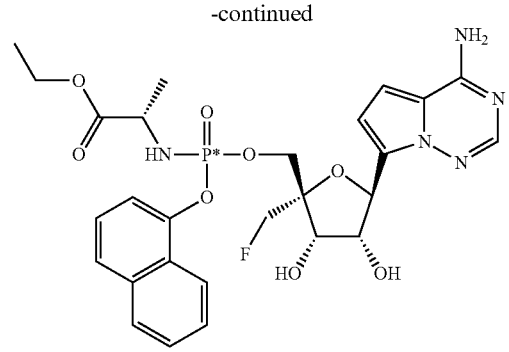
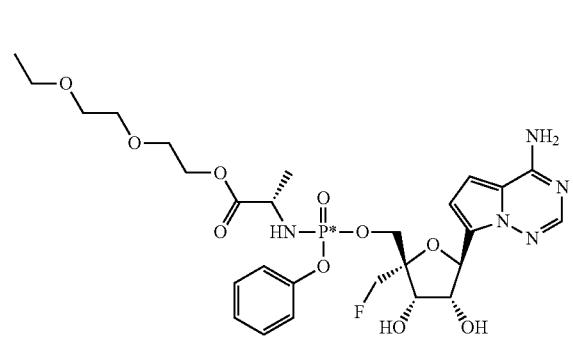
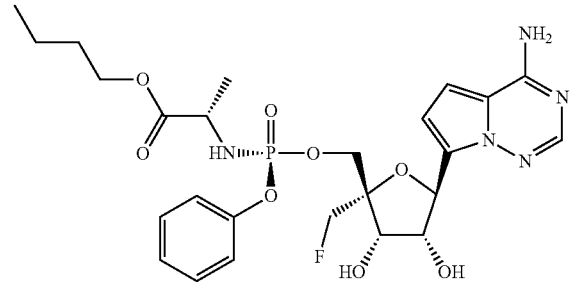
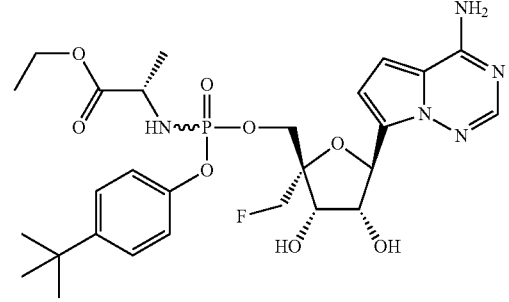
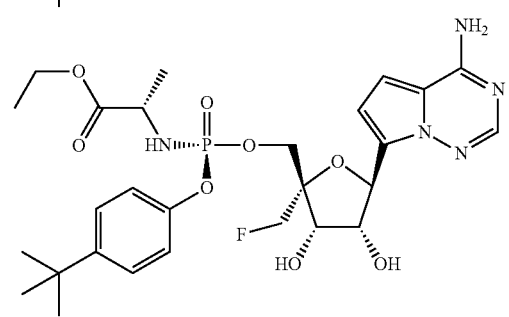

225
-continued
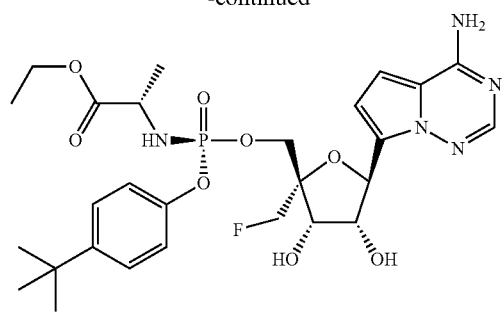
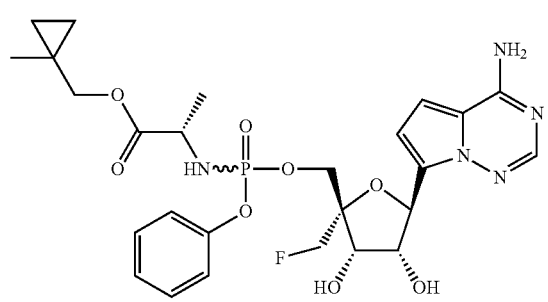
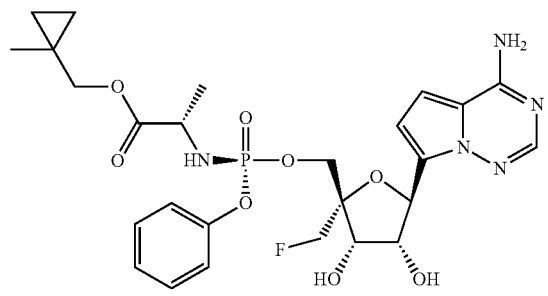
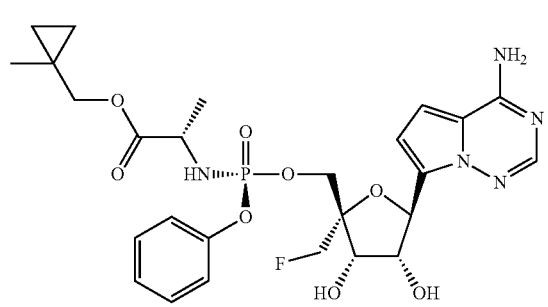
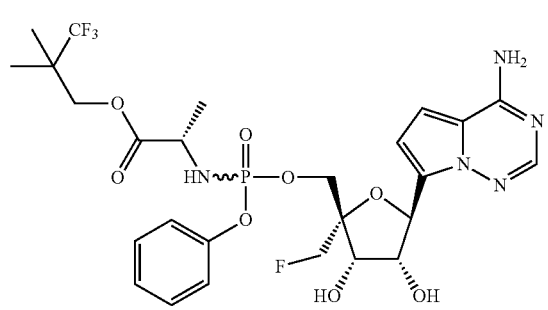
226
-continued
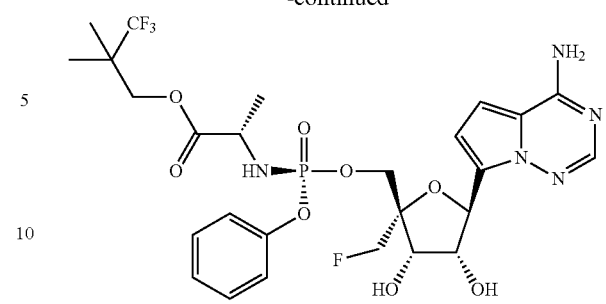
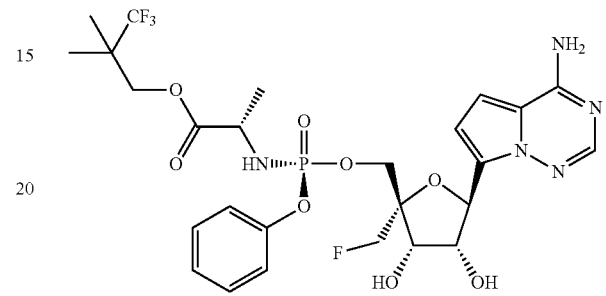
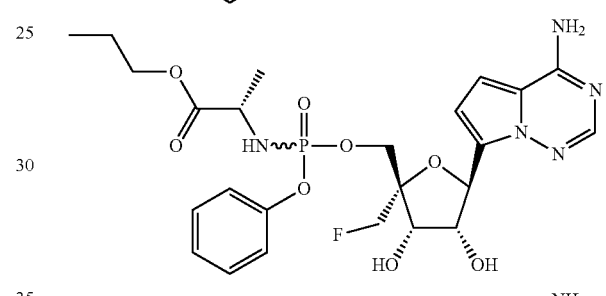
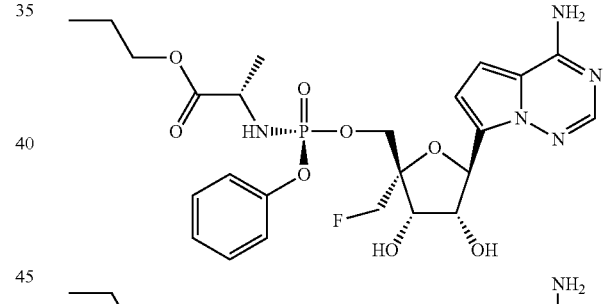
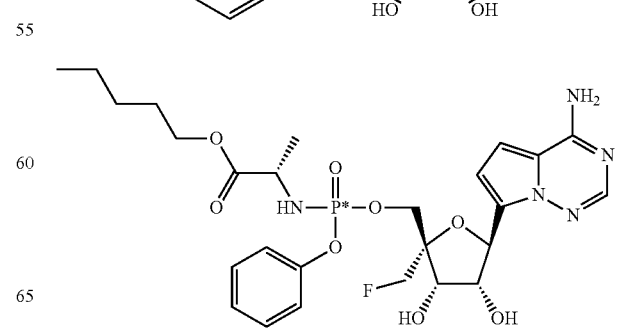

227
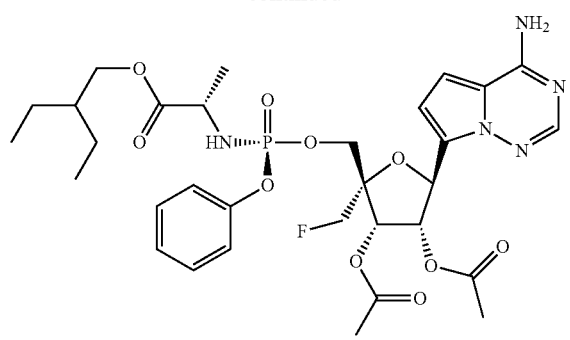
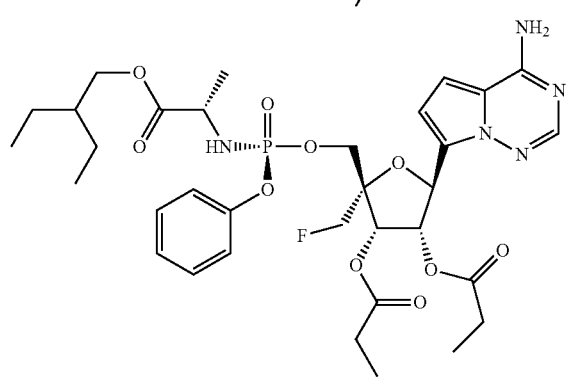
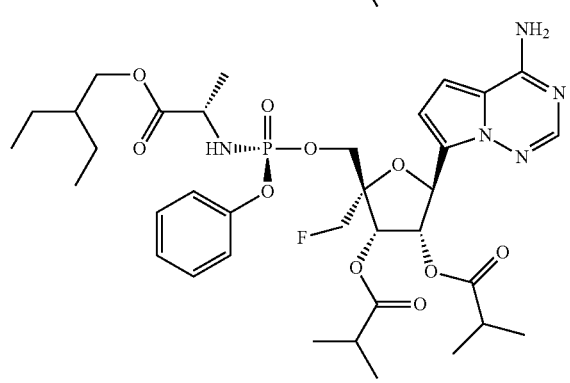
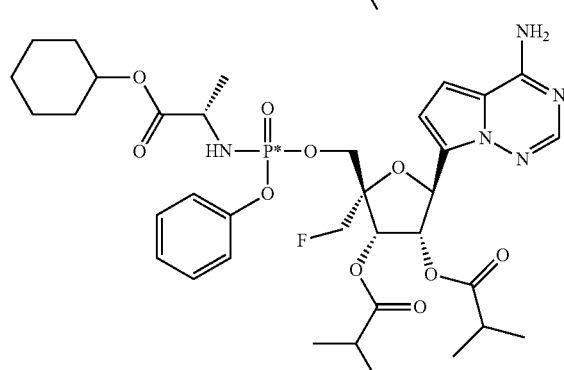
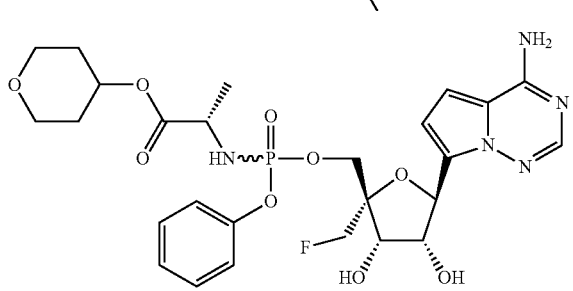
228
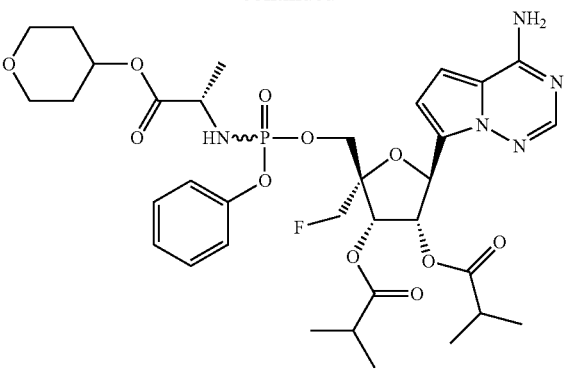
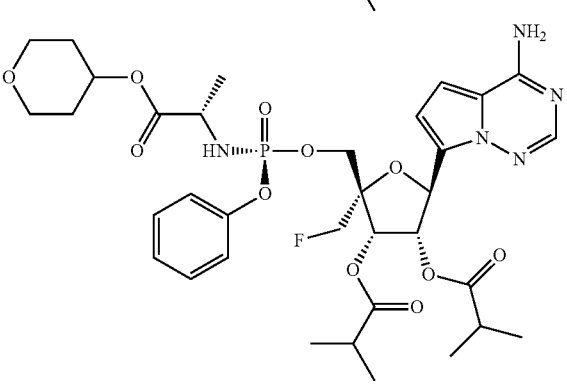
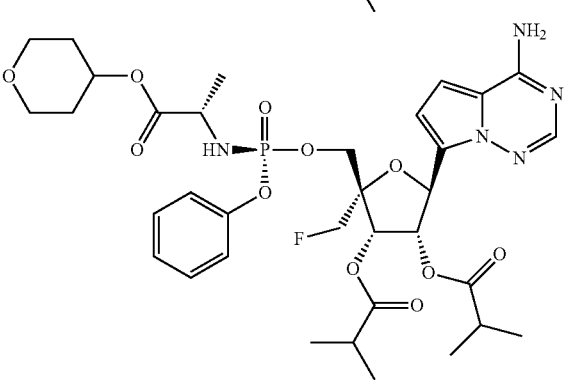
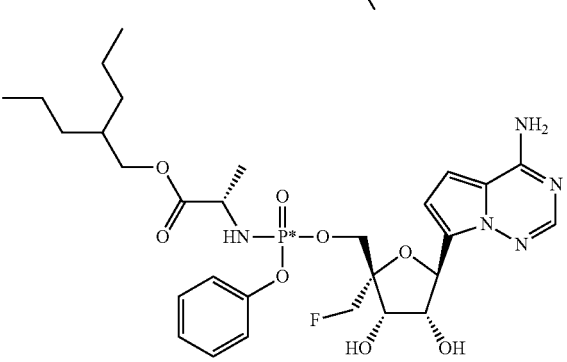
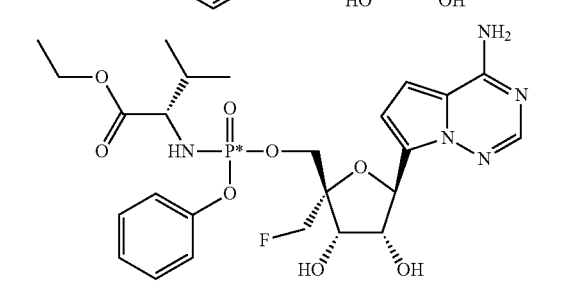

229
-continued
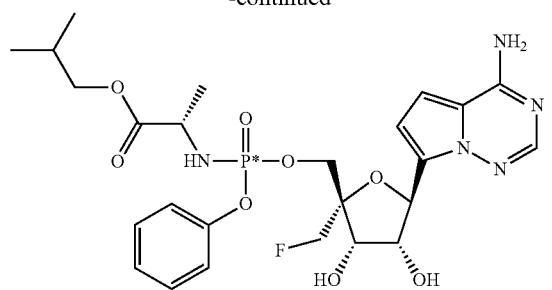
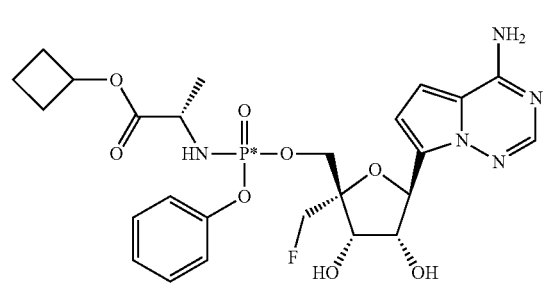
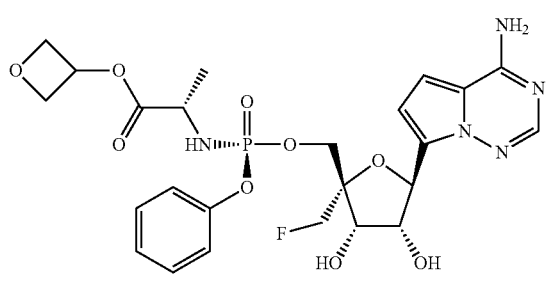
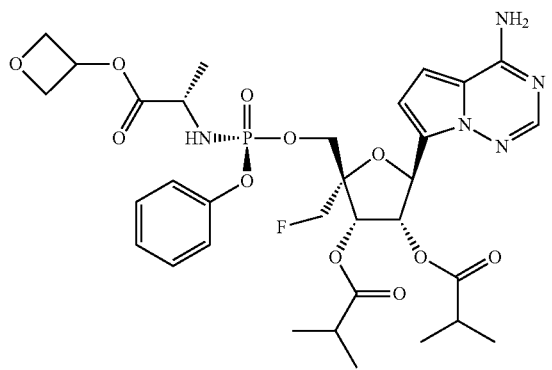
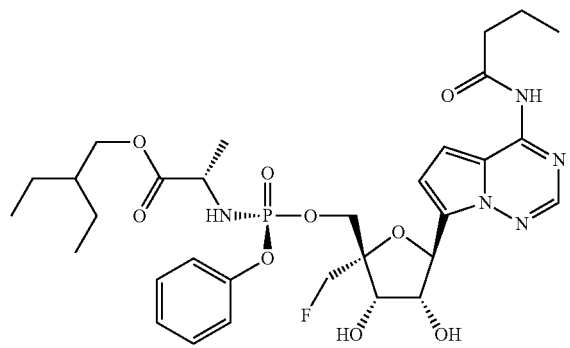
230
-continued
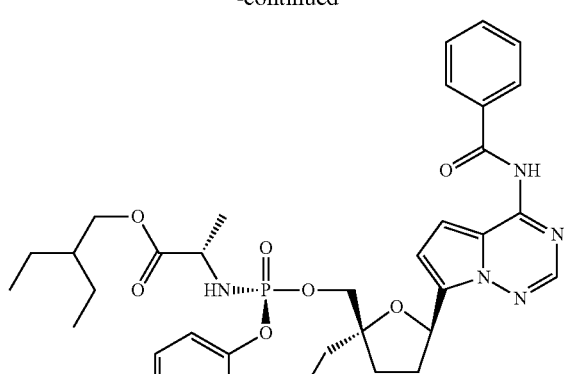
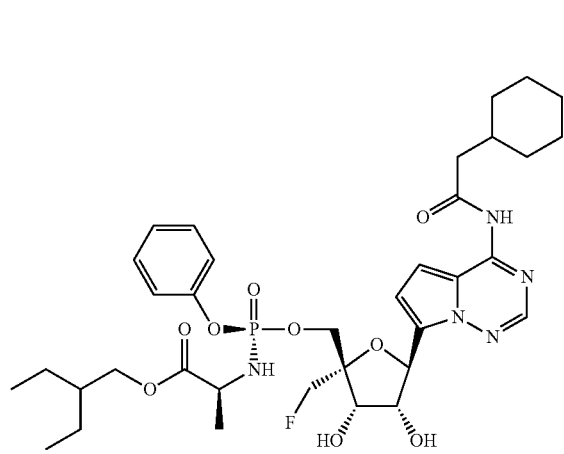
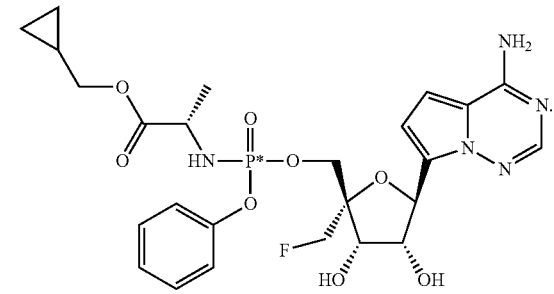
27. The compound of claim 1, or a pharmaceutically acceptable salt thereof, wherein the compound is:
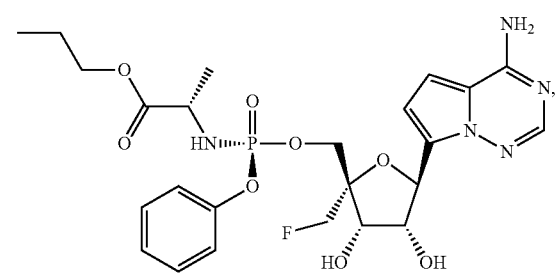

231
-continued
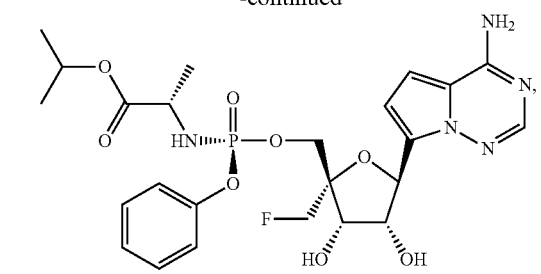
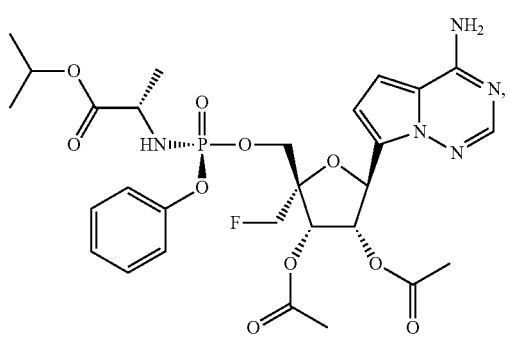
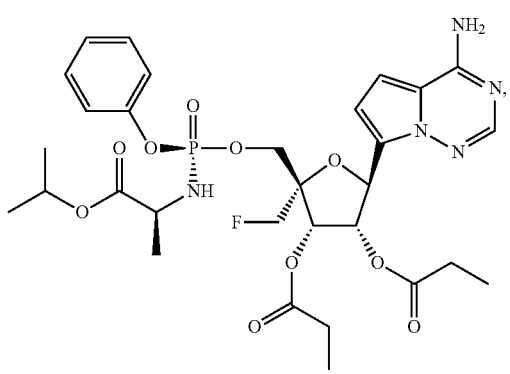
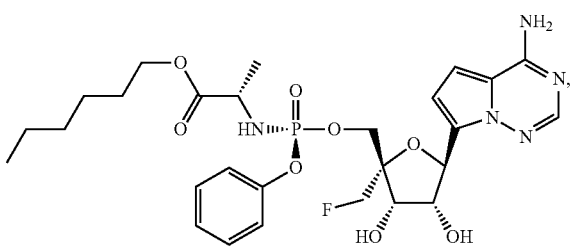
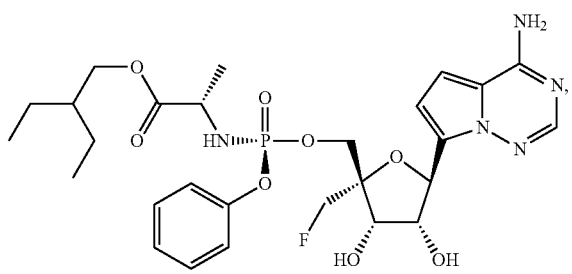
232
-continued
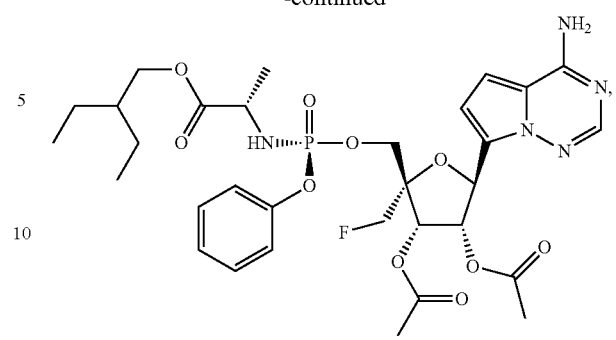
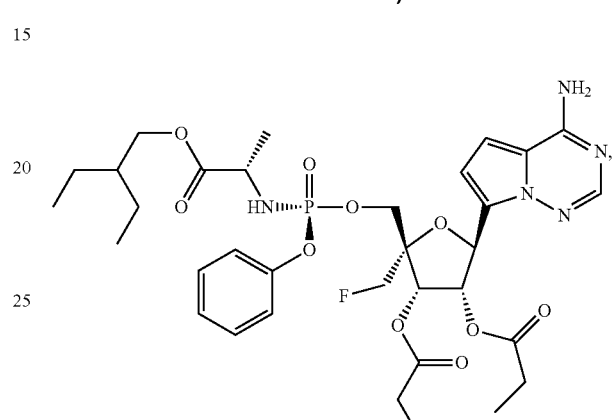
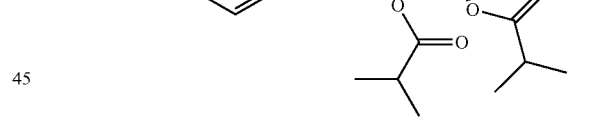
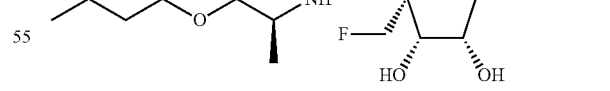
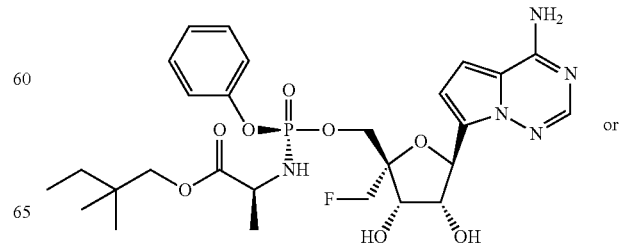
or

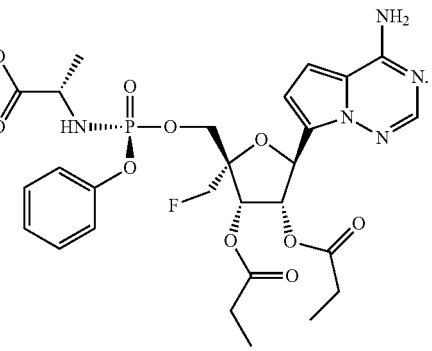

28. The compound of claim 1, or a pharmaceutically acceptable salt thereof, wherein the compound is:

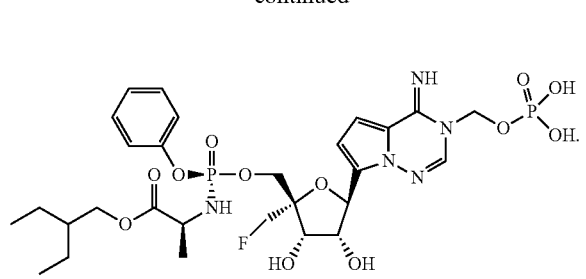

31. The compound of claim 1, or a pharmaceutically acceptable salt thereof, wherein the compound is:

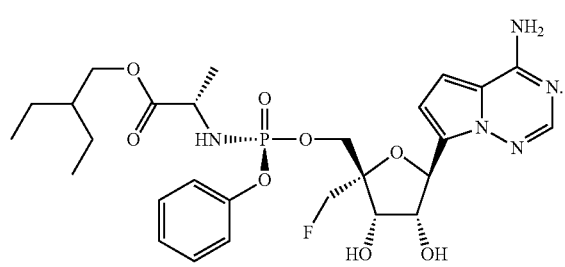 [SMILES: CCC(CC)COC(=O)[C@H](C)N[P@](=O)(OC[C@@]1(CF)O[C@@H](c2ccc3c(N)ncnn23)[C@H](O)[C@@H]1O)Oc1ccccc1]

29. The compound of claim 1, or a pharmaceutically acceptable salt thereof, wherein the compound is:

32. The compound of claim 1, or a pharmaceutically acceptable salt thereof, wherein the compound is:

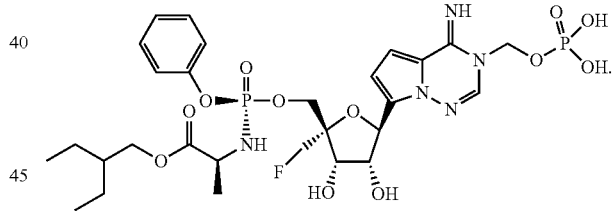

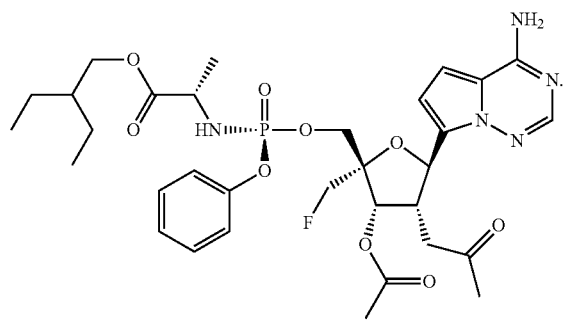 [SMILES: CCC(CC)COC(=O)[C@H](C)N[P@](=O)(OC[C@@]1(CF)O[C@@H](c2ccc3c(N)ncnn23)[C@H](CC(C)=O)[C@@H]1OC(C)=O)Oc1ccccc1]

33. A pharmaceutical formulation comprising a pharmaceutically effective amount of a compound of claim 1 or a pharmaceutically acceptable salt thereof, and a pharmaceutically acceptable carrier or excipient.

30. The compound of claim 1, or a pharmaceutically acceptable salt thereof, wherein the compound is:

* * * * *

SEQUENCE LISTING

```
<160> NUMBER OF SEQ ID NOS: 1

<210> SEQ ID NO 1
<211> LENGTH: 244
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 1
ucagucaguc agucagucag ucagucaguc agucagucag ucagucaguc agucagucag     60
ucagucaguc agucagucag uccaagucca aguccaaguc caaguccaag uccaagucca    120
aguccaaguc caaguccaag uccaagucca aguccaaguc caagucaguc agucagucag    180
ucagucaguc agucagucag ucagucaguc agucagucag ucagucaguc agucagucag    240
ucag                                                                 244
```